(12) United States Patent
Ko

(10) Patent No.: US 10,335,456 B2
(45) Date of Patent: Jul. 2, 2019

(54) METHODS OF USING ZSCAN4 FOR REJUVENATING HUMAN CELLS

(71) Applicant: Elixirgen, LLC, Baltimore, MD (US)

(72) Inventor: Minoru S. H. Ko, Cockeysville, MD (US)

(73) Assignee: Elixirgen Therapeutics, Inc., Cockeysville, MD (US)

( * ) Notice: Subject to any disclaimer, the term of this patent is extended or adjusted under 35 U.S.C. 154(b) by 470 days.

(21) Appl. No.: 14/776,707

(22) PCT Filed: Mar. 14, 2014

(86) PCT No.: PCT/US2014/029537
§ 371 (c)(1),
(2) Date: Sep. 14, 2015

(87) PCT Pub. No.: WO2014/144932
PCT Pub. Date: Sep. 18, 2014

(65) Prior Publication Data
US 2016/0030514 A1 Feb. 4, 2016

Related U.S. Application Data

(60) Provisional application No. 61/800,668, filed on Mar. 15, 2013.

(51) Int. Cl.
| | | |
|---|---|---|
| A61K 38/17 | (2006.01) |
| A61K 31/7088 | (2006.01) |
| A61K 35/28 | (2015.01) |
| A61K 35/33 | (2015.01) |
| A61K 35/545 | (2015.01) |
| A61K 9/51 | (2006.01) |
| C12N 15/113 | (2010.01) |
| C12Q 1/68 | (2018.01) |
| A61K 48/00 | (2006.01) |
| C12N 15/85 | (2006.01) |
| C12N 5/0735 | (2010.01) |
| C12N 5/075 | (2010.01) |
| C12N 5/074 | (2010.01) |
| C12Q 1/6883 | (2018.01) |

(52) U.S. Cl.
CPC ............ *A61K 38/1709* (2013.01); *A61K 9/51* (2013.01); *A61K 31/7088* (2013.01); *A61K 35/28* (2013.01); *A61K 35/33* (2013.01); *A61K 35/545* (2013.01); *A61K 48/005* (2013.01); *C12N 5/0606* (2013.01); *C12N 5/0609* (2013.01); *C12N 5/0696* (2013.01); *C12N 15/113* (2013.01); *C12N 15/85* (2013.01);

*C12Q 1/6883* (2013.01); *A61K 48/00* (2013.01); *C12N 2310/14* (2013.01); *C12N 2310/531* (2013.01); *C12N 2320/31* (2013.01); *C12N 2501/998* (2013.01); *C12N 2510/04* (2013.01); *C12N 2760/18841* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| 5,888,762 | A | 3/1999 | Joliot et al. |
| 6,110,902 | A | 8/2000 | Mohler et al. |
| 6,821,948 | B1 | 11/2004 | Braun et al. |
| 2003/0125242 | A1 | 7/2003 | Rosenecker et al. |
| 2004/0005296 | A1 | 1/2004 | Yonemitsu et al. |
| 2005/0287648 | A1 | 12/2005 | Smith et al. |
| 2006/0024331 | A1 | 2/2006 | Fernandez-Salas et al. |
| 2006/0099677 | A1 | 5/2006 | Lee et al. |
| 2006/0106197 | A1 | 5/2006 | Karas |
| 2006/0286544 | A1 | 12/2006 | Mandal et al. |
| 2010/0105043 | A1 | 4/2010 | Ko et al. |
| 2011/0028880 | A1 | 2/2011 | Uchida et al. |
| 2012/0129161 | A1 | 5/2012 | Ko et al. |
| 2012/0156305 | A1 | 6/2012 | Ko et al. |

(Continued)

FOREIGN PATENT DOCUMENTS

| JP | 2013-503638 A | 2/2013 |
| WO | 2008/118957 A2 | 10/2008 |

(Continued)

OTHER PUBLICATIONS

Widmer, et al. (2010) "Hemoglobin Can Attenuate Hydrogen Peroxide—Induced Oxidative Stress by Acting as an Antioxidative Peroxidase", Antioxidants & Redox Signalling, 12(2): 185-198.*

(Continued)

*Primary Examiner* — Robert M Kelly
(74) *Attorney, Agent, or Firm* — Morrison & Foerster LLP

(57) ABSTRACT

The present disclosure relates to methods for increasing telomere length in one or more human cells and/or increasing genome stability of one or more human cells, for example by contacting one or more human cells with an agent that increases expression of Zscan4 in the one or more human cells. Methods of treating a subject in need of telomere lengthening, treating a disease or condition associated with a genomic and/or chromosome abnormality, of rejuvenating one or more human cells, of rejuvenating tissues or organs, and of rejuvenating a subject in need thereof, for example by contacting one or more human cells in the subject with an agent that increases expression of Zscan4, or by administering to a subject in need thereof, an agent that increases expression of Zscan4 are also provided.

12 Claims, 19 Drawing Sheets
Specification includes a Sequence Listing.

(56) References Cited

U.S. PATENT DOCUMENTS

| | | |
|---|---|---|
| 2014/0287511 A1 | 9/2014 | Ko et al. |
| 2014/0322176 A1 | 10/2014 | Ko et al. |

FOREIGN PATENT DOCUMENTS

| | | |
|---|---|---|
| WO | 2011/028880 A2 | 3/2011 |
| WO | 2012/103235 A1 | 8/2012 |
| WO | 2012/129342 A1 | 9/2012 |
| WO | 2012/158561 A1 | 11/2012 |
| WO | 2012/158564 A1 | 11/2012 |
| WO | 2014/144932 A2 | 9/2014 |

OTHER PUBLICATIONS

Gungor, et al. (2003) "Nonmyeloablative allogeneic hematopoietic stem cell transplantation for treatment of Dyskeratosis Congenita", Bone Marrow Transplanation, 31(5): 407-10.*

Hermann, et al. (2004) "Efficient generation of neural stem cell-like cells from adult human bone marrow stromal cells", Journal of Cell Science, 117: 441-22.*

Kean, et al. (2013) "MSCs: Delivery Routes and Engraftment, Cell-Targeting Strategies and Immune Modulation", Stem Cells International, Article ID 732742, 13 pages long.*

Fusaki et al., "Efficient Induction of Transgene-Free Human Pluripotent Stem Cells using a Vector based on Sendai Virus, an RNA Virus that does not Integrate into the Host Genome", Proceedings of the Japan Academy. Series B, vol. 85, No. 8, 2009, pp. 348-362.

Gadalla et al., "Telomere Length in Blood, Buccal Cells, and Fibroblasts from Patients with Inherited Bone Marrow Failure Syndromes", Aging, vol. 2, No. 11, Nov. 2010, pp. 867-874.

Yegorov, Y. E., "Telomeres, Telomerase, Oncogenesis and Measure of Health", Clinical Oncohematology, Fundamental Studies and Clinical Practice, vol. 3, No. 2, 2010, pp. 184-197 (With English Summary).

Aebischer et al., "Transplantation in Humans of Encapsulated Xenogeneic Cells without Immunosuppression: A Preliminary Report", Transplantation, vol. 58, No. 11, Dec. 1994, pp. 1275-1277.

Amano et al., "Correction of Down Syndrome and Edwards Syndrome Aneuploidies in Human Cell Cultures", DNA Research, Aug. 31, 2015, pp. 1-12.

Brambrink et al., "Sequential Expression of Pluripotency Markers during Direct Reprogramming of Mouse Somatic Cells", Cell Stem Cell, vol. 2, Feb. 2008, pp. 151-159.

Carter et al., "An in Situ Hybridization-based Screen for Heterogeneously Expressed Genes in Mouse ES Cells.", Gene Expr Patterns, vol. 8, No. 3, Feb. 2008, pp. 181-198.

Elliott et al., "Intercellular Trafficking and Protein Delivery by a Herpesvirus Structural Protein", Cell , vol. 88, Jan. 24, 1997 , pp. 223-233.

Extended European Search Report (includes Supplementary European Search Report and European Search Opinion) received for European Patent Application No. 14762788.9, dated Jun. 30, 2016, 11 pages.

Falco, et al., "Zscan4: A Novel Gene Expressed Exclusively in Late 2-Cell Embryos and Embryonic Stem Cells", Developmental Biology, vol. 307, 2007, pp. 539-550.

Gadalla et al., "Telomere Biology in Hematopoiesis and Stem Cell Transplantation", Blood Reviews, vol. 25, Nov. 2011, pp. 261-269.

Hamatani et al., "Dynamics of Global Gene Expression Changes during Mouse Preimplantation Development", Developmental Cell, vol. 6, Jan. 2004, pp. 117-131.

Harley et al., "A Natural Product Telomerase Activator as Part of a Health Maintenance Program", vol. 14, No. 1, 2011, pp. 45-56.

Hawiger, Jacek, "Noninvasive Intracellular Delivery of Functional Peptides and Proteins", Current Opinion in Chemical Biology, vol. 3, 1999, pp. 89-94.

International Preliminary Report on Patentability received for PCT Application No. PCT/US2014/029537, dated Sep. 24, 2015, 16 pages.

International Search Report and Written Opinion received for PCT Patent Application No. PCT/US2014/029537 dated Oct. 17, 2014, 21 pages.

James et al., "Radiological Features of the Most Common Autosomal Disorders: Trisomy 21-22 (Mongolism or Down's Syndrome), Trisomy 18, Trisomy 13-15, and the CRI DU Chat Syndrome", Clinical Radiology, vol. 22, 1971, pp. 417-433.

Jiang et al., "Zscan4 promotes Genomic Stability during Reprogramming and Dramatically Improves the Quality of iPS Cells as Demonstrated by Tetraploid Complementation", Cell Research, vol. 23, No. 1, Jan. 2013, pp. 92-106.

Kaji et al., "Virus Free Induction of Pluripotency and Subsequent Excision of Reprogramming Factors", Nature, vol. 458, No. 7239, Apr. 9, 2009, pp. 771-775.

Kay, Mark A. et al., "State-of-the-Art Gene-based Therapies: The Road Ahead", Nature Reviews Genetics, Apr. 6, 2011, pp. 1-13.

Kim et al., "Generation of Human Induced Pluripotent Stem Cells by Direct Delivery of Reprogramming Proteins", Cell Stem Cell , vol. 4, No. 6, Jun. 5, 2009, pp. 472-476.

Ko et al., "Large-Scale cDNA Analysis Reveals Phased Gene Expression Patterns during Preimplantation Mouse Development", Development, vol. 127, 2000, pp. 1737-1749.

Laus et al., "Enhanced Major Histocompatibility Complex Class I-Dependent Presentation of Antigens Modified with Cationic and Fusogenic Peptides", Nature Biotechnology, vol. 18, Dec. 2000, pp. 1269-1272.

"Long Telomere Length Associated with Increased Lung Cancer Risk", The University of Chicago Medicine, Press, available at <http://www.uchospitals.edu/news/2015/20150729-lung-cancer.html >, Jul. 29, 2015, 3 pages.

Mi et al., "Characterization of a Class of Cationic Peptides Able to Facilitate Efficient Protein Transduction in Vitro and in Vivo", Molecular Therapy, vol. 2, No. 4, Oct. 2000, pp. 339-347.

Misra, Sanjukta, "Human Gene Therapy: A Brief Overview of the Genetic Revolution", JAPI, vol. 61, 2013, pp. 127-133.

Okita et al., "Generation of Mouse Induced Pluripotent Stem Cells Without Viral Vectors", Science, vol. 322, No. 5903, Nov. 7, 2008, pp. 949-953.

Sharov et al., "Transcriptome Analysis of Mouse Stem Cells and Early Embryos", PLoS Biology, vol. 1, No. 3, 2003, pp. 410-419.

Stadtfeld et al., "Induced Pluripotent Stem Cells Generated without Viral Integration", Science, vol. 322, No. 5903, Nov. 7, 2008, pp. 945-949.

Takahashi et al., "Induction of Pluripotent Stem Cells from Adult Human Fibroblasts by Defined Factors.", Cell, vol. 131, Nov. 30, 2007, pp. 861-872.

Wang et al., "Chromosomal Transposition of PiggyBac in Mouse Embryonic Stem Cells", PNAS, vol. 105, No. 27, Jul. 8, 2008, pp. 9290-9295.

Wernig et al., "A Drug-Inducible Transgenic System for Direct Reprogramming of Multiple Somatic Cell Types", Nat Biotechnol., vol. 26, No. 8, Aug. 2008, pp. 916-924.

Yu et al., "Human Induced Pluripotent Stem Cells Free of Vector and Transgene Sequences", Science, vol. 324, No. 5928, May 8, 2009, pp. 797-801.

Yusa et al., "Generation of Transgene-Free Induced Pluripotent Mouse Stem Cells by the PiggyBac Transposon", Nat Methods, vol. 6, No. 5, May 2009, pp. 363-369.

Zalzman et al., "Zscan4 Regulates Telomere Elongation and Genomic Stability in ES Cells", Nature, Apr. 8, 2010, pp. 858-863.

Zhou et al., "Generation of Induced Pluripotent Stem Cells Using Recombinant Proteins", Cell Stem Cell, vol. 4, No. 5, May 8, 2009, pp. 381-384.

Hirata et al., "Zscan4 Transiently Reactivates Early Embryonic Genes During the Generation of Induced Pluripotent Stem Cells," Science Reports, vol. 2, No. 208, Jan. 4, 2012, pp. 1-11.

Search Report and Written Opinion received for Singapore Patent Application No. 11201507334V, dated Sep. 27, 2016, 14 pages.

Agarwal, et al., "Telomere Elongation in Induced Pluripotent Stem Cells from Dyskeratosis Congenita Patients," Nature, vol. 464, Mar. 11, 2010, pp. 292-296.

(56) References Cited

OTHER PUBLICATIONS

Fleisig, et al., "Telomerase as a Clinical Target: Current Strategies and Potential Applications," Experimental Gerontology, vol. 42, 2007, pp. 102-112.
Westin, et al., "Telomere Restoration and Extension of Proliferative Lifespan in Dyskeratosis Congenita Fibroblasts," Aging Cell, vol. 6, Jan. 27, 2007, pp. 383-394.
Armanios et al., "The Telomere Syndromes", Nature Reviews Genetics, vol. 13, No. 10, 2012, pp. 693-704.
Bogliolo et al., "The Fanconi Anaemia Genome Stability and Tumour Suppressor Network", Mutagenesis, vol. 17, No. 6, 2002, pp. 529-538.
Alter, Blanche P., "Inherited Bone Marrow Failure Syndromes: Considerations Pre- and Posttransplant", Blood, vol. 130, No. 21, Nov. 23, 2017, pp. 2257-2264.
Brunt et al., "Stem Cells and Regenerative Medicine—Future Perspectives", Can. J. Physiol. Pharmacol., vol. 90, 2012, pp. 327-335.
Nakanishi et al., "Development of Sendai Virus Vectors and their Potential Applications in Gene Therapy and Regenerative Medicine", Current Gene Therapy, vol. 12, No. 5, 2012, pp. 410-416.
Naldini, Luigi, "Ex Vivo Gene Transfer and Correction for Cell-Based Therapies", Nature Reviews: Genetics, vol. 12, May 2011, pp. 301-315.
Nguyen et al., "Methods to Assess Stem Cell Lineage, Fate and Function", Advanced Drug Delivery Reviews, vol. 62, 2010, pp. 1175-1186.
Response filed Oct. 24, 2018 to the Office Action dated Jul. 27, 2018 in U.S. Appl. No. 14/211,638.

* cited by examiner

FIG. 14

1. SeVAG-TS15 (P3, D14) -> 6.9 kb
2. SeVAG-TS15 (P7, D62) -> 6.7 kb
3. SeVmZscan4-TS15 (P3, D14) -> 6.8 kb
4. SeVmZscan4-TS15 (P7, D62) -> 6.7 kb
5. SeVhZSCAN4-TS15 (P3, D62) -> 6.7 kb
6. SeVhZSCAN4-TS15 (P7, D62) -> 7.8 kb

SEQUENCE LISTING

```
<160> NUMBER OF SEQ ID NOS: 44

<210> SEQ ID NO 1
<211> LENGTH: 2275
<212> TYPE: DNA
<213> ORGANISM: Mus musculus

<400> SEQUENCE: 1
cacagtgcct ccctgggctt cttggcatca cccttgaagt tcactggaga aagagttgag      60
gtggaggaat aggtaaactt cccttcctag tggtcttgaa tgtcttttac agtacatcca     120
tcaactgtta gcattttcgt aaagtcacaa aacagatatt aaactactat agttgaatct     180
ttcacaccat tgtcaccaca atggcttcac agcaggcacc agcaaaagac cttcagacca     240
acaatttaga gtttactcca actgatagtt ctggtgtgca gtgggcagaa gacatctcta     300 actccaccaag tgctcagcta aacttttccc caagtaacaa tggctgctgg gcaactcagg     360
agctgcaaag tctctggaag atgttcaact cctggttgca gccagaaaag cagactaagg     420
agcagatgat ttctcaactg gtcttggagc agtttctcct cactgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtctcaatg caaggacaag     600
aagccctctt ttctgaaaac atgccattaa aagaagtcat caagctttg aaacaacagc     660 aatctgcaac aaggccaaca ccagataatg cacagatgcc agtagacacc acacaagata     720
gattattggc cacaggacaa gaaaacagtg aaaatgaatg caacacctct tgtaatgcta     780
```

```
ctgaaggaaa tgttggtgag agctgtagtg gaaatgaaat ggactcctct cttattatcc     840
agaaagaaca gtaccctgag catgaagagg ggaatgttgt ttgtcaattc cctcttgatg     900
ccagaagagc aagtcaaggc acctccagtc atcatgtaga cttcctgagt gctctgacta     960
ctgccgatgt ccccatggag gaacaaccaa aggatttatc cagagaaaac atctctgagg    1020
acaagaacaa ttgctataac acttccagga atgcagctac taaagtatat agtggtgata    1080
atattcccag gaaaaagaca gactcccttt ccattaacaa gaggatatat catcctgagc    1140
ctgaggtggg agatattcct tatggagttc ctcaggattc tacaagagca agtcaaggaa    1200
catctacatg cctgcaagag tcacttgggg gatgtttttc cgaaaaagac ctagggaggg    1260
taccagggtt gcagtctagg taagagcagc ctatctctga tcctgtcctt cttggtaaga    1320
atcatgaggc aaacttacca tgtgaaagtc atcaaaagag attctgtaga gatgccaaac    1380
tatacaagtg tgaagaatgt tctaggatgt tcaaacatgc caggagcctt tcatcccacc    1440
agagaactca cctgaataag aagagtgaat tgctttgtgt cacctgtcag aaaattttca    1500
aacgagtctc tgaccgccga acccatgaga tcatacacat gccagaaaag cctttcaagt    1560
gcagcacatg tgaaaagtcc ttcagccaca agaccaacct gaagtctcat gagatgattc    1620
acacaggaga aatgccttat gtctgttccc tatgtagccg tcgctttcgc caatcatcca    1680
cttaccatcg tcacctgagg aattatcaca gatctgactg aagtatctaa catcctcagc    1740
agagactggt agggcttcag cctcagtatg tcatcttcaa agagagaaga atgttgcaag    1800
taaattgtac tgtcccaata atgatataac atgcttgtgg attgccactt ttatgttttg    1860
ttttgttttg ttttttattt tgtgtgtgtg tatgtaattt tttgtctgta tttccatagt    1920
tccacagcat aagttattag aatactttgc tgttaattct tgagttgctt cttgctttta    1980
gacagtgtct ttctggttgg cagctttata cacctgtcct tctggcacta gagttttcaa    2040
acattttctg atctccactt ttattttcta cagtggtcct gacagaggcc tgccattccc    2100
tctgacattt ttctacatgt tggggtttca tcccaagtct tagggttgca agttaaatgc    2160
attgcctctt cagacatctc atgtcatgtc tactgcttac agttcaagaa tatttctcta    2220
cattactaga acgacgttca aagtggaata ataaataaat aaataatcaa caatt         2275
```

<210> SEQ ID NO 2
<211> LENGTH: 1774
<212> TYPE: DNA
<213> ORGANISM: Mus musculus

<400> SEQUENCE: 2

```
cacagtgcct ccctgggctt cttggcatca cccttgaagt tcactggaga aagaggtgat      60
gtggagaagt aggtaaactt cccttttcttg tggtcttgaa tgtcttttac agtacatccg     120
tcaactgtta gcatttttcct aaagtcacaa aacagatact aaactgctat agttgaatct    180
ttcagaccat tgtcaccaca atggcttcac agcaggcacc agcaaaagac cttcagacca    240
acaatttaga gtttactcca actgatagtt ctggtgtgca gtgggcagaa gacatctcta    300
actcaccaag tgctcagcta aacttttccc caagtaacaa tggctgctgg gcaactcagg    360
agctgcaaag tctctggaag atgttcaact cctggttgca gccagaaaag cagactaagg    420
agcagatgat ttctcaattg gtcttggagc agtttctcct cactgggcac tgcaaggaca    480
agtatgcttt gacagagaag tggaaagcca gtggtagcga tatgaggaga ttcatggaga    540
gtctgactga tgagtgcttg aagcctcctg tcatggtcca tgtttcaatg caaggacaag    600
aagccctctt ttctgaaaac atgccattaa agaagtcat caagctttg aaacaacagc      660
```

| | |
|---|---|
| aatctgcaac aaggccaata ccagataatg cacagatgcc agtagacacc acacaagata | 720 |
| gattattggc cacaggcaag aaaacagtga aaatgaatgc aacacctctt gcaatgctac | 780 |
| tgaagtaaat gttggtgaaa gctgtagtgg aaatgaaaag gactcccttc ttattaccca | 840 |
| gaaagaacaa aaccatgagc atgaagaggg gaatgttgtt tgtcaattcc ctcgtggtgc | 900 |
| cagaagagca agtcaagaca cctccagtca tcatgtagac ttcccgagtg ctctgactcc | 960 |
| tgcagatgtc cccatggagg aacaaccaat ggatttatcc agagaaaaca tctctgagga | 1020 |
| caagaacaat tgctataaca cttccaggaa tgcagctact caagtatata gtggtgataa | 1080 |
| tattcccagg aacaagacag actcccttt cattaacaag agaatatatc atcctgagcc | 1140 |
| tgaggtggga gatattcctt atggagttcc tcaggattct acaagagcaa gtcaaggaac | 1200 |
| atctacatgc ctgcaagagt cacttgggga atgttttct gaaaaagacc caagggaggt | 1260 |
| accagggttg cagtctaggc aagagcagcc tatctctgat cctgtccttg gtaagaatca | 1320 |
| tgaggcaaac ttaccatgtg aaagtcatca aaagagattc catagagatg ccaaactata | 1380 |
| caagtgtgaa gaatgttcta ggatgttcaa acatgccagg agccttcat cccaccagag | 1440 |
| aactcacctg aataagaaga gtgaattgct ttgcatcacc tgtcagaaaa tattcaaacg | 1500 |
| agtttctgac cttcgaaccc atgagatcat acacatgtca gaaaagcctt tcaagtgcag | 1560 |
| cacatgtgaa aagtccttca gccacaagac caacctgaag tatcatgaga tgattcacac | 1620 |
| aggagaaatg ccttatgtct gttccctatg tagccgtcgc tttcgccaat catccactta | 1680 |
| ccatcgtcac ctgaggaatt accacagatc tgactgaagt atctaacatc ctcagcagag | 1740 |
| actggtaggg cttcagcctc agtatgtcat cttc | 1774 |

<210> SEQ ID NO 3
<211> LENGTH: 2275
<212> TYPE: DNA
<213> ORGANISM: Mus musculus

<400> SEQUENCE: 3

| | |
|---|---|
| cacagtgcct ccctgggctt cttggcatca cccttgaagt tcaccggaga aagcagtgag | 60 |
| gtggaggaat aggtaaactt tccttcctag tggtcttgaa tgtctttac agtacatcca | 120 |
| tcaactgtta gcattttcgt aaagtcacaa aacagatatt aaactactat agttgaatct | 180 |
| ttcacaccat tgtcaccaca atggcttcac agcaggcacc agcaaaagac cttcagacca | 240 |
| acaatttaga gtttactcca actgatagtt ctggtgtgca gtgggcagaa gacatctcta | 300 |
| actcaccaag tgctcagcta aacttttccc caagtaacaa tggctgctgg gcaactcagg | 360 |
| agctgcaaag tctctggaag atgttcaact cctggttgca gccagaaaag cagactaagg | 420 |
| agcagatgat ttctcaactg gtcttggagc agtttctcct cactgggcac tgcaaggaca | 480 |
| agtatgcttt gacagagaag tggaaagcca gtggtagcga tatgaggaga ttcatggaga | 540 |
| gtctgactga tgagtgcttg aagcctcctg tcatggtcca tgtttcaatg caaggacaag | 600 |
| aagccctctt ttctgaaaac atgccattaa agaagtcat caagcttttg aaacaacagc | 660 |
| aatctgcaac aaggccaaca ccagataatg agcagatgcc agtagacacc acacaagata | 720 |
| gattattggc cacaggacaa gaaacagtg aaatgaatg caacaactct tgtaatgcta | 780 |
| ctgaagcaaa tgttggtgaa agctgtagtg gaaatgaaat ggactcctt cttattatcc | 840 |
| agaaagaaca gcaccctgag catgaagagg ggaatgttgt ttgtcaattc cctcatggtg | 900 |
| ccagaagagc aagtcaaggc accccagtc atcatgtaga cttcccgagt gctccgacta | 960 |

| | | | | |
|---|---|---|---|---|
| ctgccgatgt | ccccatggag | gaacaaccaa | aggatttatc | cagagaaaac atctctgagg | 1020 |
| acaagaacaa | ttgctataac | acttccagaa | atgcagctac | tcaagtatat agtggtgata | 1080 |
| atattcccag | gaacaagtca | gactcccttt | tcattaacaa | gagaatatat catcctgagc | 1140 |
| ctgaggtggg | agatattcct | tatggagttc | ctcaggattc | tacaagagca agtcaaggaa | 1200 |
| catctacatg | cctgcaagag | tcacttgggg | aatgtttttc | tgaaaacgac ccaagggagg | 1260 |
| taccagggtt | gcagtctagg | caagagcagc | ctatctctga | tcctgtcctt cttggtaaga | 1320 |
| atcatgaggc | aaacttacca | tgtgaaagtc | atcaaaagag | attctgtaga gatgccaaac | 1380 |
| tatacaagtg | tgaagaatgt | tctaggatgt | caaacatgc | caggagcctt tcatcccacc | 1440 |
| agagaactca | cctgaataag | aagagtgaat | tgctttgtgt | cacctgtcag aaaatgttca | 1500 |
| aacgagtctc | tgaccgccga | acccatgaga | tcatacacat | gccagaaaag cctttcaagt | 1560 |
| gcagcacatg | tgaaaagtcc | ttcagccaca | agaccaacct | gaagtctcat gagatgattc | 1620 |
| acacaggaga | aatgccttat | gtctgttccc | tatgtagccg | tcgctttcgc caatcatcca | 1680 |
| cttaccatcg | tcacctgagg | aattaccaca | gatctgactg | aactatctaa catcctcagc | 1740 |
| agagactggt | agggcttcag | cctcagtatg | tcatcttcaa | agagagaaga atgttgcaag | 1800 |
| taaattgtac | tgtcccaata | atgatataac | atgcttgtgg | attgccactt ttatgttttg | 1860 |
| ttttgttttg | ttwtttatkt | tgtgtgtgtg | tatgtaattt | tttgtctgta tttccatatt | 1920 |
| tccacagcat | aagttattag | aatactttgc | tgttaattct | tgagttgctt cttgctttta | 1980 |
| gacagtgtct | ttctggttgg | cagctttata | cacctgtctt | tctggcacta gagtttccaa | 2040 |
| acattttctg | atctccactt | ttattttcta | cagtgttctt | gacagaagcc tggcattccc | 2100 |
| tctgacattt | tctacatgtt | ggggttttca | tcccaagtct | taggttgca agttaaatgc | 2160 |
| attgcctctt | cagacatctc | atgccatgtc | tactgcttac | agttcaagaa tatttctcta | 2220 |
| cattactaga | acgacgttca | aagtggaata | ataaataaat | aaataatcaa caatt | 2275 |

```
<210> SEQ ID NO 4
<211> LENGTH: 2268
<212> TYPE: DNA
<213> ORGANISM: Mus musculus

<400> SEQUENCE: 4
```

| | | | | |
|---|---|---|---|---|
| cacagtgcct | ccctgggctt | cttggcatca | cccttgaagt | tcactggaca aagaggtgag | 60 |
| gtggaggagt | aggtaaactt | cccttcctag | tggtcgtgaa | tgtcttttac agtacatcca | 120 |
| tcaactgtta | gcattttcat | aaagtcacaa | aacagatact | aaactgctat agttgaatct | 180 |
| ttcacaccat | tgtcaccaca | atggcttcac | agcaggcacc | agcaaaagac cttcagacca | 240 |
| acaatttaga | gttactccaa | tctcatagtt | ctggtgtgca | gtgggtagaa gacatctcta | 300 |
| actcaccaag | tgctcagcta | aacttttctc | caagtaacaa | tggctgctgg gcaactcagg | 360 |
| agctgcaaag | tctctggaag | atgttcaact | cctggttgca | gccagaaaag cagactaagg | 420 |
| agcagatgat | ttctcaactg | gtcttggagc | agtttctcct | cattgggcac tgcaaggaca | 480 |
| agtatgcttt | gacagagaag | tggaaagcca | gtggtagcga | tatgaggaga ttcatggaga | 540 |
| gtctgactga | tgagtgcttg | aagcctcctg | tcatggtcca | tgtttcaatg caaggacaag | 600 |
| aagctctctt | ttctgaaaac | atgccattaa | agaagtcat | caagcttttg aaacaacagc | 660 |
| aatctgcaac | aaggccaaca | ccagataatg | agcagatgcc | agtagacacc acacaagata | 720 |
| gattattggc | cacaggacaa | gaaaacagtg | aaaatgaatg | caacaactct tgtaatgcta | 780 |
| ctgaagcaaa | tgttggtgaa | agctgtagtg | gaaatgaaat | ggactcccctt cttattatcc | 840 |

```
agaaagaaca gcaccctgag catgaagagg ggaatgttgt ttttcaattc cctcttgatg      900
ccagaagagc aagtcaaggc aactccagtc atcatgtaga cttccggagt gctccgactc      960
ctgcggatgt ccccatggag gaacaaccaa aggatttatc cagagaaaac atctctgagg     1020
acaagaacaa ttgctataac acttccagga atgcagctac tcaagtatat agaagtgata     1080
atattcccag gaaaaagaca gactcccttt ccattaacaa gagaatatat cattctgagc     1140
ctgaggaggg agatattcct tatggagttc ctcaggattc tacaagagca agtcaaggaa     1200
catctacatg cttgcaagag tcacttgggg aatgtttttc tgaaaaagac cctagggagc     1260
taccagggtt ggagtctagg caagaggagc ctatctctga tcctgtcttt cttggtaagg     1320
atcatgaggc aaacttacca tgtgaaagtc atcaaaagag attccgtaga gatgccaaac     1380
tattcaagtg tgaagaatgt tctaggatgt caaacatgc caggagcctt tcgtcccacc      1440
agagaactca cctgaataag aagagtgaat tgctttgtgt cacctgtcag aaaatgttca     1500
aacgagtctc tgaccgccga acccatgaga tcatacacat gccagaaaag ccttttcaagt    1560 gcagcacatg tgaaaagtcc ttcagccaca agaccaacct gaagtctcat gagatgattc     1620
acacaggaga aatgccttat gtctgttccc tatgtagccg tcgctttcgc caatcatcca     1680
cttaccatcg tcacctgagg aattaccaca gatctgactg aagtatctaa catcctcagc     1740
agagactggt agggcttcag cctcagtatg tcatcttcaa agagagaaga atgttgcaag     1800
taaattgtac tgtcccaata atgatataac atgcttgtgg attgccactt ttatgttttg     1860
ttttttattg tgtgtgtgtg tgtatgtaat tttttgtctg taatttccat agttccacag     1920
cataagttat tagaatactt tgctgttaat tcttgagttg cttcttgctt ttagacagtg     1980
tctttctggt tggcagcttt atacacctgt ctttctggca ctagagtttc caaacatttt     2040
ctgatctcca cttttattct ctacagtggt cctgacagag gcctgccatt ccctctgaca     2100 tttttttaaca tgttggggtt tcatcccaag tcttagggtt gcaagttaaa tgcattgcct     2160
cttcagacat ctcatgtcat gtctactgct tacagttcaa gaatatttct ctacattact     2220
agaatgacgt tcaaagtgga ataataaata aaaaaataat caacaatt                  2268
```

<210> SEQ ID NO 5
<211> LENGTH: 1774
<212> TYPE: DNA
<213> ORGANISM: Mus musculus

<400> SEQUENCE: 5

```
cacagtgcct ccctgggctt cttggcatca ccattgaagt tcactggaga aagaggtgag       60
gtggagaagt aggtaaactt ccctttcttg tggtcttgaa tgtcttttac agtacatccg      120
tcaactgtta gcatttctct aaagtcacaa aacagatact aaactgctat agttgaatct      180
ttcagaccat tgtcaccaca atggcttcac agcaggcacc agcaaaagac cttcagacca     240
acaatttaga gttactccac actgatagtt ctggtgtgca gtgggcagaa gacatctcta     300
actcaccaag tgctcagcta aacttttccc caagtaacaa tggctgctgg gcaactcagg     360
agctgcaaag tctctggaag atgttcaact cctggttgca gccagaaaag cagactaagg     420
agcagatgat ttctcaactg gtcttggagc agttttctcct cactgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtttcaatg caaggacaag     600
aagccctctt ttctgaaaac atgccattaa agaagtcat caagcttttg aaacaacagc      660
```

```
aatctgcaac aaggccaata ccagataatg agcagatgcc agtagacacc acacaagata      720
gattattggc cacaggcaag aaaacagtga aaatgaatgc aacacctctt gcaatgctac      780
tgaagtaaat gttggtgaaa gctgtagtgg aaatgaaaag gactcccttc ttattaccca      840
gaaagaacaa aaccatgagc atgaagaggg gaatgttgtt tgtcaattcc ctcgtggtgc      900
cagaagagca agtcaagaca cctccagtca tcatgtagac ttcccgagtg ctctgactcc      960
tgcagatgtc cccatggagg aacaaccaat ggatttatcc agagaaaaca tctctgagga     1020
caagaacaat tgctataaca cttccaggaa tgcagctact caagtatata atggtgataa     1080
tattcccagg aacaagacag actccctttt cattaacaag agaatatatc atcctgagcc     1140
tgaggtggga gatattcctt atggagttcc tcaggattct acaagagcaa gtcaaggaac     1200
atctacatgc ctgcaagagt cacttgggga atgttttttct gaaaaagacc caagggaggt     1260
accagggttg cagtctaggc aagagcagcc tatctctgat cctgtccttg gtaagaatca     1320
tgaggcaaac ttaccatgtg aaagtcatca aaagagattc catagagatg ccaaactata     1380
caagtgtgaa gaatgttcta ggatgttcaa acatgccagg agcctttcat cccaccagag     1440
aactcacctg aataagaaga gtgaattgct ttgcatcacc tgtcagaaaa tattcaaacg     1500
agtttctgac cttcgaaccc atgagatcat acacatgtca gaaaagcctt tcaagtgcag     1560
cacatgtgaa aagtccttca gccacaagac caacctgaag tatcatgaga tgattcacac     1620
aggagaaatg ccttatgtct gttccctatg tagccgtcgc tttcgccaat catccactta     1680
ccatcgtcac ctgaggaatt accacagatc tgactgaagt atctaacatc ctcagcagag     1740
actggtaggg cttcagcctc agtatgtcat cttc                                 1774

<210> SEQ ID NO 6
<211> LENGTH: 2273
<212> TYPE: DNA
<213> ORGANISM: Mus musculus

<400> SEQUENCE: 6
cacagtgcct ccctgggctt cttggcatca cccttgaagt tcactggaga aagaggtgag       60
gtggaggaat aggtaaactt tccttcctag tggtcttgaa tgtcttttac agtacatcca      120
tcaactgtta gcattttcgt aaagtcacaa acagatatt aaactactat agttgaatct      180
ttcacaccat tgtcaccaca atggcttcac agcaggcacc agcaaaagac cttcagacca      240
acaatttaga gtttactcca actgatagtt ctggtgtgca gtgggcagaa gacatctcta      300
actcaccaag tgctcagcta aacttttccc caagtaacaa tggctgctgg gcaactcagg      360
agctgcaaag tctctggaag atgttcaact cctggttgca gccagaaaag cagactaagg      420
agcagatgat ttctcaactg gtcttggagc agtttctcct cactgggcac tgcaaggaca      480
agtatgcttt gactgagaag tggaaagcca gtggtagcga tatgaggaga ttcatggaga      540
gtctgactga tgagtgcttg aagcctcctg tcatggtcca tgtttcaatg caaggacaag      600
aagccctctt ttctgaaaac atgccattaa agaagtcat caagcttttg aaacaacagc      660
aatctgcaac aaggccaaca ccagataatg agcagatgcc agtagacacc acacaagata      720
gattattggc cacaggacaa gaaaacagtg aaaatgaatg caacaactct tgtaatgcta      780
ctgaagcaaa tgttggtgaa agctgtagtg gaaatgaaat ggactccctt cttattatgc      840
agaaagaaca gcaccctgag catgaagagg ggaatgttgt ttgtcaattc cctcatggtg      900
ccagaagagc aagtcaaggc accccagtc atcatgtaga cttcccgagt gctccgacta      960
ctgccgatgt ccccatggag gaacaaccaa aggatttatc cagagaaaac atctctgagg     1020
```

| | | | | |
|---|---|---|---|---|
| acaagaacaa | ttgctataac | acttccagaa | atgcagctac | tcaagtatat agtggtgata | 1080 |
| atattcccag | gaacaagtca | gactcccttt | tcattaacaa | gagaatatat catcctgagc | 1140 |
| ctgaggtggg | agatattcct | tatggagttc | tcaggattc | tacaagagca agtcaaggaa | 1200 |
| catctacatg | cctgcaagag | tcacttgggg | aatgttttc | tgaaaagac cctagggagg | 1260 |
| taccagggtt | gcagtctagg | caagagcagc | ttatctctga | tcctgtcctt cttggtaaga | 1320 |
| atcatgaggc | aaacttacca | tgtgaaagtc | atcaaaagag | attctgtaga gatgccaaac | 1380 |
| tatacaagtg | tgaagaatgt | tctaggatgt | tcaaacatgc | caggagcctt tcatcccacc | 1440 |
| agagaactca | cctgaataag | aagagtgaat | tgctttgtgt | cacctgtcag aaaatgttca | 1500 |
| aacgagtctc | tgaccgccga | acccatgaga | tcatacacat | gccagaaaag cctttcaagt | 1560 |
| gcagcacatg | tgaaaagtcc | ttcagccaca | agaccaacct | gaagtctcat gagatgattc | 1620 |
| acacaggaga | aatgccttat | gtctgttccc | tatgtagccg | tcgctttcgc caatcatcca | 1680 |
| cttaccatcg | tcacctgagg | aattaccaca | gatctgactg | aactatctaa catcctcagc | 1740 |
| agagactggt | agggcttcag | cctcagtatg | tcatcttcaa | agagagaaga atgttgcaag | 1800 |
| taaattgtac | tgtcccaata | atgatataac | atgcttgtgg | attgccactt ttatgttttg | 1860 |
| ttttgttttt | tattttgtgt | gtgtgtgtat | gtaattttt | gtctgtattt ccatagttcc | 1920 |
| acagcataag | ttattagaat | actttgctgt | taattcttga | gttgcttctt gcttttagac | 1980 |
| agtgtctttc | tggttgacag | ctttataaac | ctgtctttct | ggcactagag tttccaaaca | 2040 |
| ttttctgatc | tccacttta | ttctctacag | tgttcttgac | agaagcctgg cattccctct | 2100 |
| gacattttc | tacatgttgg | ggttttcatc | ccaagtctta | gggttgcaag ttaaatgcat | 2160 |
| tgcctcttca | gacatctcat | gccctgtcta | ctgcttacag | ttcaagaata tttctctaca | 2220 |
| ttactagaac | gacattcaaa | gtggaataat | aaataaataa | ataatcaaca att | 2273 |

<210> SEQ ID NO 7
<211> LENGTH: 2260
<212> TYPE: DNA
<213> ORGANISM: Homo sapiens

<400> SEQUENCE: 7

| | | | | |
|---|---|---|---|---|
| ccttgtaatt | cataaatctc | tgaaaactta | aaagtttgag | caaaagtttg tcatgtttct | 60 |
| atgagtaatt | tataataaaa | cttgatcaga | atttgtgaga | ctaacgtttg tctttatatt | 120 |
| ttcctttttt | tttttttttt | ttttgagaca | cagtctcgct | ctgtcgtcca ggctggagtg | 180 |
| ccgtggcgta | atctcggctc | actgcaacct | ctgcctcctg | gattcaaaca attcttctgc | 240 |
| ctcagcctcc | tgagtagctg | ggattacagg | accagtgatg | gtatagaaca ctgtattaga | 300 |
| gacatggagc | tggggctgga | tgaagattcc | atcagtaatt | caatcaacag acaagtgtta | 360 |
| tccaatcacg | tctttaaatc | aatcactgac | atggagctgg | ggctggatga agattccatc | 420 |
| agtaattcaa | tcaacagaca | agtgttatcc | aatcacgtct | ttaaatcaat cactgatccc | 480 |
| agcccctata | aagggagca | gccttaggag | gcacatcaga | taaacccagt gtggaaagct | 540 |
| agtcacacat | cagctcagtg | ttcggcccgg | gattacccag | tcaaccaagg agcttgcagt | 600 |
| tttaaagaat | ccaccaactg | ttgaaacaaa | tccctagaga | cacaaggcaa gagactgaat | 660 |
| catcaaagta | aagtctctct | gagaattatt | gctaagaatg | gctttagatc taagaaccat | 720 |
| atttcagtgt | gaaccatccg | agaataatct | tggatcagaa | aattcagcgt tcaacaaag | 780 |
| ccaaggacct | gctgttcaga | gagaagaagg | gatttctgag | ttctcaagaa tggtgctcaa | 840 |

```
ttcatttcaa gacagcaata attcatatgc aaggcaggaa ttgcaaagac tttataggat      900
ctttcactca tggctgcaac cagaaaagca cagcaaggat gaaattattt ctctattagt      960
cctggagcag tttatgattg gtggccactg caatgacaaa gccagtgtga aagagaaatg     1020
gaaatcaagt ggcaaaaact tggagagatt catagaagac ctgactgatg acagcataaa     1080
tccacctgcc ttagtccacg tccacatgca gggacaggaa gctctctttt ctgaggatat     1140
gcccttaaga gatgtcattg ttcatctcac aaaacaagtg aatgcccaaa ccacaagaga     1200
agcaaacatg gggacaccct cccagacttc ccaagatact tccttagaaa caggacaagg     1260
atatgaagat gaacaagatg gctggaacag ttcttcgaaa actactcgag taaatgaaaa     1320
tattactaat caaggcaatc aaatagtttc cctaatcatc atccaggaag agaacggtcc     1380
taggcctgaa gagggaggtg tttcttctga aacccatac aactcaaaaa gagcagagct      1440
agtcactgct agatctcagg aagggtccat aaatggaatc actttccaag gtgtccctat     1500
ggtgatggga gcagggtgta tctctcaacc agagcagtcc tcccctgagt ctgcccttac     1560
ccaccagagc aatgagggaa attccacatg tgaggtacat cagaaaggat cccatggagt     1620
ccaaaaatca tacaaatgtg aagaatgccc caaggtcttt aagtatctct gtcacttatt     1680
agctcaccag agaagacaca ggaatgagag gccatttgtt tgtcccgagt gtcaaaaagg     1740
cttcttccag atatcagacc tacgggtgca tcagataatt cacacaggaa agaagccttt     1800
cacatgcagc atgtgtaaaa agtccttcag ccacaaaacc aacctgcggt ctcatgagag     1860
aatccacaca ggagaaaagc cttatacatg tcccttttgt aagacaagct accgccagtc     1920
atccacatac caccgccata tgaggactca tgagaaaatt accctgccaa gtgttccctc     1980
cacaccagaa gcttcctaag ctgctggtct gataatgtgt ataaatatgt atgcaagtat     2040
gtatattcct atagtattta tctacttagg atataagata taatctcctg attatgcttt     2100
caatttattg tcttgcttca ttaaaatgta aggctaagga gagcatggaa tttgtcagtt     2160
ttgttcacta aagtattcca agtggttggg aaagtggaac attccaaga accaataaat      2220 ttctgttgaa taaatgaatg aatccaaaaa aaaaaaaaaa                           2260

<210> SEQ ID NO 8
<211> LENGTH: 1302
<212> TYPE: DNA
<213> ORGANISM: Canis familiaris

<400> SEQUENCE: 8
atggcttcag atatcagaat atcatttcag ggagaaccat ctatgaatga tcctgggtca       60
gaaaacctag agcataaact tagccaagga ccagccattc aggaggaaga cgagatctat      120
gagttcccaa gcactcagct cactttattg caaaacagta actcaagtgc aaggcaggaa      180
ctgcaaaatc tctataagtt atttcactca tggctgcaac cagagaaaca cagcaaggat      240
gagattattt ctcatctggt cttggaacag tttatgatca atggccactg cagtgacagg      300
tccatgttga aaagaaatg gaatgcaagt ggcaggaacc tggagaaatt catggaagat      360
ctgactgatg atggcatgaa gctacctgga ttagtccacg tccacatgaa gggccaggac      420
gccctctttt ctgagaatat gcccttaaga gaagtcatcg ttcatttcat gaaacaattg      480
tcagcaggaa ccccaacaga agagaacatg gggacaccct cctggacttc ccaagatact      540
tccctggaaa caggacaagg tgagtgggat aaagcaaatg gctacaacat ttatcacaat      600
gacggtacta ctagtcaagg caatgcagta ccttccctgt tcattgtcca tgaggaggac      660
tgtcctcacc ctgaagagga cagtgttttct ttgaaggatc tgctcagccc tggaagaccg      720
```

```
ggtctaggta cgtccaattc ccaggaaggg tgcctgcaag gacgcccata tcaagatgtc    780
ctgatggagg gggcaccagg gtttcactct cggtcaaccg cagtcacccc tgaccctgtt    840
tctacccacc aaaaaaccga ggggaattcc acatgtgggg gacaccaaga aagattccgt    900
gacgcccaaa actcctacag atgtgaaaaa tgtcccagga tctttaggta tttctctcag    960
ctaaaagccc atcagagaag acacaacaat gagaggacat tcatttgtgc tgagtgtaac   1020
aaaggcttct tccaagcgtc agacctacac gtgcatcaga agattcacac agaagagaag   1080
cctttcaggt gcagcacatg tgaaaaatcc ttcagccaca aaaccaacct tctggcccat   1140
gagagaatcc acacgggtga aagcccctat gtatgtgcgc tttgccagag aagctaccgc   1200
cagtcatcca cctaccaccg ccacctgagg actcaccaga aaattgccgt caaaggtact   1260
ccttccacat cagaagcttc ctcagctgta gcctcagtgt aa                       1302

<210> SEQ ID NO 9
<211> LENGTH: 1251
<212> TYPE: DNA
<213> ORGANISM: Bos taurus

<400> SEQUENCE: 9
atggatttag gtttcagagc atcatttcag catgaaccat ccaatgagga cccaaagtca     60
gcaaatacag gctttatccc cagtcgagga cccactctgc aaacagcaga ggatatctct    120
cagttgcaaa acactcagcc cggcttattg caaaatggta ataactcacg tgcaaggcag    180
gaactgcaaa gactctataa gtcatttcac ttatggctgc agccagaaaa acacagcaag    240
catgaaatta ttttcaact tgccctggaa caatttatga tcaataagca ctgcagtgaa    300
aagtctactt tgaaagagaa atggaaagca agtggtggag acctggagaa attcacagaa    360
gacctgcatg atgactgcat aaagctacct gatttggtcc atgtccactt gcaggggcag    420
gaagccctct tttcagaaaa atatgtcctta aaagaaatca tctttcatct aaccaatcag    480
ttgtcaacag gaggggtgaa catgggaact ccgtcctgga ccatgcaaga tacatccctg    540
gaaacaggac aaagaaatga aggtaaagaa aatgatggca cattttctgt gaaaagtgac    600
agtattacta gtccaagcaa tcagataact tccctaatca ttgtccaaga agagaatcac    660
ctgaggctgg aagaaggagg tgtttctctg gagaatccac ggaactccag aagaggagca    720
ggcccaggcc cctccaggcc tcaggatgga tccctgaaag accctcctc tcaagatgtc     780 ctcatggaag tggaacgaga ccaggtcacc cctgggcctg tttctaccct ccagagctct    840
gaggggactt ctgcacgtgg aaacaccagg aaagatccc tcagccccc agaagtatac      900 agatgtgaga gatgtcccaa gaccttcagg tattcctctc ggttcagagt tcaccagaaa    960
agacacgata tgagagaac atatatttgt gccgagtgtg gcaaaggctt ctttcaggcc   1020
tcagacctcc atgtgcatca gaggattcat acaggagaga agccctttgt gtgcagcaca   1080
tgtgaaatgg ccttcaccca caaaaccaac cttcgggctc acgagagaac ccacacggga   1140
gagaagccct atgagtgttc cctctgccag agacgcttcc gccagtcctc cacctaccac   1200
cgccatctta ggtttcacca gaaaactacc ctcaaaagtg ctccacacta a            1251

<210> SEQ ID NO 10
<211> LENGTH: 1713
<212> TYPE: DNA
<213> ORGANISM: Equus caballus

<400> SEQUENCE: 10
```

| | |
|---|---|
| atggctttag atctcagaat ctcatttcaa ggtgaaccat ccaggaatga tcctgggtca | 60 |
| gaaaatcatg agtttaatcc ccgtcaagta cctgctgtcc aggatgggga gaggatctcc | 120 |
| aagttcccga gcactcaaca cagcttattt caaaatggca agaattcatg tgcaaggcag | 180 |
| gaactgcaaa gactctataa gttatttcac tcctggctac agccagaaaa acacagcaag | 240 |
| gatgaaatga tttctcgttt ggtcctggag caatttatga tcaatggcta ctgcagtgac | 300 |
| aggtccatgt tgaaagagaa atgggaatca agtggcagaa acctgagaa attcatggaa | 360 |
| gatctgactg atgatggcat gaagccacct ggcttagtcc acgtctgcat gcaggggcag | 420 |
| gaagctctct tttctgagaa tatgccctta agagaagtca tagttcacct caggaaacag | 480 |
| ttctcaacag gaacccaaac tggagagaac atggggaccc ctttccagac tcccaaagat | 540 |
| cattctctgg aaacagaaca aggagatgaa gacaaagaaa atggtggcaa catatctttg | 600 |
| aaaacttgtc aagtaaatga cagtatgact agtcaaggca atcaaacacc ttccctactc | 660 |
| atcatccagg gagagaaccg tcctgggcct ggagagggag gtgttccttt ggagaatcca | 720 |
| ctcagctcca gaagagcagg tctaggcagc tgcaggtccc aggaagagtc cctgaaagga | 780 |
| ccccccttatc aagatgtcct tatagaggtg agaccagggt ttctctcccg gccaaaccag | 840 |
| gttacgcctg agcgtgttcc tacccaccag agcattgagg gaaactcagc atgtggggga | 900 |
| caccaagaaa gatcccaggg agcccccaaa tcatacaaat gtgagaagtg tcccaggatc | 960 |
| tttaggtatc tgtctcggtt aaaagcccat caaagaagac acaataatga gaggacattt | 1020 |
| atttgtggcc agtgtgacaa aggcttcttc caggcatcag acctacgcat gcatcagaag | 1080 |
| attcacacag gagagaaacc tttcaagtgc agcacatgtg aaatgtcctt cagccacaaa | 1140 |
| accaaccttc gggctcatga gagaatccac acaggggaga gccctatgt gtgttccctt | 1200 |
| tgccagagaa gctaccgcca gtcatccacc taccaccgcc acctgaggac tcaccagaaa | 1260 |
| attgccttca aaagtgttcc ctctaggggg ctgtggcagc ataccagttc atggatcccc | 1320 |
| acacagcaga ttcccacaac tgtaagagga ggtgaggaca gcatgaccgg aaaacacttt | 1380 |
| tgggctctgg cccatgggag ggcccaacat gccatagtgg ccttgcctgt ggaaatgctc | 1440 |
| tacactgagt ggcggtggct cccctccacc ctagcacagt gcaggcaaga aggtgccctg | 1500 |
| cccgctcaga aggtgcccct gtctgcagag cacagtagcc agaaggatcc acagagtggt | 1560 |
| ggctcagccc ccgcatgggt gccctacacc cttagtgtag cgcaggcaag aaggcaccct | 1620 |
| gcccactcag aaggtacccc aacccacaga gcatggcagc ccacaggaac catcaagtgg | 1680 |
| cggctcagcc tctacatagc ctgcagcagc taa | 1713 |

<210> SEQ ID NO 11
<211> LENGTH: 360
<212> TYPE: PRT
<213> ORGANISM: Mus musculus

<400> SEQUENCE: 11

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu

```
                65                  70                  75                  80
Val Leu Glu Gln Phe Leu Leu Thr Gly His Cys Lys Asp Lys Tyr Ala
                    85                  90                  95
Leu Thr Glu Lys Trp Lys Ala Ser Gly Ser Asp Met Arg Arg Phe Met
                100                 105                 110
Glu Ser Leu Thr Asp Glu Cys Leu Lys Pro Val Met Val His Val
                115                 120                 125
Ser Met Gln Gly Gln Glu Ala Leu Phe Ser Glu Asn Met Pro Leu Lys
                130                 135                 140
Glu Val Ile Lys Leu Leu Lys Gln Gln Ser Ala Thr Arg Pro Thr
145                 150                 155                 160
Pro Asp Asn Ala Gln Met Pro Val Asp Thr Thr Gln Asp Arg Leu Leu
                165                 170                 175
Ala Thr Gly Gln Glu Asn Ser Glu Asn Glu Cys Asn Thr Ser Cys Asn
                180                 185                 190
Ala Thr Glu Gly Asn Val Gly Glu Ser Cys Ser Gly Asn Glu Met Asp
                195                 200                 205
Ser Ser Leu Ile Ile Gln Lys Glu Gln Tyr Pro Glu His Glu Glu Gly
                210                 215                 220
Asn Val Val Cys Gln Phe Pro Leu Asp Ala Arg Arg Ala Ser Gln Gly
225                 230                 235                 240
Thr Ser Ser His His Val Asp Phe Leu Ser Ala Leu Thr Thr Ala Asp
                245                 250                 255
Val Pro Met Glu Glu Gln Pro Lys Asp Leu Ser Arg Glu Asn Ile Ser
                260                 265                 270
Glu Asp Lys Asn Asn Cys Tyr Asn Thr Ser Arg Asn Ala Ala Thr Lys
                275                 280                 285
Val Tyr Ser Gly Asp Asn Ile Pro Arg Lys Lys Thr Asp Ser Leu Ser
                290                 295                 300
Ile Asn Lys Arg Ile Tyr His Pro Glu Pro Glu Val Gly Asp Ile Pro
305                 310                 315                 320
Tyr Gly Val Pro Gln Asp Ser Thr Arg Ala Ser Gln Gly Thr Ser Thr
                325                 330                 335
Cys Leu Gln Glu Ser Leu Gly Gly Cys Phe Ser Glu Lys Asp Pro Arg
                340                 345                 350
Glu Val Pro Gly Leu Gln Ser Arg
                355                 360

<210> SEQ ID NO 12
<211> LENGTH: 195
<212> TYPE: PRT
<213> ORGANISM: Mus musculus

<400> SEQUENCE: 12

Met Ala Ser Gln Gln Ala Pro Ala Lys Asp Leu Gln Thr Asn Asn Leu
1               5                   10                  15
Glu Phe Thr Pro Thr Asp Ser Ser Gly Val Gln Trp Ala Glu Asp Ile
                20                  25                  30
Ser Asn Ser Pro Ser Ala Gln Leu Asn Phe Ser Pro Ser Asn Asn Gly
                35                  40                  45
Cys Trp Ala Thr Gln Glu Leu Gln Ser Leu Trp Lys Met Phe Asn Ser
                50                  55                  60
Trp Leu Gln Pro Glu Lys Gln Thr Lys Glu Gln Met Ile Ser Gln Leu
65                  70                  75                  80
```

```
Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Val Met Val His Val
            115                 120                 125

Ser Met Gln Gly Gln Glu Ala Leu Phe Ser Glu Asn Met Pro Leu Lys
            130                 135                 140

Glu Val Ile Lys Leu Leu Lys Gln Gln Gln Ser Ala Thr Arg Pro Ile
145                 150                 155                 160

Pro Asp Asn Ala Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195

<210> SEQ ID NO 13
<211> LENGTH: 506
<212> TYPE: PRT
<213> ORGANISM: Mus musculus

<400> SEQUENCE: 13

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
            35                  40                  45

Cys Trp Ala Thr Gln Glu Leu Gln Ser Leu Trp Lys Met Phe Asn Ser
        50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Val Met Val His Val
            115                 120                 125

Ser Met Gln Gly Gln Glu Ala Leu Phe Ser Glu Asn Met Pro Leu Lys
            130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
            195                 200                 205

Ser Leu Leu Ile Ile Gln Lys Glu Gln His Pro Glu His Glu Glu Gly
        210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Ala Asp
                245                 250                 255
```

```
Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Asn Asp Pro Arg
            340                 345                 350

Glu Val Pro Gly Leu Gln Ser Arg Gln Glu Gln Pro Ile Ser Asp Pro
        355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505

<210> SEQ ID NO 14
<211> LENGTH: 506
<212> TYPE: PRT
<213> ORGANISM: Mus musculus

<400> SEQUENCE: 14

Met Ala Ser Gln Gln Ala Pro Ala Lys Asp Leu Gln Thr Asn Asn Leu
1               5                   10                  15

Glu Phe Thr Pro Ser His Ser Ser Gly Val Gln Trp Val Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Ile Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
```

```
            115                 120                 125
Ser Met Gln Gly Gln Glu Ala Leu Phe Ser Glu Asn Met Pro Leu Lys
130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                    165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
210                 215                 220

Asn Val Val Phe Gln Phe Pro Leu Asp Ala Arg Arg Ala Ser Gln Gly
225                 230                 235                 240

Asn Ser Ser His His Val Asp Phe Arg Ser Ala Pro Thr Pro Ala Asp
                    245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Arg Ser Asp Asn Ile Pro Arg Lys Lys Thr Asp Ser Leu Ser
290                 295                 300

Ile Asn Lys Arg Ile Tyr His Ser Glu Pro Glu Glu Gly Asp Ile Pro
305                 310                 315                 320

Tyr Gly Val Pro Gln Asp Ser Thr Arg Ala Ser Gln Gly Thr Ser Thr
                    325                 330                 335

Cys Leu Gln Glu Ser Leu Gly Glu Cys Phe Ser Glu Lys Asp Pro Arg
            340                 345                 350

Glu Leu Pro Gly Leu Glu Ser Arg Gln Glu Glu Pro Ile Ser Asp Pro
        355                 360                 365

Val Phe Leu Gly Lys Asp His Glu Ala Asn Leu Pro Cys Glu Ser His
370                 375                 380

Gln Lys Arg Phe Arg Arg Asp Ala Lys Leu Phe Lys Cys Glu Glu Cys
385                 390                 395                 400

Ser Arg Met Phe Lys His Ala Arg Ser Leu Ser Ser His Gln Arg Thr
                    405                 410                 415

His Leu Asn Lys Lys Ser Glu Leu Leu Cys Val Thr Cys Gln Lys Met
            420                 425                 430

Phe Lys Arg Val Ser Asp Arg Thr His Glu Ile Ile His Met Pro
        435                 440                 445

Glu Lys Pro Phe Lys Cys Ser Thr Cys Glu Lys Ser Phe Ser His Lys
450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                    485                 490                 495

Arg His Leu Arg Asn Tyr His Arg Ser Asp
            500                 505

<210> SEQ ID NO 15
<211> LENGTH: 195
<212> TYPE: PRT
<213> ORGANISM: Mus musculus
```

<400> SEQUENCE: 15

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
130                 135                 140

Glu Val Ile Lys Leu Leu Lys Gln Gln Gln Ser Ala Thr Arg Pro Ile
145                 150                 155                 160

Pro Asp Asn Glu Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

<210> SEQ ID NO 16
<211> LENGTH: 506
<212> TYPE: PRT
<213> ORGANISM: Mus musculus

<400> SEQUENCE: 16

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
130                 135                 140

Glu Val Ile Lys Leu Leu Lys Gln Gln Gln Ser Ala Thr Arg Pro Thr
145                 150                 155                 160
```

```
Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Met Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Lys Asp Pro Arg
            340                 345                 350

Glu Val Pro Gly Leu Gln Ser Arg Gln Glu Gln Leu Ile Ser Asp Pro
        355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505

<210> SEQ ID NO 17
<211> LENGTH: 433
<212> TYPE: PRT
<213> ORGANISM: Homo sapiens

<400> SEQUENCE: 17

Met Ala Leu Asp Leu Arg Thr Ile Phe Gln Cys Glu Pro Ser Glu Asn
1               5                   10                  15

Asn Leu Gly Ser Glu Asn Ser Ala Phe Gln Gln Ser Gln Gly Pro Ala
```

-continued

```
                20                  25                  30
Val Gln Arg Glu Glu Gly Ile Ser Glu Phe Ser Arg Met Val Leu Asn
         35                  40                  45

Ser Phe Gln Asp Ser Asn Asn Ser Tyr Ala Arg Gln Glu Leu Gln Arg
 50                  55                  60

Leu Tyr Arg Ile Phe His Ser Trp Leu Gln Pro Glu Lys His Ser Lys
 65                  70                  75                  80

Asp Glu Ile Ile Ser Leu Leu Val Leu Glu Gln Phe Met Ile Gly Gly
                     85                  90                  95

His Cys Asn Asp Lys Ala Ser Val Lys Glu Lys Trp Lys Ser Ser Gly
                 100                 105                 110

Lys Asn Leu Glu Arg Phe Ile Glu Asp Leu Thr Asp Ser Ile Asn
             115                 120                 125     Asn

Pro Pro Ala Leu Val His Val His Met Gln Gly Gln Glu Ala Leu Phe
         130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                 165                 170                 175

Thr Ser Gln Asp Thr Ser Leu Glu Thr Gly Gln Gly Tyr Glu Asp Glu
             180                 185                 190

Gln Asp Gly Trp Asn Ser Ser Lys Thr Thr Arg Val Asn Glu Asn
         195                 200                 205

Ile Thr Asn Gln Gly Asn Gln Ile Val Ser Leu Ile Ile Gln Glu
     210                 215                 220

Glu Asn Gly Pro Arg Pro Glu Glu Gly Gly Val Ser Ser Asp Asn Pro
225                 230                 235                 240

Tyr Asn Ser Lys Arg Ala Glu Leu Val Thr Ala Arg Ser Gln Glu Gly
                 245                 250                 255

Ser Ile Asn Gly Ile Thr Phe Gln Gly Val Pro Met Val Met Gly Ala
             260                 265                 270

Gly Cys Ile Ser Gln Pro Glu Gln Ser Ser Pro Glu Ser Ala Leu Thr
         275                 280                 285

His Gln Ser Asn Glu Gly Asn Ser Thr Cys Glu Val His Gln Lys Gly
     290                 295                 300

Ser His Gly Val Gln Lys Ser Tyr Lys Cys Glu Glu Cys Pro Lys Val
305                 310                 315                 320

Phe Lys Tyr Leu Cys His Leu Leu Ala His Gln Arg His Arg Asn
                 325                 330                 335

Glu Arg Pro Phe Val Cys Pro Glu Cys Gln Lys Gly Phe Phe Gln Ile
             340                 345                 350

Ser Asp Leu Arg Val His Gln Ile His Thr Gly Lys Lys Pro Phe
         355                 360                 365

Thr Cys Ser Met Cys Lys Lys Ser Phe Ser His Lys Thr Asn Leu Arg
     370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                 405                 410                 415

Thr His Glu Lys Ile Thr Leu Pro Ser Val Pro Ser Thr Pro Glu Ala
             420                 425                 430

Ser
```

<210> SEQ ID NO 18
<211> LENGTH: 433
<212> TYPE: PRT
<213> ORGANISM: Canis familiaris

<400> SEQUENCE: 18

```
Met Ala Ser Asp Ile Arg Ile Ser Phe Gln Gly Glu Pro Ser Met Asn
1               5                   10                  15

Asp Pro Gly Ser Glu Asn Leu Glu His Lys Leu Ser Gln Gly Pro Ala
            20                  25                  30

Ile Gln Glu Glu Asp Glu Ile Tyr Glu Phe Pro Ser Thr Gln Leu Thr
        35                  40                  45

Leu Leu Gln Asn Ser Asn Ser Ser Ala Arg Gln Glu Leu Gln Asn Leu
    50                  55                  60

Tyr Lys Leu Phe His Ser Trp Leu Gln Pro Glu Lys His Ser Lys Asp
65                  70                  75                  80

Glu Ile Ile Ser His Leu Val Leu Glu Gln Phe Met Ile Asn Gly His
                85                  90                  95

Cys Ser Asp Arg Ser Met Leu Lys Lys Lys Trp Asn Ala Ser Gly Arg
            100                 105                 110

Asn Leu Glu Lys Phe Met Glu Asp Leu Thr Asp Asp Gly Met Lys Leu
        115                 120                 125

Pro Gly Leu Val His Val His Met Lys Gly Gln Asp Ala Leu Phe Ser
    130                 135                 140

Glu Asn Met Pro Leu Arg Glu Val Ile Val His Phe Met Lys Gln Leu
145                 150                 155                 160

Ser Ala Gly Thr Pro Thr Glu Asn Met Gly Thr Pro Ser Trp Thr
                165                 170                 175

Ser Gln Asp Thr Ser Leu Glu Thr Gly Gln Gly Glu Trp Asp Lys Ala
            180                 185                 190

Asn Gly Tyr Asn Ile Tyr His Asn Asp Gly Thr Thr Ser Gln Gly Asn
        195                 200                 205

Ala Val Pro Ser Leu Phe Ile Val His Glu Glu Asp Cys Pro His Pro
    210                 215                 220

Glu Glu Asp Ser Val Ser Leu Lys Asp Leu Leu Ser Pro Gly Arg Pro
225                 230                 235                 240

Gly Leu Gly Thr Ser Asn Ser Gln Glu Gly Cys Leu Gln Gly Arg Pro
                245                 250                 255

Tyr Gln Asp Val Leu Met Glu Gly Ala Pro Gly Phe His Ser Arg Ser
            260                 265                 270

Thr Ala Val Thr Pro Asp Pro Val Ser Thr His Gln Lys Thr Glu Gly
        275                 280                 285

Asn Ser Thr Cys Gly Gly His Gln Glu Arg Phe Arg Asp Ala Gln Asn
    290                 295                 300

Ser Tyr Arg Cys Glu Lys Cys Pro Arg Ile Phe Arg Tyr Phe Ser Gln
305                 310                 315                 320

Leu Lys Ala His Gln Arg Arg His Asn Asn Glu Arg Thr Phe Ile Cys
                325                 330                 335

Ala Glu Cys Asn Lys Gly Phe Phe Gln Ala Ser Asp Leu His Val His
            340                 345                 350

Gln Lys Ile His Thr Glu Glu Lys Pro Phe Arg Cys Ser Thr Cys Glu
        355                 360                 365

Lys Ser Phe Ser His Lys Thr Asn Leu Leu Ala His Glu Arg Ile His
    370                 375                 380
```

```
Thr Gly Glu Lys Pro Tyr Val Cys Ala Leu Cys Gln Arg Ser Tyr Arg
385                 390                 395                 400

Gln Ser Ser Thr Tyr His Arg His Leu Arg Thr His Gln Lys Ile Ala
            405                 410                 415

Val Lys Gly Thr Pro Ser Thr Ser Glu Ala Ser Ser Ala Val Ala Ser
            420                 425                 430

Val

<210> SEQ ID NO 19
<211> LENGTH: 416
<212> TYPE: PRT
<213> ORGANISM: Bos taurus

<400> SEQUENCE: 19

Met Asp Leu Gly Phe Arg Ala Ser Phe Gln His Glu Pro Ser Asn Glu
1               5                   10                  15

Asp Pro Lys Ser Ala Asn Thr Gly Phe Ile Pro Ser Arg Gly Pro Thr
            20                  25                  30

Leu Gln Thr Ala Glu Asp Ile Ser Gln Leu Gln Asn Thr Gln Pro Gly
        35                  40                  45

Leu Leu Gln Asn Gly Asn Asn Ser Arg Ala Arg Gln Glu Leu Gln Arg
50                  55                  60

Leu Tyr Lys Ser Phe His Leu Trp Leu Gln Pro Glu Lys His Ser Lys
65                  70                  75                  80

His Glu Ile Ile Phe Gln Leu Ala Leu Glu Gln Phe Met Ile Asn Lys
                85                  90                  95

His Cys Ser Glu Lys Ser Thr Leu Lys Glu Lys Trp Lys Ala Ser Gly
            100                 105                 110

Gly Asp Leu Glu Lys Phe Thr Glu Asp Leu His Asp Asp Cys Ile Lys
        115                 120                 125

Leu Pro Asp Leu Val His Val His Leu Gln Gly Gln Glu Ala Leu Phe
130                 135                 140

Ser Glu Asn Met Ser Leu Lys Glu Ile Ile Phe His Leu Thr Asn Gln
145                 150                 155                 160

Leu Ser Thr Gly Gly Val Asn Met Gly Thr Pro Ser Trp Thr Met Gln
                165                 170                 175

Asp Thr Ser Leu Glu Thr Gly Gln Arg Asn Glu Gly Lys Glu Asn Asp
            180                 185                 190

Gly Asn Ile Ser Val Lys Ser Asp Ser Ile Thr Ser Pro Ser Asn Gln
        195                 200                 205

Ile Pro Ser Leu Ile Ile Val Gln Glu Glu Asn His Leu Arg Leu Glu
210                 215                 220

Glu Gly Gly Val Ser Leu Glu Asn Pro Arg Asn Ser Arg Arg Gly Ala
225                 230                 235                 240

Gly Pro Gly Pro Ser Arg Pro Gln Asp Gly Ser Leu Lys Gly Pro Ser
                245                 250                 255

Ser Gln Asp Val Leu Met Glu Val Glu Arg Asp Gln Val Thr Pro Gly
            260                 265                 270

Pro Val Ser Thr Leu Gln Ser Ser Glu Gly Thr Ser Ala Arg Gly Lys
        275                 280                 285

His Gln Glu Arg Ser Leu Arg Ala Pro Glu Val Tyr Arg Cys Glu Arg
    290                 295                 300

Cys Pro Lys Thr Phe Arg Tyr Ser Ser Arg Phe Arg Val His Gln Lys
305                 310                 315                 320
```

```
Arg His Asp Asn Glu Arg Thr Tyr Ile Cys Ala Glu Cys Gly Lys Gly
                325                 330                 335

Phe Phe Gln Ala Ser Asp Leu His Val His Gln Arg Ile His Thr Gly
            340                 345                 350

Glu Lys Pro Phe Val Cys Ser Thr Cys Glu Met Ala Phe Thr His Lys
        355                 360                 365

Thr Asn Leu Arg Ala His Glu Arg Thr His Thr Gly Glu Lys Pro Tyr
    370                 375                 380

Glu Cys Ser Leu Cys Gln Arg Arg Phe Arg Gln Ser Ser Thr Tyr His
385                 390                 395                 400

Arg His Leu Arg Phe His Gln Lys Thr Thr Leu Lys Ser Ala Pro His
                405                 410                 415

<210> SEQ ID NO 20
<211> LENGTH: 570
<212> TYPE: PRT
<213> ORGANISM: Equus caballus

<400> SEQUENCE: 20

Met Ala Leu Asp Leu Arg Ile Ser Phe Gln Gly Glu Pro Ser Arg Asn
1               5                   10                  15

Asp Pro Gly Ser Glu Asn His Glu Phe Asn Pro Arg Gln Val Pro Ala
            20                  25                  30

Val Gln Asp Gly Glu Arg Ile Ser Lys Phe Pro Ser Thr Gln His Ser
        35                  40                  45

Leu Phe Gln Asn Gly Lys Asn Ser Cys Ala Arg Gln Glu Leu Gln Arg
    50                  55                  60

Leu Tyr Lys Leu Phe His Ser Trp Leu Gln Pro Glu Lys His Ser Lys
65                  70                  75                  80

Asp Glu Met Ile Ser Arg Leu Val Leu Glu Gln Phe Met Ile Asn Gly
                85                  90                  95

Tyr Cys Ser Asp Arg Ser Met Leu Lys Glu Lys Trp Glu Ser Ser Gly
            100                 105                 110

Arg Asn Leu Glu Lys Phe Met Glu Asp Leu Thr Asp Asp Gly Met Lys
        115                 120                 125

Pro Pro Gly Leu Val His Val Cys Met Gln Gly Gln Glu Ala Leu Phe
    130                 135                 140

Ser Glu Asn Met Pro Leu Arg Glu Val Ile Val His Leu Arg Lys Gln
145                 150                 155                 160

Phe Ser Thr Gly Thr Gln Thr Gly Glu Asn Met Gly Thr Pro Phe Gln
                165                 170                 175

Thr Pro Lys Asp His Ser Leu Glu Thr Glu Gln Gly Asp Glu Asp Lys
            180                 185                 190

Glu Asn Gly Gly Asn Ile Ser Leu Lys Thr Cys Gln Val Asn Asp Ser
        195                 200                 205

Met Thr Ser Gln Gly Asn Gln Thr Pro Ser Leu Leu Ile Ile Gln Gly
    210                 215                 220

Glu Asn Arg Pro Gly Pro Gly Glu Gly Gly Val Pro Leu Glu Asn Pro
225                 230                 235                 240

Leu Ser Ser Arg Arg Ala Gly Leu Gly Ser Cys Arg Ser Gln Glu Glu
                245                 250                 255

Ser Leu Lys Gly Pro Pro Tyr Gln Asp Val Leu Ile Glu Val Arg Pro
            260                 265                 270

Gly Phe Leu Ser Arg Pro Asn Gln Val Thr Pro Glu Arg Val Pro Thr
```

```
            275                 280                 285
    His Gln Ser Ile Glu Gly Asn Ser Ala Cys Gly Gly His Gln Glu Arg
        290                 295                 300
    Ser Gln Gly Ala Pro Lys Ser Tyr Lys Cys Glu Lys Cys Pro Arg Ile
305                 310                 315                 320
    Phe Arg Tyr Leu Ser Arg Leu Lys Ala His Gln Arg Arg His Asn Asn
                325                 330                 335
    Glu Arg Thr Phe Ile Cys Gly Gln Cys Asp Lys Gly Phe Phe Gln Ala
                340                 345                 350
    Ser Asp Leu Arg Met His Gln Lys Ile His Thr Gly Glu Lys Pro Phe
                355                 360                 365
    Lys Cys Ser Thr Cys Glu Met Ser Phe Ser His Lys Thr Asn Leu Arg
        370                 375                 380
    Ala His Glu Arg Ile His Thr Gly Glu Lys Pro Tyr Val Cys Ser Leu
385                 390                 395                 400
    Cys Gln Arg Ser Tyr Arg Gln Ser Ser Thr Tyr His Arg His Leu Arg
                405                 410                 415
    Thr His Gln Lys Ile Ala Phe Lys Ser Val Pro Ser Arg Gly Leu Trp
                420                 425                 430
    Gln His Thr Ser Ser Trp Ile Pro Thr Gln Gln Ile Pro Thr Thr Val
                435                 440                 445
    Arg Gly Gly Glu Asp Ser Met Thr Gly Lys His Phe Trp Ala Leu Ala
        450                 455                 460
    His Gly Arg Ala Gln His Ala Ile Val Ala Leu Pro Val Glu Met Leu
465                 470                 475                 480
    Tyr Thr Glu Trp Arg Trp Leu Pro Ser Thr Leu Ala Gln Cys Arg Gln
                485                 490                 495
    Glu Gly Ala Leu Pro Ala Gln Lys Val Pro Leu Ser Ala Glu His Ser
                500                 505                 510
    Ser Gln Lys Asp Pro Gln Ser Gly Gly Ser Ala Pro Ala Trp Val Pro
                515                 520                 525
    Tyr Thr Leu Ser Val Ala Gln Ala Arg Arg His Pro Ala His Ser Glu
        530                 535                 540
    Gly Thr Pro Thr His Arg Ala Trp Gln Pro Thr Gly Thr Ile Lys Trp
545                 550                 555                 560
    Arg Leu Ser Leu Tyr Ile Ala Cys Ser Ser
                565                 570

<210> SEQ ID NO 21
<211> LENGTH: 528
<212> TYPE: DNA
<213> ORGANISM: Gorilla gorilla
<220> FEATURE:
<221> NAME/KEY: misc_feature
<222> LOCATION: 18, 19, 80, 211, 212, 519, 520, 521, 522
<223> OTHER INFORMATION: n = A,T,C or G

<400> SEQUENCE: 21
aatggaatca ctttccanng tgtccctatg gtgatgggag cagggtgtat ctctcaacca      60
gagcagtcct cccctgagtn tgcccttacc caccagagca atgagggaaa ctccacatgt     120
gaggtacatc agaaaggatc ccatggagtc cgaaaatcat acaaatgtga agaatgcccc     180
aaggtcttta agtatcactg tcacttatta nntcaccaga gaagacacag gaatgagagg     240
ccatttgttt gtcccgagtg tcaaaaaggc ttcttccaga tatcagacct acgggtgcat     300
cagataattc acacaggaaa gaagcctttc acatgcagca tgtgtaaaaa gtccttcagc     360
```

| cacaaaacca acctgcggtc tcatgagaga atccacacag gagaaaagcc ttatacatgt | 420 |
| ccctttgta agacaagcta ccgccagtca tccacatacc accgccatat gaggactcat | 480 |
| gagaaaatta ccctgccaag tgttccctcc acaccagann nntcctaa | 528 |

<210> SEQ ID NO 22
<211> LENGTH: 1302
<212> TYPE: DNA
<213> ORGANISM: Pan paniscus

<400> SEQUENCE: 22

| atggctttag atctaagaac catatttcag tgtgaaccat ccgagaataa tcttggatca | 60 |
| gaaaattcag cgtttcaaca aagccaagga cctgctgttc agagagaaga agggatttct | 120 |
| gagttctcaa gaatggtgct caattcattt caagacagca ataattcata tgcaaggcag | 180 |
| gaattgcaaa gactttatag gatctttcac tcatggctgc aaccagaaaa gcacagcaag | 240 |
| gatgaaatta tttctctatt agtcctggag cagtttatga ttggtggcca ctgcaatgac | 300 |
| aaagccggtg tgaaagagaa atggaaatca agtggcaaaa acttggagag attcatagaa | 360 |
| gacctgactg atgacagcat aaatccacct gccttagtcc acgtccacat gcagggacag | 420 |
| gaagctctct tttctgagga tatgccctta agagatgtca ttgttcatct cacaaaacaa | 480 |
| gtgaatgccc aaaccacaag agaagcaaac atggggacac cctcccagac ttcccaagat | 540 |
| acttccttag aaacaggaca aggatatgaa gatgaacaag atggctggaa cagttctttg | 600 |
| aaaactactc aagtaaatga aaatattact aatcaaggcg atcaaatagt ttccctaatc | 660 |
| atcatccagg aagagaacag tcctaggcct gaagagggag gtgtttcttc tgacaaccca | 720 |
| tacaactcaa aaagagcaga gctagtcact gctagatctc aggaagggtc cataaatgga | 780 |
| atcacttttcc aaggtgtccc tatggtgatg ggagcagggt gtatctctca accagagcag | 840 |
| tcctcccctg agtctgccct tacccaccag agcaatgagg gaaactccac atgtgaggta | 900 |
| catcagaaag gatcccatgg agtccgaaaa tcatacaaat gtgaagaatg ccccaaggtc | 960 |
| tttaagtatc tctgtcactt attagctcac cagagaagac acaggaatga gaggccatttt | 1020 |
| gtttgtcccg agtgtcaaaa aggcttcttc cagatatcag acctacgggt gcatcagata | 1080 |
| attcacacag gaaagaagcc tttcacatgc agcatatgta aaaagtcctt cagccacaaa | 1140 |
| accaacctgc ggtctcatga gagaatccac acaggagaaa agccttatac atgtccctttt | 1200 |
| tgtaagacaa gctaccgcca gtcatccaca taccaccgcc atatgaggac tcatgagaaa | 1260 |
| attaccgtgc caagtgttcc ctccacacca gaagcttcct aa | 1302 |

<210> SEQ ID NO 23
<211> LENGTH: 1302
<212> TYPE: DNA
<213> ORGANISM: Bornean orangutan

<400> SEQUENCE: 23

| atggctttag atctaagaac catatttcag tgtgaaccat ccgagaataa tcttggatca | 60 |
| gaaaattcag agtttcgaca aagccaagga cctgctgttc agagagaaga agggatttct | 120 |
| gagttctcaa gaatggtgct caattcattt caagacagca ataattcata tgcaaggcag | 180 |
| gaattgcaga gactttatag gatctttcac tcatggctgc aaccagaaaa gcacagcaag | 240 |
| gatgaaatta tttctctatt agtcctggag cagtttatga ttggtggcca ctgcaatgac | 300 |
| aaagccagtg tgaaagagaa atggaaatca agtggcaaaa acttggagag attcatagaa | 360 |

| | |
|---|---|
| gacctgactg atgacagcat aaatccacct gccttagtcc atgtccacat gcagggacag | 420 |
| gaagctctct tttctgagga tatgccctta aaagatgtca ttgttcatct cacaaaacaa | 480 |
| gtgtctgccc aaaccccaag agaagcaaat atggggacac cctcccagac ttcccaagat | 540 |
| acttccttag aaacaggaga aggatgtgaa gatgaacaag atggctgcaa cagttctttg | 600 |
| aaaactactc aagtaaatga aatattact aatcaaggca atcaaatagt ttccctaatc | 660 |
| atcatccagg aagagaacgg tcctaggtct gaagagggga gtgtttcttc tgacaatcca | 720 |
| aacaactcaa aaagagcaga gctagtcact gctagatctc aggaagggtc cataaacgga | 780 |
| atcacttttc aaggtgtccc tatggagatg ggagcagggt gtatctctca gccagagcag | 840 |
| tcctcccctg agtctgccct tacccaccag agcaatgagg gaaactccac atgtgaggta | 900 |
| catcagaaag gatcccatgg agtccgaaaa tcctacaaat gtgaagaatg ccctaaggtc | 960 |
| tttaagtatc tctgtcactt attagctcac cagagaagac acaggaatga gaggccatt | 1020 |
| gtttgtcccg agtgtcaaaa aggcttcttc cagatatcag acctacgcgt gcatcagata | 1080 |
| attcacacag gaaagaagcc tttcacatgc agcatgtgtg aaaagtcctt cagccacaaa | 1140 |
| accaacctgc ggtctcatga gagaatccac acaggagaaa agccttatac atgtcccttt | 1200 |
| tgtaagacaa gctaccgcca gtcatccaca taccaccgcc atatgaggac tcatgagaaa | 1260 |
| attccccgc caagtgttcc ctccacacca gaagcttcct aa | 1302 |

<210> SEQ ID NO 24
<211> LENGTH: 1640
<212> TYPE: DNA
<213> ORGANISM: Pongo abelii

<400> SEQUENCE: 24

| | |
|---|---|
| tccaccaact gttgaaacaa atccctagag acacaaggca agagactgaa tcatcaaagt | 60 |
| aaagtctctc tgagaattat tgctaagaat ggctttagat ctaagaacca tatttcagtg | 120 |
| tgaaccatcc gagaataatc ttggatcaga aaattcagtg tttcgacaaa gccaaggacc | 180 |
| tgctgttcag agagaagaag ggatttctga gttctcaaga atggtgctca attcatttca | 240 |
| agacagcaat aattcatatg caaggcagga attgcagaga cttatagga tctttcactc | 300 |
| atggctgcaa ccagaaaagc acagcaagga tgaaattatt tctctattag tcctggagca | 360 |
| gtttatgatt ggtggccact gcaatgacaa agccagtgtg aaagagaaat ggaaatcaag | 420 |
| tggcaaaaac ttggagagat tcatggaaga cctgactgat gacagcataa atccacctgc | 480 |
| cttagtccat gtccacatgc agggacagga agctctcttt tctgaggata tgcccttaaa | 540 |
| agatgtcatt gttcatctca aaaacaagt gtctgcccaa accccaagag aagcaaatat | 600 |
| ggggacaccc tcccagactt cccaagatac ttccttagaa acaggagaag gatgtgaaga | 660 |
| tgaacaagat ggctgcaaca gttctttgaa aactactcaa gtaaatgaaa atattactaa | 720 |
| tcaaggcaat caaatagttt ccctaatcat catccaggaa gagaacggtc ctaggtctga | 780 |
| agagggaggt gtttcttctg acaatccaaa caactcaaaa agagcagagc tagtcactgc | 840 |
| tagatctcag gaagggtcca taaacggaat cacttttcaa ggtgtcccta tggagatggg | 900 |
| agcagggtgt atctctcagc cagagcagtc tcccctgag tctgcccta cccaccagag | 960 |
| caatgaggga aactccacat gtgaggtaca tcagaaagga tcccatggag tccgaaaatc | 1020 |
| ctacaaatgt gaagaatgcc ctaaggtctt taagtatctc tgtcacttat tagctcacca | 1080 |
| gagaagacac aggaatgaga ggccattgt ttgtcccgag tgtcaaaaag gcttcttcca | 1140 |
| gatatcagac ctacgcgtgc atcagataat tcacacagga aagaagcctt tcacatgcag | 1200 |

```
catgtgtgaa aagtccttca gccacaaaac caacctgcgg tctcatgaga gaatccacac    1260
aggagaaaag ccttatacat gtcccttttg taagacaagc taccgccagt catccacata    1320
ccaccgccat atgaggactc atgagaaaat tacccgcca agtgttccct ccacaccaga    1380
agcttcctaa gctgctggtc tgataatgtg tataaatatg tatgcaagta tgtatattcc    1440
catagtattt atcgacttag gatataagat ataatttcct gattatgctt tcaatttatt    1500
gtcttgcttc attaaaatgt aaggctaagg agagcatgga atttgtcagt tttgttcact    1560
aaagtattcc aagtggttgg gaaagtggaa catttccaag aaccaataaa tttctgttga    1620
ataaatgaat gaatccaaaa                                                 1640

<210> SEQ ID NO 25
<211> LENGTH: 1002
<212> TYPE: DNA
<213> ORGANISM: Artificial Sequence
<220> FEATURE:
<223> OTHER INFORMATION: Reverse translation of SEQ ID NO: 35

<400> SEQUENCE: 25
ctgaaaattg atagctttct gtgcgaactg agcatggatg atccgggcag caaaaacaaa      60
gattttaaac cgagccaggg cccggcgctg cagaaagcgg aagaaattag cgaatttcag     120
gatagccagc atagcctgtt tcaggatgga acaacagcc atgcgaaaca ggaactgcag     180
cgcctgtata aaagcttta gctggctg cagccggaaa acatagcaa agatgaaatt       240 attttcagg tggtgctgga acagtttat attaaccgcc attgcagcgg ccgcagcacc       300
ctgaaaaaaa aatgggaaag cagcggccgc aacctggaaa aatttatgga aagcctgagc     360
gaaagcagcc tgaaaccgcc ggatctggtg catgtgcata tgcagggcca ggaagcgctg     420
tttagcgaaa acatgccgct gaaagaagtg attgtgcatc tgaccaaaca gctgagcgtg     480
ggcagcccga ccggcaccga tatggaaacc ccgagctgga ccccgcagga taccagcctg     540
gaaaccggcc agggcgaatg ggcaaaaaa gaaaacggcg ataacattta tcatattaac     600
gatagcatta ccagccaggg caacgaaatt ccgagcctgc tgattattcg cgaagaagat     660
tatccgcgcc cggaagaaga tagcgtgagc ctgaaaaacc cgctgagcag ccgcaaagcg     720
ggcctgggca tgagcggcag ccaggaaggc agcctgaaag cccgagcta tcaggatgtg     780 ctgatggaag gcgccgggg ctttctgagc cagagcattc aggtgagccc ggaaccggtg     840
ccgacccatc agcgcaccga aggcaacagc acccgcggcg ccatcagga acgctgccgc     900 gaagcgcaga acagctatcg ctgcgaaaaa tgcccgaaaa ttttcgcta ttttagccag     960 ctgaaagcgc atcagcgccg ccataacaac gaacgcacct tt                      1002

<210> SEQ ID NO 26
<211> LENGTH: 1317
<212> TYPE: DNA
<213> ORGANISM: Artificial Sequence
<220> FEATURE:
<223> OTHER INFORMATION: Reverse translation of SEQ ID NO: 36

<400> SEQUENCE: 26
atggatctgg atctgcgcct gagctttcag ggcgaaccga gccgcaacga tccgggcagc      60
gaaaacctgg cgctgaaagc gagccagggc tatgtgattc gcgatggcga aggcattagc     120
gaatttccga caccgcct gagcctgttt cagaacagca gcaacagctt tgcgcgccgc     180
gaactgcagc gcctgtataa cctgtttcat agctggctgc agccggaaaa acgcagcaaa     240
```

| | |
|---|---|
| gatgaaatga ttagctgcct ggtgctggaa cagtttgtga ttaacggcca ttgcagcgat | 300 |
| cgcagcaccc tgcaggaaaa atggaacgcg agcggccgca acctggaaaa atttatggaa | 360 |
| gatctgaccg atgatggcat gaaacagccg ggctttgtgc atgtgcatat gcagggccag | 420 |
| gaagcgctgt ttagcgaaaa catgccgctg cgcgaagtgc tggtgcattt tcgcaaacat | 480 |
| ctggcgaccg cgaccccgcg cggcgaaaac accaaagcgc cgctgtggac cccgcgcgat | 540 |
| gcgagcctgg aaaccggcca ggaaagcgaa ggcaaagaat gcggcggcaa caccagccgc | 600 |
| aaaacctgcc cggtgaccga agcctgacc tggcagggca gccagacccc gtttctgctg | 660 |
| attattccgg aagaaacctg cccgggcctg gaagaagcgg gcgtgagccc ggaaaacccg | 720 |
| ctgggcagcc gcaccgcgga accgggcctg gcggtgagcc aggaaggcag cccggaaggc | 780 |
| ccgtttggcg gcgatgtgca tctggaagcg gaacccggct ttctgagccg cccggatcag | 840 |
| gtgaccctgg aaccggtgag cgcgcatccg agcctggaag caacccggc gcgcggcaaa | 900 |
| agcccggaag gcctgccggg cgcgcagaaa gtgtttccgt gcgaaaaatg cagccaggtg | 960 |
| tttcgctatc tgagccgcct gaaagtgcat cagcgccgcc ataacgatga acgcccgttt | 1020 |
| gtgtgcgcga atgcaaaaa aggcttttt cagaccagcg atctgcgcgt gcatcagcgc | 1080 |
| attcatacca agaaaaaacc gtttcgctgc agcacctgca acgcccgtt tagccataaa | 1140 |
| accaacctgc gcgcgcatga acgcattcat accggcgaaa aaccgtatct gtgcagcctg | 1200 |
| tgccagcgcc gctatcgcca gagcagcacc tataaccgcc atctgaaaag ccatcagaaa | 1260 |
| ctggcgctga aggcgatct gagcggcgtg ccggtggtgg cgcagcgcaa acgcatt | 1317 |

<210> SEQ ID NO 27
<211> LENGTH: 1656
<212> TYPE: DNA
<213> ORGANISM: Nomascus leucogenys

<400> SEQUENCE: 27

| | |
|---|---|
| agattgcagt tttaaagaat ccaccaactg ttgaaacaaa tccctagaga cacaaggcaa | 60 |
| gagactgaat catcaaagtt aagtctctct gagaattatt gctaagaatg ctttagagc | 120 |
| taagaaccat atttcagtgt gaaccatccg agaataatct tggatcagaa aattcagagt | 180 |
| ttcgacaaag ccaaggacct gctgttcaga gagaagaagg gatttctgag ttctcaagaa | 240 |
| tggtgctcaa ttcatttcaa gacagcaata aatcatatgc aaggcaggaa ttgcaaagac | 300 |
| tttataggat ctttcactca tggctgcaac cagaaaagca cagcaaggat gaaattattt | 360 |
| ctctattagt cctggagcag tttatgattg gtggccactg caatgacaaa accagtgtga | 420 |
| aagagaaatg gaaatcaagt ggcaaaaact tggagagatt catggaagac ctgactgatg | 480 |
| acagcataaa tccacctgcc ttagtccacg tccacatgca gggacaggaa gctctctttt | 540 |
| ctgaggatat gcccttaaaa gatgtcattg ttcatctcac aaaacaagtg tctgcccaaa | 600 |
| tcccaagaga agcaaacatg gggacaccct tccagacttc caagatact tccttagaaa | 660 |
| caggacaagg acgtgaagat gaacaagatg gctgcaacag ttctttgaaa actactcaag | 720 |
| taaatgaaaa tattactaat caaggcaatc aaatagtttc cctaatcatc atccaggaag | 780 |
| agaatggtcc taggcctgaa gagggagtg tttcttctga caaccatgc aactcaaaaa | 840 |
| gagcagagct agtcactgct agatcccagg aagggtccat aaacggaatc acttttcaag | 900 |
| gtgtccctat ggagatggga gcagggtgta tctctcagcc agagcagtcc tcccctgagt | 960 |
| ctgccccta ccaccagagc aatgagggaa actccacatg tgaggtacat cagaaaggat | 1020 |
| cccatggagt ccgaaaatca tacaaatgtg aagaatgccc caaggtcttt aagtatctct | 1080 |

```
gtcacttatt agctcaccag aggagacaca ggaatgagag gccatttgtt tgtcccgagt    1140
gtcagaaagg cttcttccag acatcagacc tacgcgtgca tcaggtgatt cacacaggaa    1200
agaagccttt cacatgcagc atgtgtgaaa agtccttcag ccacaaaacc aacctgcggt    1260
cccatgagag aatccacaca ggagaaaagc cttatacatg tccctattgt aagacaagct    1320
accgccagtc atccacatac caccgccata tgaggactca tgagaaaatt acctcaccaa    1380
gtgttccctc cacgccagaa gcttcctaag ctgctggtct gataatgtgt ataaatgtgt    1440
atgcaagtat gtatattccc atagtattta tctacttagg atataagata taatttcctg    1500
attatgcttt caatttattg tctgcttcat taaaatgtaa ggctaaggag agcatggaat    1560
ttgtcagttt tgctcactaa agtattccaa gtggttggga aagtgggaac atttccaaga    1620
accaataaat ttctgttgaa taaatgaatg aatcca                              1656
```

<210> SEQ ID NO 28
<211> LENGTH: 1299
<212> TYPE: DNA
<213> ORGANISM: Macaca mulatta

<400> SEQUENCE: 28

```
atggctttag atctaagaac catatttcag catgaaccat ccgagaataa tcttggatca     60
gaaaattcag agtttcgacg aagtcaagga cctgctgttc agacagaaga agggatttct    120
gagttctcaa gaatgatgct caattcattt caagacagca ataattcata tgcaaggcag    180
gaattgcaaa gactttatag gatctttcac tcatggctgc aaccagaaaa gcacagcaag    240
gatgaaatta tttctctatt agtcctggag cagtttatga ttggtggcca ctgcaatgac    300
aaagccactg tgaaagagaa atggaaatca agtggcaaaa acctggagag attcatggaa    360
gacctgactg atgacatcat aaatccacct gccttagtcc atgtccacat gcagggacag    420
gaagctctct tttctgacaa tatgccctta aaagatgtca ttgttcatct cacaaaacaa    480
gtgtctgcca aaactccaag agaagcaaac atggggacac ccttccagac ttcccaagac    540
acttcctcag aaacaggaca aggacgtgaa gatgaacaag atggctgcaa cagttctttg    600
aaaactactc aagtaaatga agtaatact aatcaagaca atccaatagt ttctctaatc    660
atccaggaag agaatggccc taggcctaaa gagggaggtg tttcttctga caacccatac    720
aattcaagaa gaacagagct agacactgct agatcccagg aagggtccac gaacggaatt    780
atttttcaag gtgtccctat ggagatggga gcagggttta tctctcagcc agagcagtca    840
tcccctgagt ctgccctac ccaccagagc aataagggga actccacatg tgaggtacat    900
cagaaaggat cccatggagt ccgaaaatca tacaaatgtg aagaatgccc caaggtcttt    960
aagtatctct gtcacttatt agctcaccag agaagacaca ggaatgagag gccatttgtt   1020
tgtcccaagt gtcaaaaagg cttcttccag atatcagacc tacgtgtgca tcagataatt   1080
cacacaggag agaaacctt tacatgcagc atgtgtgaaa agtccttcag ccacaaaacc   1140
aacctgcggt ctcatgagag aatccacaca ggagaaaagc cttatacatg tccctattgt   1200
aagagaagct accgccagtc atccacatac caccgccata tgaggactca taagaaaatt   1260
actctgccaa ctgttccctc cacaccagaa gcttcctaa                          1299
```

<210> SEQ ID NO 29
<211> LENGTH: 1008
<212> TYPE: DNA
<213> ORGANISM: Artificial Sequence
<220> FEATURE:

<223> OTHER INFORMATION: Reverse translation of SEQ ID NO: 39

<400> SEQUENCE: 29

```
atggcgctgg atctgcgcaa aagcttttgc caggaactga gcagcaacaa cctggaaagc     60
gaagatctgg aatttagcag cacccagggc tttgcggtgc cgaaacgcga aattagcgcg    120
tttagcagca ttcagctgaa cagcctgcag tatagcgata cagcgaagc gcgcaaagaa    180
ctgcagcgcc tgtatgaatt ttttcatagc tggctgcagc cggaaaacca tagcaaagat    240
cagattattg cgcagctggc gatggaacag tttatgctga gcggccgctg ccgcgataaa    300
agcattctga aaaaaaatg gaaagcagc ggcaaaaacc tggaaaaact gctggaagat    360
ctgaccgatg attgcatgaa accgccggtg ctggtgcatg tgtgcatgca gggccaggaa    420
gcgctgttta gcaagagat gccgctgaaa gaagtgattg cgcatctgac caaacagagc    480
agcgcgaaaa cctttaccgc gggcatgggc accgcgcatc aggtgagcca gaacgcgccg    540
ctgggcaccc gccagggcaa cgaacatgaa gaagatggct gcaccagcag ctgggaagtg    600
acccaggtga acgattatat taccaacccg ggcaaagaaa ttgtgagcct gctgattatt    660
ccggaagcga cgatccgac cccggtggaa gaaagcgcga gctgggaaaa cacccatagc    720
agccgcaaag cgcgcccggt gatttgcggc ctgcaggaag aaagccagaa aggcccgagc    780
tatcaggatg tgccgatgga tgtgggcccg ggcagcagca gcctgccgca tcagagcagc    840
agcgaaccgg tgagcaacca tcattgcagc gaaggcaaca cgcgtgcga agaaagccag    900
gaacgctttc atgaaagccc gaaaagctat aaatgcgaag aatgcccgaa aacctttaaa    960
tatctgagcc attttctggc gcatcagcgc tgccatcgca gctttcgc                1008
```

<210> SEQ ID NO 30
<211> LENGTH: 990
<212> TYPE: DNA
<213> ORGANISM: Artificial Sequence
<220> FEATURE:
<223> OTHER INFORMATION: Reverse translation of SEQ ID NO: 40

<400> SEQUENCE: 30

```
atgccgagca acctgaccaa cagctgccag tgcaaaacca gccagaacga ttttgaactg     60
ggcaacaccc aatttcgccg cacccagggc agcgcggtgc agaacggcga aatttttagc    120
gaatttagca gcagccagct gaacagcctg ccggataacg gcaacagcaa cgcgcgcaaa    180
gaactgcagc gcctgcatgg catttttcat agctggctgc agccggaaaa acatagcaaa    240
gatgaaatta ttagccgcct ggtgctggaa cagtttatga ttaacggcaa ctgccgcgat    300
cgcagcattc tgaaagaaaa atgggaaagc agcggccgca acctggaaaa actgatggaa    360
gatctgaccg atgattgcat ggaaccgccg gtgctggtgc gcgtgcatat gcagggccag    420
gaagcgctgt ttagcgaaaa catgccgctg aaagaagtga ttgtgcatct gaaaaaacag    480
ctgagcgcgg aaaacaccac cggcgaaaac aaaggcatga gcctgcaggc gccgcaggat    540
accccgctgg aaacccgcca gggcaacgaa gataaagaaa acgcgtgcaa caacttttgg    600
aaaaacaccc aggtggatga tagcattacc tgccagggca cccagacccc gagcctgctg    660
attattcagg aagatcattg cctgcgcctg gaagatggcg cgcgagctg cgaaaacccg    720
cataacagcc gccgcggcgt gaccagccat agcgaaaaag gcccgctgga aggcccgagc    780
tatcagaaca ttccggtggg cgaacagccg gaatttctgc cgaccagcga tcagagcagc    840
agcgaatttg tgccggcgca tcagagcaac aaaggcgata gcacctgcgg cggccatcat    900
gaaaaatatc gcggcgcgca gaaaagctat aaatgcaaag aatgcccgaa aatttttcgc    960
```
tatctgtgcc attttctggc gcatcagcgc                                           990

<210> SEQ ID NO 31
<211> LENGTH: 175
<212> TYPE: PRT
<213> ORGANISM: Gorilla gorilla
<220> FEATURE:
<221> NAME/KEY: VARIANT
<222> LOCATION: 6, 7, 27, 71, 173, 174
<223> OTHER INFORMATION: Xaa = Any Amino Acid

<400> SEQUENCE: 31

Asn Gly Ile Thr Phe Xaa Xaa Val Pro Met Val Met Gly Ala Gly Cys
1               5                   10                  15

Ile Ser Gln Pro Glu Gln Ser Ser Pro Glu Xaa Ala Leu Thr His Gln
            20                  25                  30

Ser Asn Glu Gly Asn Ser Thr Cys Glu Val His Gln Lys Gly Ser His
        35                  40                  45

Gly Val Arg Lys Ser Tyr Lys Cys Glu Glu Cys Pro Lys Val Phe Lys
    50                  55                  60

Tyr His Cys His Leu Leu Xaa His Gln Arg Arg His Arg Asn Glu Arg
65                  70                  75                  80

Pro Phe Val Cys Pro Glu Cys Gln Lys Gly Phe Phe Gln Ile Ser Asp
                85                  90                  95

Leu Arg Val His Gln Ile Ile His Thr Gly Lys Lys Pro Phe Thr Cys
            100                 105                 110

Ser Met Cys Lys Lys Ser Phe Ser His Lys Thr Asn Leu Arg Ser His
        115                 120                 125

Glu Arg Ile His Thr Gly Glu Lys Pro Tyr Thr Cys Pro Phe Cys Lys
    130                 135                 140

Thr Ser Tyr Arg Gln Ser Ser Thr Tyr His Arg His Met Arg Thr His
145                 150                 155                 160

Glu Lys Ile Thr Leu Pro Ser Val Pro Ser Thr Pro Xaa Xaa Ser
                165                 170                 175

<210> SEQ ID NO 32
<211> LENGTH: 433
<212> TYPE: PRT
<213> ORGANISM: Pan paniscus

<400> SEQUENCE: 32

Met Ala Leu Asp Leu Arg Thr Ile Phe Gln Cys Glu Pro Ser Glu Asn
1               5                   10                  15

Asn Leu Gly Ser Glu Asn Ser Ala Phe Gln Gln Ser Gln Gly Pro Ala
            20                  25                  30

Val Gln Arg Glu Glu Gly Ile Ser Glu Phe Ser Arg Met Val Leu Asn
        35                  40                  45

Ser Phe Gln Asp Ser Asn Asn Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Ala Gly Val Lys Glu Lys Trp Lys Ser Ser Gly
            100                 105                 110

Lys Asn Leu Glu Arg Phe Ile Glu Asp Leu Thr Asp Asp Ser Ile Asn
        115                 120                 125

Pro Pro Ala Leu Val His Val His Met Gln Gly Gln Glu Ala Leu Phe
    130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                165                 170                 175

Thr Ser Gln Asp Thr Ser Leu Glu Thr Gly Gln Gly Tyr Glu Asp Glu
            180                 185                 190

Gln Asp Gly Trp Asn Ser Ser Leu Lys Thr Thr Gln Val Asn Glu Asn
        195                 200                 205

Ile Thr Asn Gln Gly Asp Gln Ile Val Ser Leu Ile Ile Gln Glu
    210                 215                 220

Glu Asn Ser Pro Arg Pro Glu Glu Gly Gly Val Ser Ser Asp Asn Pro
225                 230                 235                 240

Tyr Asn Ser Lys Arg Ala Glu Leu Val Thr Ala Arg Ser Gln Glu Gly
                245                 250                 255

Ser Ile Asn Gly Ile Thr Phe Gln Gly Val Pro Met Val Met Gly Ala
            260                 265                 270

Gly Cys Ile Ser Gln Pro Glu Gln Ser Ser Pro Glu Ser Ala Leu Thr
        275                 280                 285

His Gln Ser Asn Glu Gly Asn Ser Thr Cys Glu Val His Gln Lys Gly
    290                 295                 300

Ser His Gly Val Arg Lys Ser Tyr Lys Cys Glu Glu Cys Pro Lys Val
305                 310                 315                 320

Phe Lys Tyr Leu Cys His Leu Leu Ala His Gln Arg His Arg Asn
                325                 330                 335

Glu Arg Pro Phe Val Cys Pro Glu Cys Gln Lys Gly Phe Phe Gln Ile
            340                 345                 350

Ser Asp Leu Arg Val His Gln Ile Ile His Thr Gly Lys Lys Pro Phe
        355                 360                 365

Thr Cys Ser Ile Cys Lys Lys Ser Phe Ser His Lys Thr Asn Leu Arg
    370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Val Pro Ser Val Pro Ser Thr Pro Glu Ala
            420                 425                 430

Ser

<210> SEQ ID NO 33
<211> LENGTH: 433
<212> TYPE: PRT
<213> ORGANISM: Pongo pygmaeus

<400> SEQUENCE: 33

Met Ala Leu Asp Leu Arg Thr Ile Phe Gln Cys Glu Pro Ser Glu Asn
1               5                   10                  15

Asn Leu Gly Ser Glu Asn Ser Glu Phe Arg Gln Ser Gln Gly Pro Ala
                20                  25                  30

Val Gln Arg Glu Glu Gly Ile Ser Glu Phe Ser Arg Met Val Leu Asn
            35                  40                  45

Ser Phe Gln Asp Ser Asn Asn Ser Tyr Ala Arg Gln Glu Leu Gln Arg
        50                  55                  60

Leu Tyr Arg Ile Phe His Ser Trp Leu Gln Pro Glu Lys His Ser Lys
 65                  70                  75                  80

Asp Glu Ile Ile Ser Leu Leu Val Leu Glu Gln Phe Met Ile Gly Gly
                 85                  90                  95

His Cys Asn Asp Lys Ala Ser Val Lys Glu Lys Trp Lys Ser Ser Gly
            100                 105                 110

Lys Asn Leu Glu Arg Phe Met Glu Asp Leu Thr Asp Asp Ser Ile Asn
        115                 120                 125

Pro Pro Ala Leu Val His Val His Met Gln Gly Gln Glu Ala Leu Phe
    130                 135                 140

Ser Glu Asp Met Pro Leu Lys Asp Val Ile Val His Leu Thr Lys Gln
145                 150                 155                 160

Val Ser Ala Gln Thr Pro Arg Glu Ala Asn Met Gly Thr Pro Ser Gln
                165                 170                 175

Thr Ser Gln Asp Thr Ser Leu Glu Thr Gly Glu Gly Cys Glu Asp Glu
            180                 185                 190

Gln Asp Gly Cys Asn Ser Ser Leu Lys Thr Thr Gln Val Asn Glu Asn
        195                 200                 205

Ile Thr Asn Gln Gly Asn Gln Ile Val Ser Leu Ile Ile Ile Gln Glu
    210                 215                 220

Glu Asn Gly Pro Arg Ser Glu Glu Gly Val Ser Ser Asp Asn Pro
225                 230                 235                 240

Asn Asn Ser Lys Arg Ala Glu Leu Val Thr Ala Arg Ser Gln Glu Gly
                245                 250                 255

Ser Ile Asn Gly Ile Thr Phe Gln Gly Val Pro Met Glu Met Gly Ala
            260                 265                 270

Gly Cys Ile Ser Gln Pro Glu Gln Ser Ser Pro Glu Ser Ala Leu Thr
        275                 280                 285

His Gln Ser Asn Glu Gly Asn Ser Thr Cys Glu Val His Gln Lys Gly
    290                 295                 300

Ser His Gly Val Arg Lys Ser Tyr Lys Cys Glu Glu Cys Pro Lys Val
305                 310                 315                 320

Phe Lys Tyr Leu Cys His Leu Leu Ala His Gln Arg Arg His Arg Asn
                325                 330                 335

Glu Arg Pro Phe Val Cys Pro Cys Gln Lys Gly Phe Phe Gln Ile
            340                 345                 350

Ser Asp Leu Arg Val His Gln Ile Ile His Thr Gly Lys Lys Pro Phe
        355                 360                 365

Thr Cys Ser Met Cys Glu Lys Ser Phe Ser His Lys Thr Asn Leu Arg
    370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Pro Pro Ser Val Pro Ser Thr Pro Glu Ala
            420                 425                 430

Ser

<210> SEQ ID NO 34
<211> LENGTH: 433
<212> TYPE: PRT
<213> ORGANISM: Pongo abelii

<400> SEQUENCE: 34

```
Met Ala Leu Asp Leu Arg Thr Ile Phe Gln Cys Glu Pro Ser Glu Asn
1               5                   10                  15

Asn Leu Gly Ser Glu Asn Ser Glu Phe Arg Gln Ser Gln Gly Pro Ala
            20                  25                  30

Val Gln Arg Glu Glu Gly Ile Ser Glu Phe Ser Arg Met Val Leu Asn
        35                  40                  45

Ser Phe Gln Asp Ser Asn Asn Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Ala Ser Val Lys Glu Lys Trp Lys Ser Ser Gly
            100                 105                 110

Lys Asn Leu Glu Arg Phe Met Glu Asp Leu Thr Asp Asp Ser Ile Asn
            115                 120                 125

Pro Pro Ala Leu Val His Val His Met Gln Gly Gln Glu Ala Leu Phe
            130                 135                 140

Ser Glu Asp Met Pro Leu Lys Asp Val Ile Val His Leu Thr Lys Gln
145                 150                 155                 160

Val Ser Ala Gln Thr Pro Arg Glu Ala Asn Met Gly Thr Pro Ser Gln
            165                 170                 175

Thr Ser Gln Asp Thr Ser Leu Glu Thr Gly Glu Gly Cys Glu Asp Glu
            180                 185                 190

Gln Asp Gly Cys Asn Ser Ser Leu Lys Thr Thr Gln Val Asn Glu Asn
            195                 200                 205

Ile Thr Asn Gln Gly Asn Gln Ile Val Ser Leu Ile Ile Ile Gln Glu
            210                 215                 220

Glu Asn Gly Pro Arg Ser Glu Glu Gly Gly Val Ser Ser Asp Asn Pro
225                 230                 235                 240

Asn Asn Ser Lys Arg Ala Glu Leu Val Thr Ala Arg Ser Gln Glu Gly
            245                 250                 255

Ser Ile Asn Gly Ile Thr Phe Gln Gly Val Pro Met Glu Met Gly Ala
            260                 265                 270

Gly Cys Ile Ser Gln Pro Glu Gln Ser Ser Pro Glu Ser Ala Leu Thr
            275                 280                 285

His Gln Ser Asn Glu Gly Asn Ser Thr Cys Glu Val His Gln Lys Gly
            290                 295                 300

Ser His Gly Val Arg Lys Ser Tyr Lys Cys Glu Glu Cys Pro Lys Val
305                 310                 315                 320

Phe Lys Tyr Leu Cys His Leu Leu Ala His Gln Arg His Arg His Arg Asn
            325                 330                 335

Glu Arg Pro Phe Val Cys Pro Glu Cys Gln Lys Gly Phe Phe Gln Ile
            340                 345                 350

Ser Asp Leu Arg Val His Gln Ile Ile His Thr Gly Lys Lys Pro Phe
            355                 360                 365

Thr Cys Ser Met Cys Glu Lys Ser Phe Ser His Lys Thr Asn Leu Arg
            370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
            405                 410                 415
```

```
Thr His Glu Lys Ile Thr Pro Pro Ser Val Pro Ser Thr Pro Glu Ala
            420                 425                 430
Ser

<210> SEQ ID NO 35
<211> LENGTH: 334
<212> TYPE: PRT
<213> ORGANISM: Ailuropoda melanoleuca

<400> SEQUENCE: 35

Leu Lys Ile Asp Ser Phe Leu Cys Glu Leu Ser Met Asp Asp Pro Gly
1               5                   10                  15

Ser Lys Asn Lys Asp Phe Lys Pro Ser Gln Gly Pro Ala Leu Gln Lys
            20                  25                  30

Ala Glu Glu Ile Ser Glu Phe Gln Asp Ser Gln His Ser Leu Phe Gln
            35                  40                  45

Asp Gly Asn Asn Ser His Ala Lys Gln Glu Leu Gln Arg Leu Tyr Lys
        50                  55                  60

Ser Phe Tyr Ser Trp Leu Gln Pro Glu Lys His Ser Lys Asp Glu Ile
65              70                  75                  80

Ile Phe Gln Val Val Leu Glu Gln Phe Met Ile Asn Arg His Cys Ser
                85                  90                  95

Gly Arg Ser Thr Leu Lys Lys Lys Trp Glu Ser Ser Gly Arg Asn Leu
            100                 105                 110

Glu Lys Phe Met Glu Ser Leu Ser Glu Ser Ser Leu Lys Pro Pro Asp
        115                 120                 125

Leu Val His Val His Met Gln Gly Gln Glu Ala Leu Phe Ser Glu Asn
130                 135                 140

Met Pro Leu Lys Glu Val Ile Val His Leu Thr Lys Gln Leu Ser Val
145                 150                 155                 160

Gly Ser Pro Thr Gly Thr Asp Met Glu Thr Pro Ser Trp Thr Pro Gln
                165                 170                 175

Asp Thr Ser Leu Glu Thr Gly Gln Gly Glu Trp Gly Lys Lys Glu Asn
            180                 185                 190

Gly Asp Asn Ile Tyr His Ile Asn Asp Ser Ile Thr Ser Gln Gly Asn
        195                 200                 205

Glu Ile Pro Ser Leu Leu Ile Ile Arg Glu Glu Asp Tyr Pro Arg Pro
210                 215                 220

Glu Glu Asp Ser Val Ser Leu Lys Asn Pro Leu Ser Ser Arg Lys Ala
225                 230                 235                 240

Gly Leu Gly Met Ser Gly Ser Gln Glu Gly Ser Leu Lys Gly Pro Ser
                245                 250                 255

Tyr Gln Asp Val Leu Met Glu Gly Gly Pro Gly Phe Leu Ser Gln Ser
            260                 265                 270

Ile Gln Val Ser Pro Glu Pro Val Pro Thr His Gln Arg Thr Glu Gly
        275                 280                 285

Asn Ser Thr Arg Gly Gly His Gln Glu Arg Cys Arg Glu Ala Gln Asn
290                 295                 300

Ser Tyr Arg Cys Glu Lys Cys Pro Lys Ile Phe Arg Tyr Phe Ser Gln
305                 310                 315                 320

Leu Lys Ala His Gln Arg Arg His Asn Asn Glu Arg Thr Phe
                325                 330

<210> SEQ ID NO 36
<211> LENGTH: 439
```

<212> TYPE: PRT
<213> ORGANISM: Sus scrofa

<400> SEQUENCE: 36

```
Met Asp Leu Asp Leu Arg Leu Ser Phe Gln Gly Glu Pro Ser Arg Asn
1               5                   10                  15

Asp Pro Gly Ser Glu Asn Leu Ala Leu Lys Ala Ser Gln Gly Tyr Val
            20                  25                  30

Ile Arg Asp Gly Glu Gly Ile Ser Glu Phe Pro Asn Thr Arg Leu Ser
        35                  40                  45

Leu Phe Gln Asn Ser Ser Asn Ser Phe Ala Arg Arg Glu Leu Gln Arg
    50                  55                  60

Leu Tyr Asn Leu Phe His Ser Trp Leu Gln Pro Glu Lys Arg Ser Lys
65                  70                  75                  80

Asp Glu Met Ile Ser Cys Leu Val Leu Glu Gln Phe Val Ile Asn Gly
                85                  90                  95

His Cys Ser Asp Arg Ser Thr Leu Gln Glu Lys Trp Asn Ala Ser Gly
            100                 105                 110

Arg Asn Leu Glu Lys Phe Met Glu Asp Leu Thr Asp Asp Gly Met Lys
        115                 120                 125

Gln Pro Gly Phe Val His Val His Met Gln Gly Gln Glu Ala Leu Phe
    130                 135                 140

Ser Glu Asn Met Pro Leu Arg Glu Val Leu Val His Phe Arg Lys His
145                 150                 155                 160

Leu Ala Thr Ala Thr Pro Arg Gly Glu Asn Thr Lys Ala Pro Leu Trp
                165                 170                 175

Thr Pro Arg Asp Ala Ser Leu Glu Thr Gly Gln Glu Ser Glu Gly Lys
            180                 185                 190

Glu Cys Gly Gly Asn Thr Ser Arg Lys Thr Cys Pro Val Thr Glu Ser
        195                 200                 205

Leu Thr Trp Gln Gly Ser Gln Thr Pro Phe Leu Leu Ile Ile Pro Glu
    210                 215                 220

Glu Thr Cys Pro Gly Leu Glu Glu Ala Gly Val Ser Pro Glu Asn Pro
225                 230                 235                 240

Leu Gly Ser Arg Thr Ala Glu Pro Gly Leu Ala Val Ser Gln Glu Gly
                245                 250                 255

Ser Pro Glu Gly Pro Phe Gly Gly Asp Val His Leu Glu Ala Glu Pro
            260                 265                 270

Gly Phe Leu Ser Arg Pro Asp Gln Val Thr Leu Glu Pro Val Ser Ala
        275                 280                 285

His Pro Ser Leu Glu Gly Asn Pro Ala Arg Gly Lys Ser Pro Glu Gly
    290                 295                 300

Leu Pro Gly Ala Gln Lys Val Phe Pro Cys Glu Lys Cys Ser Gln Val
305                 310                 315                 320

Phe Arg Tyr Leu Ser Arg Leu Lys Val His Gln Arg Arg His Asn Asp
                325                 330                 335

Glu Arg Pro Phe Val Cys Ala Lys Cys Lys Gly Phe Phe Gln Thr
            340                 345                 350

Ser Asp Leu Arg Val His Gln Arg Ile His Thr Lys Glu Lys Pro Phe
        355                 360                 365

Arg Cys Ser Thr Cys Lys Arg Pro Phe Ser His Lys Thr Asn Leu Arg
    370                 375                 380

Ala His Glu Arg Ile His Thr Gly Glu Lys Pro Tyr Leu Cys Ser Leu
385                 390                 395                 400
```

```
Cys Gln Arg Arg Tyr Arg Gln Ser Ser Thr Tyr Asn Arg His Leu Lys
                405                 410                 415

Ser His Gln Lys Leu Ala Leu Lys Gly Asp Leu Ser Gly Val Pro Val
            420                 425                 430

Val Ala Gln Arg Lys Arg Ile
            435

<210> SEQ ID NO 37
<211> LENGTH: 433
<212> TYPE: PRT
<213> ORGANISM: Nomascus leucogenys

<400> SEQUENCE: 37

Met Ala Leu Glu Leu Arg Thr Ile Phe Gln Cys Glu Pro Ser Glu Asn
1               5                   10                  15

Asn Leu Gly Ser Glu Asn Ser Glu Phe Arg Gln Ser Gln Gly Pro Ala
            20                  25                  30

Val Gln Arg Glu Glu Gly Ile Ser Glu Phe Ser Arg Met Val Leu Asn
        35                  40                  45

Ser Phe Gln Asp Ser Asn Lys Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Thr Ser Val Lys Glu Lys Trp Lys Ser Ser Gly
            100                 105                 110

Lys Asn Leu Glu Arg Phe Met Glu Asp Leu Thr Asp Asp Ser Ile Asn
        115                 120                 125

Pro Pro Ala Leu Val His Val His Met Gln Gly Gln Glu Ala Leu Phe
    130                 135                 140

Ser Glu Asp Met Pro Leu Lys Asp Val Ile Val His Leu Thr Lys Gln
145                 150                 155                 160

Val Ser Ala Gln Ile Pro Arg Glu Ala Asn Met Gly Thr Pro Phe Gln
                165                 170                 175

Thr Ser Gln Asp Thr Ser Leu Glu Thr Gly Gln Gly Arg Glu Asp Glu
            180                 185                 190

Gln Asp Gly Cys Asn Ser Ser Leu Lys Thr Thr Gln Val Asn Glu Asn
        195                 200                 205

Ile Thr Asn Gln Gly Asn Gln Ile Val Ser Leu Ile Ile Ile Gln Glu
    210                 215                 220

Glu Asn Gly Pro Arg Pro Glu Glu Gly Val Ser Ser Asp Asn Pro
225                 230                 235                 240

Cys Asn Ser Lys Arg Ala Glu Leu Val Thr Ala Arg Ser Gln Glu Gly
                245                 250                 255

Ser Ile Asn Gly Ile Thr Phe Gln Gly Val Pro Met Glu Met Gly Ala
            260                 265                 270

Gly Cys Ile Ser Gln Pro Glu Gln Ser Ser Pro Glu Ser Ala Pro Thr
        275                 280                 285

His Gln Ser Asn Glu Gly Asn Ser Thr Cys Glu Val His Gln Lys Gly
    290                 295                 300

Ser His Gly Val Arg Lys Ser Tyr Lys Cys Glu Glu Cys Pro Lys Val
305                 310                 315                 320

Phe Lys Tyr Leu Cys His Leu Leu Ala His Gln Arg Arg His Arg Asn
```

```
            325                 330                 335
Glu Arg Pro Phe Val Cys Pro Glu Cys Gln Lys Gly Phe Phe Gln Thr
            340                 345                 350

Ser Asp Leu Arg Val His Gln Val Ile His Thr Gly Lys Lys Pro Phe
            355                 360                 365

Thr Cys Ser Met Cys Glu Lys Ser Phe Ser His Lys Thr Asn Leu Arg
        370                 375                 380

Ser His Glu Arg Ile His Thr Gly Glu Lys Pro Tyr Thr Cys Pro Tyr
385                 390                 395                 400

Cys Lys Thr Ser Tyr Arg Gln Ser Ser Thr Tyr His Arg His Met Arg
                405                 410                 415

Thr His Glu Lys Ile Thr Ser Pro Ser Val Pro Ser Thr Pro Glu Ala
                420                 425                 430

Ser
```

<210> SEQ ID NO 38
<211> LENGTH: 432
<212> TYPE: PRT
<213> ORGANISM: Macaca mulatta

<400> SEQUENCE: 38

```
Met Ala Leu Asp Leu Arg Thr Ile Phe Gln His Glu Pro Ser Glu Asn
1               5                   10                  15

Asn Leu Gly Ser Glu Asn Ser Glu Phe Arg Arg Ser Gln Gly Pro Ala
            20                  25                  30

Val Gln Thr Glu Glu Gly Ile Ser Glu Phe Ser Arg Met Met Leu Asn
        35                  40                  45

Ser Phe Gln Asp Ser Asn Asn Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Ala Thr Val Lys Glu Lys Trp Lys Ser Ser Gly
            100                 105                 110

Lys Asn Leu Glu Arg Phe Met Glu Asp Leu Thr Asp Asp Ile Ile Asn
        115                 120                 125

Pro Pro Ala Leu Val His Val His Met Gln Gly Gln Glu Ala Leu Phe
    130                 135                 140

Ser Asp Asn Met Pro Leu Lys Asp Val Ile Val His Leu Thr Lys Gln
145                 150                 155                 160

Val Ser Ala Lys Thr Pro Arg Glu Ala Asn Met Gly Thr Pro Phe Gln
                165                 170                 175

Thr Ser Gln Asp Thr Ser Ser Glu Thr Gly Gln Gly Arg Glu Asp Glu
            180                 185                 190

Gln Asp Gly Cys Asn Ser Ser Leu Lys Thr Thr Gln Val Asn Glu Ser
        195                 200                 205

Asn Thr Asn Gln Asp Asn Pro Ile Val Ser Leu Ile Ile Gln Glu Glu
    210                 215                 220

Asn Gly Pro Arg Pro Lys Glu Gly Gly Val Ser Ser Asp Asn Pro Tyr
225                 230                 235                 240

Asn Ser Arg Arg Thr Glu Leu Asp Thr Ala Arg Ser Gln Glu Gly Ser
                245                 250                 255

Thr Asn Gly Ile Ile Phe Gln Gly Val Pro Met Glu Met Gly Ala Gly
```

```
            260                 265                 270
Phe Ile Ser Gln Pro Glu Gln Ser Pro Glu Ser Ala Pro Thr His
        275                 280                 285

Gln Ser Asn Lys Gly Asn Ser Thr Cys Glu Val His Gln Lys Gly Ser
    290                 295                 300

His Gly Val Arg Lys Ser Tyr Lys Cys Glu Glu Cys Pro Lys Val Phe
305                 310                 315                 320

Lys Tyr Leu Cys His Leu Leu Ala His Gln Arg Arg His Arg Asn Glu
                325                 330                 335

Arg Pro Phe Val Cys Pro Lys Cys Gln Lys Gly Phe Phe Gln Ile Ser
            340                 345                 350

Asp Leu Arg Val His Gln Ile Ile His Thr Gly Glu Lys Pro Phe Thr
        355                 360                 365

Cys Ser Met Cys Glu Lys Ser Phe Ser His Lys Thr Asn Leu Arg Ser
    370                 375                 380

His Glu Arg Ile His Thr Gly Glu Lys Pro Tyr Thr Cys Pro Tyr Cys
385                 390                 395                 400

Lys Arg Ser Tyr Arg Gln Ser Ser Thr Tyr His Arg His Met Arg Thr
                405                 410                 415

His Lys Lys Ile Thr Leu Pro Thr Val Pro Ser Thr Pro Glu Ala Ser
            420                 425                 430

<210> SEQ ID NO 39
<211> LENGTH: 336
<212> TYPE: PRT
<213> ORGANISM: Cavia porcellus

<400> SEQUENCE: 39

Met Ala Leu Asp Leu Arg Lys Ser Phe Cys Gln Glu Leu Ser Ser Asn
1               5                   10                  15

Asn Leu Glu Ser Glu Asp Leu Glu Phe Ser Ser Thr Gln Gly Phe Ala
            20                  25                  30

Val Pro Lys Arg Glu Ile Ser Ala Phe Ser Ser Ile Gln Leu Asn Ser
        35                  40                  45

Leu Gln Tyr Ser Asp Asn Ser Glu Ala Arg Lys Glu Leu Gln Arg Leu
    50                  55                  60

Tyr Glu Phe Phe His Ser Trp Leu Gln Pro Glu Asn His Ser Lys Asp
65                  70                  75                  80

Gln Ile Ile Ala Gln Leu Ala Met Glu Gln Phe Met Leu Ser Gly Arg
                85                  90                  95

Cys Arg Asp Lys Ser Ile Leu Lys Lys Lys Trp Glu Ser Ser Gly Lys
            100                 105                 110

Asn Leu Glu Lys Leu Leu Glu Asp Leu Thr Asp Asp Cys Met Lys Pro
        115                 120                 125

Pro Val Leu Val His Val Cys Met Gln Gly Gln Glu Ala Leu Phe Ser
    130                 135                 140

Glu Asp Met Pro Leu Lys Glu Val Ile Ala His Leu Thr Lys Gln Ser
145                 150                 155                 160

Ser Ala Lys Thr Phe Thr Ala Gly Met Gly Thr Ala His Gln Val Ser
                165                 170                 175

Gln Asn Ala Pro Leu Gly Thr Arg Gln Gly Asn Glu His Glu Glu Asp
            180                 185                 190

Gly Cys Thr Ser Ser Trp Glu Val Thr Gln Val Asn Asp Tyr Ile Thr
        195                 200                 205
```

```
Asn Pro Gly Lys Glu Ile Val Ser Leu Leu Ile Ile Pro Glu Ala Asn
    210                 215                 220

Asp Pro Thr Pro Val Glu Glu Ser Ala Ser Trp Glu Asn Thr His Ser
225                 230                 235                 240

Ser Arg Lys Ala Arg Pro Val Ile Cys Gly Leu Gln Glu Glu Ser Gln
                245                 250                 255

Lys Gly Pro Ser Tyr Gln Asp Val Pro Met Asp Val Gly Pro Gly Ser
                260                 265                 270

Ser Ser Leu Pro His Gln Ser Ser Glu Pro Val Ser Asn His His
                275                 280                 285

Cys Ser Glu Gly Asn Ser Ala Cys Glu Glu Ser Gln Glu Arg Phe His
290                 295                 300

Glu Ser Pro Lys Ser Tyr Lys Cys Glu Glu Cys Pro Lys Thr Phe Lys
305                 310                 315                 320

Tyr Leu Ser His Phe Leu Ala His Gln Arg Cys His Arg Ser Phe Arg
                325                 330                 335

<210> SEQ ID NO 40
<211> LENGTH: 330
<212> TYPE: PRT
<213> ORGANISM: Spermophilus tridecemlineatus

<400> SEQUENCE: 40

Met Pro Ser Asn Leu Thr Asn Ser Cys Gln Cys Lys Thr Ser Gln Asn
1               5                   10                  15

Asp Phe Glu Leu Gly Asn Thr Glu Phe Arg Arg Thr Gln Gly Ser Ala
                20                  25                  30

Val Gln Asn Gly Glu Ile Phe Ser Glu Phe Ser Ser Ser Gln Leu Asn
                35                  40                  45

Ser Leu Pro Asp Asn Gly Asn Ser Asn Ala Arg Lys Glu Leu Gln Arg
50                  55                  60

Leu His Gly Ile Phe His Ser Trp Leu Gln Pro Glu Lys His Ser Lys
65                  70                  75                  80

Asp Glu Ile Ile Ser Arg Leu Val Leu Glu Gln Phe Met Ile Asn Gly
                85                  90                  95

Asn Cys Arg Asp Arg Ser Ile Leu Lys Glu Lys Trp Glu Ser Ser Gly
                100                 105                 110

Arg Asn Leu Glu Lys Leu Met Glu Asp Leu Thr Asp Asp Cys Met Glu
                115                 120                 125

Pro Pro Val Leu Val Arg Val His Met Gln Gly Gln Glu Ala Leu Phe
                130                 135                 140

Ser Glu Asn Met Pro Leu Lys Glu Val Ile Val His Leu Lys Lys Gln
145                 150                 155                 160

Leu Ser Ala Glu Asn Thr Thr Gly Glu Asn Lys Gly Met Ser Leu Gln
                165                 170                 175

Ala Pro Gln Asp Thr Pro Leu Val Thr Arg Gln Gly Asn Glu Asp Lys
                180                 185                 190

Glu Asn Ala Cys Asn Asn Phe Trp Lys Asn Thr Gln Val Asp Asp Ser
                195                 200                 205

Ile Thr Cys Gln Gly Thr Gln Thr Pro Ser Leu Leu Ile Ile Gln Glu
                210                 215                 220

Asp His Cys Leu Arg Leu Glu Asp Gly Ala Ser Cys Glu Asn Pro
225                 230                 235                 240

His Asn Ser Arg Arg Gly Val Thr Ser His Ser Glu Lys Gly Pro Leu
                245                 250                 255
```

```
Glu Gly Pro Ser Tyr Gln Asn Ile Pro Val Gly Glu Gln Pro Glu Phe
            260                 265                 270

Leu Pro Thr Ser Asp Gln Ser Ser Glu Phe Val Pro Ala His Gln
        275                 280                 285

Ser Asn Lys Gly Asp Ser Thr Cys Gly Gly His His Glu Lys Tyr Arg
    290                 295                 300

Gly Ala Gln Lys Ser Tyr Lys Cys Lys Glu Cys Pro Lys Ile Phe Arg
305                 310                 315                 320

Tyr Leu Cys His Phe Leu Ala His Gln Arg
                325                 330

<210> SEQ ID NO 41
<211> LENGTH: 39
<212> TYPE: DNA
<213> ORGANISM: Artificial Sequence
<220> FEATURE:
<223> OTHER INFORMATION: Synthetic Construct

<400> SEQUENCE: 41
cggtttgttt gggtttgggt ttgggtttgg gtttgggtt                              39

<210> SEQ ID NO 42
<211> LENGTH: 39
<212> TYPE: DNA
<213> ORGANISM: Artificial Sequence
<220> FEATURE:
<223> OTHER INFORMATION: Synthetic Construct

<400> SEQUENCE: 42
ggcttgcctt acccttaccc ttaccttac ccttaccct                               39

<210> SEQ ID NO 43
<211> LENGTH: 23
<212> TYPE: DNA
<213> ORGANISM: Artificial Sequence
<220> FEATURE:
<223> OTHER INFORMATION: Synthetic Construct

<400> SEQUENCE: 43
cagcaagtgg gaaggtgtaa tcc                                               23

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
cccattctat catcaacggg tacaa                                             25
```

METHODS OF USING ZSCAN4 FOR REJUVENATING HUMAN CELLS

CROSS REFERENCE TO RELATED APPLICATIONS

This is a U.S. National Phase patent application of PCT/US2014/029537, filed Mar. 14, 2014, which claims the benefit of U.S. Provisional patent application Ser. No. 61/800,668, filed Mar. 15, 2013, which are both hereby incorporated by reference, in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699442000830SEQLIST.TXT, date recorded: Sep. 14, 2015, size: 104 KB).

FIELD

The present disclosure relates to methods for increasing telomere length in one or more human cells and/or increasing genome stability of one or more human cells, for example by contacting one or more human cells with an agent that increases expression of Zscan4 in the one or more human cells. The present disclosure further provides methods of treating a subject in need of telomere lengthening, treating a disease or condition associated with a genomic and/or chromosome abnormality, of rejuvenating one or more human cells, of rejuvenating tissues or organs, and of rejuvenating a subject in need thereof, for example by contacting one or more human cells in the subject with an agent that increases expression of Zscan4, or by administering to a subject in need thereof, an agent that increases expression of Zscan4.

BACKGROUND

Telomeres are repetitive DNA sequences accompanied by proteins that cap and protect the end of each chromosome from continuous degradation in each cell cycle, thereby securing and protecting chromosomal integrity. Telomere shortening may also lead to cancer by contributing to genomic instability (Raynaud et al., *Crit. Rev Oncol Hematol* 66:99-117, 2008), and has been associated with aging and cellular senescence (Yang, *Cytogenet Genome Res* 122:211-218, 2008). It is well established that telomeres get gradually shorter during the course of normal aging. It has been reported that up to 200 base pairs of telomere DNA are lost with each round of DNA replication. For example, in new-born humans, peripheral blood lymphocytes have approximately 10 kb of telomere DNA at both ends of each chromosome, which gradually shorten to approximately 6 kb by the age of 70. It is also known that environmental factors and life-style factors can accelerate telomere shortening. It is believed that such telomere shorting is associated with age-related cellular decline. It is also believed that telomere shortening limits the number of cell divisions, which ultimately results in limiting human life span. It is also known that humans are born with differing lengths of telomeres. For example, some humans start with approximately 8 kb of telomeres, while others start with approximately 12 kb of telomeres. Accordingly, humans with shorter telomeres may be more susceptible to developing certain age-related pathological conditions at an earlier age than those with longer telomeres. Such pathological conditions include, for example, immunological deficiencies, chronic ulcers, atherosclerosis, age-related blindness due to a proliferative decline of retinal pigmented epithelial cells, and cancer.

Moreover, there are various diseases and disorders that are also associated with telomere shortening (Armanios and Blackburn, *Nat Rev Genet.* 2012 October; 13(10):693-704). Examples of genetic diseases that can cause telomere shortening include dyskeratosis congenita, Hoyeraal-Hreidarsson syndrome, Revesz syndrome, and Coats plus syndrome. Additionally, it was recently shown that a significant fraction of idiopathic pulmonary fibrosis (IPF) is caused by telomere shortening. Similarly, some liver cirrhosis and pancreatic fibrosis may be caused by telomere shortening. Considering the prevalence of such pathological conditions, it appears that diseases caused by telomere shortening are more common than previously thought.

Another example of a disease associated with telomere shortening is Fanconi anemia. Fanconi anemia is a rare autosomal recessive disease. Fanconi anemia is an inherited bone marrow failure syndrome that is characterized by progressive pancytopenia and cancer susceptibility (Bogliolo et al., *Mutagenesis.* 2002 November; 17(6):529-38). It has been reported that Fanconi anemia patients show accelerated telomere shortening (Leteurte et al., *Br. J. Haematol.,* 1999; Ball et al., *Blood,* 1998; Hanson et al., *Cytogenet. Cell Genet.* 2001; and Callen, et al., *Hum Mol Genet.* 2002 Feb. 15; 11(4):439-44).

One potential method of treating these various telomere shortening-associated diseases and disorders is to use telomerase to lengthen the shortened telomeres. Telomerase has been identified as the major enzyme known to be involved in telomere elongation maintenance. While telomerase is active in embryonic stem cells, telomerase is usually not expressed in non-embryonic (i.e., adult cells), such as somatic cells. Thus the reactivation of telomerase or forced expression of telomerase in adult cells may be used to increase telomere length. However, one potential problem with the use of telomerase is that the continuous expression of telomerase is often associated with tumorigenesis and cancerous transformation. Accordingly, expression of telomerase is not an ideal way to increase telomere length in patients suffering from diseases or conditions associated with telomere shortening.

Another potential method to lengthen telomeres is to use a recently discovered component of a Chinese herb (TA-65) that can potentially increase telomere length (Harley et al., *Rejuvenation Research* 14:45-56, 2011). However, it has not been well established that this herb can effectively lengthen telomeres. Moreover, use of this herb would require long-term continuous administration of drugs to treat patients in need of telomere lengthening.

Additionally, it has recently been shown that Zscan4 (Zinc finger and scan domain-containing protein 4) is required for the maintenance of genome stability and normal karyotype in mouse embryonic stem cells and is expressed in mouse embryos and embryonic stem cells (Falco et al., *Dev Biol* 307:539-550, 2007; Zalzman et al., *Nature* 464:858-863, 2010; PCT Publication Nos. WO 2008/118957, WO 2011/02880, WO 2012/103235, WO 2012/129342, WO 2012/158561, and WO 2012158564; and U.S. Patent Application Publication Nos. US 2010/0105043, US 2012/0129161, and US 2012/0156305). It has also been shown that Zscan4 expression in mouse embryonic stem cells is associated with telomere elongation (Zalzman et al., *Nature* 464:858-863, 2010; PCT Publication Nos. WO 2011/02880, WO 2012/129342, and WO 2012158564; and U.S. Patent Application Publication No. US 2012/0156305). While, it has been shown that the human genome also contains a ZSCAN4 gene, none of Falco et al., *Dev Biol* 307:539-550, 2007; Zalzman et al., *Nature* 464:858-863, 2010; PCT Publication Nos. WO 2008/118957, WO 2011/02880, WO 2012/103235, WO 2012/129342, WO 2012/158561, and WO 2012158564; or U.S. Patent Application Publication Nos. US 2010/0105043, US 2012/0129161, and US 2012/0156305 provide experimental support demonstrating that Zscan4 expression leads to same effects in human cells as it does in mouse embryonic cells. It is particularly unclear whether human ZSCAN4 would have the same function as mouse Zscan4, as the mouse genome contains six Zscan4 genes and three Zscan4 pseudogenes while the human genome only contains one ZSCAN4 gene (PCT Publication No. WO 2008/118957). Moreover, it is unknown whether ZSCAN4 expression in human cells, such as somatic cells involved in diseases and conditions associated with telomere shortening, would have the same effect as shown for mouse embryonic stem cells.

SUMMARY

Accordingly, there exists a need for improved approaches for increasing telomere length and correcting genomic and/or chromosome abnormalities in human cells in order to treat diseases or conditions associated with telomere shortening and genomic abnormalities.

In order to meet the above need, the present disclosure provides novel methods of increasing telomere length, increasing chromosome and/or genome stability in human cells, correcting chromosome and/or karyotype abnormalities (e.g., trisomy 21), in human cells, and/or rejuvenating human cells, by contacting the human cells with an agent that increases expression of Zscan4 (Zinc finger and scan domain-containing protein 4) in the cells. As used herein, the term "Zscan4" refers to Zscan4 polypeptides and polynucleotides, such as genes, encoding Zscan4 polypeptides from any species, including mouse and human. As used herein, the term "ZSCAN4" refers specifically to human Zscan4 polypeptides and polynucleotides, such as genes, encoding Zscan4 polypeptides.

The present disclosure also provides novel methods of treating a disease or condition associate with a telomere, chromosome and/or karyotype abnormality, increasing genomic stability and correcting karyotype abnormalities in human oocyte cells, human fertilized oocytes, and human preimplantation embryos, rejuvenating a tissue or organ, and/or rejuvenating a subject in need thereof, by administering to a subject in need thereof an agent that increases expression of Zscan4. In some embodiments, the human cells are human adult cells (i.e., non-embryonic cells).

Moreover, the present disclosure is based, at least in part, on the surprising discovery that Zscan4 expression in human cells, such as fibroblast cells, rapidly and dramatically increases the length of telomeres in the cells after just two days. In particular, as disclosed in the Example 8 below, Zscan4 expression in human fibroblast resulted in about a 40% increase in telomere length within three days. Additionally, expression of Zscan4 in human fibroblasts isolated from a patient with Fanconi anemia resulted in about a 160% increase in telomere length within three days. Surprisingly, Zscan4 expression in a population of fibroblast cells isolated from a Down syndrome patient was also able to dramatically reduce the percentage of cells in the population with trisomy 21. In particular, as disclosed in Example 15 below, Zscan4 expression in a population of fibroblast cells isolated from a Down syndrome patient was able to correct the trisomy 21 abnormality in approximately 55% of the cells.

The results disclosed herein are particularly surprising given that it is believed that it has never before been shown that Zscan4 expression can increase telomere length in human cells. The results disclosed herein are also unexpected. While Zscan4 expression has been previously shown to increase telomere length in mouse embryonic stem (ES) cells, the differences not only between human ZSCAN4 and mouse Zscan4, but also between the biology of human cells and mouse cells, as well as between ES cells and non-ES cells such as adult cells, would not lead one to expect that Zscan4 expression in human cells would also increase telomere length. This is particularly relevant given that it has been previously demonstrated that transcriptional regulatory elements in the human and mouse genomes differ dramatically. This is exceptionally striking when considering that even transcription factors with conserved function in both human and mouse exhibit a significant degree of species-specific binding event preferences (Odom et al., *Nature Genetics* 6:39, 2007).

Advantageously, utilizing agents that increase Zscan4 expression, such as nucleic acid molecules encoding Zscan4, can be used to increase the success rate of in vitro fertilization (IVF) and successful pregnancies in older women by rejuvenating and/or correcting genomic and/or chromosomal abnormalities, such as aneuploidy, in oocyte cells, fertilized oocytes, or preimplantation embryos. Additionally, utilizing agents that increase Zscan4 expression, such as nucleic acid molecules encoding Zscan4, can be used to treat a patient suffering from a disease or condition associated with telomere shortening, such as Fanconi anemia, by increasing the length of telomeres in cells of the patient affected by the disease or condition. Furthermore, agents that increase Zscan4 expression, such as nucleic acid molecules encoding Zscan4, can be used to also rejuvenate cells in an individual, tissues in an individual, or organs in an individual; or to rejuvenate individuals by increasing the length of telomeres in aged cells, tissues, organs and individuals caused by telomere shortening.

Accordingly, certain aspects of the present disclosure relate to a method of increasing telomere length in one or more human cells, by contacting the one or more human cells with an agent that increases expression of Zscan4 in the human cell, where increased expression of Zscan4 induces telomere lengthening in the one or more human cells as compared to one or more corresponding human cells that are not contacted with the agent.

Other aspects of the present disclosure relate to a method of treating a subject in need of telomere lengthening, by contacting one or more human cells in the subject with an agent that increases expression of Zscan4 in the one or more human cells, where increased expression of Zscan4 induces telomere lengthening in the one or more human cells.

Other aspects of the present disclosure relate to a method of treating a subject in need of telomere lengthening, by: i. isolating one or more human cells in need of telomere lengthening from the subject; ii. contacting the one or more human cells with an agent that increases expression of Zscan4 in the one or more human cells, where increasing expression of Zscan4 induces telomere lengthening in the one or more human cells; and iii. administering the contacted one or more human cells to the subject.

Other aspects of the present disclosure relate to a method of treating a disease or condition associated with a telomere abnormality, by administering to a subject in need thereof an agent that increases expression of Zscan4 in one or more human cells in the subject, where increasing expression of Zscan4 induces telomere lengthening in the one or more human cells to treat the disease or condition associated with a telomere abnormality.

Other aspects of the present disclosure relate to a method of treating a disease or condition associated with a telomere abnormality, by: i. isolating one or more human cells from a subject suffering from a disease or condition associated with a telomere abnormality; ii. contacting the one or more human cells with an agent that increases expression of Zscan4 in the one or more human cells, where increasing expression of Zscan4 induces telomere lengthening in the one or more human cells; and iii. administering the contacted one or more human cells to the subject to treat the disease or condition associated with a telomere abnormality.

Other aspects of the present disclosure relate to a method of treating a disease or condition associated with a chromosome abnormality, by administering to a subject in need thereof an agent that increases expression of Zscan4 in one or more human cells in the subject, where increasing expression of Zscan4 induces correction of the chromosome abnormality in the one or more human cells to treat the disease or condition associated with a chromosome abnormality.

Other aspects of the present disclosure relate to a method of treating a disease or condition associated with a chromosome abnormality, by: i. isolating one or more human cells from a subject suffering from a disease or condition associated with a chromosome abnormality; ii. contacting the one or more human cells with an agent that increases expression of Zscan4 in the one or more human cells, where increasing expression of Zscan4 induces correction of the chromosome abnormality in the one or more human cells; and iii. administering the contacted one or more human cells to the subject to treat the disease or condition associated with a chromosome abnormality.

Other aspects of the present disclosure relate to a method of treating a disease or condition associated with a karyotype abnormality, by administering to a subject in need thereof an agent that increases expression of Zscan4 in one or more human cells in the subject, where increasing expression of Zscan4 induces correction of the karyotype abnormality in the one or more human cells to treat the disease or condition associated with a karyotype abnormality.

Other aspects of the present disclosure relate to a method of treating a disease or condition associated with a karyotype abnormality, by: i. isolating one or more human cells from a subject suffering from a disease or condition associated with a karyotype abnormality; ii. contacting the one or more human cells with an agent that increases expression of Zscan4 in the one or more human cells, where increasing expression of Zscan4 induces correction of the karyotype abnormality in the one or more human cells; and iii. administering the contacted one or more human cells to the subject to treat the disease or condition associated with a karyotype abnormality.

In some embodiments that may be combined with any of the preceding embodiments, the karyotype abnormality is selected from a chromosome nullisomy, a chromosome monosomy, a chromosome trisomy, a chromosome tetrasomy, and a chromosome pentasomy. In some embodiments that may be combined with any of the preceding embodiments, the karyotype abnormality is selected from trisomy 21, trisomy 16, trisomy 18, trisomy 13, monosomy X, XXX aneuploidy, XXY aneuploidy, XYY aneuploidy, and 1p36 duplication. In some embodiments that may be combined with any of the preceding embodiments, the disease or condition associated with a karyotype abnormality is selected from dup(17)(p11.2p11.2) syndrome, Pelizaeus-Merzbacher disease, dup(22)(q11.2q11.2) syndrome, cat-eye syndrome, Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azoospermia (factor a), Azoospermia (factor b), Azoospermia (factor c), and 1p36 deletion. In some embodiments that may be combined with any of the preceding embodiments, the disease or condition is one or more diseases or conditions selected from diseases of telomere shortening, bone marrow failure syndromes, age-related telomere shortening diseases or disorders, and premature aging diseases or disorders. In some embodiments that may be combined with any of the preceding embodiments, the disease or condition is a disease of telomere shortening selected from dyskeratosis congenita, Hoyeraal-Hreidarsson syndrome, Revesz syndrome, Coats plus syndrome, idiopathic pulmonary fibrosis, liver cirrhosis, pancreatic fibrosis, Alzheimer's disease, and osteoarthritis. In some embodiments that may be combined with any of the preceding embodiments, the disease or condition is a bone marrow failure syndrome selected from Fanconi anemia, amegakaryocytic thrombocytopenia, aplastic anemia, Diamond Blackfan anemia, dyskeratosis congenita, paroxysmal nocturnal hemoglobinuria (PNH), Pearson syndrome, Shwachman Diamond syndrome, thrombocytopenia, and myelodysplastic syndrome. In some embodiments that may be combined with any of the preceding embodiments, the disease or condition is an age-related telomere shortening disease or disorder, a premature aging disease or disorder, or both selected from Werner syndrome, Bloom's syndrome, Hutchinson-Gilford progeria syndrome, Cockayne syndrome, Xeroderma pigmentosa, Ataxia telangiectasia, Rothmund Thomson syndrome, Trichothiodystrophy, Juberg-Marsidi syndrome, and Down syndrome. In some embodiments that may be combined with any of the preceding embodiments, the disease or condition is one or more diseases or conditions selected from immunological deficiencies, an autoimmune disease, an autoimmune disorder, chronic ulcers, atherosclerosis, cancer, a neurologic injury, a degenerative disorder, a neurodegenerative disorder, wound healing, muscle repair, cardiac muscle repair, cartilage replacement, arthritis, osteoarthritis, tooth regeneration, blindness, age-related blindness due to proliferative decline of retinal pigmented epithelial cells, deafness, bone marrow failure, bone marrow transplant, diabetes, muscular dystrophy, Duchenne muscular dystrophy, a genetic disease, a genetic mutation, and DNA damage. In some embodiments that may be combined with any of the preceding embodiments, the disease or condition is a cancer selected from cancers of the heart (e.g., angiosarcoma, fibrosarcoma, rhabdomyosarcoma, liposarcoma, myxoma, rhabdomyoma, fibroma, lipoma and teratoma), lung cancers (e.g., bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma); gastrointestinal tract cancers (e.g., esophagus (squamous cell carcinoma, adenocarcinoma, leiomyosarcoma, lymphoma); stomach cancers (carcinoma, lymphoma, leiomyosarcoma);

pancreatic cancers (ductal adenocarcinoma, insulinoma, glucagonoma, gastrinoma, carcinoid tumors, vipoma); small bowel cancers (adenocarcinoma, lymphoma, carcinoid tumors, Kaposi's sarcoma, leiomyoma, hemangioma, lipoma, neurofibroma, fibroma); large bowel cancers (adenocarcinoma, tubular adenoma, villous adenoma, hamartoma, leiomyoma); genitourinary tract cancers (e.g., kidney (adenocarcinoma, Wilms' tumor, nephroblastoma, lymphoma, leukemia); bladder and urethra cancers (squamous cell carcinoma, transitional cell carcinoma, adenocarcinoma); prostate cancers (adenocarcinoma, sarcoma); testis cancers (seminoma, teratoma, embryonal carcinoma, teratocarcinoma, choriocarcinoma, sarcoma, interstitial cell carcinoma, fibroma, fibroadenoma, adenomatoid tumors, lipoma); liver cancers (e.g., hepatoma (hepatocellular carcinoma), cholangiocarcinoma, hepatoblastoma, angiosarcoma, hepatocellular adenoma, hemangioma); bone cancers (e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxofibroma, osteoid osteoma and giant cell tumors); nervous system cancers (e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma, pinealoma, glioblastoma multiforme, oligodendroglioma, schwannoma, retinoblastoma, congenital tumors), spinal cord (neurofibroma, meningioma, glioma, sarcoma)); gynecological cancers (e.g., uterus (endometrial carcinoma), cervix (cervical carcinoma, pre-tumor cervical dysplasia), ovaries (ovarian carcinoma, serous cystadenocarcinoma, mucinous cystadenocarcinoma, endometrioid tumors, Brenner tumor, clear cell carcinoma, unclassified carcinoma, granulosa-theca cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma, embryonal rhabdomyosarcoma, fallopian tubes (carcinoma)); hematologic cancers (e.g., blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma)); skin cancers (e.g., malignant melanoma, basal cell carcinoma, squamous cell carcinoma, Kaposi's sarcoma, moles, dysplastic nevi, lipoma, angioma, dermatofibroma, keloids, psoriasis); and adrenal gland cancers (e.g., neuroblastoma). In some embodiments that may be combined with any of the preceding embodiments, the disease or condition is an autoimmune disease selected from thyroiditis, Goodpasture's disease, rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease, Crohn's disease, ulcerative colitis, autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Addison's disease, systemic sclerosis, polymyositis, dermatomyositis, autoimmune hemolytic anemia, and pernicious anemia. In some embodiments that may be combined with any of the preceding embodiments, the disease or condition is a neurodegenerative disease selected from adrenoleukodystrophy (ALD), alcoholism, Alexander's disease, Alper's disease, Alzheimer's disease, amyotrophic lateral sclerosis, Lou Gehrig's Disease, ataxia telangiectasia, Batten disease, Spielmeyer-Vogt-Sjogren-Batten disease, bovine spongiform encephalopathy (BSE), Canavan disease, cerebral palsy, Cockayne syndrome, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, Spinocerebellar ataxia type 3, Multiple System Atrophy, multiple sclerosis, narcolepsy, Niemann Pick disease, Parkinson's disease, Pelizaeus-Merzbacher Disease, Pick's disease, primary lateral sclerosis, prion diseases, progressive supranuclear palsy, Refsum's disease, Sandhoff disease, Schilder's disease, subacute combined degeneration of spinal cord secondary to Pernicious Anaemia, Spielmeyer-Vogt-Sjogren-Batten disease, Batten disease, spinocerebellar ataxia, spinal muscular atrophy, Steele-Richardson-Olszewski disease, Tabes dorsalis, and toxic encephalopathy.

Other aspects of the present disclosure relate to a method of treating a cancer, by administering to a subject in need thereof an agent that increases expression of Zscan4 in one or more cancer cells in the subject, where increasing expression of Zscan4 represses growth of the one or more cancer cells, thereby treating the cancer. Other aspects of the present disclosure relate to a method of improving responsiveness to chemotherapy in a cancer patient, by administering to a subject in need thereof an agent that reduces expression of endogenous ZSCAN4 in one or more cancer stem cells in the subject, where reducing expression of endogenous ZSCAN4 reduces or eliminates resistance to one or more chemotherapeutic agents in the one or more cancer stem cells, thereby improving responsiveness to the one or more chemotherapeutic agents in the subject. In some embodiments, the agent that reduces expression of endogenous ZSCAN4 is an siRNA or shRNA specific for ZSCAN4. In some embodiments, the cancer selected from cancers of the heart (e.g. angiosarcoma, fibrosarcoma, rhabdomyosarcoma, liposarcoma, myxoma, rhabdomyoma, fibroma, lipoma and teratoma), lung cancers (e.g., bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma); gastrointestinal tract cancers (e.g., esophagus (squamous cell carcinoma, adenocarcinoma, leiomyosarcoma, lymphoma); stomach cancers (carcinoma, lymphoma, leiomyosarcoma); pancreatic cancers (ductal adenocarcinoma, insulinoma, glucagonoma, gastrinoma, carcinoid tumors, vipoma); small bowel cancers (adenocarcinoma, lymphoma, carcinoid tumors, Kaposi's sarcoma, leiomyoma, hemangioma, lipoma, neurofibroma, fibroma); large bowel cancers (adenocarcinoma, tubular adenoma, villous adenoma, hamartoma, leiomyoma); genitourinary tract cancers (e.g., kidney (adenocarcinoma, Wilms' tumor, nephroblastoma, lymphoma, leukemia); bladder and urethra cancers (squamous cell carcinoma, transitional cell carcinoma, adenocarcinoma); prostate cancers (adenocarcinoma, sarcoma); testis cancers (seminoma, teratoma, embryonal carcinoma, teratocarcinoma, choriocarcinoma, sarcoma, interstitial cell carcinoma, fibroma, fibroadenoma, adenomatoid tumors, lipoma); liver cancers (e.g., hepatoma (hepatocellular carcinoma), cholangiocarcinoma, hepatoblastoma, angiosarcoma, hepatocellular adenoma, hemangioma); bone cancers (e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxofibroma, osteoid osteoma and giant cell tumors); nervous system cancers (e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma, pinealoma, glioblastoma multiforme, oligodendroglioma, schwannoma, retinoblastoma, congenital tumors), spinal cord (neurofibroma, meningioma, glioma, sarcoma)); gynecological cancers (e.g., uterus (endometrial carcinoma), cervix (cervical carcinoma, pre-tumor cervical dysplasia), ovaries (ovarian carcinoma, serous cystadenocarcinoma, mucinous cystadenocarcinoma, endometrioid tumors, Brenner tumor, clear cell carcinoma, unclassified carcinoma, granulosa-theca cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma, embryonal rhabdomyosarcoma, fallopian tubes (carcinoma)); hematologic cancers (e.g., blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma)); skin cancers (e.g., malignant melanoma, basal cell carcinoma, squamous cell carcinoma, Kaposi's sarcoma, moles, dysplastic nevi, lipoma, angioma, dermatofibroma, keloids, psoriasis); and adrenal gland cancers (e.g., neuroblastoma).

Other aspects of the present disclosure relate to a method of increasing genome stability of one or more human cells, by contacting the one or more human cells with an agent that increases expression of Zscan4 in the one or more human cells, where increased expression of Zscan4 increases genome stability in the one or more human cells as compared to one or more corresponding human cells that are not contacted with the agent.

Other aspects of the present disclosure relate to a method of increasing DNA repair capacity of one or more human cells, by contacting the one or more human cells with an agent that increases expression of Zscan4 in the one or more human cells, where increased expression of Zscan4 increases DNA repair capacity in the one or more human cells as compared to one or more corresponding human cells that are not contacted with the agent.

Other aspects of the present disclosure relate to a method of rejuvenating one or more human cells, by contacting the one or more human cells with an agent that increases expression of Zscan4 in the one or more human cells, where increased expression of Zscan4 rejuvenates the one or more human cells as compared to one or more corresponding human cells that are not contacted with the agent.

Other aspects of the present disclosure relate to a method of rejuvenating skin, treating atopic dermatitis, and/or a skin lesion, by topically administering to the skin of a subject in need thereof an agent that increases expression of Zscan4.

Other aspects of the present disclosure relate to a method of treating hair loss, by topically administering to the scalp of a subject in need thereof an agent that increases expression of Zscan4.

Other aspects of the present disclosure relate to a method of preventing hair graying, treating hair graying, or both, by administering to one or more hair follicles of a subject in need thereof an agent that increases expression of Zscan4.

Other aspects of the present disclosure relate to a method of rejuvenating a cornea, by administering to a cornea of a subject in need thereof an agent that increases expression of Zscan4.

Other aspects of the present disclosure relate to a method of treating dry eye, by administering to a cornea of a subject in need thereof an agent that increases expression of Zscan4.

Other aspects of the present disclosure relate to a method of treating idiopathic pulmonary fibrosis, by administering to a lung of a subject in need thereof an agent that increases expression of Zscan4.

Other aspects of the present disclosure relate to a method of treating atherosclerosis, a coronary heart disease, or both, by administering to the bloodstream of a subject in need thereof an agent that increases expression of Zscan4.

Other aspects of the present disclosure relate to a method of providing resistance to one or more genotoxic agents in one or more human cells, by contacting the one or more human cells with an agent that increases expression of Zscan4 in the one or more human cells, where increased expression of Zscan4 increases resistance to one or more genotoxic agents in the one or more human cells as compared to one or more corresponding human cells that are not contacted with the agent. In some embodiments, the genotoxic agent is mitomycin C or cisplatin.

In some embodiments that may be combined with any of the preceding embodiments, the one or more human cells are human adult cells. In some embodiments, the one or more human cells are adult stem cells, tissue stem cells, progenitor cells, or induced pluripotent stem cells. In some embodiments that may be combined with any of the preceding embodiments, the one or more human cells are one or more adult stem cells, tissue stem cells, or progenitor cells selected from hematopoietic stem cells, mesenchymal stem cells, adipose stem cells, neuronal stem cells, and germ stem cells. In some embodiments that may be combined with any of the preceding embodiments, the one or more human cells are somatic cells, mature cells, or differentiated cells. In some embodiments that may be combined with any of the preceding embodiments, the one or more human cells are somatic cells, mature cells, or differentiated cells. In some embodiments that may be combined with any of the preceding embodiments, the one or more human cells are one or more somatic cells, mature cells, or differentiated cells selected from epidermal cells, fibroblasts, lymphocytes, hepatocytes, epithelial cells, myocytes, chondrocytes, osteocytes, adipocytes, cardiomyocytes, pancreatic β cells, keratinocytes, erythrocytes, peripheral blood cells, neurocytes, astrocytes, germ cells, sperm cells, and oocytes.

Other aspects of the present disclosure relate to a method for inducing a human embryonic stem cell-like DNA methylation pattern in one or more human induced pluripotent stem (iPS) cells, by contacting the one or more human iPS cells with an agent that increases expression of Zscan4 in the one or more human iPS cells, where increased expression of Zscan4 induces a human embryonic stem cell-like DNA methylation pattern in the one or more human iPS cells as compared to one or more corresponding human iPS cells that are not contacted with the agent.

Other aspects of the present disclosure relate to a method of rejuvenating one or more human oocyte cells, by contacting the one or more human oocyte cells with an agent that increases expression of Zscan4 in the one or more human oocyte cells, where increased expression of Zscan4 rejuvenates the one or more human oocyte cells as compared to one or more corresponding human oocyte cells that are not contacted with the agent.

Other aspects of the present disclosure relate to a method of increasing genome stability of one or more human oocyte cells, by contacting the one or more human oocyte cells with an agent that increases expression of Zscan4 in the one or more human oocyte cells, where increased expression of Zscan4 increases genome stability in the one or more human oocyte cells as compared to one or more corresponding human oocyte cells that are not contacted with the agent. Other aspects of the present disclosure relate to a method of correcting one or more karyotype abnormalities in one or more human oocyte cells, by contacting the one or more human oocyte cells with an agent that increases expression of Zscan4 in the one or more human oocyte cells, where increased expression of Zscan4 induces correction of the one or more karyotype abnormalities in the one or more human oocyte cells as compared to one or more corresponding human oocyte cells that are not contacted with the agent. In some embodiments, the one or more human oocyte cells are isolated from a subject prior to contacting with the agent that increases expression of Zscan4. In some embodiments, after contacting with the agent that increases expression of Zscan4 the one or more human oocyte cells undergo in vitro fertilization.

Other aspects of the present disclosure relate to an in vitro method of increasing genome stability of one or more fertilized human oocytes, by contacting the one or more fertilized human oocytes with an agent that increases expression of Zscan4 in the one or more fertilized human oocytes, where increased expression of Zscan4 increases genome stability in the one or more fertilized human oocytes as compared to one or more corresponding fertilized human oocytes embryo that are not contacted with the agent. Other aspects of the present disclosure relate to an in vitro method of correcting one or more karyotype abnormalities in one or more fertilized human oocytes, by contacting the one or more fertilized human oocytes with an agent that increases expression of Zscan4 in the one or more fertilized human oocytes, where increased expression of Zscan4 induces correction of the one or more karyotype abnormalities in the one or more fertilized human oocytes as compared to one or more corresponding fertilized human oocytes that are not contacted with the agent. In some embodiments, the one or more fertilized human oocytes were fertilized by in vitro fertilization. In some embodiments, prior to being fertilized, the one or more human oocytes were isolated from a subject. In some embodiments, the one or more fertilized oocytes are embryos between the one-cell stage and the blastocyst stage.

Other aspects of the present disclosure relate to a method of treating a disease or condition associated with a telomere abnormality, by: i. isolating human bone marrow cells from a subject suffering from a disease or condition associated with a telomere abnormality; ii. contacting the human bone marrow cells with an agent that increases expression of Zscan4 in the human bone marrow cells, where increasing expression of Zscan4 induces telomere lengthening in the human bone marrow cells; and iii. engrafting the contacted human bone marrow cells into the subject to treat the disease or condition associated with a telomere abnormality.

Other aspects of the present disclosure relate to a method of treating a disease or condition associated with a chromosome abnormality, by: i. isolating human bone marrow cells from a subject suffering from a disease or condition associated with a chromosome abnormality; ii. contacting the human bone marrow cells with an agent that increases expression of Zscan4 in the human bone marrow cells, increasing expression of Zscan4 induces correction of the chromosome abnormality in the human bone marrow cells; and iii. engrafting the contacted human bone marrow cells into the subject to treat the disease or condition associated with a chromosome abnormality.

In some embodiments that may be combined with any of the preceding embodiments, the disease or condition is one or more diseases or conditions selected from diseases of telomere shortening, bone marrow failure syndromes, age-related telomere shortening diseases or disorders, and premature aging diseases or disorders. In some embodiments that may be combined with any of the preceding embodiments, the disease or condition is a disease of telomere shortening selected from dyskeratosis congenita, Hoyeraal-Hreidarsson syndrome, Revesz syndrome, Coats plus syndrome, idiopathic pulmonary fibrosis, liver cirrhosis, pancreatic fibrosis, Alzheimer's disease, and osteoarthritis. In some embodiments that may be combined with any of the preceding embodiments, the disease or condition is a bone marrow failure syndrome selected from Fanconi anemia, amegakaryocytic thrombocytopenia, aplastic anemia, Diamond Blackfan anemia, dyskeratosis congenita, paroxysmal nocturnal hemoglobinuria (PNH), Pearson syndrome, Shwachman Diamond syndrome, thrombocytopenia, and myelodysplastic syndrome. In some embodiments that may be combined with any of the preceding embodiments, the disease or condition is an age-related telomere shortening disease or disease, a premature aging disease or disease, or both selected from Werner syndrome, Bloom's syndrome, Hutchinson-Gilford progeria syndrome, Cockayne syndrome, Xeroderma pigmentosa, Ataxia telangiectasia, Rothmund Thomson syndrome, Trichothiodystrophy, Juberg-Marsidi syndrome, and Down syndrome.

Other aspects of the present disclosure relate to a method of rejuvenating a tissue or organ in a subject, by administering to a subject in need thereof an agent that increases expression of Zscan4 in the tissue or organ, where increasing expression of Zscan4 rejuvenates the tissue or organ.

Other aspects of the present disclosure relate to a method of rejuvenating a subject in need thereof, by administering to the subject an agent that increases expression of Zscan4, where increasing expression of Zscan4 rejuvenates the subject.

Other aspects of the present disclosure relate to a method of extending lifespan of one or more human cells, by contacting the one or more human cells with an agent that increases expression of Zscan4 in one or more human cells in the subject, where increasing expression of Zscan4 extends the lifespan of the one or more human cells as compared to one or more corresponding human cells that are not contacted with the agent.

Other aspects of the present disclosure relate to a method of extending lifespan of a tissue or organ in a subject, by administering to a subject in need thereof an agent that increases expression of Zscan4 in the tissue or organ, where increasing expression of Zscan4 extends the lifespan of the tissue or organ.

Other aspects of the present disclosure relate to a method of extending lifespan of a subject, by administering to a subject in need thereof an agent that increases expression of Zscan4 in one or more human cells in the subject, where increasing expression of Zscan4 extends the lifespan of the one or more human cells, thereby extending the lifespan of the subject.

Other aspects of the present disclosure relate to a method of extending lifespan of a subject, by: i. isolating one or more human cells from the subject; ii. contacting the one or more human cells with an agent that increases expression of Zscan4 in the one or more human cells, where increasing expression of Zscan4 extends the lifespan of the one or more human cells; and iii. administering the contacted one or more human cells to the subject to extend the lifespan of the subject.

Other aspects of the present disclosure relate to a method for determining one or more Zscan4-induced effects in one or more human cells, by: i. contacting the one or more human cells with an agent that increases expression of Zscan4 in one or more human cells; ii. measuring expression levels of SERPINB4, DNMT3L, and/or DUX4 in the one or more human cells; and iii. comparing the expression levels of SERPINB4, DNMT3L, and/or DUX4 in the one or more human cells to the expression levels of SERPINB4, DNMT3L, and/or DUX4 in one or more corresponding human cells that are not contacted with the agent, where an increase in the expression levels of SERPINB4, DNMT3L, and/or DUX4 in the one or more human cells indicates the presence of one or more Zscan4-induced effects in the one or more human cell.

In some embodiments that may be combined with any of the preceding embodiments, the increased expression of Zscan4 is transient. In some embodiments that may be combined with any of the preceding embodiments, the agent increases Zscan4 expression for about 1 hour to about 23 hours. In some embodiments that may be combined with any of the preceding embodiments, the agent increases Zscan4 expression for about 1 day to about 10 days. In some embodiments that may be combined with any of the preceding embodiments, the agent interacts directly with endogenous Zscan4 to increase expression of Zscan4. In some embodiments that may be combined with any of the preceding embodiments, the agent is an isolated nucleic acid molecule encoding Zscan4. In some embodiments that may be combined with any of the preceding embodiments, the isolated nucleic acid molecule is a synthetic mRNA. In some embodiments that may be combined with any of the preceding embodiments, the isolated nucleic acid molecule contains a vector. In some embodiments that may be combined with any of the preceding embodiments, the vector is a viral vector. In some embodiments that may be combined with any of the preceding embodiments, the viral vector is a paramyxovirus vector, a retrovirus vector, a lentivirus vector or an adenovirus vector. In some embodiments that may be combined with any of the preceding embodiments, the viral vector is a paramyxovirus vector. In some embodiments that may be combined with any of the preceding embodiments, the paramyxovirus vector is a Sendai virus vector. In some embodiments that may be combined with any of the preceding embodiments, the vector is a plasmid vector. In some embodiments that may be combined with any of the preceding embodiments, the vector encodes Zscan4 operably linked to a promoter. In some embodiments that may be combined with any of the preceding embodiments, the promoter is a constitutive promoter. In some embodiments that may be combined with any of the preceding embodiments, the promoter is an inducible promoter. In some embodiments that may be combined with any of the preceding embodiments, the Zscan4 is a Zscan4-ERT2 fusion protein. In some embodiments that may be combined with any of the preceding embodiments, the Zscan4 is a Zscan4-ΔC protein. In some embodiments that may be combined with any of the preceding embodiments, the Zscan4-ΔC protein includes a deletion of at least one zinc finger domain. In some embodiments that may be combined with any of the preceding embodiments, the Zscan4 is mouse Zscan4, human ZSCAN4, or a homolog thereof. In some embodiments that may be combined with any of the preceding embodiments, the Zscan4 is selected from Zscan4a, Zscan4b, Zscan4c, Zscan4d, Zscan4e, and Zscan4f. In some embodiments that may be combined with any of the preceding embodiments, the isolated nucleic acid molecule contains a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence selected from SEQ ID Nos: 1-10 and 21-30. In some embodiments that may be combined with any of the preceding embodiments, the Zscan4 is human ZSCAN4. In some embodiments that may be combined with any of the preceding embodiments, the isolated nucleic acid molecule contains a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 7. In some embodiments that may be combined with any of the preceding embodiments, the agent is a Zscan4 protein. In some embodiments that may be combined with any of the preceding embodiments, the Zscan4 protein is fused to a cell-penetrating peptide. In some embodiments that may be combined with any of the preceding embodiments, the cell-penetrating peptide contains a protein transduction domain. In some embodiments that may be combined with any of the preceding embodiments, the cell-penetrating peptide contains a poly-arginine peptide tag. In some embodiments that may be combined with any of the preceding embodiments, the Zscan4 protein is encapsulated in a nanoparticle. In some embodiments that may be combined with any of the preceding embodiments, the Zscan4 protein is a mouse Zscan4 protein, a human ZSCAN4 protein, or a homolog thereof. In some embodiments that may be combined with any of the preceding embodiments, the Zscan4 protein is selected from a Zscan4a protein, a Zscan4b protein, a Zscan4c protein, a Zscan4d protein, a Zscan4e protein, and a Zscan4f protein. In some embodiments that may be combined with any of the preceding embodiments, the Zscan4 protein contains an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an amino acid sequence selected from SEQ ID NOs: 11-20 and 31-40. In some embodiments that may be combined with any of the preceding embodiments, the Zscan4 protein is a human ZSCAN4 protein. In some embodiments that may be combined with any of the preceding embodiments, the Zscan4 protein contains an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 17. In some embodiments that may be combined with any of the preceding embodiments, the Zscan4 protein is a Zscan4-ERT2 fusion protein. In some embodiments that may be combined with any of the preceding embodiments, the Zscan4 protein is a Zscan4-ΔC protein. In some embodiments that may be combined with any of the preceding embodiments, the Zscan4-ΔC protein contains a mouse Zscan4 protein, a human ZSCAN4 protein, or a homolog thereof, and where the Zscan4 protein contains a deletion of at least one zinc finger domain. In some embodiments that may be combined with any of the preceding embodiments, the Zscan4-ΔC protein contains a Zscan4 protein selected from a Zscan4a protein, a Zscan4b protein, a Zscan4c protein, a Zscan4d protein, a Zscan4e protein, and a Zscan4f protein, and where the Zscan4 protein contains a deletion of at least one zinc finger domain. In some embodiments that may be combined with any of the preceding embodiments, the Zscan4-ΔC protein contains a human ZSCAN4 protein, and where the Zscan4 protein contains a deletion of at least one zinc finger domain. In some embodiments that may be combined with any of the preceding embodiments, the agent is a retinoid, an agent that induces oxidative stress, or both.

Other aspects of the present disclosure relate to a method of increasing telomere length in one or more human cells, by contacting the one or more human cells with an agent that increases expression of Zscan4 in the human cell, where the agent is a synthetic mRNA molecule encoding Zscan4 or a viral vector, preferably a Sendai viral vector, encoding Zscan4, and where increased expression of Zscan4 induces telomere lengthening in the one or more human cells as compared to one or more corresponding human cells that are not contacted with the agent.

Other aspects of the present disclosure relate to a method of treating a subject in need of telomere lengthening, by contacting one or more human cells in the subject with an agent that increases expression of Zscan4 in the one or more human cells, where the agent is a synthetic mRNA molecule encoding Zscan4 or a viral vector, preferably a Sendai viral vector, encoding Zscan4, and where increased expression of Zscan4 induces telomere lengthening in the one or more human cells.

Other aspects of the present disclosure relate to a method of treating a subject in need of telomere lengthening, by: i. isolating one or more human cells in need of telomere lengthening from the subject; ii. contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increasing expression of Zscan4 induces telomere lengthening in the one or more human cells; and iii. administering the contacted one or more human cells to the subject.

Other aspects of the present disclosure relate to a method of treating a disease or condition associated with a telomere abnormality, by administering to a subject in need thereof an agent that increases expression of Zscan4 in one or more human cells in the subject, where the agent is a synthetic mRNA molecule encoding Zscan4 or a viral vector, preferably a Sendai viral vector, encoding Zscan4, and where increasing expression of Zscan4 induces telomere lengthening in the one or more human cells to treat the disease or condition associated with a telomere abnormality.

Other aspects of the present disclosure relate to a method of treating a disease or condition associated with a telomere abnormality, by: i. isolating one or more human cells from a subject suffering from a disease or condition associated with a telomere abnormality; ii. contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increasing expression of Zscan4 induces telomere lengthening in the one or more human cells; and iii. administering the contacted one or more human cells to the subject to treat the disease or condition associated with a telomere abnormality.

Other aspects of the present disclosure relate to a method of treating a disease or condition associated with a chromosome abnormality, by administering to a subject in need thereof an agent that increases expression of Zscan4 in one or more human cells in the subject, where the agent is a synthetic mRNA molecule encoding Zscan4 or a viral vector, preferably a Sendai viral vector, encoding Zscan4, and where increasing expression of Zscan4 induces correction of the chromosome abnormality in the one or more human cells to treat the disease or condition associated with a chromosome abnormality.

Other aspects of the present disclosure relate to a method of treating a disease or condition associated with a chromosome abnormality, by: i. isolating one or more human cells from a subject suffering from a disease or condition associated with a chromosome abnormality; ii. contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increasing expression of Zscan4 induces correction of the chromosome abnormality in the one or more human cells; and iii. administering the contacted one or more human cells to the subject to treat the disease or condition associated with a chromosome abnormality.

Other aspects of the present disclosure relate to a method of treating a disease or condition associated with a karyotype abnormality, by administering to a subject in need thereof an agent that increases expression of Zscan4 in one or more human cells in the subject, where the agent is a synthetic mRNA molecule encoding Zscan4 or a viral vector, preferably a Sendai viral vector, encoding Zscan4, and where increasing expression of Zscan4 induces correction of the karyotype abnormality in the one or more human cells to treat the disease or condition associated with a karyotype abnormality.

Other aspects of the present disclosure relate to a method of treating a disease or condition associated with a karyotype abnormality, by: i. isolating one or more human cells from a subject suffering from a disease or condition associated with a karyotype abnormality; ii. contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increasing expression of Zscan4 induces correction of the karyotype abnormality in the one or more human cells; and iii. administering the contacted one or more human cells to the subject to treat the disease or condition associated with a karyotype abnormality.

In some embodiments that may be combined with any of the preceding embodiments, the karyotype abnormality is selected from a chromosome nullisomy, a chromosome monosomy, a chromosome trisomy, a chromosome tetrasomy, and a chromosome pentasomy. In some embodiments that may be combined with any of the preceding embodiments, the karyotype abnormality is selected from trisomy 21, trisomy 16, trisomy 18, trisomy 13, monosomy X, XXX aneuploidy, XXY aneuploidy, XYY aneuploidy, and 1p36 duplication. In some embodiments that may be combined with any of the preceding embodiments, the disease or condition associated with a karyotype abnormality is selected from dup(17)(p11.2p11.2) syndrome, Pelizaeus-Merzbacher disease, dup(22)(q11.2q11.2) syndrome, cat-eye syndrome, Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azoospermia (factor a), Azoospermia (factor b), Azoospermia (factor c), and 1p36 deletion. In some embodiments that may be combined with any of the preceding embodiments, the disease or condition is one or more diseases or conditions selected from diseases of telomere shortening, bone marrow failure syndromes, age-related telomere shortening diseases or disorders, and premature aging diseases or disorders. In some embodiments that may be combined with any of the preceding embodiments, the disease or condition is a disease of telomere shortening selected from dyskeratosis congenita, Hoyeraal-Hreidarsson syndrome, Revesz syndrome, Coats plus syndrome, idiopathic pulmonary fibrosis, liver cirrhosis, pancreatic fibrosis, Alzheimer's disease, and osteoarthritis. In some embodiments that may be combined with any of the preceding embodiments, the disease or condition is a bone marrow failure syndrome selected from Fanconi anemia, amegakaryocytic thrombocytopenia, aplastic anemia, Diamond Blackfan anemia, dyskeratosis congenita, paroxysmal nocturnal hemoglobinuria (PNH), Pearson syndrome, Shwachman Diamond syndrome, thrombocytopenia, and myelodysplastic syndrome. In some embodiments that may be combined with any of the preceding embodiments, the disease or condition is an age-related telomere shortening disease or disorder, a premature aging disease or disorder, or both selected from Werner syndrome, Bloom's syndrome, Hutchinson-Gilford progeria syndrome, Cockayne syndrome, Xeroderma pigmentosa, Ataxia telangiectasia, Rothmund Thomson syndrome, Trichothiodystrophy, Juberg-Marsidi syndrome, and Down syndrome. In some embodiments that may be combined with any of the preceding embodiments, the disease or condition is one or more diseases or conditions selected from immunological deficiencies, an autoimmune disease, an autoimmune disorder, chronic ulcers, atherosclerosis, cancer, a neurologic injury, a degenerative disorder, a neurodegenerative disorder, wound healing, muscle repair, cardiac muscle repair, cartilage replacement, arthritis, osteoarthritis, tooth regeneration, blindness, age-related blindness due to proliferative decline of retinal pigmented epithelial cells, deafness, bone marrow failure, bone marrow transplant, diabetes, muscular dystrophy, Duchenne muscular dystrophy, a genetic disease, a genetic mutation, and DNA damage. In some embodiments that may be combined with any of the preceding embodiments, the disease or condition is a cancer selected from cancers of the heart (e.g., angiosarcoma, fibrosarcoma, rhabdomyosarcoma, liposarcoma, myxoma, rhabdomyoma, fibroma, lipoma and teratoma), lung cancers (e.g., bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma); gastrointestinal tract cancers (e.g., esophagus (squamous cell carcinoma, adenocarcinoma, leiomyosarcoma, lymphoma); stomach cancers (carcinoma, lymphoma, leiomyosarcoma); pancreatic cancers (ductal adenocarcinoma, insulinoma, glucagonoma, gastrinoma, carcinoid tumors, vipoma); small bowel cancers (adenocarcinoma, lymphoma, carcinoid tumors, Kaposi's sarcoma, leiomyoma, hemangioma, lipoma, neurofibroma, fibroma); large bowel cancers (adenocarcinoma, tubular adenoma, villous adenoma, hamartoma, leiomyoma); genitourinary tract cancers (e.g., kidney (adenocarcinoma, Wilms' tumor, nephroblastoma, lymphoma, leukemia); bladder and urethra cancers (squamous cell carcinoma, transitional cell carcinoma, adenocarcinoma); prostate cancers (adenocarcinoma, sarcoma); testis cancers (seminoma, teratoma, embryonal carcinoma, teratocarcinoma, choriocarcinoma, sarcoma, interstitial cell carcinoma, fibroma, fibroadenoma, adenomatoid tumors, lipoma); liver cancers (e.g., hepatoma (hepatocellular carcinoma), cholangiocarcinoma, hepatoblastoma, angiosarcoma, hepatocellular adenoma, hemangioma); bone cancers (e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxofibroma, osteoid osteoma and giant cell tumors); nervous system cancers (e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma, pinealoma, glioblastoma multiforme, oligodendroglioma, schwannoma, retinoblastoma, congenital tumors), spinal cord (neurofibroma, meningioma, glioma, sarcoma)); gynecological cancers (e.g., uterus (endometrial carcinoma), cervix (cervical carcinoma, pre-tumor cervical dysplasia), ovaries (ovarian carcinoma, serous cystadenocarcinoma, mucinous cystadenocarcinoma, endometrioid tumors, Brenner tumor, clear cell carcinoma, unclassified carcinoma, granulosa-theca cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma, embryonal rhabdomyosarcoma, fallopian tubes (carcinoma)); hematologic cancers (e.g., blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma)); skin cancers (e.g., malignant melanoma, basal cell carcinoma, squamous cell carcinoma, Kaposi's sarcoma, moles, dysplastic nevi, lipoma, angioma, dermatofibroma, keloids, psoriasis); and adrenal gland cancers (e.g., neuroblastoma). In some embodiments that may be combined with any of the preceding embodiments, the disease or condition is an autoimmune disease selected from thyroiditis, Goodpasture's disease, rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease, Crohn's disease, ulcerative colitis, autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Addison's disease, systemic sclerosis, polymyositis, dermatomyositis, autoimmune hemolytic anemia, and pernicious anemia. In some embodiments that may be combined with any of the preceding embodiments, the disease or condition is a neurodegenerative disease selected from adrenoleukodystrophy (ALD), alcoholism, Alexander's disease, Alper's disease, Alzheimer's disease, amyotrophic lateral sclerosis, Lou Gehrig's Disease, ataxia telangiectasia, Batten disease, Spielmeyer-Vogt-Sjogren-Batten disease, bovine spongiform encephalopathy (BSE), Canavan disease, cerebral palsy, Cockayne syndrome, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, Spinocerebellar ataxia type 3, Multiple System Atrophy, multiple sclerosis, narcolepsy, Niemann Pick disease, Parkinson's disease, Pelizaeus-Merzbacher Disease, Pick's disease, primary lateral sclerosis, prion diseases, progressive supranuclear palsy, Refsum's disease, Sandhoff disease, Schilder's disease, subacute combined degeneration of spinal cord secondary to Pernicious Anaemia, Spielmeyer-Vogt-Sjogren-Batten disease, Batten disease, spinocerebellar ataxia, spinal muscular atrophy, Steele-Richardson-Olszewski disease, Tabes dorsalis, and toxic encephalopathy.

Other aspects of the present disclosure relate to a method of treating a cancer, by administering to a subject in need thereof an agent that increases expression of Zscan4 in one or more cancer cells in the subject, where the agent is a synthetic mRNA molecule encoding Zscan4 or a viral vector, preferably a Sendai viral vector, encoding Zscan4, and where increasing expression of Zscan4 represses growth of the one or more cancer cells, thereby treating the cancer. Other aspects of the present disclosure relate to a method of improving responsiveness to chemotherapy in a cancer patient, by administering to a subject in need thereof an agent that reduces expression of endogenous ZSCAN4 in one or more cancer stem cells in the subject, where the agent is a synthetic mRNA molecule encoding Zscan4 or a viral vector, preferably a Sendai viral vector, encoding Zscan4, and where reducing expression of endogenous ZSCAN4 reduces or eliminates resistance to one or more chemotherapeutic agents in the one or more cancer stem cells, thereby improving responsiveness to the one or more chemotherapeutic agents in the subject. In some embodiments, the agent that reduces expression of endogenous ZSCAN4 is an siRNA or shRNA specific for ZSCAN4. In some embodiments, the cancer selected from cancers of the heart (e.g. angiosarcoma, fibrosarcoma, rhabdomyosarcoma, liposarcoma, myxoma, rhabdomyoma, fibroma, lipoma and teratoma), lung cancers (e.g., bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma); gastrointestinal tract cancers (e.g., esophagus (squamous cell carcinoma, adenocarcinoma, leiomyosarcoma, lymphoma); stomach cancers (carcinoma, lymphoma, leiomyosarcoma); pancreatic cancers (ductal adenocarcinoma, insulinoma, glucagonoma, gastrinoma, carcinoid tumors, vipoma); small bowel cancers (adenocarcinoma, lymphoma, carcinoid tumors, Kaposi's sarcoma, leiomyoma, hemangioma, lipoma, neurofibroma, fibroma); large bowel cancers (adenocarcinoma, tubular adenoma, villous adenoma, hamartoma, leiomyoma); genitourinary tract cancers (e.g., kidney (adenocarcinoma, Wilms' tumor, nephroblastoma, lymphoma, leukemia); bladder and urethra cancers (squamous cell carcinoma, transitional cell carcinoma, adenocarcinoma); prostate cancers (adenocarcinoma, sarcoma); testis cancers (seminoma, teratoma, embryonal carcinoma, teratocarcinoma, choriocarcinoma, sarcoma, interstitial cell carcinoma, fibroma, fibroadenoma, adenomatoid tumors, lipoma); liver cancers (e.g., hepatoma (hepatocellular carcinoma), cholangiocarcinoma, hepatoblastoma, angiosarcoma, hepatocellular adenoma, hemangioma); bone cancers (e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxofibroma, osteoid osteoma and giant cell tumors); nervous system cancers (e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma, pinealoma, glioblastoma multiforme, oligodendroglioma, schwannoma, retinoblastoma, congenital tumors), spinal cord (neurofibroma, meningioma, glioma, sarcoma)); gynecological cancers (e.g., uterus (endometrial carcinoma), cervix (cervical carcinoma, pre-tumor cervical dysplasia), ovaries (ovarian carcinoma, serous cystadenocarcinoma, mucinous cystadenocarcinoma, endometrioid tumors, Brenner tumor, clear cell carcinoma, unclassified carcinoma, granulosa-theca cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma, embryonal rhabdomyosarcoma, fallopian tubes (carcinoma)); hematologic cancers (e.g., blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma)); skin cancers (e.g., malignant melanoma, basal cell carcinoma, squamous cell carcinoma, Kaposi's sarcoma, moles, dysplastic nevi, lipoma, angioma, dermatofibroma, keloids, psoriasis); and adrenal gland cancers (e.g., neuroblastoma).

Other aspects of the present disclosure relate to a method of increasing genome stability of one or more human cells, by contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increased expression of Zscan4 increases genome stability in the one or more human cells as compared to one or more corresponding human cells that are not contacted with the agent.

Other aspects of the present disclosure relate to a method of increasing DNA repair capacity of one or more human cells, by contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increased expression of Zscan4 increases DNA repair capacity in the one or more human cells as compared to one or more corresponding human cells that are not contacted with the agent.

Other aspects of the present disclosure relate to a method of rejuvenating one or more human cells, by contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increased expression of Zscan4 rejuvenates the one or more human cells as compared to one or more corresponding human cells that are not contacted with the agent.

Other aspects of the present disclosure relate to a method of rejuvenating skin, treating atopic dermatitis, and/or a skin lesion, by topically administering to the skin of a subject in need thereof an agent that increases expression of Zscan4, where the agent is a synthetic mRNA molecule encoding Zscan4 or a viral vector, preferably a Sendai viral vector, encoding Zscan4.

Other aspects of the present disclosure relate to a method of treating hair loss, by topically administering to the scalp of a subject in need thereof an agent that increases expression of Zscan4, where the agent is a synthetic mRNA molecule encoding Zscan4 or a viral vector, preferably a Sendai viral vector, encoding Zscan4.

Other aspects of the present disclosure relate to a method of preventing hair graying, treating hair graying, or both, by administering to one or more hair follicles of a subject in need thereof an agent that increases expression of Zscan4, where the agent is a synthetic mRNA molecule encoding Zscan4 or a viral vector, preferably a Sendai viral vector, encoding Zscan4.

Other aspects of the present disclosure relate to a method of rejuvenating a cornea, by administering to a cornea of a subject in need thereof an agent that increases expression of Zscan4, where the agent is a synthetic mRNA molecule encoding Zscan4 or a viral vector, preferably a Sendai viral vector, encoding Zscan4.

Other aspects of the present disclosure relate to a method of treating dry eye, by administering to a cornea of a subject in need thereof an agent that increases expression of Zscan4, where the agent is a synthetic mRNA molecule encoding Zscan4 or a viral vector, preferably a Sendai viral vector, encoding Zscan4.

Other aspects of the present disclosure relate to a method of treating idiopathic pulmonary fibrosis, by administering to a lung of a subject in need thereof an agent that increases expression of Zscan4, where the agent is a synthetic mRNA molecule encoding Zscan4 or a viral vector, preferably a Sendai viral vector, encoding Zscan4.

Other aspects of the present disclosure relate to a method of treating atherosclerosis, a coronary heart disease, or both, by administering to the bloodstream of a subject in need thereof an agent that increases expression of Zscan4, where the agent is a synthetic mRNA molecule encoding Zscan4 or a viral vector, preferably a Sendai viral vector, encoding Zscan4.

Other aspects of the present disclosure relate to a method of providing resistance to one or more genotoxic agents in one or more human cells, by contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increased expression of Zscan4 increases resistance to one or more genotoxic agents in the one or more human cells as compared to one or more corresponding human cells that are not contacted with the agent. In some embodiments, the genotoxic agent is mitomycin C or cisplatin.

In some embodiments that may be combined with any of the preceding embodiments, the one or more human cells are human adult cells. In some embodiments that may be combined with any of the preceding embodiments, the one or more human cells are adult stem cells, tissue stem cells, progenitor cells, or induced pluripotent stem cells. In some embodiments that may be combined with any of the preceding embodiments, the one or more human cells are one or more adult stem cells, tissue stem cells, or progenitor cells selected from hematopoietic stem cells, mesenchymal stem cells, adipose stem cells, neuronal stem cells, and germ stem cells. In some embodiments that may be combined with any of the preceding embodiments, the one or more human cells are somatic cells, mature cells, or differentiated cells. In some embodiments that may be combined with any of the preceding embodiments, the one or more human cells are somatic cells, mature cells, or differentiated cells. In some embodiments that may be combined with any of the preceding embodiments, the one or more human cells are one or more somatic cells, mature cells, or differentiated cells selected from epidermal cells, fibroblasts, lymphocytes, hepatocytes, epithelial cells, myocytes, chondrocytes, osteocytes, adipocytes, cardiomyocytes, pancreatic β cells, keratinocytes, erythrocytes, peripheral blood cells, neurocytes, astrocytes, germ cells, sperm cells, and oocytes.

Other aspects of the present disclosure relate to a method for inducing a human embryonic stem cell-like DNA methylation pattern in one or more human induced pluripotent stem (iPS) cells, by contacting the one or more human iPS cells with an agent that increases expression of Zscan4 in the one or more human iPS cells, where the agent is a synthetic mRNA molecule encoding Zscan4 or a viral vector, preferably a Sendai viral vector, encoding Zscan4, and where increased expression of Zscan4 induces a human embryonic stem cell-like DNA methylation pattern in the one or more human iPS cells as compared to one or more corresponding human iPS cells that are not contacted with the agent.

Other aspects of the present disclosure relate to a method of rejuvenating one or more human oocyte cells, by contacting the one or more human oocyte cells with an agent that increases expression of Zscan4 in the one or more human oocyte cells, where the agent is a synthetic mRNA molecule encoding Zscan4 or a viral vector, preferably a Sendai viral vector, encoding Zscan4, and where increased expression of Zscan4 rejuvenates the one or more human oocyte cells as compared to one or more corresponding human oocyte cells that are not contacted with the agent.

Other aspects of the present disclosure relate to a method of increasing genome stability of one or more human oocyte cells, by contacting the one or more human oocyte cells with an agent that increases expression of Zscan4 in the one or more human oocyte cells, where the agent is a synthetic mRNA molecule encoding Zscan4 or a viral vector, preferably a Sendai viral vector, encoding Zscan4, and where increased expression of Zscan4 increases genome stability in the one or more human oocyte cells as compared to one or more corresponding human oocyte cells that are not contacted with the agent. Other aspects of the present disclosure relate to a method of correcting one or more karyotype abnormalities in one or more human oocyte cells, by contacting the one or more human oocyte cells with an agent that increases expression of Zscan4 in the one or more human oocyte cells, where the agent is a synthetic mRNA molecule encoding Zscan4 or a viral vector, preferably a Sendai viral vector, encoding Zscan4, and where increased expression of Zscan4 induces correction of the one or more karyotype abnormalities in the one or more human oocyte cells as compared to one or more corresponding human oocyte cells that are not contacted with the agent. In some embodiments, the one or more human oocyte cells are isolated from a subject prior to contacting with the agent that increases expression of Zscan4. In some embodiments, after contacting with the agent that increases expression of Zscan4 the one or more human oocyte cells undergo in vitro fertilization.

Other aspects of the present disclosure relate to an in vitro method of increasing genome stability of one or more fertilized human oocytes, by contacting the one or more fertilized human oocytes with an agent that increases expression of Zscan4 in the one or more fertilized human oocytes, where the agent is a synthetic mRNA molecule encoding Zscan4 or a viral vector, preferably a Sendai viral vector, encoding Zscan4, and where increased expression of Zscan4 increases genome stability in the one or more fertilized human oocytes as compared to one or more corresponding fertilized human oocytes embryo that are not contacted with the agent. Other aspects of the present disclosure relate to an in vitro method of correcting one or more karyotype abnormalities in one or more fertilized human oocytes, by contacting the one or more fertilized human oocytes with an agent that increases expression of Zscan4 in the one or more fertilized human oocytes, where the agent is a synthetic mRNA molecule encoding Zscan4 or a viral vector, preferably a Sendai viral vector, encoding Zscan4, and where increased expression of Zscan4 induces correction of the one or more karyotype abnormalities in the one or more fertilized human oocytes as compared to one or more corresponding fertilized human oocytes that are not contacted with the agent. In some embodiments, the one or more fertilized human oocytes were fertilized by in vitro fertilization. In some embodiments, prior to being fertilized, the one or more human oocytes were isolated from a subject. In some embodiments, the one or more fertilized oocytes are embryos between the one-cell stage and the blastocyst stage.

Other aspects of the present disclosure relate to a method of treating a disease or condition associated with a telomere abnormality, by: i. isolating human bone marrow cells from a subject suffering from a disease or condition associated with a telomere abnormality; ii. contacting the human bone marrow cells with an agent that increases expression of Zscan4 in the human bone marrow cells, where the agent is a synthetic mRNA molecule encoding Zscan4 or a viral vector, preferably a Sendai viral vector, encoding Zscan4, and where increasing expression of Zscan4 induces telomere lengthening in the human bone marrow cells; and iii. engrafting the contacted human bone marrow cells into the subject to treat the disease or condition associated with a telomere abnormality.

Other aspects of the present disclosure relate to a method of treating a disease or condition associated with a chromosome abnormality, by: i. isolating human bone marrow cells from a subject suffering from a disease or condition associated with a chromosome abnormality; ii. contacting the human bone marrow cells with an agent that increases expression of Zscan4 in the human bone marrow cells, where the agent is a synthetic mRNA molecule encoding Zscan4 or a viral vector, preferably a Sendai viral vector, encoding Zscan4, and where increasing expression of Zscan4 induces correction of the chromosome abnormality in the human bone marrow cells; and iii. engrafting the contacted human bone marrow cells into the subject to treat the disease or condition associated with a chromosome abnormality.

In some embodiments that may be combined with any of the preceding embodiments, the disease or condition is one or more diseases or conditions selected from diseases of telomere shortening, bone marrow failure syndromes, age-related telomere shortening diseases or disorders, and premature aging diseases or disorders. In some embodiments that may be combined with any of the preceding embodiments, the disease or condition is a disease of telomere shortening selected from dyskeratosis congenita, Hoyeraal-Hreidarsson syndrome, Revesz syndrome, Coats plus syndrome, idiopathic pulmonary fibrosis, liver cirrhosis, pancreatic fibrosis, Alzheimer's disease, and osteoarthritis. In some embodiments that may be combined with any of the preceding embodiments, the disease or condition is a bone marrow failure syndrome selected from Fanconi anemia, amegakaryocytic thrombocytopenia, aplastic anemia, Diamond Blackfan anemia, dyskeratosis congenita, paroxysmal nocturnal hemoglobinuria (PNH), Pearson syndrome, Shwachman Diamond syndrome, thrombocytopenia, and myelodysplastic syndrome. In some embodiments that may be combined with any of the preceding embodiments, the disease or condition is an age-related telomere shortening disease or disease, a premature aging disease or disease, or both selected from Werner syndrome, Bloom's syndrome, Hutchinson-Gilford progeria syndrome, Cockayne syndrome, Xeroderma pigmentosa, Ataxia telangiectasia, Rothmund Thomson syndrome, Trichothiodystrophy, Juberg-Marsidi syndrome, and Down syndrome.

Other aspects of the present disclosure relate to a method of rejuvenating a tissue or organ in a subject, by administering to a subject in need thereof an agent that increases expression of Zscan4 in the tissue or organ, where the agent is a synthetic mRNA molecule encoding Zscan4 or a viral vector, preferably a Sendai viral vector, encoding Zscan4, and where increasing expression of Zscan4 rejuvenates the tissue or organ.

Other aspects of the present disclosure relate to a method of rejuvenating a subject in need thereof, by administering to the subject an agent that increases expression of Zscan4, where the agent is a synthetic mRNA molecule encoding Zscan4 or a viral vector, preferably a Sendai viral vector, encoding Zscan4, and where increasing expression of Zscan4 rejuvenates the subject.

Other aspects of the present disclosure relate to a method of extending lifespan of one or more human cells, by contacting the one or more human cells with an agent that increases expression of Zscan4 in one or more human cells in the subject, where the agent is a synthetic mRNA molecule encoding Zscan4 or a viral vector, preferably a Sendai viral vector, encoding Zscan4, and where increasing expression of Zscan4 extends the lifespan of the one or more human cells as compared to one or more corresponding human cells that are not contacted with the agent.

Other aspects of the present disclosure relate to a method of extending lifespan of a tissue or organ in a subject, by administering to a subject in need thereof an agent that increases expression of Zscan4 in the tissue or organ, where the agent is a synthetic mRNA molecule encoding Zscan4 or a viral vector, preferably a Sendai viral vector, encoding Zscan4, and where increasing expression of Zscan4 extends the lifespan of the tissue or organ.

Other aspects of the present disclosure relate to a method of extending lifespan of a subject, by administering to a subject in need thereof an agent that increases expression of Zscan4 in one or more human cells in the subject, where the agent is a synthetic mRNA molecule encoding Zscan4 or a viral vector, preferably a Sendai viral vector, encoding Zscan4, and where increasing expression of Zscan4 extends the lifespan of the one or more human cells, thereby extending the lifespan of the subject.

Other aspects of the present disclosure relate to a method of extending lifespan of a subject, by: i. isolating one or more human cells from the subject; ii. contacting the one or more human cells with an agent that increases expression of Zscan4 in the one or more human cells, where the agent is a synthetic mRNA molecule encoding Zscan4 or a viral vector, preferably a Sendai viral vector, encoding Zscan4, and where increasing expression of Zscan4 extends the lifespan of the one or more human cells; and iii. administering the contacted one or more human cells to the subject to extend the lifespan of the subject.

Other aspects of the present disclosure relate to a method for determining one or more Zscan4-induced effects in one or more human cells, by: i. contacting the one or more human cells with an agent that increases expression of Zscan4 in one or more human cells, where the agent is a synthetic mRNA molecule encoding Zscan4 or a viral vector, preferably a Sendai viral vector, encoding Zscan4; ii. measuring expression levels of SERPINB4, DNMT3L, and/or DUX4 in the one or more human cells; and iii. comparing the expression levels of SERPINB4, DNMT3L, and/or DUX4 in the one or more human cells to the expression levels of SERPINB4, DNMT3L, and/or DUX4 in one or more corresponding human cells that are not contacted with the agent, where an increase in the expression levels of SERPINB4, DNMT3L, and/or DUX4 in the one or more human cells indicates the presence of one or more Zscan4-induced effects in the one or more human cell.

In some embodiments that may be combined with any of the preceding embodiments, the increased expression of Zscan4 is transient. In some embodiments that may be combined with any of the preceding embodiments, the agent increases Zscan4 expression for about 1 hour to about 23 hours. In some embodiments that may be combined with any of the preceding embodiments, the agent increases Zscan4 expression for about 1 day to about 10 days. In some embodiments that may be combined with any of the preceding embodiments, the agent interacts directly with endogenous Zscan4 to increase expression of Zscan4. In some embodiments that may be combined with any of the preceding embodiments, the vector encodes Zscan4 operably linked to a promoter. In some embodiments that may be combined with any of the preceding embodiments, the promoter is a constitutive promoter. In some embodiments that may be combined with any of the preceding embodiments, the promoter is an inducible promoter. In some embodiments that may be combined with any of the preceding embodiments, the Zscan4 is a Zscan4-ERT2 fusion protein. In some embodiments that may be combined with any of the preceding embodiments, the Zscan4 is a Zscan4-ΔC protein. In some embodiments that may be combined with any of the preceding embodiments, the Zscan4-ΔC protein includes a deletion of at least one zinc finger domain. In some embodiments that may be combined with any of the preceding embodiments, the Zscan4 is mouse Zscan4, human ZSCAN4, or a homolog thereof. In some embodiments that may be combined with any of the preceding embodiments, the Zscan4 is selected from Zscan4a, Zscan4b, Zscan4c, Zscan4d, Zscan4e, and Zscan4f. In some embodiments that may be combined with any of the preceding embodiments, the isolated nucleic acid molecule contains a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence selected from SEQ ID Nos: 1-10 and 21-30. In some embodiments that may be combined with any of the preceding embodiments, the Zscan4 is human ZSCAN4. In some embodiments that may be combined with any of the preceding embodiments, the isolated nucleic acid molecule contains a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 7. In some embodiments that may be combined with any of the preceding embodiments, the agent is a Zscan4 protein. In some embodiments that may be combined with any of the preceding embodiments, the Zscan4 protein is fused to a cell-penetrating peptide. In some embodiments that may be combined with any of the preceding embodiments, the cell-penetrating peptide contains a protein transduction domain. In some embodiments that may be combined with any of the preceding embodiments, the cell-penetrating peptide contains a poly-arginine peptide tag. In some embodiments that may be combined with any of the preceding embodiments, the Zscan4 protein is encapsulated in a nanoparticle. In some embodiments that may be combined with any of the preceding embodiments, the Zscan4 protein is a mouse Zscan4 protein, a human ZSCAN4 protein, or a homolog thereof. In some embodiments that may be combined with any of the preceding embodiments, the Zscan4 protein is selected from a Zscan4a protein, a Zscan4b protein, a Zscan4c protein, a Zscan4d protein, a Zscan4e protein, and a Zscan4f protein. In some embodiments that may be combined with any of the preceding embodiments, the Zscan4 protein contains an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an amino acid sequence selected from SEQ ID NOs: 11-20 and 31-40. In some embodiments that may be combined with any of the preceding embodiments, the Zscan4 protein is a human ZSCAN4 protein. In some embodiments that may be combined with any of the preceding embodiments, the Zscan4 protein contains an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 17. In some embodiments that may be combined with any of the preceding embodiments, the Zscan4 protein is a Zscan4-ERT2 fusion protein. In some embodiments that may be combined with any of the preceding embodiments, the Zscan4 protein is a Zscan4-ΔC protein. In some embodiments that may be combined with any of the preceding embodiments, the Zscan4-ΔC protein contains a mouse Zscan4 protein, a human ZSCAN4 protein, or a homolog thereof, and where the Zscan4 protein contains a deletion of at least one zinc finger domain. In some embodiments that may be combined with any of the preceding embodiments, the Zscan4-ΔC protein contains a Zscan4 protein selected from a Zscan4a protein, a Zscan4b protein, a Zscan4c protein, a Zscan4d protein, a Zscan4e protein, and a Zscan4f protein, and where the Zscan4 protein contains a deletion of at least one zinc finger domain. In some embodiments that may be combined with any of the preceding embodiments, the Zscan4-ΔC protein contains a human ZSCAN4 protein, and where the Zscan4 protein contains a deletion of at least one zinc finger domain. In some embodiments that may be combined with any of the preceding embodiments, the agent is a retinoid, an agent that induces oxidative stress, or both.

The foregoing and other objects and features of the disclosure will become more apparent from the following detailed description, which proceeds with reference to the accompanying figures.

BRIEF DESCRIPTION OF THE DRAWINGS

FIG. 1A depicts the experimental procedure. FIG. 1B depicts the percent of euploid mouse ES cells transfected with hZSCAN4 mRNAs.

FIG. 2A depicts the percent of euploid mouse ES cells infected with SeVmZscan4 or SeVhZSCAN4. FIG. 2B depicts the percent of euploid mouse ES cells infected with SeVmZERT2 or SeVhZERT2.

FIG. 3A depicts the percent of euploid mouse ES cells infected with SeVmZscan4-TS15 or SeVhZSCAN4-TS15, followed by culturing at 35° C. for three days. FIG. 3B depicts the percent of euploid mouse ES cells infected with SeVmZscan4-TS15 or SeVhZSCAN4-TS15 followed by culturing at 35° C. for six days. FIG. 3C depicts the percent of euploid mouse ES cells infected with SeVmZscan4-TS15 or SeVhZSCAN4-TS15, followed by culturing at 35° C. for three days and then at 37° C. for three days.

FIG. 4A depicts the effects of transfecting mouse ES cells with hZSCAN4 mRNAs. FIG. 4B depicts the effects of infecting mouse ES cells with Sendai virus vectors expressing Zscan4. FIG. 4C depicts the effects of infecting mouse ES cells with temperature-sensitive Sendai virus vectors expressing mZscan4 or hZSCAN4.

FIG. 5A depicts the effects of transfecting human iPS cells with Zscan4 mRNAs. FIG. 5B depicts the effects of infecting human iPS cells with Sendai virus vectors expressing Zscan4. FIG. 5C depicts the effects of infecting human iPS cells with temperature-sensitive Sendai virus vectors expressing mZscan4 or hZSCAN4.

FIG. 13A depicts the results of a growth assay of HDFa cells transfected with hZSCAN4 mRNAs or GFP mRNAs and cultured for approximately 50 days. FIG. 13B depicts the results of a growth assay of HDFa cells transfected with hZSCAN4 mRNAs or GFP mRNAs and cultured for approximately 30 days. FIG. 13C depicts the results of a growth assay of HDFa cells transfected with mZscan4 mRNAs, hZSCAN4 mRNAs, or GFP mRNAs and cultured for approximately 20 days.

FIG. 14 depicts the results of extension of telomere lengths in human mesenchymal stem (MS) cells infected with temperature-sensitive Sendai virus vectors expressing mouse Zscan4 or human ZSCAN4.

FIG. 16A depicts typical results of FISH analyses. Three dots indicate trisomy 21 and two dots indicate normal diploid chromosome 21. FIG. 16B depicts DS cells transfected once with hZSCAN4 mRNAs. FIG. 16C depicts DS cells transfected twice with hZSCAN4 mRNAs. In the figure, "n" indicates the number of examined nuclei.

DETAILED DESCRIPTION

Overview

Figure 1:
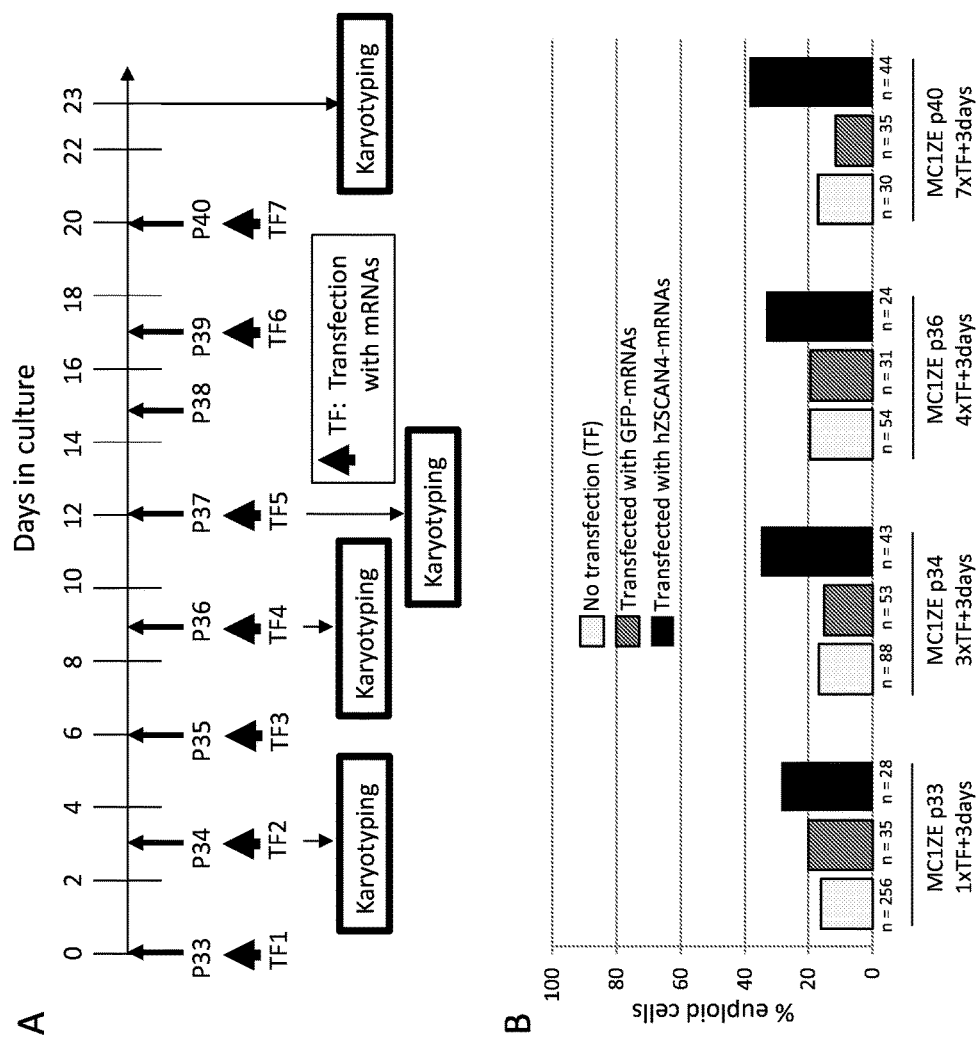
FIG. 1 depicts the correction of chromosome abnormalities in mouse ES cells transfected with hZSCAN4-mRNAs.

As discussed above, it has been previously shown that expression of mouse Zscan4 in mouse embryonic stem cells is associated telomere elongation. Given that the mouse genome contains six Zscan4 genes and three Zscan4 pseudo-genes, while the human genome only contains one Zscan4 gene, one of ordinary skill in the art would not have been able to extrapolate the results of Zscan4 expression in mouse cells to human cells. However, as disclosed in the Example 8 below, applicant has for the first time shown that expression of human ZSCAN4 in fully differentiated, adult human fibroblasts results in about 40% increase in telomere length in the fibroblasts. Moreover, applicant has shown that expression of Zscan4 in human fibroblasts isolated from a patient with Fanconi anemia resulted in about a 160% increase in telomere length in the fibroblasts. These results surprisingly demonstrate that Zscan4 is an upstream effector, rather than a downstream actor in telomere elongation, as Zscan4 expression alone was shown to be sufficient to increase telomere length in human fibroblasts isolated from a patient with Fanconi anemia. As such, activating or increasing expression of Zscan4 in cells can be an effective treatment for Fanconi anemia or any other disease or condition associated with telomere shortening. Further, as disclosed in Example 15 below, applicant has also for the first time shown that Zscan4 expression goes far beyond mere promotion of genome stability. Zscan4 expression in a population of human fibroblast cells having trisomy 21 induces the correction of the trisomy 21 abnormality in approximately 55% of the cells. Accordingly, activating or increasing expression of Zscan4 can be used to treat aneuploidy in cells, as well as increase the success rate of in vitro fertilization (IVF) and successful pregnancies in older women by rejuvenating and/or correcting chromosomal abnormalities, such as aneuploidy, in oocyte cells and fertilized oocytes.

Accordingly, the methods of the present disclosure generally relate to increasing the expression of Zscan4 (e.g., Zscan4 protein expression) in human cells to increase telomere length and/or increase genome stability. Various aspects of the present disclosure relate to increasing telomere length in one or more human cells, treating a subject in need of telomere lengthening, treating a disease or condition associated with a telomere abnormality, treating a disease or condition associated with a chromosome abnormality, increasing genome stability of one or more human cells, rejuvenating one or more human cells, rejuvenating a tissue or organ in a subject, and rejuvenating a subject in need thereof.

In one aspect, the present disclosure relates to a method of increasing telomere length in one or more human cells, including contacting the one or more human cells with an agent that increases expression of Zscan4 in the human cell, where increased expression of Zscan4 induces telomere lengthening in the one or more human cells as compared to one or more corresponding human cells that are not contacted with the agent.

In another aspect, the present disclosure relates to a method of treating a subject in need of telomere lengthening, including contacting one or more human cells in the subject with an agent that increases expression of Zscan4 in the one or more human cells, where increased expression of Zscan4 induces telomere lengthening in the one or more human cells.

In another aspect, the present disclosure relates to a method of treating a subject in need of telomere lengthening, including: i.) isolating one or more human cells in need of telomere lengthening from the subject; ii.) contacting the one or more human cells with an agent that increases expression of Zscan4 in the one or more human cells, where increasing expression of Zscan4 induces telomere lengthening in the one or more human cells; and iii.) administering the contacted one or more human cells to the subject.

In another aspect, the present disclosure relates to a method of treating a disease or condition associated with a telomere abnormality, including administering to a subject in need thereof an agent that increases expression of Zscan4 in one or more human cells in the subject, where increasing expression of Zscan4 induces telomere lengthening in the one or more human cells to treat to treat the to treat the disease or condition associated with a telomere abnormality.

In another aspect, the present disclosure relates to a method of treating a disease or condition associated with a telomere abnormality, including: i.) isolating one or more human cells from a subject suffering from a disease or condition associated with a telomere abnormality; ii.) contacting the one or more human cells with an agent that increases expression of Zscan4 in the one or more human cells, where increasing expression of Zscan4 induces telomere lengthening in the one or more human cells; and iii.) administering the contacted one or more human cells to the subject to treat the disease or condition associated with a telomere abnormality.

In another aspect, the present disclosure relates to a method of treating a disease or condition associated with a chromosome abnormality, by administering to a subject in need thereof an agent that increases expression of Zscan4 in one or more human cells in the subject, where increasing expression of Zscan4 induces correction of the chromosome abnormality in the one or more human cells to treat the disease or condition associated with a chromosome abnormality.

In another aspect, the present disclosure relates to a method of treating a disease or condition associated with a chromosome abnormality, by: i.) isolating one or more human cells from a subject suffering from a disease or condition associated with a chromosome abnormality; ii.) contacting the one or more human cells with an agent that increases expression of Zscan4 in the one or more human cells, where increasing expression of Zscan4 induces correction of the chromosome abnormality in the one or more human cells; and iii.) administering the contacted one or more human cells to the subject to treat the disease or condition associated with a chromosome abnormality.

In another aspect, the present disclosure relates to a method of treating a disease or condition associated with a karyotype abnormality, by administering to a subject in need thereof an agent that increases expression of Zscan4 in one or more human cells in the subject, where increasing expression of Zscan4 induces correction of the karyotype abnormality in the one or more human cells to treat the disease or condition associated with a karyotype abnormality.

In another aspect, the present disclosure relates to a method of treating a disease or condition associated with a karyotype abnormality, by: i.) isolating one or more human cells from a subject suffering from a disease or condition associated with a karyotype abnormality; ii.) contacting the one or more human cells with an agent that increases expression of Zscan4 in the one or more human cells, where increasing expression of Zscan4 induces correction of the karyotype abnormality in the one or more human cells; and iii.) administering the contacted one or more human cells to the subject to treat the disease or condition associated with a karyotype abnormality.

In another aspect, the present disclosure relates to a method of treating a cancer, by administering to a subject in need thereof an agent that increases expression of Zscan4 in one or more cancer cells in the subject, where increasing expression of Zscan4 represses growth of the one or more cancer cells, thereby treating the cancer.

In another aspect, the present disclosure relates to a method of improving responsiveness to chemotherapy in a cancer patient, by administering to a subject in need thereof an agent that reduces expression of endogenous ZSCAN4 in one or more cancer stem cells in the subject, where reducing expression of endogenous ZSCAN4 reduces or eliminates resistance to one or more chemotherapeutic agents in the one or more cancer stem cells, thereby improving responsiveness to the one or more chemotherapeutic agents in the subject.

In another aspect, the present disclosure relates to a method of increasing genome stability of one or more human cells, including contacting the one or more human cells with an agent that increases expression of Zscan4 in the one or more human cells, where increased expression of Zscan4 increases genome stability in the one or more human cells as compared to one or more corresponding human cells that are not contacted with the agent.

In another aspect, the present disclosure relates to a method of increasing DNA repair capacity of one or more human cells, by contacting the one or more human cells with an agent that increases expression of Zscan4 in the one or more human cells, where increased expression of Zscan4 increases DNA repair capacity in the one or more human cells as compared to one or more corresponding human cells that are not contacted with the agent.

In another aspect, the present disclosure relates to a method of rejuvenating one or more human cells, including contacting the one or more human cells with an agent that increases expression of Zscan4 in the one or more human cells, where increased expression of Zscan4 rejuvenates the one or more human cells as compared to one or more corresponding human cells that are not contacted with the agent.

In another aspect, the present disclosure relates to a method of providing resistance to one or more genotoxic agents in one or more human cells, by contacting the one or more human cells with an agent that increases expression of Zscan4 in the one or more human cells, where increased expression of Zscan4 increases resistance to one or more genotoxic agents in the one or more human cells as compared to one or more corresponding human cells that are not contacted with the agent.

In another aspect, the present disclosure relates to a method for inducing a human embryonic stem cell-like DNA methylation pattern in one or more human induced pluripotent stem (iPS) cells, by contacting the one or more human iPS cells with an agent that increases expression of Zscan4 in the one or more human iPS cells, where increased expression of Zscan4 induces a human embryonic stem cell-like DNA methylation pattern in the one or more human iPS cells as compared to one or more corresponding human iPS cells that are not contacted with the agent.

In another aspect, the present disclosure relates to a method of rejuvenating one or more human oocyte cells, by contacting the one or more human oocyte cells with an agent that increases expression of Zscan4 in the one or more human oocyte cells, where increased expression of Zscan4 rejuvenates the one or more human oocyte cells as compared to one or more corresponding human oocyte cells that are not contacted with the agent.

In another aspect, the present disclosure relates to a method of increasing genome stability of one or more human oocyte cells, by contacting the one or more human oocyte cells with an agent that increases expression of Zscan4 in the one or more human oocyte cells, where increased expression of Zscan4 increases genome stability in the one or more human oocyte cells as compared to one or more corresponding human oocyte cells that are not contacted with the agent.

In another aspect, the present disclosure relates to a method of correcting one or more karyotype abnormalities in one or more human oocyte cells, by contacting the one or more human oocyte cells with an agent that increases expression of Zscan4 in the one or more human oocyte cells, wherein increased expression of Zscan4 induces correction of the one or more karyotype abnormalities in the one or more human oocyte cells as compared to one or more corresponding human oocyte cells that are not contacted with the agent.

In another aspect, the present disclosure relates to an in vitro method of increasing genome stability of one or more fertilized human oocytes, by contacting the one or more fertilized human oocytes with an agent that increases expression of Zscan4 in the one or more fertilized human oocytes, where increased expression of Zscan4 increases genome stability in the one or more fertilized human oocytes as compared to one or more corresponding fertilized human oocytes that are not contacted with the agent.

In another aspect, the present disclosure relates to an in vitro method of correcting one or more karyotype abnormalities in one or more fertilized human oocytes, by contacting the one or more fertilized human oocytes with an agent that increases expression of Zscan4 in the one or more fertilized human oocytes, where increased expression of Zscan4 induces correction of the one or more karyotype abnormalities in the one or more fertilized human oocytes as compared to one or more corresponding fertilized human oocytes that are not contacted with the agent.

In another aspect, the present disclosure relates to a method of treating a disease or condition associated with a telomere abnormality, including: i.) isolating human bone marrow cells from a subject suffering from a disease or condition associated with a telomere abnormality; ii.) contacting the human bone marrow cells with an agent that increases expression of Zscan4 in the human bone marrow cells, where increasing expression of Zscan4 induces telomere lengthening in the human bone marrow cells; and iii.) engrafting the contacted human bone marrow cells into the subject to treat the disease or condition associated with a telomere abnormality.

In another aspect, the present disclosure relates to a method of treating a disease or condition associated with a chromosome abnormality, including: i.) isolating human bone marrow cells from a subject suffering from a disease or condition associated with a chromosome abnormality; ii.) contacting the human bone marrow cells with an agent that increases expression of Zscan4 in the human bone marrow cells, where increasing expression of Zscan4 induces correction of the chromosome abnormality in the human bone marrow cells; and iii.) engrafting the contacted human bone marrow cells into the subject to treat the disease or condition associated with a chromosome abnormality.

In another aspect, the present disclosure relates to a method of rejuvenating a tissue or organ in a subject, including administering to a subject in need thereof an agent that increases expression of Zscan4 in the tissue or organ, where increasing expression of Zscan4 rejuvenates the tissue or organ.

In another aspect, the present disclosure relates to a method of rejuvenating a subject in need thereof, including administering to the subject an agent that increases expression of Zscan4, where increasing expression of Zscan4 rejuvenates the subject.

In another aspect, the present disclosure relates to a method of extending lifespan of one or more human cells, by contacting the one or more human cells with an agent that increases expression of Zscan4 in one or more human cells in the subject, where increasing expression of Zscan4 extends the lifespan of the one or more human cells as compared to one or more corresponding human cells that are not contacted with the agent.

In another aspect, the present disclosure relates to a method of extending lifespan of a tissue or organ in a subject, by administering to a subject in need thereof an agent that increases expression of Zscan4 in the tissue or organ, where increasing expression of Zscan4 extends the lifespan of the tissue or organ.

In another aspect, the present disclosure relates to a method of extending lifespan of a subject, by administering to a subject in need thereof an agent that increases expression of Zscan4 in one or more human cells in the subject, where increasing expression of Zscan4 extends the lifespan of the one or more human cells, thereby extending the lifespan of the subject.

In another aspect, the present disclosure relates to a method of extending lifespan of a subject, by: i. isolating one or more human cells from the subject; ii. contacting the one or more human cells with an agent that increases expression of Zscan4 in the one or more human cells, where increasing expression of Zscan4 extends the lifespan of the one or more human cells; and iii. administering the contacted one or more human cells to the subject to extend the lifespan of the subject.

In another aspect, the present disclosure relates to a method for determining one or more Zscan4-induced effects in one or more human cells, by: i. contacting the one or more human cells with an agent that increases expression of Zscan4 in one or more human cells; ii. measuring expression levels of SERPINB4, DNMT3L, and/or DUX4 in the one or more human cells; and iii. comparing the expression levels of SERPINB4, DNMT3L, and/or DUX4 in the one or more human cells to the expression levels of SERPINB4, DNMT3L, and/or DUX4 in one or more corresponding human cells that are not contacted with the agent, where an increase in the expression levels of SERPINB4, DNMT3L, and/or DUX4 in the one or more human cells indicates the presence of one or more Zscan4-induced effects in the one or more human cell.

Zscan4

Zinc finger and SCAN domain containing 4 (Zscan4) genes represent a group of genes that have previously been identified as exhibiting 2-cell-specific expression and ES cell-specific expression (PCT Publication No. WO 2008/118957). The Zscan4 gene was identified by expression profiling of all pre-implantation stages of mouse embryos using a large-scale cDNA sequencing project (Ko et al., *Development* 127: 1737-1749, 2000; Sharov et al., *PLoS Biol* 1:E74, 2003) and DNA microarray analysis (Hamatani et al, *Dev Cell* 6:117-131, 2004). In mice, the term "Zscan4" refers to a collection of genes including three pseudogenes (Zscan4-ps1, Zscan4-ps2 and Zscan4-ps3) and six expressed genes (Zscan4a, Zscan4b, Zscan4c, Zscan4d, Zscan4e and Zscan4f). Among the six paralogs, the open reading frames of Zscan4c, Zscan4d, and Zscan4f encode a SCAN domain, predicted to mediate protein-protein interactions, as well as four zinc finger domains, suggesting their potential role as transcription factors. In contrast to mice, the human genome contains only one copy of Zscan4. Zscan4 may refer to Zscan4 polypeptides and Zscan4 may refer to polynucleotides encoding the Zscan4 polypeptides.

It has recently been shown that Zscan4 (Zinc finger and scan domain-containing protein 4), which, in mice, is expressed specifically in 2-cell stage embryos and ES cells (Falco et al., *Dev Biol* 307:539-550, 2007), is required for the maintenance of genome stability and normal karyotype in ES cells (Zalzman et al., *Nature* 464:858-863, 2010). Although only a small fraction (~1% to ~5%) of undifferentiated ES cells express Zscan4 at a given time (Falco et al., *Dev Biol* 307:539-550, 2007), essentially all of the ES cells in culture undergo the transient Zscane state within 9 passages (Zalzman et al., *Nature* 464:858-863, 2010). Upon short hairpin RNA (shRNA)-mediated repression of Zscan4, after about 8 passages ES cells undergo massive karyotype deterioration. Prior studies have also shown that the Zscan4$^+$ state of mouse ES cells is associated with telomere extension (Zalzman et al., *Nature* 464:858-863, 2010). Although ES cells have the best capacity to maintain their genome integrity in culture, it is also widely recognized that even ES cells, in long-term culture, gradually lose their developmental potency. A telomere may refer to the end of a eukaryotic chromosome, a specialized structure involved in the replication and stability of the chromosome. Telomeres contain many repeats of a short DNA sequence in a specific orientation. Telomere functions include protecting the ends of the chromosome so that chromosomes do not end up joined together, and allowing replication of the extreme ends of the chromosomes (by telomerase). The number of repeats of telomeric DNA at the end of a chromosome decreases with age.

It has also been shown previously that forced expression of mouse Zscan4 in mouse ES cells for three days increases the average length of telomeres from the standard length of approximately 40 kb to approximately 66 kb (Zalzman et al., 2010). This indicates that Zscan4 alone can efficiently and rapidly increase telomere length. However, it is unknown whether Zscan4 can increase the length of telomeres in non-embryonic human cells, such as adult stem cells and somatic cells.

Human Cells

Certain aspects of the present disclosure relate to increasing telomere length in one or more human cells, including without limitation, human adult cells, by utilizing an agent that increases Zscan4 expression (e.g., Zscan4 protein expression) in the one or more human cells. In certain embodiments, the one or more human cells are in a subject in need of telomere lengthening, or suffering or diagnosed with a disease or condition associated with a telomere abnormality.

Various human cells find use in the methods described herein. As disclosed herein, the term "human cell(s)" refers to any cell(s) found throughout the human body during and after embryonic development, such as human embryonic cells, stem cells, pluripotent cells, differentiated cells, mature cells, somatic cells, and adult cells. In some embodiments, human cells of the present disclosure are human adult cells. As disclosed herein, the term "human adult cell(s)" refers to any cell(s) found throughout the human body after embryonic development (i.e., non-embryonic cells). Human cells of the present disclosure include, without limitation, sperm cells, oocyte cells, fertilized oocytes (i.e., zygotes), embryonic cells, mature cells, differentiated cells, somatic cells, progenitor cells, embryonic stem (ES) cells, induced pluripotent stem (iPS) cells, adult stem cells, somatic stem cells, and tissue stem cells. Adult stem cells, which are also known as somatic stem cells or tissue stem cells, may refer to undifferentiated cells, found throughout the body after embryonic development, which multiply by cell division to replenish dying cells and regenerate damaged tissues. Progenitor cells may refer to oligopotent or unipotent cells that differentiate into a specific type of cell or cell lineage. Progenitor cells are similar to stem cells but are more differentiated and exhibit limited self-renewal. Exemplary adult stem cells, tissue stem cells, and/or progenitor cells may include, without limitation, hematopoietic stem cells, mesenchymal stem cells, adipose stem cells, neuronal stem cells, intestinal stem cells, skin stem cells, and germ cells (such as, sperm cells and oocytes).

Human cells may also include, without limitation, somatic cells, mature cells, and differentiated cells. Somatic cells may refer to any cell of the body, including, without limitation, germ cells, tissue stem cells, progenitor cells, induced pluripotent stem (iPS) cells, and differentiated cells. Exemplary somatic cells, mature cells, and/or differentiated cells may include, without limitation, epidermal cells, fibroblasts, lymphocytes, hepatocytes, epithelial cells, myocytes, chondrocytes, osteocytes, adipocytes, cardiomyocytes, pancreatic β cells, keratinocytes, erythrocytes, peripheral blood cells, bone marrow cells, neurocytes, astrocytes, and germ cells. Germ cells may refer to the cells that give rise to the gametes (i.e., eggs and sperm) of organisms that reproduce sexually. In certain embodiments, germ cells include, without limitation, oocytes, and sperm cells. In some embodiment, somatic cells, mature cells, and/or differentiated cells of the present disclosure also include, without limitation, preimplantation embryos.

Agents that Increase Expression of Zscan4

Certain aspects of the present disclosure relate to utilizing an agent that increases Zscan4 expression (e.g., Zscan4 protein expression) in human cells to increase telomere length in the human cells. An agent may refer to any nucleic acid molecule, protein, compound, small molecule, organic compound, inorganic compound, or other molecule of interest. In some embodiments, the agent is any agent that increases expression of Zscan4 either by directly interacting with the endogenous Zscan4 gene (including any upstream or downstream regulatory sequences) or by interacting with genes and/or proteins that lead to the induction of Zscan4 expression. In some embodiments, the agent can be a nucleic acid molecule encoding Zscan4 including, without limitation, a synthetic mRNA and an expression vector including, without limitation, a viral vector such as Sendai virus vectors. In other embodiments, the agent can be a polypeptide containing a Zscan4 protein or a functional portion thereof such as Zscan4-ΔC. In some embodiments, the agent can be a retinoid, or an agent that induces oxidative stress.

In some embodiments, an agent of the present disclosure that increases Zscan4 expression (e.g., Zscan4 protein expression) in human cells transiently increases Zscan4 expression. For example, an agent of the present disclosure that increases Zscan4 expression in human cells may increase Zscan4 expression for about 1 hour to about 23 hours (e.g., for about 1 hour, about 2 hours, about 3 hours, about 4 hours, about 5 hours, about 6 hours, about 7 hours, about 8 hours, about 9 hours, about 10 hours, 11 hours, about 12 hours, about 13 hours, about 14 hours, about 15 hours, about 16 hours, about 17 hours, about 18 hours, about 19 hours, about 20 hours, about 21 hours, about 22 hours, or about 23 hours); or about 1 day to about 10 days (e.g., about 1 day, about 1.25 days, about 1.5 days, about 1.75 days, about 2 days, about 2.25 days, about 2.5 days, about 2.75 days, about 3 days, about 3.25 days, about 3.5 days, about 3.75 days, about 4 days, about 4.25 days, about 4.5 days, about 4.75 days, about 5 days, about 6.25 days, about 6.5 days, about 6.75 days, about 7 days, about 7.25 days, about 7.5 days, about 7.75 days, about 8 days, about 8.25 days, about 8.5 days, about 8.75 days, about 9 days, about 9.25 days, about 9.5 days, about 9.75 days, or about 10 days).

In some embodiments, the disclosed beneficial effects of increased Zscan4 expression (e.g., Zscan4 protein expression) in human cells may be enhanced by repeated transient increases in Zscan4 expression. Accordingly, in certain embodiments, an agent of the present disclosure that increases Zscan4 expression (e.g., Zscan4 protein expression) in human cells may be used to repeatedly increase Zscan4 expression in human cells at an interval of every 4 hours, every 8 hours, every 12 hours, every 16 hours, every 24 hours, every 32 hours, every 40 hours, every 48 hours, every three days, every four days, every five days, every six days, every week, every two weeks, every three weeks, every four weeks, every month, every two months, every three months, every four months, every six months, every seven months, every eight months, every nine months, every 10 months, every 11 months, every year, every two years, every three years, every four years, every five years, every six years, every seven years, every eight years, every nine years, every 10 years, every 11 years, every 12 years, every 13 years, every 14 years, every 15 years, every 16 years, every 17 years, every 18 years, every 19 years, every 20 years, every 21 years, every 22 years, every 23 years, every 24 years, every 25 years, every 26 years, every 27 years, every 28 years, every 29 years, every 30 years, every 35 years, every 40 years, every 45 years, or every 50 years.

As disclosed herein, human cells do not generally express ZSCAN protein in any significant amount. As such, agents of the present disclosure that increases Zscan4 expression increase Zscan4 protein expression in treated cells. In some embodiments, treating a human cell with an agent of the present disclosure that increases Zscan4 expression may result in at least a 1.5 fold increase to at least a 1,000,000 fold increase in Zscan4 protein expression.

Accordingly, in certain embodiments, an agent of the present disclosure that increases Zscan4 expression in human cells, increases Zscan4 protein expression by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, at least 10 fold, at least 100 fold, at least 200 fold, at least 300 fold, at least 400 fold, at least 500 fold, at least 600 fold, at least 700 fold, at least 800 fold, at least 900 fold, at least 1,000 fold, at least 2,000 fold, at least 3,000 fold, at least 4,000 fold, at least 5,000 fold, at least 6,000 fold, at least 7,000 fold, at least 8,000 fold, at least 9,000 fold, at least 10,000 fold, at least 25,000 fold, at least 50,000 fold, at least 75,000 fold, at least 100,000 fold, at least 125,000 fold, at least 150,000 fold, at least 175,000 fold, at least 200,000 fold, at least 225,000 fold, at least 250,000 fold, at least 275,000 fold, at least 300,000 fold, at least 325,000 fold, at least 350,000 fold, at least 375,000 fold, at least 400,000 fold, at least 425,000 fold, at least 450,000 fold, at least 475,000 fold, at least 500,000 fold, at least 525,000 fold, at least 550,000 fold, at least 575,000 fold, at least 600,000 fold, at least 625,000 fold, at least 650,000 fold, at least 675,000 fold, at least 700,000 fold, at least 725,000 fold, at least 750,000 fold, at least 775,000 fold, at least 800,000 fold, at least 825,000 fold, at least 850,000 fold, at least 875,000 fold, at least 900,000 fold, at least 925,000 fold, at least 950,000 fold, at least 975,000 fold, or at least 1,000,000 fold, for example, relative to Zscan4 protein expression in a human cell that has not been contacted with the agent.

Any method known in the art and disclosed herein for determining Zscan4 protein expression in a cell, or for quantifying the number of proteins (i.e., protein stoichiometry) per cell may be used. In some embodiments, not all cells in a cell population or subject treated with the agent will be affected by the agent. For example, in embodiments where the agent is a viral vector expressing Zscan4, the viral vector may not infect every cell in a treated cell population or subject. As such, a "fold increase" in Zscan4 protein expression as used herein refers to the average increase in Zscan4 protein expression in the cells in a treated cell population or subject that are affected by the agent. For example in embodiments where the agent is a viral vector, a fold increase in Zscan4 protein expression may refer to the average increase in Zscan4 protein expression in infected cells of a treated cell population or subject.

Zscan4 Polynucleotides

In some embodiments, an agent of the present disclosure that increases expression of Zscan4 is a nucleic acid molecule including a nucleic acid sequence encoding a Zscan4 protein. A polynucleotide may refer to a nucleic acid sequence (such as a linear sequence) of any length. Therefore, a polynucleotide includes oligonucleotides, and also gene sequences found in chromosomes. An oligonucleotide is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Nucleic acid molecules encoding a Zscan4 polypeptide are termed Zscan4 polynucleotides or nucleic acid molecules. These polynucleotides include DNA, cDNA and RNA sequences, such as mRNA sequences, which encode a Zscan4. It is understood that all polynucleotides encoding a Zscan4 polypeptide are also included herein, as long as they encode a polypeptide with a recognized Zscan4 activity, such as the ability to modulate genome stability or telomere length. Genome stability may refer to the ability of a cell to faithfully replicate DNA and maintain integrity of the DNA replication machinery. Long telomeres are thought to provide a buffer against cellular senescence and be generally indicative of genome stability and overall cell health. Chromosome stability (e.g., few mutations, no chromosomal rearrangements or change in number) is also associated with genome stability. A loss of genome stability is associated with cancer, neurological disorders and premature aging. Signs of genome instability include elevated mutation rates, gross chromosomal rearrangements, alterations in chromosome number, and shortening of telomeres.

Zscan4 nucleic acid sequences have been previously described in the art (see, for example, WO 2008/118957, the disclosure of which is herein incorporated by reference; Falco et al., Dev. Biol. 307(2):539-550, 2007; and Carter et al., Gene Expr. Patterns. 8(3):181-198, 2008). Zscan4 nucleic acids may include, without limitation, any one of a group of mouse Zscan4 genes exhibiting 2-cell embryonic stage- or ES cell-specific expression (including Zscan4a, Zscan4b, Zscan4c, Zscan4d, Zscan4e and Zscan4f), the human ortholog ZSCAN4, or any other species ortholog of Zscan4.

As disclosed herein, the nucleotide sequence of the mouse Zscan4a gene is set forth in SEQ ID NO: 1, the nucleotide sequence of the mouse Zscan4b gene is set forth in SEQ ID NO: 2, the nucleotide sequence of the mouse Zscan4c gene is set forth in SEQ ID NO: 3, the nucleotide sequence of the mouse Zscan4d gene is set forth in SEQ ID NO: 4, the nucleotide sequence of the mouse Zscan4e gene is set forth in SEQ ID NO: 5, and the nucleotide sequence of the mouse Zscan4f gene is set forth in SEQ ID NO: 6. Additionally, the nucleotide sequence of the human ZSCAN4 gene is set forth in SEQ ID NO: 7.

Zscan4 nucleic acid sequences from other species are publically available, including dog Zscan4 (GenBank Accession Nos. XM.sub.—541370.2 and XM.sub.—848557.1; SEQ ID NO: 8); cow Zscan4 (GenBank Accession No. XM.sub.—001789250.1; SEQ ID NO: 9); horse Zscan4 (GenBank Accession No. XM.sub.—001493944.1; SEQ ID NO: 10); gorilla Zscan4 (nucleotide sequence of UniProt Accession No. A1YEQ9; SEQ ID NO: 21); bonobo Zscan4 (nucleotide sequence of UniProt Accession No. A1YFX5; SEQ ID NO: 22); Bornean orangutan Zscan4 (nucleotide sequence of UniProt Accession No. A2T7G6; SEQ ID NO: 23); Sumatran orangutan (nucleotide sequence of UniProt Accession No. H2P0E3; SEQ ID NO: 24); panda Zscan4 (nucleotide sequence of UniProt Accession No. G1LE29; SEQ ID NO: 25); pig Zscan4 (nucleotide sequence of UniProt Accession No. F1SCQ2; SEQ ID NO: 26); Northern white-cheeked gibbon Zscan4 (nucleotide sequence of UniProt Accession No. G1RJD4; SEQ ID NO: 27); Rhesus macaque Zscan4 (nucleotide sequence of UniProt Accession No. F7GH55; SEQ ID NO: 28); guinea pig Zscan4 (nucleotide sequence of UniProt Accession No. H0V5E8; SEQ ID NO: 29); and Thirteen-lined ground squirrel (nucleotide sequence of UniProt Accession No. I3N7T3; SEQ ID NO: 30). Each of the above-listed GenBank Accession numbers is herein incorporated by reference as it appears in the GenBank database on Aug. 11, 2009. Each of the above-listed UniProt Accession numbers is herein incorporated by reference as it appears in the UniProt database on Mar. 15, 2013.

In a specific example, Zscan4 is mouse Zscan4c or human ZSCAN4. Zscan4 nucleic acids may also include, without limitation, Zscan4 nucleic acids, or homologs thereof, that encode Zscan4 polypeptides that are capable of increasing genome stability and/or increasing telomere length.

Fragments and variants of Zscan4 polynucleotides can readily be prepared by one of skill in the art using molecular techniques. In some embodiments, a fragment of a Zscan4 polynucleotide includes at least 250, at least 500, at least 750, at least 1000, at least 1500, or at least 2000 consecutive nucleic acids of a Zscan4 polynucleotide. In some embodiments, a fragment of Zscan4 is a fragment that confers a function of Zscan4 when expressed in a cell of interest, such as, but not limited to, increasing genome stability and/or increasing telomere length.

Minor modifications of the Zscan4 polynucleotide sequences may result in expression of peptides which have substantially equivalent activity as compared to the unmodified counterpart polynucleotides described herein. Such modifications may be deliberate, as by site-directed mutagenesis, or may be spontaneous. All of the polynucleotides produced by these modifications are included herein.

Zscan4 polynucleotides may include recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA. A recombinant nucleic acid or polypeptide is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

In some embodiments, a degenerative variant of any of the Zscan4 polynucleotides described herein may be used in the methods of the present disclosure. A degenerative variant may refer to a polynucleotide encoding a polypeptide, such as a Zscan4 polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

A Zscan4 coding sequence may be operably linked to a heterologous promoter to direct transcription of the Zscan4 coding nucleic acid sequence. A promoter may refer to nucleic acid control sequences which direct transcription of a nucleic acid. A promoter includes necessary nucleic acid sequences near the start site of transcription. A promoter also optionally includes distal enhancer or repressor elements. A constitutive promoter is a promoter that is continuously active and is not subject to regulation by external signals or molecules. In contrast, the activity of an inducible promoter is regulated by an external signal or molecule (for example, a transcription factor). A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and where necessary to join two protein coding regions, in the same reading frame. A heterologous polypeptide or polynucleotide refers to a polypeptide or polynucleotide derived from a different source or species. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In one example, the promoter is a constitutive promoter, such as the CAG-promoter (Niwa et al., Gene 108(2):193-9, 1991), or the phosphoglycerate kinase (PGK)-promoter. In some embodiments, the promoter is an inducible promoter such as a tetracycline-inducible promoter (Masui et al., Nucleic Acids Res. 33:e43, 2005). Other exemplary promoters that can be used to drive Zscan4 expression include but are not limited to: lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, and the promoter of the yeast alpha-mating factors. In some embodiments, a native Zscan4 promoter is used. Zscan4 polynucleotides of the present disclosure may be under the control of a constitutive promoter, an inducible promoter, or any other suitable promoter described herein or other suitable promoter that will be readily recognized by one skilled in the art.

The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

The terms "identical" or percent "identity," in the context of two or more sequences (e.g., nucleic acid sequences or amino acid sequences), may refer to two or more sequences or subsequences that are the same. Two sequences are substantially identical if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastp, the default parameters are Gap opening penalty=11 and Gap extension penalty=1. For blastn, the default parameters are Gap opening penalty=5 and Gap extension penalty=2.

A comparison window may include reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8):2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17): 3389-3402 and Altschul et al. (1990) J. Mol Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word length of 3, and expectation (E) of 10, and the BLOSUM62 scoring matrix [see Henikoff and Henikoff, (1992) Proc Natl Acad Sci USA 89(22):10915-10919] alignments (B) of 50, expectation (E) of 10, M=5, N=−4, and a comparison of both strands. For nucleotide sequences, the BLASTN program uses as defaults a word length (W) of 11, an expectation (E) or 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

One indication that two nucleic acid molecules are closely related is that the two molecules hybridize to each other under stringent conditions. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

Moreover, one indication that two polypeptides are substantially identical is that the first polypeptide is immunologically cross-reactive with antibodies raised against the second polypeptide. Thus, a polypeptide is typically substantially identical to a second polypeptide, for example, where the two peptides differ only by conservative substitutions.

Various aspects of the present disclosure relate to isolated entities, such as isolated nucleic acids or synthetic mRNA molecules. An isolated nucleic acid has been substantially separated or purified away from other nucleic acid sequences and from the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. Similarly, isolated proteins have been substantially separated or purified from other proteins of the cells of an organism in which the protein naturally occurs, and encompasses proteins prepared by recombination expression in a host cell as well as chemically synthesized proteins. Similarly, isolated cells have been substantially separated away from other cell types.

Accordingly, in certain embodiments, the polynucleotides of the present disclosure include sequences that are degenerate as a result of the genetic code. There are 20 natural amino acids, most of which are specified by more than one codon. Therefore, all degenerate nucleotide sequences are included as long as the amino acid sequence of the Zscan4 polypeptide encoded by the nucleotide sequence is functionally unchanged. A Zscan4 polynucleotide encodes a Zscan4 polypeptide, as disclosed herein. Exemplary polynucleotide sequences encoding Zscan4 polypeptides may include, for example, the nucleotide sequence from any one of SEQ ID NOs: 1-10 and 21-30. Further, non-human homologs of human ZSCAN4 may be used to increase Zscan4 expression in a human subject in accordance with any of the methods of the present disclosure, as expression of such non-human Zscan4 homologs is transient, and as such would not lead to an adverse immunogenic response in the human subject.

In some embodiments, the Zscan4 polynucleotide encoding a Zscan4 polypeptide is a human ZSCAN4 polynucleotide or a homolog thereof. In some embodiments, the Zscan4 polynucleotide encoding a Zscan4 polypeptide is a mouse Zscan4 polynucleotide or a homolog thereof. In some embodiments, the Zscan4 polynucleotide encoding a Zscan4 polypeptide is a Zscan4a polynucleotide, a Zscan4b polynucleotide, a Zscan4c polynucleotide, a Zscan4d polynucleotide, a Zscan4e polynucleotide, or a Zscan4f polynucleotide. In some embodiments, the Zscan4 polynucleotide encoding a Zscan4 polypeptide is a dog Zscan4 polynucleotide, a cow Zscan4 polynucleotide, a horse Zscan4 polynucleotide, or a homolog thereof. In some embodiments, the Zscan4 polynucleotide encoding a Zscan4 polypeptide includes a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleotide sequence from any one of SEQ ID NO: 1-10 and 21-30.

In certain embodiments, the Zscan4 polynucleotide encoding a Zscan4 polypeptide is a human ZSCAN4 polynucleotide or homolog thereof. In some embodiments, the Zscan4 polynucleotide encoding a Zscan4 polypeptide includes a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleotide sequence of SEQ ID NO: 7.

Methods of Introducing Zscan4 Polynucleotides into Human Cells

In some embodiments, Zscan4 polynucleotides are introduced into human cells. Introducing a nucleic acid molecule or a protein into a cell encompasses any means of delivering the nucleic acid molecule or protein into the cell. For example, nucleic acid molecules can be transfected, transduced or electroporated into a cell. Delivery of proteins into cells can be achieved, for example, by fusing the protein to a cell-penetrating peptide, such as a peptide with a protein transduction domain (e.g., HIV-1 Tat), or a poly-arginine peptide tag (Fuchs and Raines, *Protein Science* 14:1538-1544, 2005). Protein transduction domains may refer to small cationic peptides that facilitate entry of larger molecules (proteins, nucleic acid molecules etc.) into a cell by a mechanism that is independent of classical endocytosis. A poly-arginine peptide tag may refer to a short peptide (generally 7 to 11 residues) comprised of arginine residues that facilitates delivery of larger molecules (such as proteins and nucleic acid molecules) into cells (see, for example, Fuchs and Raines, *Protein Science* 14:1538-1544, 2005).

Introduction of Zscan4 polynucleotides into human cells may involve using a viral vector (such as integrating or non-integrating viral vectors) or a plasmid vector, delivery of mRNA molecules encoding the Zscan4 polynucleotides, or direct delivery of the Zscan4 proteins. Each of these methods has been described in the art and is therefore within the capabilities of one of skill in the art. A brief summary of each method that can be used to deliver Zscan4 to a human cell is provided herein. A vector may refer to a nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). For example, an expression vector contains the necessary regulatory sequences to allow transcription and translation of inserted gene or genes. A vector may also include one or more selectable marker genes and other genetic elements known in the art. Vectors may include, for example, virus vectors and plasmid vectors.

Zscan4 Promoter Sequences and Expression Vectors

An expression vector including a Zscan4 promoter sequence operably linked to a nucleic acid sequence encoding a heterologous polypeptide (such as a reporter gene) can be used to identify cells that express Zscan4. Methods of detecting expression of the reporter gene vary depending upon the type of reporter gene and are well known in the art. For example, when a fluorescent reporter is used, detection of expression can be achieved by FACS or fluorescence microscopy. Identification of human cells expressing Zscan4 can be achieved with alternative methods, including, but not limited to, using antibodies specific for Zscan4 or by in situ hybridization.

In some embodiments, a heterologous nucleic acid sequence (such as a reporter molecule) is expressed under the control of a Zscan4 promoter (for example in a vector). A Zscan4 promoter may be a promoter sequence that regulates the expression of an endogenous Zscan4 polynucleotide described herein. Identification of Zscan4 promoters is well within the capabilities of one skilled in the art and in view of the present disclosure. Other expression control sequences, including appropriate enhancers, transcription terminators, a start codon (i.e., ATG) in front of a protein-encoding gene, splicing signals for introns, and stop codons can be included with the Zscan4 promoter in an expression vector. Generally the promoter includes at least a minimal sequence sufficient to direct transcription of a heterologous nucleic acid sequence. In some embodiments, the heterologous nucleic acid sequence encodes a reporter molecule.

In some embodiments, a heterologous nucleic acid sequence (such as a reporter molecule) is incorporated into a subject's genomic DNA, such as by homologous recombination. For example, the coding sequence for GFP could be inserted into the coding region of Zscan4, or could replace the coding region of Zscan4, such that GFP is expressed in the same manner as endogenous Zscan4. Gene "knock-in" methods by homologous recombination are well known in the art.

The heterologous protein encoded by the heterologous nucleic acid sequence is typically a reporter molecule, such as a marker, an enzyme, a fluorescent protein, a polypeptide that confers antibiotic resistance to the cell or an antigen that can be identified using conventional molecular biology procedures. Reporter molecules can be used to identify a cell, or a population of cells, of interest, such as human cells that have been contacted with an agent that increases Zscan4 expression in a human cell. In some embodiments, the heterologous protein is a fluorescent marker (such as a green fluorescent protein, or a variant thereof, e.g. Emerald (Invitrogen, Carlsbad, Calif.)) an antigenic marker (such as human growth hormone, human insulin, human HLA antigens); a cell-surface marker (such as CD4, or any cell surface receptor); or an enzymatic marker (such as lacZ, alkaline phosphatase). Expression of the reporter gene indicates the cell expresses Zscan4. Methods of detecting expression of the reporter gene vary depending upon the type of reporter gene and are well known in the art. For example, when a fluorescent reporter is used, detection of expression can be achieved by FACS or fluorescence microscopy.

Expression vectors typically contain an origin of replication as well as specific genes which allow phenotypic selection of the transformed cells, such as an antibiotic resistance gene. Vectors suitable for use herein are well known in the art, including viral vectors and plasmid vectors (such as those described herein). In some embodiments, an enhancer is located upstream of the Zscan4 promoter, but enhancer elements can generally be located anywhere on the vector and still have an enhancing effect. However, the amount of increased activity will generally diminish with distance. Additionally, two or more copies of an enhancer sequence can be operably linked one after the other to produce an even greater increase in promoter activity.

Expression vectors including a Zscan4 promoter can be used to transfect host cells, such as, for example, human cells. Biologically functional viral and plasmid DNA vectors capable of expression and replication in a host are known in the art, and can be used to transfect any cell of interest. A host cell may refer to cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

A transfected cell may refer to a host cell into which (or into an ancestor of which) has been introduced a nucleic acid molecule (e.g., DNA molecule), such as a DNA molecule including a Zscan4 promoter element. The process of transfecting or transfection may refer to the process of introducing a nucleic acid into a cell or tissue. Transfection can be achieved by any one of a number of methods, such as, but not limited to, liposomal-mediated transfection, electroporation and injection. Transfection of a host cell with a recombinant nucleic acid molecule may be carried out by conventional techniques as are well known to those skilled in the art. Transfection may include liposomal-mediated transfection, electroporation, injection or any other suitable technique for introducing a nucleic acid molecule into a cell.

Viral Vectors

In some embodiments, the vectors used in the methods of the present disclosure are viral vectors. Various viral vectors are known in the art and are described herein.

Paramyxoviruses may be used in the methods of the present disclosure. A paramyxovirus vector may include, without limitation, a vector (or carrier) that is derived from the Paramyxovirus and that is used for gene transfer, such as a Zscan4 polynucleotide, to host cells, such as human cells. The paramyxovirus vector may be ribonucleoprotein (RNP) or a virus particle having infectivity. Infectivity may refer to the ability of a paramyxovirus vector to transfer, through its cell adhesion and membrane fusion abilities, a gene contained in the vector to cells to which the vector is adhered. The paramyxovirus vector may have replication ability or may be a defective vector without the replication ability. Replication ability may refer to the ability of paramyxovirus vectors to replicate and produce infective virus particles in host cells infected with the virus vectors. (See e.g. US 2004/0005296).

A paramyxovirus is a virus of the Paramyxoviridae family or a derivative thereof. Paramyxoviruses may include, without limitation, viruses belonging to the Paramyxoviridae such as Sendai virus, Newcastle disease virus, Mumps virus, Measles virus, Respiratory syncytial virus, rinderpest virus, distemper virus, simian parainfluenza virus (SV5), and type I, II, and III human parainfluenza virus. A viral vector used herein may be based on a virus of the genus Paramyxovirus or a derivative thereof. A viral vector used herein may be based on a variety of paramyxoviruses including, without limitation, type I human parainfluenza virus (HPI-V-1), type III human parainfluenza virus (HPIV-3), type III bovine parainfluenza virus (BPIV-3), Sendai virus (also referred to as "type I mouse parainfluenza virus"), or type x simian parainfluenza virus (SPIV-10). These viruses may be naturally occurring, wild-type, mutant, laboratory-passaged, or artificially constructed strains. Incomplete viruses such as, for example, the DI particle (Willenbrink W. and Neubert W. J., J. Virol., 1994, 68, 8413-8417) and synthesized oligonucleotides may also be utilized as a material for generating a paramyxovirus viral vector used herein. (See e.g. US 2004/0005296).

Genes encoding proteins of a paramyxovirus include NP, P, M, F, HN, and L genes. The NP, P, M, F, HN, and L genes represent those encoding the nucleocapsid protein, phosphoprotein, matrix protein, fusion protein, hemagglutinin-neuraminidase, and large protein, respectively. The NP gene may also be indicated as the N gene. The aforementioned paramyxovirus proteins are well known in the art. For instance, the accession numbers of each gene of the Sendai virus, for example, classified as a Respirovirus of Paramyxoviridae in the nucleotide sequence database, are M29343, M30202, M30203, M30204, M51331, M55565, M69046, and X17218 for NP gene; M30202, M30203, M30204, M55565, M69046, X00583, X17007, and X17008 for P gene; D11446, K02742, M30202, M30203, M30204, M69046, U31956, X00584, and X53056 for M gene; D00152, D11446, D17334, D17335, M30202, M30203, M30204, M69046, X00152, and X02131 for F gene; D26475, M12397, M30202, M30203, M30204, M69046, X00586, X02808, and X56131 for HN gene; and D00053, M30202, M30203, M30204, M69040, X00587, and X58886 for L gene. (See e.g. US 2004/0005296). Note that paramyxovirus-based vectors, such as Sendai virus-based vectors, used herein may include modifications, such as deletions of endogenous viral proteins.

Paramyxovirus-based viral vectors are useful expression of a nucleic acid in a host cell. Since paramyxovirus vectors are not pathogenic in humans, they can be suggested to be preferably utilized in clinical trials of human gene therapy in view of safety. It is a major obstacle in high efficient gene transfer that, in most cases, introduced DNA must be transported into the nucleus or nuclear membrane must be eliminated for the expression of an exogenous gene via plasmid DNA or such. In the case of Sendai virus, however, expression of an exogenous gene is driven by both cellular tubulin and its RNA polymerase (L protein) in the cytoplasm when viruses replicate. This suggests that the Sendai virus does not interact with chromosomes of host cells, which avoids risks such as cancerization and immortalization of cells. Furthermore, the Sendai virus is known to be pathogenic in rodents causing pneumonia, but not in humans, which is supported by studies showing that the intranasal administration of the wild type Sendai virus does not do harm in nonhuman primates (Hurwitz J. L. et al., Vaccine, 1997, 15, 533-540). These features suggest that Sendai virus vector can be utilized in human therapy, and further, support the notion that Sendai virus vectors can be a promising tool, in particular for use in contacting a human cell with an agent that increases Zscan4 expression in a human cell. (See e.g. US 2004/0005296). Accordingly, in certain embodiments, the virus vector is a Sendai virus vector. In some embodiments, the Sendai vector is a temperature-sensitive Sendai vector. For example, the TS15 temperature-sensitive Sendai vector is functional at 35° C., but can be inactivated when cultured at 37° C. (See e.g., Ban et al., *Proc Natl Acad Sci USA*. 2011; 108(34):14234-14239). Examples of further temperature-sensitive Sendai vectors include, without limitation, the TS7 and the TS13 Sendai vectors, which are functional at 32° C., 35° C., and 37 C; but can be inactivated when cultured at 38° C. or 39° C. (See e.g., Ban et al., *Proc Natl Acad Sci USA*. 2011; 108(34):14234-14239). Any other variant Sendai vector known in the art may also be used to express a Zscan4 of the present disclosure.

Further, retrovirus vectors (e.g., Moloney murine leukemia virus (MMLV)-based vectors) may also be used herein (See e.g. Takahashi et al., *Cell* 126:663-666, 2006; Takahashi et al., *Cell* 31:861-872, 2007; Okita et al., *Nature* 313-317, 2007; Park et al., *Nature* 451:141-146; U.S. Patent Application Publication No. 2009/0047263). Studies utilizing lentivirus-based vectors (Brambrink et al., *Cell Stem Cell* 2:151-159, 2008; Wernig et al., *Nat Biotechnol* 26:916-924, 2008; Stadtfeld et al., *Science* 322:945-949, 2008) demonstrated the advantage of these vectors as being able to infect both dividing and non-dividing cells, thereby improving the rate of cell transduction. In addition, lentiviruses can be pseudotyped to expand viral tropism. For example, pseudotyping with vesicular stomatitis virus glycoprotein (VSVg) enables infection of a wide range of cell types (Lai et al., *J Assist Reprod Genet* 28(4):291-301, 2011). Lentiviruses also allow for both constitutive and inducible expression of the proteins. Examples of drug-inducible lentivirus expression systems are described by Hockmeyer et al. (*Cell Stem Cell* 3:346-353, 2008) and Wernig et al. (*Nat Biotechnol* 26:916-924, 2008).

Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980, 289).

Non-integrating viral vectors, such as adenovirus vectors, have also been used to deliver nucleic acid molecules encoding proteins to cells. For example adenovirus vectors, which remain in episomal form in cells, have been successfully used to deliver proteins into mouse fibroblasts and liver cells (Stadtfeld et al., *Science* 322:945-949, 2008).

In some embodiments, vectors containing the promoter and enhancer regions of the SV40 or long terminal repeat (LTR) of the Rous Sarcoma virus and polyadenylation and splicing signal from SV40 (Mulligan and Berg, 1981, Proc. Natl. Acad. Sci. USA 78:2072-6; Gorman et al., 1982, Proc. Natl. Acad. Sci. USA 78:6777-81) are used. In some embodiments, the vector is a viral vector, such as an adenoviral vector, an adeno-associated virus (AAV), such as described in U.S. Pat. No. 4,797,368 (Carter et al.) and in McLaughlin et al. (J. Virol. 62:1963-73, 1988) and AAV type 4 (Chiorini et al. J. Virol. 71:6823-33, 1997) and AAV type 5 (Chiorini et al. J. Virol. 73:1309-19, 1999), or retroviral vector (such as the Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus). Other viral transfection systems may also be utilized, including Vaccinia virus (Moss et al., 1987, Annu. Rev. Immunol. 5:305-24), Bovine Papilloma virus (Rasmussen et al., 1987, Methods Enzymol. 139:642-54) or members of the herpes virus group such as Epstein-Ban virus (Margolskee et al., 1988, Mol. Cell. Biol. 8:2837-47). In addition, vectors may contain antibiotic selectable markers (such as neomycin, hygromycin or mycophenolic acid) to permit selection of transfected cells that exhibit stable, long-term expression of the vectors (and therefore the Zscan4 nucleic acid).

The vectors can be maintained in the cells as episomal, freely replicating entities by using regulatory elements of viruses such as papilloma (Sarver et al., 1981, Mol. Cell. Biol. 1:486) or Epstein-Barr (Sugden et al., 1985, Mol. Cell. Biol. 5:410). Alternatively, one can also produce cell lines that have integrated the vector into genomic DNA. Both of these types of cell lines produce the gene product on a continuous basis. One of skill in the art can also produce cell lines that have amplified the number of copies of the vector (and therefore of the cDNA as well) to create cell lines that can produce high levels of the gene product.

Plasmid Vectors

In some instances, it is desirable to use non-viral vectors, such as to avoid integration into the host cell genome. Thus, Zscan4-encoding polynucleotides can be delivered to a human cell using one or more plasmid vectors. Plasmid vectors are episomally maintained and generally exhibit a short duration of gene expression (Lai et al., *J Assist Reprod Genet* 28(4):291-301, 2011). As one example, Okita et al. (Science 322:949-953, 2008) describe the use of the pCX plasmid, containing a CAG promoter, for the expression of proteins in somatic cells.

Episomal plasmid vectors are a further option for introducing Zscan4-encoding polynucleotides into a human cell. Episomal plasmid vectors are capable of replicating themselves autonomously as extrachromosomal elements, and therefore exhibit prolonged gene expression in target cells. An episomal plasmid vector derived from the Epstein Barr virus (oriP/EBNA1) has been used to express proteins in human somatic cells (Yu et al., *Science* 324:797-801, 2009).

Selection of an appropriate vector is well within the capabilities of one of skill in the art. Expression vectors typically contain an origin of replication, a promoter, and optionally include specific genes to allow for phenotypic selection of the transformed cells (e.g. an antibiotic resistance cassette). Generally, the expression vector will include a promoter. The promoter can be inducible or constitutive. The promoter can also be tissue specific. Exemplary promoters include the CAG promoter, thymidine kinase promoter (TK), metallothionein I, polyhedron, neuron specific enolase, tyrosine hydroxylase, beta-actin, CMV immediate early promoter, or other promoters. Optionally, an enhancer element is also included, and can generally be located anywhere on the vector and still have an enhancing effect on gene expression.

Plasmid vectors can be introduced into human cells using any suitable method. In some embodiments, the vector is delivered to a cell by transfection using a lipid of cationic polymer. In particular examples, the transfection reagent is LIPOFECTAMINE™, or a similar reagent. In other examples, delivery is achieved using the nucleofection transfection technology (Amaxa, Cologne, Germany). This technology is based on an electroporation technique using the NUCLEOFECTOR™ delivery device to introduce DNA directly into the host cell nucleus (Lakshmipathy et al., *Stem Cells* 22:531-543, 2004). In yet another example, the transfection reagent includes poly-β-amino esters.

The transfer of DNA into human or other mammalian cells is a conventional technique. For example, an isolated Zscan4 nucleic acid sequence (for example as a naked DNA or as part of an expression vector) can be introduced into the recipient cells for example by precipitation with calcium phosphate (Graham and vander Eb, 1973, Virology 52:466) or strontium phosphate (Brash et al., 1987, Mol. Cell. Biol. 7:2013), electroporation (Neumann et al., 1982, EMBO J. 1:841), lipofection (Felgner et al., 1987, Proc. Natl. Acad. Sci. USA 84:7413), DEAE dextran (McCuthan et al., 1968, J. Natl. Cancer Inst. 41:351), microinjection (Mueller et al., 1978, Cell 15:579), protoplast fusion (Schafner, 1980, Proc. Natl. Acad. Sci. USA 77:2163-7), or pellet guns (Klein et al., 1987, Nature 327:70).

Excision Strategies

Excision of exogenous polynucleotides from genomic integration sites may be desirable. Two excision-based methods have been previously described, CreloxP recombination and piggyBac transposition. Soldner et al. (*Cell* 136:964-977, 2009) described the use of the Cre-lox system. This strategy included positioning a loxP site in the 3' LTR of a lentivirus vector that contained a Dox-inducible minimal CMV promoter to drive expression of the reprogramming factors. During proviral replication, loxP was duplicated into the 5' LTR, resulting in genomic integration of the reprogramming factors flanked by two loxP sites. Transient expression of Cre-recombinase resulted in excision of the floxed reprogramming factors.

The piggyBac transposon is capable of excising itself without leaving any remnants of exogenous DNA in the cell genome (Elick et al., *Genetica* 98:33-41, 1996; Fraser et al., *Insect Mol Biol* 5:141-151, 1996). Using this method, more than two proteins have been successfully produced in human cells by delivery of a polycistronic construct carrying genes linked with a 2A peptide linker positioned between the piggyBac transposon 5' and 3' terminal repeats. Precise excision of the integrated reprogramming genes is observed upon expression of the transposase (Kaji et al., *Nature* 458:771-775, 2009; Wang et al., *Proc Natl Acad Sci USA* 105:9290-9295, 2008; Yusa et al., *Nat Methods* 6:363-369, 2009).

mRNAs

Another strategy for introducing Zscan4 into human cells is by delivery of synthetic mRNAs encoding Zscan4. It has been shown that a specific protein can be efficiently produced by transfecting synthetic mRNA encoding the protein into cells (Warren et al., *Cell Stem Cell* 7(5):618-630, 2010). In the study by Warren et al., the mRNA was modified to overcome innate antiviral responses. Transfection of mRNAs was carried out repeatedly—once a day for up to a few weeks to compensate the transient nature of this method, because mRNAs were quickly degraded in the cells. This particular feature may be advantageous for Zscan4, whose expression is required only for a short time (e.g., in the order of hours and days) to achieve the desired effects (i.e., extending telomeres and increasing genome stability). In certain embodiments, synthetic mRNAs encoding Zscan4 are encapsulated in a viral envelope. Preferably, the viral envelope coating contains envelope proteins that recognize cell surface receptors, and as such increase the efficiency of delivery of the synthetic Zscan4 mRNAs into the cells. In certain embodiments, synthetic mRNAs encoding Zscan4 are encapsulated in nanoparticle or liposomes coated with viral envelope proteins. Any suitable viral envelope known in the art may be used. In some embodiments, the viral envelope is a Sendai virus envelope. Methods of encapsulating polynucleotides, such as synthetic mRNAs, in viral envelopes or viral envelope proteins are well known in the art.

Cells Including Zscan4 Polynucleotides

Further provided herein are isolated cells containing a Zscan4 nucleic acid molecule or Zscan4-containing vector as described herein. In some embodiments, the cell is a human cell. The origin of the human cell may be from any suitable species. The human cell may include any type of human cell described herein.

Zscan4 Polypeptides

In certain embodiments, an agent of the present disclosure that increases expression of Zscan4 is a Zscan4 polypeptide. A polypeptide may refer to a polymer in which the monomers are amino acid residues which are joined together through amide bonds. When the amino acids are alpha-amino acids, either the L-optical isomer or the D-optical isomer can be used, the L-isomers being preferred. The terms "polypeptide or "protein" are intended to encompass any amino acid sequence and include modified sequences such as glycoproteins. The term "polypeptide" is specifically intended to cover naturally occurring proteins, as well as those which are recombinantly or synthetically produced.

Various Zscan4 polypeptides are known in the art and may be used in the methods described herein. One skilled in the art will appreciate that the various Zscan4 polypeptides described herein that retain Zscan4 activity, such as the ability to increase telomere length and/or genome stability in a cell, may be used in the methods described herein.

Exemplary Zscan4 polypeptides are provided herein. For example, the amino acid sequence of the mouse Zscan4a polypeptide is set forth in SEQ ID NO: 11, the amino acid sequence of the mouse Zscan4b polypeptide is set forth in SEQ ID NO: 12, the amino acid sequence of the mouse Zscan4c polypeptide is set forth in SEQ ID NO: 13, the amino acid sequence of the mouse Zscan4d polypeptide is set forth in SEQ ID NO: 14, the amino acid sequence of the mouse Zscan4e polypeptide is set forth in SEQ ID NO: 15, and the amino acid sequence of the mouse Zscan4f polypeptide is set forth in SEQ ID NO: 16. Additionally, the amino acid sequence of the human ZSCAN4 polypeptide is set forth in SEQ ID NO: 17.

Zscan4 amino acid sequences from various other species are publically available, including dog Zscan4 (GenBank Accession Nos. XP.sub.—541370.2 and XP.sub.—853650.1; SEQ ID NO: 18); cow Zscan4 (GenBank Accession No. XP.sub.—001789302.1; SEQ ID NO: 19); horse Zscan4 (GenBank Accession No. XP.sub.—001493994.1; SEQ ID NO: 20); gorilla Zscan4 (UniProt Accession No. A1YEQ9; SEQ ID NO: 31); bonobo Zscan4 (nucleotide sequence of UniProt Accession No. A1YFX5; SEQ ID NO: 32); Bornean orangutan Zscan4 (UniProt Accession No. A2T7G6; SEQ ID NO: 33), Sumatran orangutan Zscan4 (UniProt Accession No. H2P0E3; SEQ ID NO: 34); panda Zscan4 (UniProt Accession No. G1LE29; SEQ ID NO: 35); pig Zscan4 (UniProt Accession No. F1SCQ2; SEQ ID NO: 36); Northern white-cheeked gibbon Zscan4 (UniProt Accession No. G1RJD4; SEQ ID NO: 37); Rhesus macaque Zscan4 (UniProt Accession No. F7GH55; SEQ ID NO: 38); guinea pig Zscan4 (UniProt Accession No. H0V5E8; SEQ ID NO: 39); and Thirteen-lined ground squirrel (UniProt Accession No. 13N7T3; SEQ ID NO: 40). Each of the above-listed GenBank Accession numbers is herein incorporated by reference as it appears in the GenBank database on Aug. 11, 2009. Each of the above-listed UniProt Accession numbers is herein incorporated by reference as it appears in the UniProt database on Mar. 15, 2013.

In some embodiments, the Zscan4 polypeptide is a human ZSCAN4 polypeptide, or a homolog or ortholog thereof. In some embodiments, the Zscan4 polypeptide is a mouse Zscan4 polypeptide or a homolog or ortholog thereof. In some embodiments, the Zscan4 polypeptide is a Zscan4a polypeptide, a Zscan4b polypeptide, a Zscan4c polypeptide, a Zscan4d polypeptide, a Zscan4e polypeptide, or a Zscan4f polypeptide. In some embodiments, the Zscan4 polypeptide is a dog Zscan4 polypeptide, or a homolog or ortholog thereof. In some embodiments, the Zscan4 polypeptide is a cow Zscan4 polypeptide, or a homolog or ortholog thereof. In some embodiments, the Zscan4 polypeptide is a horse Zscan4 polypeptide, or a homolog or ortholog thereof. In some embodiments, the Zscan4 polypeptide includes an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence from any one of SEQ ID NOs: 11-20 and 31-40.

In some embodiments, the Zscan4 polypeptide is a human ZSCAN4 polypeptide or homolog or ortholog thereof. In some embodiments, the Zscan4 polypeptide includes an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 17.

Fragments and variants of a Zscan4 polypeptide can readily be prepared by one of skill in the art using molecular techniques. A polypeptide fragment may refer to a portion of a polypeptide which exhibits at least one useful epitope. The term "functional fragments of a polypeptide" refers to all fragments of a polypeptide that retain an activity of the polypeptide, such as a Zscan4. Biologically functional fragments, for example, can vary in size from a polypeptide fragment as small as an epitope capable of binding an antibody molecule to a large polypeptide capable of participating in the characteristic induction or programming of phenotypic changes within a cell, including affecting cell proliferation or differentiation. An epitope is a region of a polypeptide capable of binding an immunoglobulin generated in response to contact with an antigen. Thus, smaller peptides containing the biological activity of Zscan4, or conservative variants of Zscan4, are thus included as being of use. In some embodiments, a fragment of a Zscan4 polypeptide includes at least 50, at least 100, at least 150, at least 200, at least 250, at least 300, at least 350, at least 400, at least 450 or at least 500 consecutive amino acids of the Zscan4 polypeptide. In some embodiments, a fragment of Zscan4 is a fragment that confers a function of Zscan4 when transferred into a cell of interest, such as, but not limited to, increasing genome stability and/or increasing telomere length.

Minor modifications of the Zscan4 polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

One of skill in the art can readily produce fusion proteins including a Zscan4 polypeptide and a second polypeptide of interest. Optionally, a linker can be included between the Zscan4 polypeptide and the second polypeptide of interest. Fusion proteins include, but are not limited to, a polypeptide including a Zscan4 polypeptide and a marker protein. In some embodiments, the marker protein can be used to identify or purify a Zscan4 polypeptide. Exemplary fusion proteins include, but are not limited to, green fluorescent protein, six histidine residues, or myc and a Zscan4 polypeptide.

One skilled in the art will appreciate that such variants, fragments, and fusions of Zscan4 useful for the disclosed methods are those that retain Zscan4 activity (such as the ability to increase genome stability and increase telomere length or both in a human cell).

Various aspects of the present disclosure relate to substantially purified polypeptides. A substantially purified polypeptide may refer to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Polypeptides of the present disclosure, such as Zscan4 polypeptides, may also include conservative substitutions of the amino acids composing the polypeptide. Conservative substitutions replace one amino acid with another amino acid that is similar in size, hydrophobicity, etc. Examples of conservative substitutions are shown below:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |

-continued

| Original Residue | Conservative Substitutions |
| --- | --- |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. Thus, in several non-limiting examples, a Zscan4 polypeptide includes at most two, at most five, at most ten, at most twenty, or at most fifty conservative substitutions. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide.

In certain embodiments, Zscan4 polypeptides of the present disclosure are encapsulated in a viral envelope. Preferably, the viral envelope coating contains envelope proteins that recognize cell surface receptors, and as such increase the efficiency of delivery of the Zscan4 polypeptide into cells. In certain embodiments, Zscan4 polypeptides are encapsulated in nanoparticle or liposomes coated with viral envelope proteins. Any suitable viral envelope known in the art may be used. In some embodiments, the viral envelope is a Sendai virus envelope. Methods of encapsulating polypeptides in viral envelopes or viral envelope proteins are well known in the art.

Cells Including Zscan4 Polypeptides

Further provided herein are isolated cells containing a Zscan4 polypeptide as described herein. In some embodiments, the cell is a human cell. The origin of the human cell may be from any suitable species. The human cell may include any type of human cell described herein.

Compositions, Vectors and Cells Including a Modified Zscan4

Provided herein are isolated nucleic acid molecules encoding a modified Zscan4 protein, where the protein has been modified so that the activity of the protein is regulatable (i.e., inducible or repressible). For example, the Zscan4 protein may be a fusion protein that contains an inducible receptor or ligand bind domain. Any inducible receptor and/or ligand bind domain known in the art may be used. In some embodiments, the inducible receptor and/or ligand bind domain may include, without limitation, an estrogen receptor (ER); a mutant estrogen receptor that is sensitive to Tamoxifen or its metabolite 4-hydroxy-tamoxifen (4OHT), such as ERT or ERT2; a glucocorticoid receptor (GR) that is glucocorticoid receptor that is sensitive to mifepristone (MIFEPREX); a drug-regulatable ligand binding domain; and a steroid-inducible receptor, such as an ecdysone-inducible receptor.

In certain embodiments, isolated nucleic acid molecules of the present disclosure encode a fusion protein, wherein the fusion protein includes a Zscan4 protein fused to an ERT2 protein. ERT2 is a mutated version of the ligand binding domain of human estrogen receptor. ERT2 does not bind its natural ligand (17β-estradiol) at physiological concentrations, but is highly sensitive to nanomolar concentrations of Tamoxifen or its metabolite 4-hydroxy-tamoxifen (4OHT) (Feil et al., *Biochem Biophys Res Commun* 237(3): 752-757, 1997). A fusion protein may refer to a protein containing at least a portion of two different (heterologous) proteins. In some examples such proteins are generated by expression of a nucleic acid sequence engineered from nucleic acid sequences encoding at least a portion of two different (heterologous) proteins. To create a fusion protein, the nucleic acid sequences must be in the same reading frame and contain no internal stop codons.

In some embodiments, the nucleic acid molecule encoding the Zscan4 portion of a modified Zscan4 protein of the present disclosure, such as the Zscan4-ERT2 fusion protein, is a human ZSCAN4, mouse Zscan4c, mouse Zscan4d or mouse Zscan4f, or a functional fragment or variant thereof. The nucleic acid molecule encoding the modified Zscan4 protein, such as the Zscan4-ERT2 fusion protein, may include any Zscan4 polynucleotide, or homolog, fragment, or variant thereof described herein. Functional fragments and variants of Zscan4 include, for example, any Zscan4 fragment or variant that retains one or more biological activities of Zscan4, such as the capacity to increase pluripotency of a stem cell, promote genomic stability or increase telomere length.

In some embodiments, the nucleic acid molecule encoding the Zscan4 portion of a modified Zscan4 protein of the present disclosure, such as the Zscan4-ERT2 fusion protein, may include, for example, the nucleotide sequence from any one of SEQ ID NOs: 1-10 and 21-30. In some embodiments, the nucleic acid molecule encoding the Zscan4 portion of a modified Zscan4 protein of the present disclosure, such as the Zscan4-ERT2 fusion protein, is a mouse Zscan4 polynucleotide or a homolog thereof. In some embodiments, the nucleic acid molecule encoding the Zscan4 portion of a modified Zscan4 protein of the present disclosure, such as the Zscan4-ERT2 fusion protein, is a human ZSCAN4 polynucleotide or a homolog thereof. In some embodiments, the nucleic acid molecule encoding the Zscan4 portion of a modified Zscan4 protein of the present disclosure, such as the Zscan4-ERT2 fusion protein, is a Zscan4a polynucleotide, a Zscan4b polynucleotide, a Zscan4c polynucleotide, a Zscan4d polynucleotide, a Zscan4e polynucleotide, or a Zscan4f polynucleotide. In some embodiments, the nucleic acid molecule encoding the Zscan4 portion of a modified Zscan4 protein of the present disclosure, such as the Zscan4-ERT2 fusion protein, includes a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence from any one of SEQ ID NOs: 1-10 and 21-30.

In some embodiments, the nucleic acid molecule encoding the Zscan4 portion of a modified Zscan4 protein of the present disclosure, such as the Zscan4-ERT2 fusion protein, is a human ZSCAN4 polynucleotide or homolog thereof. In some embodiments, the nucleic acid molecule encoding the Zscan4 portion of a modified Zscan4 protein of the present disclosure, such as the Zscan4-ERT2 fusion protein, includes a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleotide sequence of SEQ ID NO: 7.

In some embodiments, the nucleic acid molecule encoding a Zscan4-fusion protein, such as the Zscan4-ERT2 fusion protein, includes a linker sequence between the Zscan4 and the inducible receptor and/or ligand bind domain sequence, such as the ERT2 coding sequence. Linkers are well known in the art and selection of an appropriate linker is well within the capabilities of one of ordinary skill in the art. A linker may refer to one or more nucleotides or amino acids that serve as a spacer between two molecules, such as between two nucleic acid molecules or two peptides (such as in a fusion protein). In some embodiments, a linker is 1 to 100 amino acids, such as 1 to 50 or 5 to 10 amino acids. In some embodiments, the linker is at least 2 amino acids (aa), at least 3, at least 5, at least 10, at least 20, at least 50 or at least 100 aa, such as 2 to 50 or 2 to 10 aa. In some embodiments, the linker includes the amino acid sequence Ala-Ser.

Also provided are vectors that include a modified Zscan4, such as Zscan4-ERT2, encoding nucleic acid molecule disclosed herein. Any suitable expression vector, such as an expression (plasmid) vector (e.g., pPyCAG-BstXI-IP), or viral vector (e.g., a paramyxovirus such as a Sendai virus, an adenovirus, adeno-associated virus, lentivirus or retrovirus vector), is contemplated. Numerous expression vectors and viral vectors are known in the art and the selection of an appropriate vector is well within the capabilities of one of ordinary skill in the art.

Further provided herein are isolated cells containing a modified Zscan4, such as a Zscan4-ERT2, nucleic acid molecule or vector as described herein. In some embodiments, the cell is a human cell. The origin of the human cell may be from any suitable species. The human cell may include any type of human cell described herein.

Compositions including a nucleic acid molecule or vector encoding a modified Zscan4 protein, such as a Zscan4-ERT2 fusion protein, are also provided herein. The compositions may further include a carrier or diluent, such as a pharmaceutically acceptable carrier or diluent. Modified Zscan4 proteins, such as Zscan4-ERT2 fusion proteins, encoded by the nucleic acid molecules and vectors described herein are further provided.

Also provided herein are recombinant modified Zscan4 proteins, such as Zscan4-ERT2 fusion proteins. In some embodiments, the recombinant modified Zscan4 protein, such as the Zscan4-ERT2 fusion protein, is human ZSCAN4, mouse Zscan4c, mouse Zscan4d or mouse Zscan4f, or a functional fragment or variant thereof. The Zscan4 portion of the modified Zscan4 protein, such as the Zscan4-ERT2 recombinant fusion protein, may include any Zscan4 polypeptide, homolog, ortholog, fragment, or variant described herein. Functional fragments and variants of Zscan4 include, for example, any Zscan4 fragment or variant that retains one or more biological activities of Zscan4, such as the capacity to increase genomic stability or increase telomere length.

In some embodiments, the Zscan4 protein portion of the modified Zscan4 protein, such as the Zscan4-ERT2 fusion protein, is a mouse Zscan4 polypeptide or a homolog or ortholog thereof. In some embodiments, the Zscan4 protein portion of the modified Zscan4 protein, such as Zscan4-ERT2 fusion protein, is a human ZSCAN4 polypeptide, or a homolog or ortholog thereof. In some embodiments, the Zscan4 protein portion of the modified Zscan4 protein, such as Zscan4-ERT2 fusion protein, is a Zscan4a polypeptide, a Zscan4b polypeptide, a Zscan4c polypeptide, a Zscan4d polypeptide, a Zscan4e polypeptide, or a Zscan4f polypeptide. In some embodiments, the Zscan4 protein portion of the modified Zscan4 protein, such as Zscan4-ERT2 fusion protein, includes an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an amino acid sequence from any one of SEQ ID Nos: 11-20 and 31-40.

In some embodiments, the Zscan4 protein portion of the modified Zscan4 protein, such as Zscan4-ERT2 fusion protein, is a human ZSCAN4 polypeptide or homolog or ortholog thereof. In some embodiments, the Zscan4 protein portion of the modified Zscan4 protein, such as Zscan4-ERT2 fusion protein, includes an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 17.

Fragments and variants of a Zscan4 protein can readily be prepared by one of skill in the art using molecular techniques. In some embodiments, a fragment of a Zscan4 protein includes at least 50, at least 100, at least 150, at least 200, at least 250, at least 300, at least 350, at least 400, at least 450 or at least 500 consecutive amino acids of the Zscan4 polypeptide. In a further embodiment, a fragment of Zscan4 is a fragment that confers a function of Zscan4, such as, but not limited to, increasing genome stability and/or increasing telomere length.

Compositions including a modified Zscan4 protein, such as Zscan4-ERT2 fusion protein, are also provided herein. The compositions may further include a carrier or diluent, such as a pharmaceutically acceptable carrier or diluent, for example saline.

Compositions, Vectors and Cells Including Zscan4-ΔC

Also provided herein are isolated nucleic acid molecules encoding a Zscan4 protein with a C-terminal truncation (referred to herein as Zscan4-ΔC). The C-terminally truncated Zscan4 includes a deletion of at least one zinc finger domain. Thus, in some embodiments, the Zscan4-ΔC protein has a deletion of one, two, three or four zinc finger domains.

In some embodiments, the nucleic acid molecule encoding the Zscan4-ΔC protein is a C-terminally truncated human ZSCAN4, mouse Zscan4c, mouse Zscan4d or mouse Zscan4f. In some embodiments, the Zscan4-ΔC protein is either human ZSCAN4 or mouse Zscan4c with a deletion of all four zinc finger domains. The nucleic acid molecule encoding the Zscan4-ΔC protein may contain a C-terminal truncation of any Zscan4 polynucleotide described herein.

In some embodiments, the Zscan4 portion of the nucleic acid molecule encoding the Zscan4-ΔC protein may include, for example, the nucleotide sequence from any one of SEQ ID Nos: 1-10 and 21-30. In some embodiments, the Zscan4 portion of the nucleic acid molecule encoding the Zscan4-ΔC protein is a mouse Zscan4 polynucleotide or a homolog thereof. In some embodiments, the Zscan4 portion of the nucleic acid molecule encoding the Zscan4-ΔC protein is a human ZSCAN4 polynucleotide or a homolog thereof. In some embodiments, the Zscan4 portion of the nucleic acid molecule encoding the Zscan4-ΔC protein is a Zscan4a polynucleotide, a Zscan4b polynucleotide, a Zscan4c polynucleotide, a Zscan4d polynucleotide, a Zscan4e polynucleotide, or a Zscan4f polynucleotide. In some embodiments, the Zscan4 portion of the nucleic acid molecule encoding the Zscan4-ΔC protein includes a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence from any one of SEQ ID Nos: 1-10 and 21-30.

In some embodiments, the Zscan4 portion of the nucleic acid molecule encoding the Zscan4-ΔC protein is a human ZSCAN4 polynucleotide or homolog thereof. In some embodiments, the Zscan4 portion of the nucleic acid molecule encoding the Zscan4-ΔC protein includes a nucleotide sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 7.

The Zscan4-ΔC nucleic acid sequences contemplated herein include sequences that are degenerate as a result of the genetic code. There are 20 natural amino acids, most of which are specified by more than one codon. Therefore, all degenerate nucleotide sequences are included as long as the amino acid sequence of the Zscan4-ΔC polypeptide encoded by the nucleotide sequence is functionally unchanged.

Also provided are vectors that include a Zscan4-ΔC encoding nucleic acid molecule disclosed herein. Any suitable expression vector, such as an expression (plasmid) vector (e.g., pPyCAG-BstXI-IP), or viral vector (e.g., a paramyxovirus such as a Sendai virus, an adenovirus, adeno-associated virus, lentivirus or retrovirus vector), is contemplated. Numerous expression vectors and viral vectors are known in the art and the selection of an appropriate vector is well within the capabilities of one of ordinary skill in the art.

Further provided herein are isolated cells containing a Zscan4-ΔC nucleic acid molecule or vector as described herein. In some embodiments, the cell is a human cell. The origin of the human cell may be from any suitable species. The human cell may include any type of human cell described herein.

Compositions including a nucleic acid molecule or vector encoding a Zscan4ΔC protein are also provided herein. The compositions may further include a carrier or diluent, such as a pharmaceutically acceptable carrier or diluent.

Zscan4-ΔC proteins encoded by the nucleic acid molecules and vectors described herein are further provided.

Also provided herein are recombinant Zscan4-ΔC proteins. In some embodiments, the recombinant Zscan4-ΔC protein is a C-terminally truncated human ZSCAN4, mouse Zscan4c, mouse Zscan4d or mouse Zscan4f. The Zscan4 portion of a recombinant Zscan4-ΔC protein may include any Zscan4 polypeptide, homolog, ortholog, fragment, or variant described herein.

In some embodiments, the Zscan4 protein portion of the recombinant Zscan4-ΔC protein is a mouse Zscan4 polypeptide or a homolog or ortholog thereof. In some embodiments, the Zscan4 protein portion of the recombinant Zscan4-ΔC protein is a human ZSCAN4 polypeptide, or a homolog or ortholog thereof. In some embodiments, the Zscan4 protein portion of the recombinant Zscan4-ΔC protein is a Zscan4a polypeptide, a Zscan4b polypeptide, a Zscan4c polypeptide, a Zscan4d polypeptide, a Zscan4e polypeptide, or a Zscan4f polypeptide. In some embodiments, the Zscan4 protein portion of the recombinant Zscan4-ΔC protein includes an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence from any one of SEQ ID Nos: 11-20 and 31-40.

In some embodiments, the Zscan4 protein portion of the recombinant Zscan4-ΔC protein is a human ZSCAN4 polypeptide or homolog or ortholog thereof. In some embodiments, the Zscan4 protein portion of the recombinant Zscan4-ΔC protein includes an amino acid sequence that is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence from SEQ ID NO: 17.

Further provided herein are isolated cells including a Zscan4-ΔC protein disclosed herein. In some embodiments, the cells are human cells. The origin of the human cell may be from any suitable species. The human cell may include any type of human cell described herein.

Compositions including a Zscan4-ΔC protein are also provided herein. The compositions may further include a carrier or diluent, such as a pharmaceutically acceptable carrier or diluent, for example saline.

Methods of Introducing Zscan4 Polypeptide into Human Cells

It is possible to introduce Zscan4 polypeptides by directly delivering the respective proteins to cells, such as human cells. Protein delivery can be accomplished using, for example, electroporation, microinjection, cationic lipids or nanoparticles according to standard methods. Alternatively, the proteins can be modified by fusion with a cell-penetrating peptide (CPP) to facilitate entry of the protein into the cell. The use of CPPs and nanoparticles is discussed in greater detail herein.

Cell-Penetrating Peptides (CPPs)

CPPs are a family of polypeptides that facilitate transduction of proteins, nucleic acids or other compounds across membranes in a receptor-independent manner (Wadia and Dowdy, *Curr. Protein Pept. Sci.* 4(2):97-104, 2003). Typically, CPPs are short polycationic sequences that can facilitate cellular uptake of compounds to which they are linked into endosomes of cells. Examples of CPPs include poly-arginine tags and protein transduction domains. Any protein transduction domain known in the art may be used. Examples of suitable protein transduction domains include, without limitation, HIV Tat, HIV Vpr, HIV Vp22, homeodomains (HD) from HD-containing proteins, and synthetic protein transduction domains.

The capacity of certain peptides to deliver proteins or nucleic acids into cells was originally described for the HIV-encoded Tat protein, which was shown to cross membranes and initiate transcription. It was then discovered that the portion of the Tat protein that was required for the transduction of the protein was only an 11 amino acid polypeptide, referred to as the Tat peptide. When fused with other proteins, the Tat peptide has been demonstrated to deliver these proteins, varying in size from 15 to 120 kDa, into cells in tissue culture (Frankel and Pabo, *Cell* 55(6): 1189-93, 1988; Green and Loewenstein, *J. Gen. Microbiol.* 134(3):849-55, 1988; Vives et al., *J. Biol. Chem.* 272(25): 16010-7, 1997; Yoon et al., *J. Microbiol.* 42(4):328-35, 2004; Cai et al., *Eur. J. Pharm. Sci.* 27(4):311-9, 2006).

Other known CPPs include PENETRATIN™, a 16 amino acid peptide derived from the third helix of the *Drosophila* Antennapedia homeobox gene (U.S. Pat. No. 5,888,762; Derossi et al., *J. Biol. Chem.* 269:10444-10450, 1994; Schwarze et al., *Trends Pharmacol. Sci.* 21:45-48, 2000); transportan, a 27 amino acid chimeric peptide comprised of 12 amino acids from the N-terminus of the neuropeptide galanin and the 14-amino acid protein mastoparan, connected via a lysine (U.S. Pat. No. 6,821,948; Pooga, *FASEB J.* 12:67-77, 1998; Hawiger, *Curr. Opin. Chem. Biol.* 3:89-94, 1999); peptides from the VP22 protein of herpes simplex virus (HSV) type 1 (Elliott et al., *Cell* 88:223-233, 1997); the UL-56 protein of HSV-2 (U.S. Pre-Grant Publication No. 2006/0099677); and the Vpr protein of HIV-1 (U.S. Pre-Grant Publication No. 2005/0287648). In addition, a number of artificial peptides also are known to function as CPPs, such as poly-arginine, poly-lysine and others (see, for example, U.S. Pre-Grant Publication Nos. 2006/0106197; 2006/0024331; 2005/0287648; and 2003/0125242; Zhibao et al., *Mol. Ther.* 2:339-347, 2000; and Laus et al. *Nature Biotechnol.* 18:1269-1272, 2000).

Zhou et al. (*Cell Stem Cell* 4:381-384, 2009) describe the successful use of poly-arginine peptide tags. In addition, Kim et al. (*Cell Stem Cell* 4:472-476, 2009) describe the successful use of the HIV-TAT protein transduction domain to deliver proteins to human fetal fibroblasts.

Nanoparticles

Nanoparticles are submicron (less than about 1000 nm) sized drug delivery vehicles that can carry encapsulated drugs such as synthetic small molecules, proteins, peptides, cells and nucleic acid based biotherapeutics for either rapid or controlled release. A variety of molecules (e.g., proteins, peptides and nucleic acid molecules) can be efficiently encapsulated in nanoparticles using processes well known in the art. A molecule encapsulated in a nanoparticle may refer to a molecule (such as a Zscan4 nucleic acid or protein) that is either contained within the nanoparticle or attached to the surface of the nanoparticle, or a combination thereof.

In some examples, an agent that increases Zscan4 expression in a human cell is encapsulated by a nanoparticle to aid in delivery to the cells. Suitable nanoparticles for use with the disclosed methods are known in the art and are described briefly below.

The nanoparticles for use with the methods described herein can be any type of biocompatible nanoparticle, such as biodegradable nanoparticles, such as polymeric nanoparticles, including, but not limited to polyamide, polycarbonate, polyalkene, polyvinyl ethers, and cellulose ether nanoparticles. In some embodiments, the nanoparticles are made of biocompatible and biodegradable materials. In some embodiments, the nanoparticles include, but are not limited to nanoparticles including poly(lactic acid) or poly(glycolic acid), or both poly(lactic acid) and poly(glycolic acid). In some embodiments, the nanoparticles are poly(D,L-lactic-co-glycolic acid) (PLGA) nanoparticles.

Other biodegradable polymeric materials are contemplated for use with the methods described herein, such as poly(lactic acid) (PLA) and polyglycolide (PGA). Additional useful nanoparticles include biodegradable poly(alkylcyanoacrylate) nanoparticles (Vauthier et al., *Adv. Drug Del. Rev.* 55: 519-48, 2003).

Various types of biodegradable and biocompatible nanoparticles, methods of making such nanoparticles, including PLGA nanoparticles, and methods of encapsulating a variety of synthetic compounds, proteins and nucleic acids, has been well described in the art (see, for example, U.S. Publication No. 2007/0148074; U.S. Publication No. 20070092575; U.S. Patent Publication No. 2006/0246139; U.S. Pat. No. 5,753,234; U.S. Pat. No. 7,081,489; and PCT Publication No. WO/2006/052285).

Retinoids

In certain embodiments, an agent of the present disclosure that increases expression of Zscan4 is a retinoid. A retinoid may refer to a class of chemical compounds that are related chemically to vitamin A. Retinoids are used in medicine, primarily due to the way they regulate epithelial cell growth. Retinoids have many important and diverse functions throughout the body including roles in vision, regulation of cell proliferation and differentiation, growth of bone tissue, immune function, and activation of tumor suppressor genes. Examples of retinoids include, but are not limited to, all-trans retinoic acid (atRA), 9-cis retinoic acid (9-cis RA), 13-cis RA and vitamin A (retinol).

Various retinoids are known in the art and may be used in the methods described herein. Retinoids may include, without limitation, all-trans retinoic acid, 9-cis retinoic acid, 13-cis retinoic acid, or vitamin A.

Agents that Induce Oxidative Stress

In certain embodiments, an agent of the present disclosure that increases expression of Zscan4 is an agent that induces oxidative stress. Oxidative stress may refer to an imbalance between the production of reactive oxygen species and a biological system's ability to readily detoxify the reactive intermediates or to repair the resulting damage. Disturbances in the normal redox state of tissues can cause toxic effects through the production of peroxides and free radicals that damage all components of the cell, including proteins, lipids, and DNA. In some embodiments of the disclosed methods, the agent that induces oxidative stress is hydrogen peroxide ($H_2O_2$).

Various agents that induce oxidative stress are known in the art and may be used in the methods described herein.

Increasing Telomere Length and Genome Stability

Certain aspects of the present disclosure relate to methods of increasing telomere length and/or increasing genome stability in one or more human cells by, for example, contacting one or more human cells with an agent that increases expression (e.g., protein expression) of Zscan4 in the one or more human cells. As disclosed herein, a transient increase in expression and/or increased expression for only a short period of time (e.g., from about 1 hour to about 23 hours, or from about 1 day to about 10 days) is sufficient to increase telomere length and/or increase genome stability in the human cells. Moreover, in some embodiments, repeating the transient increase in Zscan4 expression in the human cells enhances the effects of the increase in Zscan4 expression. In certain embodiments, the transient increase in Zscan4 expression is repeated every 4 hours, every 8 hours, every 12 hours, every 16 hours, every 24 hours, every 32 hours, every 40 hours, every 48 hours, every three days, every four days, every five days, every six days, every week, every two weeks, every three weeks, every four weeks, every month, every two months, every three months, every four months, every six months, every seven months, every eight months, every nine months, every 10 months, every 11 months, every year, every two years, every three years, every four years, every five years, every six years, every seven years, every eight years, every nine years, every 10 years, every 11 years, every 12 years, every 13 years, every 14 years, every 15 years, every 16 years, every 17 years, every 18 years, every 19 years, every 20 years, every 21 years, every 22 years, every 23 years, every 24 years, every 25 years, every 26 years, every 27 years, every 28 years, every 29 years, every 30 years, every 35 years, every 40 years, every 45 years, or every 50 years.

Contacting may refer to placement in direct physical association; including both in solid and liquid form. "Contacting" may be used interchangeably with "exposed." In some cases, "contacting" includes transfecting, such as transfecting a nucleic acid molecule into a cell. Methods of measuring genome stability and telomere length are routine in the art, and the disclosure is not limited to particular methods. The particular examples provided herein are exemplary.

In some embodiments, telomere length is increased in human cells contacted with an agent that increases Zscan4 protein expression in the human cells, by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, at least 10 fold, at least 100 fold, at least 200 fold, at least 300 fold, at least 400 fold, at least 500 fold, at least 600 fold, at least 700 fold, at least 800 fold, at least 900 fold, at least 1,000 fold, at least 2,000 fold, at least 3,000 fold, at least 4,000 fold, at least 5,000 fold, at least 6,000 fold, at least 7,000 fold, at least 8,000 fold, at least 9,000 fold, at least 10,000 fold, at least 25,000 fold, at least 50,000 fold, at least 75,000 fold, at least 100,000 fold, at least 125,000 fold, at least 150,000 fold, at least 175,000 fold, at least 200,000 fold, at least 225,000 fold, at least 250,000 fold, at least 275,000 fold, at least 300,000 fold, at least 325,000 fold, at least 350,000 fold, at least 375,000 fold, at least 400,000 fold, at least 425,000 fold, at least 450,000 fold, at least 475,000 fold, at least 500,000 fold, at least 525,000 fold, at least 550,000 fold, at least 575,000 fold, at least 600,000 fold, at least 625,000 fold, at least 650,000 fold, at least 675,000 fold, at least 700,000 fold, at least 725,000 fold, at least 750,000 fold, at least 775,000 fold, at least 800,000 fold, at least 825,000 fold, at least 850,000 fold, at least 875,000 fold, at least 900,000 fold, at least 925,000 fold, at least 950,000 fold, at least 975,000 fold, or at least 1,000,000 fold, for example, relative to Zscan4 protein expression in a corresponding human cell that has not contacted with the agent that increases Zscan4 expression. Any method known in the art and disclosed herein for determining Zscan4 protein expression in a cell, or for quantifying the number of proteins (i.e., protein stoichiometry) per cell may be used.

In other embodiments, methods of increasing telomere length and/or genome stability in one or more human cells includes contacting the one or more human cells with a nucleic acid molecule or vector encoding a modified Zscan4 protein of the present disclosure, such as a Zscan4-ERT2 fusion protein. In other embodiments, the method includes contacting the human cell or human cell population with a modified Zscan4 protein of the present disclosure, such as a Zscan4-ERT2 fusion protein.

In yet other embodiments, methods increasing telomere length and/or genome stability in one or more human cells includes contacting the human cell or human cell population with a nucleic acid molecule or vector encoding a Zscan4-ΔC protein disclosed herein. In other embodiments, the method includes contacting the human cell or human cell population with a Zscan4-ΔC protein disclosed herein.

Methods of delivering nucleic acid molecules encoding Zscan4-ERT2 or Zscan4-ΔC, and Zscan4-ERT2 or Zscan4-ΔC proteins to human cells are known in the art and are described herein.

In some embodiments, telomere length is increased in human cells by at least 20%, at least 30%, at least 40%, at least 50%, at least 60%, at least 70%, at least 80%, at least 90%, at least 100%, at least 110%, at least 115%, at least 120%, at least 125%, at least 130%, at least 135%, at least 140%, at least 145%, at least 150%, at least 155%, or at least 160%, for example, relative to a human cell that has not been contacted with a modified Zscan4 protein, such as a Zscan4-ERT2 or Zscan4-ΔC protein, or a nucleic acid encoding a modified Zscan4 protein, such as a Zscan4-ERT2 or Zscan4-ΔC protein (or compared to a value or range of values expected in a human cell that has not undergone frequent activation of Zscan4). In some embodiments, telomere length is increased in human cells by at least at least 1.2-fold, at least 1.3-fold, at least 1.4-fold, at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, relative to a human cell that has not been contacted with a modified Zscan4 protein, such as a Zscan4-ERT2 or Zscan4-AC protein, or a nucleic acid encoding a modified Zscan4 protein, such as a Zscan4-ERT2 or Zscan4-ΔC protein (or compared to a value or range of values expected in a human cell that has not undergone frequent activation of Zscan4).

In some embodiments, telomere length is measured in the one or more human cells that have been contacted with an agent that increases Zscan4 expression in the human cells. In some examples, telomere length is increased in a human cell if the length of the telomeres is greater, for example, relative to telomere length in a human cell not contacted with the agent that increases Zscan4 expression. For example, telomere length can be detected in a human cell by fluorescence in situ hybridization (FISH), quantitative FISH (Q-FISH), or telomere qPCR.

Genome Stability

In some embodiments, genome stability is increased in one or more human cells contacted with an agent of the present disclosure that increases expression of Zscan4 in the human cells by at least 20%, at least 40%, at least 50%, at least 60%, at least 75%, at least 80%, at least 90%, at least 95%, or at least 98%, for example, relative to a corresponding human cell not contacted with the agent that increases expression of Zscan4.

Methods of measuring genome stability are routine in the art, and the disclosure is not limited to particular methods. The particular examples provided herein are exemplary.

In some examples, genome stability in a human cell, such as a human cell contacted with an agent that increases Zscan4 expression (e.g., agent that increases expression of Zscan4, such as a Zscan4 nucleic acid, Zscan4 protein, Zscan4-ERT or Zscan4-ΔC), is measured by performing karyotype analysis. Genome stability is increased if the presence of karyotype abnormalities (such as chromosome fusions and fragmentations) is decreased or even absent, for example relative to a cell that has not been contacting with the agent that increases expression of Zscan4. For example, karyotype analysis can be performed in human cells by inducing metaphase arrests, then preparing metaphase chromosome spreads.

In some examples, genome stability in a human cell, such as a human cell contacted with a Zscan4, Zscan4-ERT, or Zscan4-ΔC protein or nucleic acid, is measured by measuring sister chromatid exchange (SCE). Genome stability is increased if the presence of SCE is decreased relative to a control, such as a stem cell that has not undergone frequent activation of Zscan4. For example, SCE can be measured in a stem cell by detecting SCE in a metaphase spread.

Therapeutic Uses of Zscan4

It is disclosed herein that expression of Zscan4 increases telomere length, increases genome stability, corrects genome and/or chromosome abnormalities, protects cells against DNA damage, and/or enhances DNA repair. DNA repair may refer to a collection of processes by which a cell identifies and corrects damage to the DNA molecules that encode its genome. Thus, provided herein are methods related to increasing the expression of Zscan4 in human cells to increase genome stability, protect cells against DNA damage, enhance DNA repair, and increase telomere length in human cells.

Methods are provided for treating subjects in need of human cell therapy, such as a subject having human cells in need of telomere lengthening or of correcting telomere and/or chromosome abnormalities. These methods may include the use of human cells. In some embodiments, the methods may include contacting one or more human cells with an agent that increases expression of Zscan4 in the human cell. Increased expression of Zscan4 in the one or more human cells induces telomere lengthening in the one or more human cells as compared to one or more corresponding human cells that are not contacted with the agent.

Methods are provided for treating a subject in need of telomere lengthening. In some embodiments, the methods may include contacting one or more human cells in the subject with an agent that increases expression of Zscan4 in the one or more human cells, where increased expression of Zscan4 induces telomere lengthening in the one or more human cells. In some embodiments, the methods may include isolating one or more human cells, contacting the one or more human cells with an agent that increases expression of Zscan4 in the one or more human cells, and administering the contacted one or more human cells to the subject. Increasing expression of Zscan4 induces telomere lengthening in the one or more human cells.

Methods are also provided for treating a disease or condition associated with a telomere and/or chromosome abnormality. In some embodiments, the methods may include administering to a subject in need thereof an agent that increases expression of Zscan4 in one or more human cells in the subject, where increasing expression of Zscan4 induces telomere lengthening and/or correction of telomere and/or chromosome abnormalities in the one or more human cells to treat to treat the to treat the disease or condition associated with a telomere and/or chromosome abnormality. In some embodiments, the methods may include isolating one or more human cells from a subject suffering from a disease or condition associated with a telomere and/or chromosome abnormality, contacting the one or more human cells with an agent that increases expression of Zscan4 in the one or more human cells, and administering the contacted one or more human cells to the subject to treat the associated with a telomere and/or chromosome abnormality. Increasing expression of Zscan4 induces telomere lengthening and/or correction of telomere and/or chromosome abnormalities in the one or more human cells. In some embodiments, the methods may include isolating human bone marrow cells from a subject suffering from a disease or condition associated with a telomere and/or chromosome abnormality, contacting the human bone marrow cells with an agent that increases expression of Zscan4 in the human bone marrow cells, and engrafting the contacted human bone marrow cells into the subject to treat the disease or condition associated with a telomere and/or chromosome abnormality. Increasing expression of Zscan4 induces telomere lengthening and/or correction of telomere and/or chromosome abnormalities in the human bone marrow cells.

Methods are also provided for increasing genome stability of one or more human cells. In some embodiments, the methods may include contacting the one or more human cells with an agent that increases expression of Zscan4 in the one or more human cells, where increased expression of Zscan4 increases genome stability in the one or more human cells as compared to one or more corresponding human cells that are not contacted with the agent.

Methods are also provided for increasing DNA repair capacity of one or more human cells. In some embodiments, the methods may include contacting the one or more human cells with an agent that increases expression of Zscan4 in the one or more human cells, where increased expression of Zscan4 increases DNA repair capacity in the one or more human cells as compared to one or more corresponding human cells that are not contacted with the agent.

Methods are also provided for rejuvenating one or more human cells and/or extending lifespan of one or more human cells. In some embodiments, the methods may include contacting the one or more human cells with an agent that increases expression of Zscan4 in the one or more human cells, where increased expression of Zscan4 rejuvenates and/or extends the lifespan of the one or more human cells as compared to one or more corresponding human cells that are not contacted with the agent.

Methods are provided for rejuvenating a tissue or organ in a subject and/or extending lifespan of a tissue or organ in a subject. In some embodiments, the methods may include administering to a subject in need thereof an agent that increases expression of Zscan4 in the tissue or organ, wherein increasing expression of Zscan4 rejuvenates and/or extends the lifespan of the tissue or organ.

Methods are provided for treating a disease or condition associated with one or more deficiencies in resident tissue stem cells (i.e., tissue stem cells resident in the organ and/or tissue of the human body), such as Duchenne muscular dystrophy. In some embodiments, the methods may include administering to resident tissue stem cells in a subject in need thereof an agent that increases expression of Zscan4 in the resident tissue stem cells, wherein increasing expression of Zscan4 prevents the deterioration of the cells.

Methods are provided for rejuvenating a subject in need thereof and/or extending lifespan of a subject in need thereof. In some embodiments, the methods may include administering to the subject an agent that increases expression of Zscan4, wherein increasing expression of Zscan4 rejuvenates and/or extends the lifespan of the subject. In certain embodiments, the methods may include isolating one or more human cells from the subject; contacting the one or more human cells with an agent that increases expression of Zscan4 in the one or more human cells, where increasing expression of Zscan4 rejuvenates and/or extends the lifespan of the one or more human cells, and administering the contacted one or more human cells to the subject to rejuvenate and/or extend the lifespan of the subject. In some embodiments, administering the agent that increases expression of Zscan4 may include, without limitation, injecting the agent to each organ and tissue of the body, injecting the agent to the circulating blood of the subject, injecting the agent into the cerebrospinal fluids of the subject, injecting the agent into the lymphatic system of the subject, administering the agent into the lung tissue of the subject, administering the agent into the digestive organs and tissues, including the esophagus, stomach, and intestines of the subject, injecting the agent into portal veins of the subject, and topically administering the agent the skin and skin appendages, such as hair follicles and sweat glands to rejuvenate the tissue stem cells, progenitor cells, and/or terminally differentiated cells residing in the treated organ and/or tissue. It is believed that the overall effects of the rejuvenation of tissue stem cells, progenitor cells, and/or terminally differentiated cells in the treated subject are the rejuvenation of the subject and/or the slowing down of the aging process of the subject. It is also believed that rejuvenation of tissue stem cells, progenitor cells, and/or terminally differentiated cells in the treated subject will result in lifespan extension of the subject.

For example, provided herein is a method of treating a subject with cancer by administering to the subject a Zscan4 polypeptide or polynucleotide. A subject may refer to living multi-cellular vertebrate organisms, a category that includes human and non-human mammals. In some embodiments, the method further includes selecting a patient in need of such therapy, such as a subject that has been diagnosed with cancer. Cancer may refer to a malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. Metastatic disease may refer to cancer cells that have left the original tumor site and migrate to other parts of the body for example via the bloodstream or lymph system.

In some embodiments of the methods disclosed herein, the subject is administered a Zscan4 polynucleotide. In some examples, the subject is administered a vector including a Zscan4 polynucleotide. Methods of generating and using Zscan4-expressing vectors are described in other sections of the application. In some embodiments, the Zscan4 polynucleotide (or vector including the Zscan4 polynucleotide) is administered directly to tumor cells to tumor tissue, such as by injection.

In some embodiments, the subject is administered a Zscan4 polypeptide. In some embodiments, a Zscan4 polynucleotide and/or Zscan4 polypeptide of the present disclosure is encapsulated by a nanoparticle to aid in delivery of the Zscan4 polynucleotide, Zscan4 polypeptide, and/or agent that induces Zscan4 expression to tumor cells. Suitable nanoparticles for use with the disclosed methods are known in the art and are described below.

Nanoparticles are submicron (less than about 1000 nm) sized drug delivery vehicles that can carry encapsulated drugs such as synthetic small molecules, proteins, peptides and nucleic acid based biotherapeutics for either rapid or controlled release. A variety of molecules (e.g., proteins, peptides and nucleic acid molecules) can be efficiently encapsulated in nanoparticles using processes well known in the art.

The nanoparticles for use with the compositions and methods described herein can be any type of biocompatible nanoparticle, such as biodegradable nanoparticles, such as polymeric nanoparticles, including, but not limited to polyamide, polycarbonate, polyalkene, polyvinyl ethers, and cellulose ether nanoparticles. In some embodiments, the nanoparticles are made of biocompatible and biodegradable materials. In some embodiments, the nanoparticles include, but are not limited to nanoparticles including poly(lactic acid) or poly(glycolic acid), or both poly(lactic acid) and poly(glycolic acid). In some embodiments, the nanoparticles are poly(D,L-lactic-co-glycolic acid) (PLGA) nanoparticles.

PLGA is an FDA-approved biomaterial that has been used in resorbable sutures and biodegradable implants. PLGA nanoparticles have also been used in drug delivery systems for a variety of drugs via numerous routes of administration including, but not limited to, subcutaneous, intravenous, ocular, oral and intramuscular. Administration may refer to providing or giving a subject an agent by any effective route. An exemplary route of administration includes, but is not limited to, injection (such as subcutaneous, intramuscular, intradermal, intraperitoneal, intravenous or intra-arterial). PLGA degrades into its monomer constituents, lactic and glycolic acid, which are natural byproducts of metabolism, making the material highly biocompatible. In addition, PLGA is commercially available as a clinical-grade material for synthesis of nanoparticles.

Other biodegradable polymeric materials are contemplated for use with the compositions and methods described herein, such as poly(lactic acid) (PLA) and polyglycolide (PGA). Additional useful nanoparticles include biodegradable poly(alkylcyanoacrylate) nanoparticles (Vauthier et al., Adv. Drug Del. Rev. 55: 519-48, 2003). Oral adsorption also may be enhanced using poly(lactide-glycolide) nanoparticles coated with chitosan, which is a mucoadhesive cationic polymer. The manufacture of such nanoparticles is described, for example, by Takeuchi et al. (Adv. Drug Del. Rev. 47: 39-54, 2001).

Among the biodegradable polymers currently being used for human applications, PLA, PGA, and PLGA are known to be generally safe because they undergo in vivo hydrolysis to harmless lactic acid and glycolic acid. These polymers have been used in making sutures when post-surgical removal is not required, and in formulating encapsulated leuprolide acetate, which has been approved by the FDA for human use (Langer and Mose, Science 249:1527, 1990); Gilding and Reed, Polymer 20:1459, 1979; Morris, et al., Vaccine 12:5, 1994). The degradation rates of these polymers vary with the glycolide/lactide ratio and molecular weight thereof. Therefore, the release of the encapsulated molecule (such as a protein or peptide) can be sustained over several months by adjusting the molecular weight and glycolide/lactide ratio of the polymer, as well as the particle size and coating thickness of the capsule formulation (Holland, et al., J. Control. Rel. 4:155, 1986).

In some embodiments, the nanoparticles for use with the compositions and methods described herein range in size from about 50 nm to about 1000 nm in diameter. In some embodiments, the nanoparticles are less than about 600 nm. In some embodiments, the nanoparticles are about 100 to about 600 nm in diameter. In some embodiments, the nanoparticles are about 200 to about 500 nm in diameter. In some embodiments, the nanoparticles are about 300 to about 450 nm in diameter. One skilled in the art would readily recognize that the size of the nanoparticle may vary depending upon the method of preparation, clinical application, and imaging substance used.

Various types of biodegradable and biocompatible nanoparticles, methods of making such nanoparticles, including PLGA nanoparticles, and methods of encapsulating a variety of synthetic compounds, proteins and nucleic acids, has been well described in the art (see, for example, U.S. Publication No. 2007/0148074; U.S. Publication No. 20070092575; U.S. Patent Publication No. 2006/0246139; U.S. Pat. No. 5,753,234; U.S. Pat. No. 7,081,489; and PCT Publication No. WO/2006/052285).

In some embodiments, one or more human cells are contacted with an agent that increases expression of Zscan4 in the one or more human cells. As used herein, a human cell that has been contacted with an agent that increases the expression of Zscan4 is referred to as a "Zscane human cell". As disclosed herein, "Zscan4+ cells" include, without limitation, cells that transiently express Zscan4. That is, Zscan4+ cells do not necessarily continue to have a contact with Zscan4 or continually express Zscan4. As disclosed in some embodiments of the present disclosure, the action of Zscan4 is rapid and usually requires only transient and short contact (e.g., in the order of hours to days). In the case of telomeres, once telomeres are extended by the transient Zscan4 action, Zscan4 is not required for a long time as the telomeres get shorter only gradually. Accordingly, "Zscan4+ human cells" can include both cells that are contacted with an agent of the present disclosure that increases expression of Zscan4, and cells that were contacted with an agent of the present disclosure that increases expression of Zscan4, but are no longer in contact with the agent. Zscan4+ human cells may be administered to a subject in need thereof to treat a disorder or disease.

Subjects that can be treated using the methods provided herein may include mammalian subjects, such as a veterinary or human subject. Subjects may include a fetus, newborns, infants, children, and/or adults. In some embodiments, the subject to be treated is selected, such as selecting a subject that would benefit from human cell therapy, particularly therapy that includes administration of Zscan4+ human cells and/or an agent that increases Zscan4 expression in human cells.

Examples of disorders or diseases that can benefit from administration of Zscan4+ human cells and/or an agent that increases Zscan4 expression in human cells include those disorders or diseases that are associated with telomere-shortening. Further examples of disorders or diseases that can benefit from administration of Zscan4+ human cells and/or an agent that increases Zscan4 expression in human cells include cancer, autoimmune diseases, and diseases in which cell regeneration is beneficial, such as neurologic injuries or a neurodegenerative disorders, as well as blindness, deafness, tooth loss, arthritis, myocardial infarctions, bone marrow transplants, baldness, Crohn's disease, diabetes, muscular dystrophy, and Duchenne muscular dystrophy. In particular examples, a subject having one or more of these disorders is selected for the treatments herein disclosed.

In some embodiments, a subject of the present disclosure in need of Zscan4 treatment has a disease or condition associated with a telomere abnormality. A telomere abnormality may refer to any change in a telomere, such as telomere shortening, disruption of telomeric DNA repeats, or telomere DNA mutation, that disrupts one or more telomere function. Exemplary diseases or conditions associated with telomere abnormality that may benefit from Zscan4+ human cells and/or an agent that increases Zscan4 expression in human cells may include, without limitation, diseases of telomere shortening, bone marrow failure syndromes, age-related telomere shortening diseases, and premature aging disorders.

A disease or condition of telomere shortening that may benefit from Zscan4+ human cells and/or an agent that increases Zscan4 expression in human cells may include, without limitation, dyskeratosis congenita, Hoyeraal-Hreidarsson syndrome, Revesz syndrome, Coats plus syndrome, idiopathic pulmonary fibrosis, liver cirrhosis, pancreatic fibrosis, and degenerative diseases, such as Alzheimer's disease and osteoarthritis.

A disease or condition of a bone marrow failure syndrome that may benefit from Zscan4+ human cells and/or an agent that increases Zscan4 expression in human cells may include, without limitation, Fanconi anemia, amegakaryocytic thrombocytopenia, aplastic anemia, Diamond Blackfan anemia, dyskeratosis congenita, paroxysmal nocturnal hemoglobinuria (PNH), Pearson syndrome, Shwachman Diamond syndrome, thrombocytopenia, and myelodysplastic syndrome.

A disease or condition that is an age-related telomere shortening disease or a premature aging disease that may benefit from Zscan4+ human cells and/or an agent that increases Zscan4 expression in human cells may include, without limitation, Werner syndrome, Bloom's syndrome, Hutchinson-Gilford progeria syndrome, Cockayne syndrome, Xeroderma pigmentosa, Ataxia telangiectasia, Rothmund Thomson syndrome, Trichothiodystrophy, Juberg-Marsidi syndrome, and Down syndrome.

In some embodiments, a subject of the present disclosure has a disease or condition associated with a chromosome abnormality. A chromosome abnormality may refer to any anomaly, aberration, or mutation in a chromosome that results in a missing, extra, or irregular portion of chromosomal DNA. In certain embodiments, a chromosome abnormality may result in an atypical number of chromosomes or a structural abnormality in one or more chromosomes. In certain embodiments, a chromosome abnormality may include a karyotype abnormality, such as aneuploidy. As used herein, aneuploidy may refer to an abnormal number of whole chromosomes or parts of chromosomes, including, without limitation, chromosome nullisomy, chromosome monosomy, chromosome trisomy, chromosome tetrasomy, and chromosome pentasomy. Examples of human aneuploidies include, without limitation, trisomy 21, trisomy 16, trisomy 18 (Edwards syndrome), trisomy 13 (Patau syndrome), monosomy X (Turner's syndrome), XXX aneuploidy, XXY aneuploidy, and XYY aneuploidy. Examples of human segmental aneuploidy include, without limitation, 1p36 duplication, dup(17)(p11.2p11.2) syndrome, Pelizaeus-Merzbacher disease, dup(22)(q11.2q11.2) syndrome, and cat-eye syndrome. In some embodiments, an aneuploidy may include one or more deletions of sex or autosomal chromosomes, which can result in a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azoospermia (factor a), Azoospermia (factor b), Azoospermia (factor c), or 1p36 deletion. Accordingly, in certain embodiments, Zscan4+ human cells and/or an agent that increases Zscan4 expression in human cells may be used to treat aneuploidy or a disease, disorder, or condition associated with an aneuploidy.

Various types of diseases, disorders, and conditions may benefit from Zscan4+ human cells and/or an agent that increases Zscan4 expression in human cells including, without limitation, immunological deficiencies, an autoimmune disease, an autoimmune disorder, chronic ulcers, atherosclerosis, cancer, a neurologic injury, a degenerative disorder, a neurodegenerative disorder, wound healing, muscle repair, cardiac muscle repair, cartilage replacement, arthritis, osteoarthritis, tooth regeneration, blindness, age-related blindness due to proliferative decline of retinal pigmented epithelial cells, deafness, bone marrow failure, bone marrow transplant, diabetes, muscular dystrophy, Duchenne muscular dystrophy, a genetic disease, a genetic mutation, and DNA damage.

Cancers include malignant tumors that are characterized by abnormal or uncontrolled cell growth. Cancers are frequently associated with genome instability, chromosome abnormalities, DNA mutations, and aberrant telomere regulation. Based on the Zscan4 activities described herein, such as increasing the genome stability and correcting chromosome abnormalities, Zscan4 biologics of the present disclosure (e.g., agents of the present disclosure that increase Zscan4 expression in human cells) may be administered to treat cancer patients. As disclosed herein in Example 17, applicant has shown that Zscan4 biologics can slow down the proliferation of cancer cells. Accordingly, in some embodiments, an agent of the present disclosure that increases Zscan4 expression in human cells may be administered to prevent cancer cells from becoming more aggressive due to genome instability, chromosome abnormalities, DNA mutations, and/or aberrant telomere regulation. Furthermore, Zscan4+ human cells, such as immune cells, may be administered to cancer patients to enhance their physical abilities to suppress the growth of cancer cells. In other embodiments, Zscan4+ human cells may be used in patients who have had a tumor removed, wherein specific cells differentiated from Zscan4+ cells are used to reconstruct the removed tissues and/or organs. In other embodiments, an agent of the present disclosure that increases Zscan4 expression in human cells may be administered to represses the growth (e.g., proliferation) of the cancer cells.

It is known that human cancer tissues (e.g., tumors) contain cancer stem cells, which are not actively proliferating and are resistant to cancer chemotherapy (e.g., treatment with chemotherapeutic agents such as cisplatin). It is believed that cancer stem cells can survive treatment with chemotherapy, and thus results in the recurrence of the cancer after the treatment. It is also believed that endogenous ZSCAN4 expression occurs in certain cancer stem cells, thus providing the cells with protection from the chemotherapeutic agents. As such, it is believed that agents that reduce the expression of endogenous ZSCAN4, such as siRNAs or shRNAs specific for ZSCAN4, may be administered to cancer patients who are undergoing or will undergo chemotherapy to reduce or eliminate resistance to one or more chemotherapeutic agents in the cancer stem cells, thereby improving responsiveness to the one or more chemotherapeutic agents in the patient.

Exemplary cancers that can benefit from Zscan4+ human cells and/or an agent that increases Zscan4 expression in human cells provided herein include but are not limited to cancers of the heart (e.g., sarcoma (angiosarcoma, fibrosarcoma, rhabdomyosarcoma, liposarcoma), myxoma, rhabdomyoma, fibroma, lipoma and teratoma), lung (e.g., bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma); gastrointestinal tract (e.g., esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), genitourinary tract (e.g., kidney (adenocarcinoma, Wilms' tumor, nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma), liver (e.g., hepatoma (hepatocellular carcinoma), cholangiocarcinoma, hepatoblastoma, angiosarcoma, hepatocellular adenoma, hemangioma), bone (e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxofibroma, osteoid osteoma and giant cell tumors), nervous system (e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma>pinealoma!, glioblastoma multiforme, oligodendroglioma, schwannoma, retinoblastoma, congenital tumors), spinal cord (neurofibroma, meningioma, glioma, sarcoma)), gynecological cancers (e.g., uterus (endometrial carcinoma), cervix (cervical carcinoma, pre-tumor cervical dysplasia), ovaries (ovarian carcinoma, serous cystadenocarcinoma, mucinous cystadenocarcinoma, endometrioid tumors, Brenner tumor, clear cell carcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma, embryonal rhabdomyosarcoma, fallopian tubes (carcinoma)), hematologic cancers (e.g., blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma)), skin (e.g., malignant melanoma, basal cell carcinoma, squamous cell carcinoma, Kaposi's sarcoma, moles, dysplastic nevi, lipoma, angioma, dermatofibroma, keloids, psoriasis), and adrenal glands (e.g., neuroblastoma).

In some embodiments, a patient with an autoimmune disease is selected for treatment. An autoimmune disease may refer to a disease resulting from an aberrant immune response, such as the production of antibodies or cytotoxic T cells specific for a self-antigen or a subject's own cells or tissues. Autoimmune diseases can result from an overactive immune response of the body against substances and tissues normally present in the body. In some examples, the autoimmune disease is be restricted to certain organs (e.g., in thyroiditis) or can involve a particular tissue in different places (e.g., Goodpasture's disease which may affect the basement membrane in both the lung and the kidney). Accordingly, in some embodiments, Zscan4+ human cells, such as hematopoietic stem cells and/or immune cells, and/or an agent of the present disclosure that increases Zscan4 expression in human cells, may be used to treat an autoimmune disease in a subject, by correcting the immune system of a patient with an autoimmune disease. Exemplary autoimmune diseases that can benefit from Zscan4+ human cells and/or an agent that increases Zscan4 expression in human cells provided herein include but are not limited to, rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, and pernicious anemia.

In some embodiments, the subject selected is one who has suffered a neurologic injury or suffers from a neurodegenerative disorder. A neurological injury may refer to a trauma to the nervous system (such as to the brain or spinal cord or particular neurons), which adversely affects the movement and/or memory of the injured patient. For example, such patients may suffer from dysarthria (a motor speech disorder), hemiparesis or hemiplegia. Neurologic injuries can result from a trauma to the nervous system (such as to the brain or spinal cord or particular neurons), which adversely affects the movement and/or memory of the injured patient. Such traumas may be caused by an infectious agent (e.g., a bacterium or virus), a toxin, an injury due to a fall or other type of accident, or genetic disorder, or for other unknown reasons. Accordingly, in some embodiments, Zscan4+ human cells, such as hematopoietic stem cells, neural stem cells, mesenchymal stem cells, and/or immune cells, and/or an agent of the present disclosure that increases Zscan4 expression in human cells, may be used to treat a neurologic injury in a subject, by rejuvenating tissue stem cells in the nervous system of a patient that has suffered a neurologic injury, where rejuvenating tissue stem cells in the nervous system produces neurons and glial cells, thereby repairing defects in nervous system. In some embodiments, the patient may have suffered a neurologic injury, such as a brain or spinal cord injury resulting from an accident, such as an automobile or diving accident, or from a stroke.

A neurodegenerative disease is a condition in which cells of the brain and spinal cord are lost. Neurodegenerative diseases result from deterioration of neurons or their myelin sheath which over time lead to dysfunction and disabilities. Conditions that result can cause problems with movement (such as ataxia) and with memory (such as dementia). Accordingly, in some embodiments, Zscan4+ human cells, such as hematopoietic stem cells, neural stem cells, mesenchymal stem cells, and/or immune cells, and/or an agent of the present disclosure that increases Zscan4 expression in human cells, may be used to treat a neurodegenerative disease in a subject, by rejuvenating tissue stem cells in the nervous system of a patient suffering from a neurodegenerative disease, where rejuvenating tissue stem cells in the nervous system produces neurons and glial cells, thereby repairing defects in nervous system. In some embodiments, the Zscan4+ human cells and/or agent rejuvenate the nervous system of the subject and revert the degenerative conditions of the disease. Exemplary neurodegenerative diseases Zscan4+ human cells and/or an agent that increases Zscan4 expression in human cells provided herein include but are not limited to: adrenoleukodystrophy (ALD), alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, cerebral palsy, Cockayne syndrome, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), Multiple System Atrophy, multiple sclerosis, narcolepsy, Niemann Pick disease, Parkinson's disease, Pelizaeus-Merzbacher Disease, Pick's disease, primary lateral sclerosis, prion diseases, progressive supranuclear palsy, Refsum's disease, Sandhoff disease, Schilder's disease, subacute combined degeneration of spinal cord secondary to Pernicious Anaemia, Spielmeyer-Vogt-Sjogren-Batten disease (also known as Batten disease), spinocerebellar ataxia, spinal muscular atrophy, Steele-Richardson-Olszewski disease, Tabes dorsalis, toxic encephalopathy.

Zscan4+ human cells can be obtained or generated using the methods described herein. Methods of administering Zscan4+ human cells to mammalian subjects are known in the art. For example, Zscan4+ human cells administered to a subject in need of such therapy via injection, such as subcutaneous, intramuscular, intradermal, intraperitoneal, intravenous or intra-arterial administration. In some embodiments, Zscan4+ human cells are administered directly to the area in need of treatment, such as to a cancerous organ or tissue, or to the brain or spinal cord. In some embodiments, Zscan4+ human cells are administered alone, in the presence of a pharmaceutically acceptable carrier (such as encapsulated in a suitable polymer) or in the presence of other therapeutic agents. In some embodiments, a subject is administered at least 20,000 Zscan4+ human cells, such as at least 50,000, at least 100,000, at least 500,000, at least 1,000,000, or at least 2,000,000 Zscan4+ human cells.

In some aspects, the methods of the present disclosure involve the use of a therapeutic amount of an agent that increases expression of Zscan4. A therapeutic amount of an agent may refer to the amount of a therapeutic agent sufficient to achieve the intended purpose. For example, a therapeutic amount of Zscan4+ human cells and/or an agent that increases Zscan4 expression in a human cell to treat a disease or condition associated with a telomere abnormality is an amount sufficient to reduce the disease or condition or one or more symptoms of the disease or condition. A therapeutic amount may in some example not treat the disease or condition or symptoms of the disease or condition 100%. However, a decrease in any known feature or symptom of the disease or condition, such as a decrease of at least 10%, at least 15%, at least 25%, at least 30%, at least 50%, at least 60%, at least 70%, at least 75%, at least 85%, at least 95%, or greater, can be therapeutic. The therapeutic amount of a given therapeutic agent will vary with factors such as the nature of the agent, the route of administration, the size and/or age of the subject to receive the therapeutic agent, and the purpose of the administration. The therapeutic amount in each individual case can be determined empirically without undue experimentation by a skilled artisan according to established methods in the art.

In some aspects, the methods of the present disclosure involve the use of a pharmaceutical agent. A pharmaceutical agent may refer to a chemical compound, small molecule, or other composition, such as a Zscan4+ human cell, capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

The pharmaceutically acceptable carriers of use in the present disclosure are conventional. Remington's Pharmaceutical Sciences, by E. W. Martin, Mack Publishing Co., Easton, Pa., 15th Edition (1975), describes compositions and formulations suitable for pharmaceutical delivery of the Zscan4 proteins, Zscan4 nucleic acid molecules, retinoids, agents that induce oxidative stress, and cells disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

In one example, Zscan4+ human cells and/or an agent that increases Zscan4 expression in human cells are encapsulated into a semipermeable polymer membrane and the polymer membrane transplanted into a tissue site of a host subject. Such methods may achieve local, long-term chronic delivery of a therapeutic substance with the capability of regulating release of the substance. See U.S. Pat. No. 5,573,528 for description of encapsulation of compounds and cells. In one embodiment, Zscan4+ human cells and/or an agent that increases Zscan4 expression in human cells are encapsulated within a polymer membrane. The encapsulated polymer membrane is then transplanted into a tissue site of a host subject. In one embodiment, the tissue site is central nervous system, such as brain or spinal cord.

The semipermeable polymer membrane can be synthetic or natural. Examples of polymer that can be used include polyethersulfone (PES), polyacrylonitrile-co-vinyl chloride (P[AN/VC], poly(lactic acid), poly(lactic-co-glycolic acid), methylcellulose, hyaluronic acid, collagen, and the like. Delivery of encapsulated Zscan4+ human cells and/or an agent that increases Zscan4 expression in human cells within a polymer membrane can avoid host rejection and immune response to cells, and problems associated with rejection and inflammation. In addition, cells contained within the polymer membrane are shielded by the wall of the polymer (i.e., the walls of the individual fibers, fibrils, films, sprays, droplets, particles, etc.) from immune surveillance while still maintaining cell viability and allowing transport of molecules, nutrients and metabolic products through the polymer walls. The grafting of polymer-encapsulated cells has been developed by Aebischer et al., 1991, Transplant, 111:269-275, and has been successfully used with both non-human primates and humans (Aebischer et al., 1994, Transplant, 58:1275-1277). See also U.S. Pat. No. 6,110,902.

In one embodiment, Zscan4+ human cells are encapsulated by first embedding them into a matrix of either collagen, agarose or PVA (polyvinylalcohol). Subsequently, the embedded cells are injected into hollow fibers made of polypropylene of a 60:40 copolymer of polyacrylonitrile:polyvinylchloride. The fibers are cut into pieces and end-sealed for implantation. In one embodiment, the encapsulated cells have about 20,000 to about 2,000,000 Zscan4+ human cells.

In some examples, the Zscan4+ human cells are of exogenous origin. Exogenous cells may refer to cells obtained from sources other than the subject in which they are implanted for treatment. Exogenous cells can be from other organisms of the same species (such as human-derived cells for use in a human patient). Exogenous cells can also be from heterologous sources, i.e., from a species distinct from the subject to be therapeutically treated (such as mouse cells for use in a human). Zscan4+ human cells can also be taken from an isogenic source, i.e., from the subject who is to receive the cells. After harvesting the cells from the subject, the cells can be genetically modified (e.g., a nucleic acid encoding Zscan4 is introduced) or selected/enriched for Zscan4+ human cells, then re-implanted back to the subject. Since the cells are isogeneic, no immune response is expected.

In one aspect, the Zscan4+ human cells are immortalized. For example and not by way of limitation, cells can be conditionally immortalized (such that the cells grow well in tissue culture at reduced temperatures, yet discontinue division once implanted into a patient and maintained at 37° C.) or constitutively immortalized (e.g., transfection with constructs expressing large T antigen, or immortalization by Epstein Barr virus) by methods well known in the art. Another method of delivering Zscan4+ human cells into a host subject is to directly transplant the cells into the target area of a tissue site. Once transplanted, these cells survive, migrate and integrate seamlessly into the host tissue. In one embodiment, the Zscan4+ human cells are directly transplanted into the nervous system of the host subject, such as a developing nervous system or a nervous system that has suffered a trauma or in a subject having a neurological disorder. When transplanted into a developing nervous system, the Zscan4+ human cells will participate in processes of normal development and will respond to the host's developmental cues. The transplanted neural precursor cells will migrate along established migratory pathways, will spread widely into disseminated areas of the nervous system and will differentiate in a temporally and regionally appropriate manner into progeny from both the neuronal and glial lineages in concert with the host developmental program. The transplanted Zscan4+ human cell is capable of non-disruptive intermingling with the host neural precursor cells as well as differentiated cells. The transplanted cells can replace specific deficient neuronal or glial cell populations, restore defective functions and can express foreign genes in a wide distribution.

The Zscan4+ human cells can also be transplanted into a developed nervous system. The transplanted neural precursor cells can form a stable graft, migrate within the host nervous system, intermingle and interact with the host neural progenitors and differentiated cells. They can replace specific deficient neuronal or glial cell populations, restore deficient functions and activate regenerative and healing processes in the host's nervous system. In one embodiment, the stable graft is a graft established in the central nervous system or the peripheral nervous system.

Similar methods can be used to directly transplant Zscan4+ human cells into any region in need of human cell therapy. Such cells may be undifferentiated or differentiated into the desired cell type in vitro (then administered to a subject in need thereof). For example, where organ regeneration is desired, for example for replacement of organs or tissues removed to treat cancer or lost for other reasons (e.g., teeth, hair, cells of the ear or eyes, skin or muscle). In one embodiment, Zscan4+ human cells are directly transplanted into the heart, for example to regenerate cardiac tissue or cells lost to myocardial infarction. In one embodiment, Zscan4+ human cells are directly transplanted into the pancreas, for example to regenerate cells in a subject with diabetes. In one embodiment, Zscan4+ human cells are directly transplanted into the bone or administered systemically, for example to regenerate bone marrow cells in a subject having cancer.

The therapeutic dose and regimen most appropriate for patient treatment will vary with diseases or conditions to be treated, and according to the patient's weight and other parameters. An effective dosage and treatment protocol can be determined by conventional means, starting with a low dose in laboratory animals and then increasing the dosage while monitoring the effects, and systematically varying the dosage regimen. Numerous factors can be taken into consideration by a clinician when determining an optimal dosage for a given subject. Factors include the size of the patient, the age of the patient, the general condition of the patient, the particular disease being treated, the severity of the disease, the presence of other drugs in the patient, and the like. The trial dosages would be chosen after consideration of the results of animal studies and the clinical literature.

Accordingly, Zscan4+ human cells and/or an agent that increases Zscan4 expression in human cells are administered to subjects so as to reduce or ameliorate symptoms associated with a particular disorder, particularly those associated with telomere abnormalities. Therapeutic endpoints for the treatment of cancer can include a reduction in the size or volume of a tumor, reduction in angiogenesis to the tumor, or reduction in metastasis of the tumor. If the tumor has been removed, another therapeutic endpoint can be regeneration of the tissue or organ removed. Effectiveness of cancer treatment can be measured using methods in the art, for example imaging of the tumor or detecting tumor markers or other indicators of the presence of the cancer. Therapeutic endpoints for the treatment of autoimmune diseases can include a reduction in the autoimmune response. Effectiveness of autoimmune disease treatment can be measured using methods in the art, for example measuring of autoimmune antibodies, wherein a reduction in such antibodies in the treated subject indicates that the therapy is successful. Therapeutic endpoints for the treatment of neurodegenerative disorders can include a reduction in neurodegenerative-related deficits, e.g., an increase in motor, memory or behavioral deficits. Effectiveness of treating neurodegenerative disorders can be measured using methods in the art, for example by measuring cognitive impairment, wherein a reduction in such impairment in the treated subject indicates that the therapy is successful. Therapeutic endpoints for the treatment of neurologic injuries can include a reduction in injury-related deficits, e.g., an increase in motor, memory or behavioral deficits. Effectiveness of treating neurologic injuries can be measured using methods in the art, for example by measuring mobility and flexibility, wherein an increase in such in the treated subject indicates that the therapy is successful. Treatment does not require 100% effectiveness. A reduction in the disease (or symptoms thereof) of at least about 10%, about 15%, about 25%, about 40%, about 50%, or greater, for example relative to the absence of treatment with Zscan4+ human cells and/or an agent that increases Zscan4 expression in human cells, is considered effective.

In some examples, Zscan4+ human cells are administered at a dose from about $1 \times 10^4$ cells to about $1 \times 10^7$ cells in a mouse or other small mammal, or a dose from about $1 \times 10^4$ cells to about $1 \times 10^{10}$ cells in a human or other large mammal. In one specific, non-limiting embodiment, a therapeutically effective amount is about $1 \times 10^6$ cells. Other therapeutic agents (for example, chemical compounds, small molecules, or peptides) can be administered in a therapeutically effective dose in combination with the Zscan4+ human cells (for example shortly before or after, or simultaneously) in order to achieve a desired effect in a subject being treated. An effective amount of Zscan4+ human cells may be administered in a single dose, or in several doses, for example daily, during a course of treatment. However, one skilled in the art will appreciate that the effective amount of Zscan4+ human cells will be dependent on the agent applied, the subject being treated, the severity and type of the affliction, and the manner of administration of the agent.

Agents of the present disclosure that increase expression of Zscan4 may also be used to rejuvenate skin, treat atopic dermatitis, or skin lesions in a subject in need thereof, by, for example, applying an agent of the present disclosure that increase expression of Zscan4 to the skin of the subject.

Agents of the present disclosure that increase expression of Zscan4 may also be used to treat hair loss by stimulating hair growth in a subject in need thereof, by, for example, applying an agent of the present disclosure that increase expression of Zscan4 to the scalp of the subject. Agents of the present disclosure that increase expression of Zscan4 may also be used to prevent or treat hair graying in a subject in need thereof by applying an agent of the present disclosure that increase expression of Zscan4 to the scalp to increasing telomere length and/or genome stability melanocyte stem cells in hair follicles, whose dysfunction causes gray hair.

As disclosed herein, limbal stem cells regenerate corneas, and as such, it is believed that increasing telomere length and/or genome stability in limbal stem cells by increasing expression of Zscan4 would rejuvenate corneas in a subject in need thereof. Increasing expression of Zscan4 in corneas may also be used to treat dry eyes in a subject in need thereof. Accordingly, agents of the present disclosure that increase expression of Zscan4 may also be used to rejuvenate corneas and/or treat dry eye in a subject in need thereof, by, for example, applying an agent of the present disclosure that increase expression of Zscan4 to a cornea of the subject.

As disclosed herein, idiopathic pulmonary fibrosis is known to be caused by the telomere shortening. Accordingly, agents of the present disclosure that increase expression of Zscan4 may also be used to treat idiopathic pulmonary fibrosis in a subject in need thereof, by, for example, formulating an agent of the present disclosure that increases expression of Zscan4 (e.g., a Zscan4 polynucleotide of the present disclosure) such that it can be inhaled by the subject in order to treat the idiopathic pulmonary fibrosis.

Agents of the present disclosure that increase expression of Zscan4 may also be used to treat atherosclerosis and/or a coronary heart disease in a subject in need thereof, by, for example, administering an agent of the present disclosure to the bloodstream of the subject such that the agent contacts and increases telomere length and/or genome stability of vascular endothelial cells, thereby treating atherosclerosis and/or a coronary heart disease in the subject.

Agents of the present disclosure that increase expression of Zscan4 may also be used to provide resistance to one or more genotoxic agents in one or more human cells and/or a subject in need thereof, by, for example, contacting the one or more human cells with an agent of the present disclosure that increases expression of Zscan4 (e.g., a Zscan4 polynucleotide of the present disclosure) or administering such an agent to a subject in need thereof, such that increasing expression of Zscan4 increases resistance to one or more genotoxic agents in the one or more human cells or subject. Advantageously, Zscan4 expression can be used to provide resistance for any known genotoxic agent or drug, including, without limitation, mitomycin C and cisplatin.

It is known that there are regions in the genome of iPS cells where DNA methylation patterns differ from those of human embryonic stem (ES) cells, which is believed to cause problems in the iPS cells (e.g., see Ohi, Y et al., Nat Cell Biol. 2011 May; 13(5):541-9). Without wishing to be bound by theory, it is believed that agents of the present disclosure that increase expression of Zscan4 will improve iPS cells by inducing a DNA methylation pattern in human iPS cells that is more similar to that of human ES cells. It is further believed that inducing a more human ES cell-like DNA methylation pattern in human iPS can may such cells safer for therapeutic use. Accordingly, in certain embodiments, agents of the present disclosure that increase expression of Zscan4 may be used to induce a human embryonic stem cell-like DNA methylation pattern in one or more human induced pluripotent stem (iPS) cells, by, for example, contacting one or more human iPS cells with an agent of the present disclosure that increases expression of Zscan4 (e.g., a Zscan4 polynucleotide of the present disclosure), such that increasing expression of Zscan4 induces a human embryonic stem cell-like DNA methylation pattern in the one or more human iPS cells.

Agents of the present disclosure that increase expression of Zscan4 may also be used to rejuvenate aged oocytes and correct karyotype abnormalities in both oocyte cells and in vitro fertilized oocytes, such as zygotes or preimplantation embryos between the one-cell stage and the blastocyst stage to increase the success rate of in vitro fertilization (IVF); to increase the success rate of healthy full-term pregnancies in, for example, older women; to correct karyotype abnormalities, such as aneuploidy; and to reduce the risk of developmental disorders, such as Down syndrome. Such treatments may be of particular use for in vitro fertilization (IVF) and in IVF clinics. Accordingly, in certain embodiments, agents of the present disclosure that increase expression of Zscan4 may be used to rejuvenate one or more human oocyte cells, increase genome stability in one or more human oocyte cells, and/or correct one or more karyotype abnormalities in one or more human oocyte cells by, for example, contacting one or more human oocyte cells with an agent of the present disclosure that increases expression of Zscan4 (e.g., a Zscan4 polynucleotide of the present disclosure), such that increasing expression of Zscan4 rejuvenates the one or more human oocyte cells, increases genome stability in the one or more human oocyte cells, and/or corrects one or more karyotype abnormalities in the one or more human oocyte cells. In some embodiments, the one or more human oocyte cells are isolated from a subject prior to contacting with the agent that increases expression of Zscan4. In other embodiments, once the one or more human oocyte cells have been treated with the agent that increases expression of Zscan4, the cells undergo in vitro fertilization.

In other embodiments, agents of the present disclosure that increase expression of Zscan4 may be used to increase genome stability and/or correct one of more karyotype abnormalities in one or more fertilized human oocytes by, for example, contacting the one or more fertilized human oocytes with an agent of the present disclosure that increases expression of Zscan4 (e.g., a Zscan4 polynucleotide of the present disclosure), such that increasing expression of Zscan4 increases genome stability and/or corrects the one or more karyotype abnormalities in the one or more fertilized human oocytes. In some embodiments, the one or more fertilized human oocytes were fertilized by in vitro fertilization prior to being contacted with agent that increases expression of Zscan4. In other embodiments, the one or more human oocytes are isolated from a subject prior to being fertilized. In yet other embodiments, the one or more fertilized oocytes are preimplantation embryos between the one-cell stage and the blastocyst stage.

In certain embodiments, the agent of the present disclosure that increases expression of Zscan4 corrects one or more karyotype abnormalities that include, without limitation, an aneuploidy, such as trisomy 21 (Down syndrome), trisomy 16, trisomy 18 (Edwards syndrome), trisomy 13 (Patau syndrome), monosomy X (Turner's syndrome), XXX aneuploidy, XXY aneuploidy, and XYY aneuploidy; a segmental aneuploidy, such as 1p36 duplication, dup(17)(p11.2p11.2) syndrome, Pelizaeus-Merzbacher disease, dup(22)(q11.2q11.2) syndrome, and cat-eye syndrome; and a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azoospermia (factor a), Azoospermia (factor b), Azoospermia (factor c), and 1p36 deletion.

As disclosed herein, the human genes SERPINB4, DNMT3L, and DUX4 are marker genes, whose expression is unregulated when Zscan4 gene is expressed in human cells. As such, it is believed that SERPINB4, DNMT3L, and DUX4 may be used as markers for the effects of Zscan4 in human cells. Accordingly, in some embodiments methods are provided for determining one or more Zscan4-induced effects in one or more human cells, for example, by contacting the one or more human cells with an agent that increases expression of Zscan4 in one or more human cells; measuring expression levels of SERPINB4, DNMT3L, and/or DUX4 in the one or more human cells; and comparing the expression levels of SERPINB4, DNMT3L, and/or DUX4 in the one or more human cells to the expression levels of SERPINB4, DNMT3L, and/or DUX4 in one or more corresponding human cells that are not contacted with the agent, where an increase in the expression levels of SERPINB4, DNMT3L, and/or DUX4 in the one or more human cells indicates the presence of one or more Zscan4-induced effects in the one or more human cell.

In some embodiments, the subjects of the present disclosure are non-human animals. Non-human animals may refer to all animals other than humans. A non-human animal includes, but is not limited to, a non-human primate, a farm animal such as swine, cattle, and poultry, a sport animal or pet such as dogs, cats, horses, hamsters, rodents, such as mice, or a zoo animal such as lions, tigers or bears. In one embodiment, the non-human animal is a mouse.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The following examples are provided to illustrate certain particular features and/or embodiments. These examples should not be construed to limit the disclosure to the particular features or embodiments described.

EXAMPLES

Example 1: Zscan4 Expression Corrects Chromosome Abnormalities in Mouse Embryonic Stem Cells This example describes the finding that expression of Zscan4, either by a synthetic mRNA encoding Zscan4 or a Sendai virus vector expressing Zscan4, can correct chromosome abnormalities in mouse embryonic stem (ES). This example also demonstrates that synthetic mRNAs encoding Zscan4 and Sendai virus vector expressing Zscan4 can be used as therapeutic biologics.

Materials and Methods

Cell Culture

The MC1ZE mouse ES cell line was previously reported (Amano et al., *Nat Commun*, 2013; 4:1966.). MC1ZE cells were used as typical mouse ES cells which show poor karyotypes (i.e., only about 20% of cells carry euploidy) due to long-term cultures (passage number 33), and the integration of an exogenous gene. Cells were cultured at 37° C. in 5% CO2 in the complete ES medium as previously described (Amano et al., *Nat Commun*, 2013; 4:1966.): DMEM (Gibco), 15% FBS (Atlanta Biologicals), 1000 U/ml leukemia inhibitory factor (LIF) (ESGRO, Chemicon), 1 mM sodium pyruvate, 0.1 mM non-essential amino acids (NEAA), 2 mM GlutaMAX, 0.1 mM beta-mercaptoethanol, and penicillin/streptomycin (50 U/50 µg/ml). Medium was changed daily and cells were passaged every 2 to 3 days routinely.

Synthetic mRNA

For synthesis of modified mRNA, mRNA synthesis was performed as reported previously by Warren et al. (Warren et al., *Cell Stem Cell*, 2010 Nov. 5; 7(5):618-30). Using these protocol from Warren et al., mRNAs were synthesized by in vitro transcription of template DNAs encoding human ZSCAN4 or green fluorescent protein (GFP) with mixtures of modified dNTPs to increase RNA stability as well as translation efficiency in mammalian cells. The following modified dNTPs were used: 3'-O-Me-m7G(5')ppp(5')G ARCA cap analog, 5-methylcytidine triphosphate, and pseudouridine triphosphate.

Sendai Virus Vectors

Sendai vectors that express either mouse Zscan4c (SeV18+mZscan4/ΔF) or human ZSCAN4 (SeV18+hZSCAN4/ΔF) were custom-made by MBL (Medical & Biological Laboratories Co, LTD). These vectors are referred to as "SeVmZscan4' or "SeVhZSCAN4", respectively, herein. As a control, the same Sendai vector was used, but the vector expressed a green fluorescent protein variant, rather than Zscan4. These Sendai vectors lack the F protein, and thus, are not transmissible (Inoue et al., *J Virol*. 77: 23238-3246, 2003).

Sendai vectors that express either mouse Zscan4c fused to a Tamoxifen-controllable ERT2 domain (SeV18+mZERT2/ΔF), or human ZSCAN4 fused to Tamoxifen-controllable ERT2 domain (SeV18+hZERT2/ΔF) were custom-made by MBL (Medical & Biological Laboratories Co, LTD). These vectors are referred to as "SeVmZERT2' or "SeVhZERT2", respectively, herein. These Sendai vectors also lack the F protein, and thus, are not transmissible (Inoue et al., *J Virol.* 77: 23238-3246, 2003).

Additionally, temperature-sensitive Sendai vectors that express either mouse Zscan4 (SeV18+mZscan4/TS15ΔF) or human ZSCAN4 (SeV18+hZSCAN4/TS15ΔF) were custom-made by MBL (Medical & Biological Laboratories Co, LTD). These vectors are referred to as "SeVmZscan4-TS15" or "SeVhZSCAN4-TS15", respectively, herein. These Sendai vectors are functional at 35° C., and inactive at 37° C. (Ban et al., *Proc Natl Acad Sci USA.* 2011; 108(34):14234-14239). As a control, the same Sendai vector was used, but the vector expressed a green fluorescent protein variant, rather than Zscan4. This vector is referred to as "SeVAG-TS15" herein. These Sendai vectors also lacks the F protein, and thus, it is not transmissible (Inoue et al., *J Virol.* 77: 23238-3246, 2003).

Karyotype Analysis

Karyotype analysis was performed by G-banding carried out as described in Amano et al., Nat Commun, 2013; 4:1966.

Results

Synthetic mRNAs Encoding Mouse or Human ZSCAN4 Correct Chromosome Abnormalities in Mouse Embryonic Stem Cells FIG. 1A shows the experimental procedure: MC1ZE mouse ES cells (at passage 33) were plated in a 6 well dish at a concentration of $5 \times 10^4$ cells/well and transfected with either 1 µg of synthetic GFP mRNAs (control) or 1 µg of synthetic human ZSCAN4 mRNAs using 5 µl of Lipofectamine (RNAiMAX: Life Technologies, California, USA). In addition to cells transfected with GFP mRNAs, non-transfected cells were also used as controls. Cells were passaged every 2-3 days, followed by the transfection with synthetic mRNAs. Karyotyping of cells was carried out at passage 33 (3 days after one-time transfection), at passage 34 (3 days after three-time transfection), at passage 36 (3 days after 4-time transfection), and at passage 40 (3 days after seven-time transfection).

As shown in FIG. 1B, the transfection of mouse ES cells with synthetic mRNAs of human ZSCAN4 corrected chromosome abnormalities and increased the number of cells with a normal karyotype (euploidy). Although the one-time transfection was sufficient to see a significant level of correction, repeated transfections (e.g., seven times) further increased the number of cells with euploidy from around 20% to 40%. These results indicate that the introduction of human ZSCAN4 mRNAs into cells can correct abnormalities in chromosome numbers.

Figure 2:
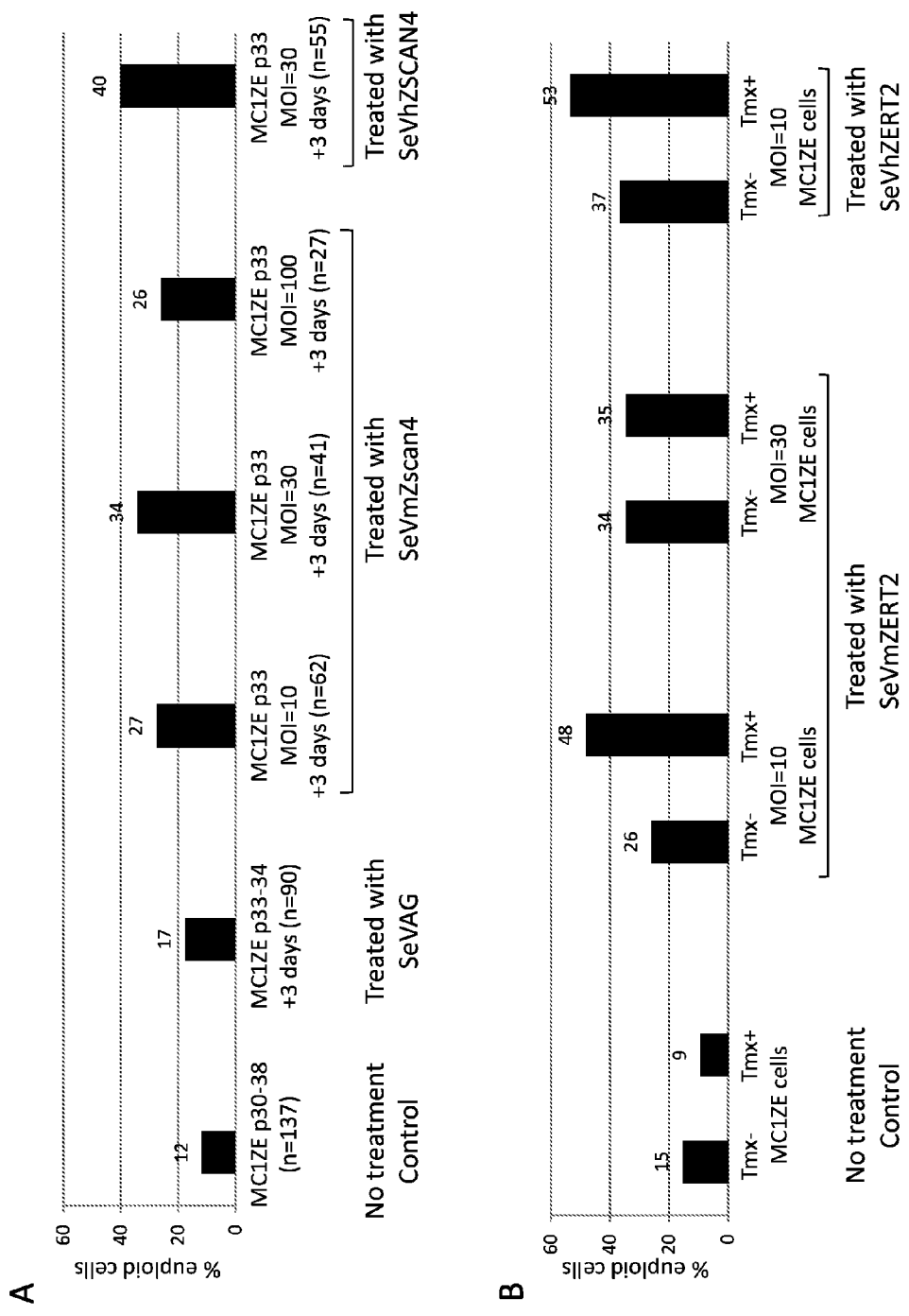
FIG. 2 depicts the correction of chromosome abnormalities in mouse ES cells infected with Sendai virus vectors expressing mZscan4 or hZSCAN4.

Sendai Virus Vectors Expressing Human ZSCAN4 Correct Chromosome Abnormalities in Mouse Embryonic Stem Cells FIG. 2A shows a summary of the karyotype analysis after treating mouse ES cells with a Sendai virus vector expressing either mouse Zscan4c or human ZSCAN4. MC1ZE mouse ES cells (at passage 33 or 34) were plated in a 6 well dish at a concentration of; $5 \times 10^4$ cells/well and treated with either SeVAG (control), SeVmZscan4, or SeVhZSCAN4 at the MOI indicated in FIG. 2A. As an additional control, MC1ZE cells without any treatment were used. After 3 days, the karyotype of cells was analyzed. As shown in FIG. 2A, the karyotype of mouse ES cells can be dramatically improved by contacting with SeVmZscan4 or SeVhZS-CAN4. Interestingly, the results show that human ZSCAN4 worked better than mouse Zscan4c.

FIG. 2B shows a summary of karyotype analysis after treating mouse MC1ZE ES cells with a Sendai virus vector expressing either a mouse Zscan4c-ERT2 fusion protein or a human ZSCAN4-ERT2 fusion protein. It is known that the protein fused with the ERT2 domain can be activated by the presence of Tamoxifen (Tmx) in the cell culture medium. MC1ZE mouse ES cells (at passage 33 or 34) were plated in a 6 well dish at a concentration of $5 \times 10^4$ cells/well and treated with either SeVmZERT2 or SeVhZERT2 at the MOI indicated in FIG. 2B. As a control, MC1ZE cells without any treatment were used. As shown in FIG. 2B, treatment with either SeVmZERT2 or SeVhZERT2 can correct chromosome abnormalities even without Tmx. Addition of Tmx, however, further enhanced the ability of SeVmZERT2 and SeVhZERT2 to correct chromosome abnormalities. The results also show that human ZSCAN4 works better than mouse Zscan4c: the fusion protein, human ZSCAN4-ERT2, in the presence of Tmx, increased the number of cells with euploidy from 15% to 53%.

Figure 3:
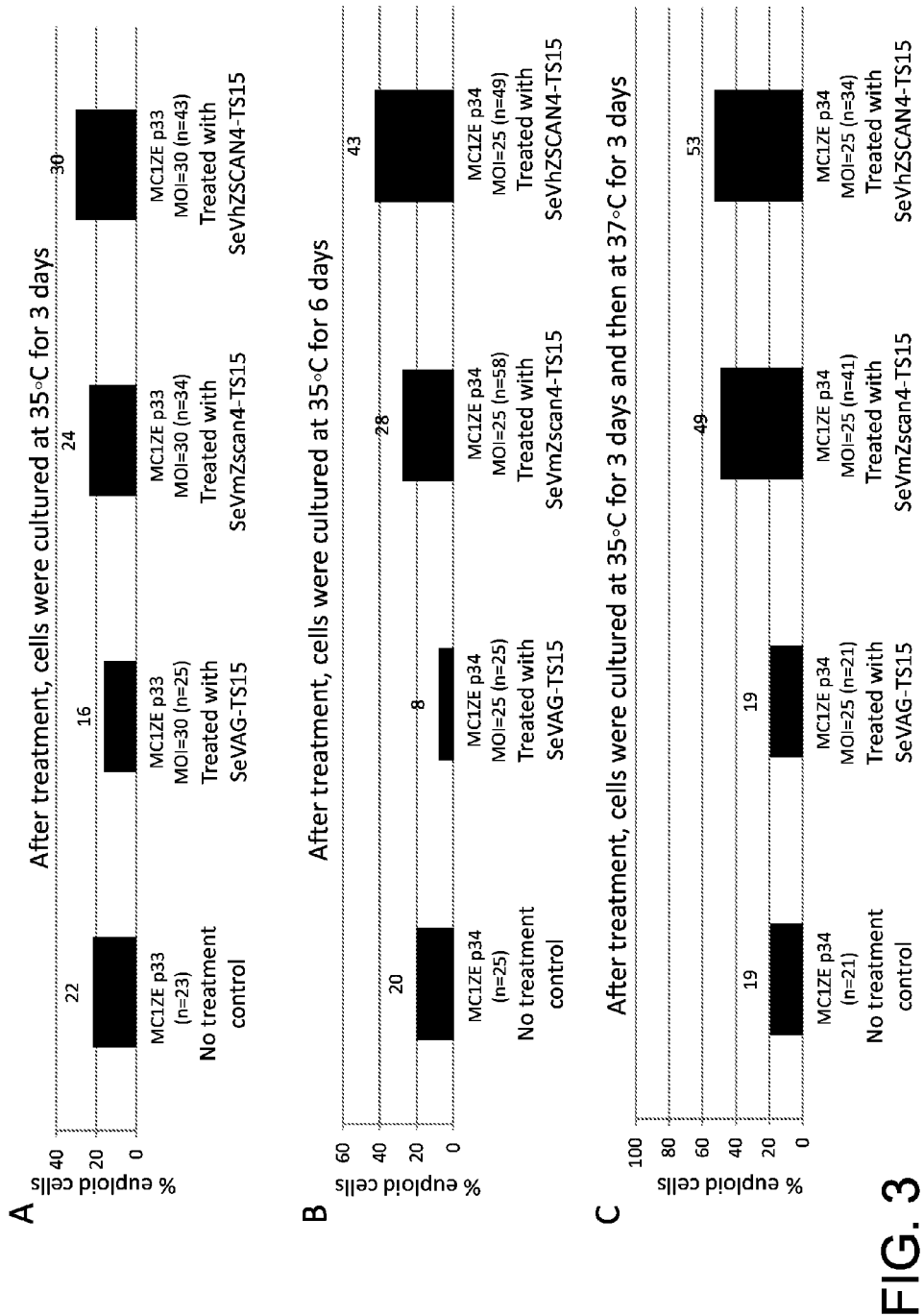
FIG. 3 depicts the correction of chromosome abnormalities in mouse ES cells infected with temperature-sensitive Sendai virus vectors expressing mZscan4 or hZSCAN4.

FIG. 3 shows a summary of karyotype analysis after treating MC1ZE mouse ES cells with a temperature-sensitive Sendai virus vector expressing either mouse Zscan4c or human ZSCAN4. MC1ZE mouse ES cells (at passage 33 or 34) were plated in a 6 well dish at a concentration of $5 \times 10^4$ cells/well and treated with either SeVAG-TS15 (control), SeVmZscan4-TS15, or SeVhZSCAN4-TS15 at the MOI indicated in FIG. 3. As an additional control, MC1ZE cells without any treatment were used. After contacting the cells with these vectors, cells were cultured at 35° C. for three days (FIG. 3A), at 35° C. for six days (FIG. 3B), and at 35° C. for three days, followed by culturing at 37° C. for three days (FIG. 3C). The correction of chromosome abnormalities by contacting cells with either SeVmZscan4-TS15 or SeVhZSCAN4-TS15 was observed in all three conditions. Surprisingly, human ZSCAN4 was found to work better than mouse Zscan4c at correcting chromosome abnormalities. Thus, these results demonstrate that even in mouse cells, human ZSCAN4 produces surprisingly superior results over mouse Zscan4c. Indeed, the best result was obtained by treating cells with human ZSCAN4 (i.e., SeVhZSCAN4-TS15) and culturing cells at 35° C. for three days, followed by the culture at 37° C. for three days: the treatment increased the number of cells with euploidy from 19% to 53%. In these experiments, culturing cells treated with the temperature-sensitive Sendai vectors at the permissive temperature of 35° C. for three days followed by culturing at the inactivating temperature of 37° C. for three days represents transient expression of Zscan4. In contrast culturing cells treated with the temperature-sensitive Sendai vectors at the permissive temperature of 35° C. for the full six days represents continuous Zscan4 expression. Based on these conditions, the results indicate the transient expression of Zscan4 works better than continuous expression of Zscan4 at correcting chromosome abnormalities.

Example 2: Effects of Zscan4 Biologics on Mouse Embryonic Stem Cells

It has been shown previously that the forced expression of exogenous mouse Zscan4c from a plasmid vector integrated into the mouse genome induces the expression of a unique set of genes, including Tmem92, Stra8, and endogenous Zscan4 genes (Amano et al., *Nat Commun,* 2013; 4:1966.).

This example demonstrates that Zscan4 biologics (e.g., expression of Zscan4, either by a synthetic mRNA encoding Zscan4 or a Sendai virus vector expressing Zscan4) exert the same function in mouse embryonic stem (ES) cells.

Materials and Methods

Cell Culture

The MC1 mouse embryonic stem (ES) cell line was previously used as typical mouse pluripotent stem cells to demonstrate the function of exogenously introduced Zscan4c gene, which was integrated into the mouse genome (Amano et al., Nat Commun, 2013; 4:1966.). MC1 cells were cultured at 37° C. in 5% CO2 in complete ES medium, as previously described (Amano et al., Nat Commun, 2013; 4:1966.): DMEM (Gibco), 15% FBS (Atlanta Biologicals), 1000 U/ml leukemia inhibitory factor (LIF) (ESGRO, Chemicon), 1 mM sodium pyruvate, 0.1 mM non-essential amino acids (NEAA), 2 mM GlutaMAX, 0.1 mM beta-mercaptoethanol, and penicillin/streptomycin (50 U/50 μg/ml). The medium was changed daily and cells were passaged every 2 to 3 days routinely.

Synthetic mRNA

For synthesis of modified mRNA, mRNA synthesis was performed as reported previously by Warren et al. (Warren et al., Cell Stem Cell, 2010 Nov. 5; 7(5):618-30). Using these protocol from Warren et al., mRNAs were synthesized by in vitro transcription of template DNAs encoding human ZSCAN4 or green fluorescent protein (GFP) with mixtures of modified dNTPs to increase RNA stability as well as translation efficiency in mammalian cells. The following modified dNTPs were used: 3'-O-Me-m7G(5')ppp(5')G ARCA cap analog, 5-methylcytidine triphosphate, and pseudouridine triphosphate.

Sendai Virus Vectors

Sendai vectors that express either mouse Zscan4c (SeV18+mZscan4/ΔF) or human ZSCAN4 (SeV18+hZS-CAN4/ΔF) were custom-made by MBL (Medical & Biological Laboratories Co, LTD). These vectors are referred to as "SeVmZscan4' or "SeVhZSCAN4", respectively, herein. As a control, the same Sendai was used, but the vector expressed a green fluorescent protein variant rather than Zscan4. These Sendai vectors lack the F protein, and thus, are not transmissible (Inoue et al., J Virol. 77: 23238-3246, 2003).

Sendai vectors that express either mouse Zscan4c fused to a Tamoxifen-controllable ERT2 domain (SeV18+mZERT2/ ΔF), or human ZSCAN4 fused to Tamoxifen-controllable ERT2 domain (SeV18+hZERT2/ΔF) were custom-made by MBL (Medical & Biological Laboratories Co, LTD). These vectors are referred to as "SeVmZERT2' or "SeVhZERT2", respectively, herein. These Sendai vectors also lack the F protein, and thus, are not transmissible (Inoue et al., J Virol. 77: 23238-3246, 2003).

Additionally, temperature-sensitive Sendai vectors that express either mouse Zscan4 (SeV18+mZscan4/TS15ΔF) or human ZSCAN4 (SeV18+hZSCAN4/TS15ΔF) were custom-made by MBL (Medical & Biological Laboratories Co, LTD). These vectors are referred to as "SeVmZscan4-TS15" or "SeVhZSCAN4-TS15", respectively, herein. These Sendai vectors are functional at 35° C., and inactive at 37° C. (Ban et al., Proc Natl Acad Sci USA. 2011; 108(34):14234-14239). As a control, the same temperature-sensitive Sendai vector was used, but the vector expressed a green fluorescent protein variant rather than Zscan4. This vector is referred to as "SeVAG-TS15" herein. These Sendai vectors also lack the F protein, and thus, it is not transmissible (Inoue et al., J Virol. 77: 23238-3246, 2003).

Results

Figure 4:
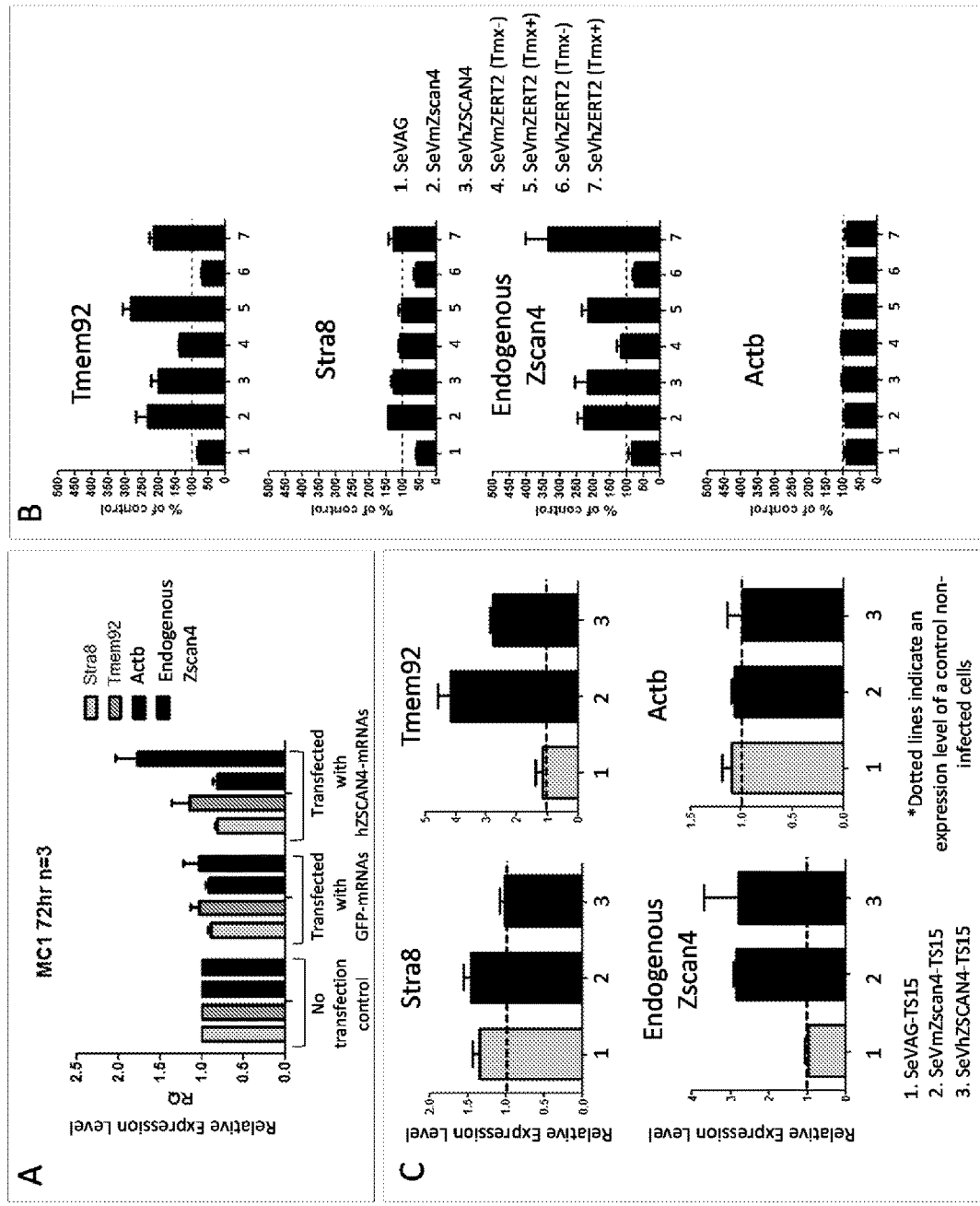
FIG. 4 depicts the effects of Zscan4 biologics on mouse ES cells.

FIG. 4A shows the results of qRT-PCR analysis, monitoring the expression levels of Tmem92, Stra8, Actb (beta-actin control), and endogenous Zscan4 genes after transfection of MC1 mouse ES cells with synthetic mRNAs. Compared to control cells transfected with GFP mRNAs, human ZSCAN4 mRNAs increased the expression of the endogenous mouse Zscan4 gene.

FIG. 4B shows the results of qRT-PCR analysis, monitoring the expression levels of Tmem92, Stra8, Actb (beta-actin control), and endogenous Zscan4 genes after contacting MC1 mouse ES cells with Sendai virus vectors expressing either mouse Zscan4c or human ZSCAN4. Compared to control cells contacted with an empty Sendai vector (SeVAG), both SeVmZscan4 and SeVhZSCAN4 increased the expression of Tmem92, Stra8, and endogenous Zscan4 genes. SeVmZERT2 and SeVhZERT2 also function in the presence of Tmx. Similarly, temperature-sensitive Sendai vectors expressing either mouse Zscan4c or human ZSCAN4 also functioned in the MC1 cells (FIG. 4C).

These results indicate that Zscan4 biologics, in the form of Sendai vectors expressing Zscan4 or synthetic Zscan4 mRNAs, can function in mouse ES cells in a manner similar to the mouse Zscan4c transgene integrated into the mouse genome. Without wishing to be bound by theory, it is believed that Zscan4 biologics have an advantage as reagents for mouse cells and therapeutics for human cells, because of the ease of use and the elimination of unwanted DNA integration into the genome. Moreover, rather than expending a great amount of time to genetically engineer the cells, Zscan4 biologics require only a simple procedure of adding a Zscan4 biologic to the cell culture media.

Example 3: Effects of Zscan4 Biologics on Human Induced Pluripotent Stem Cells

The genes SERPINB4, DNMT3L, and DUX4 are identified as marker genes that are upregulated when mouse Zscan4c or human ZSCAN4 gene is overexpressed by a transgene-based gene expression system.

This example demonstrates that Zscan4 biologics (e.g., expression of Zscan4, either by a synthetic mRNA encoding Zscan4 or a Sendai virus vector expressing Zscan4) can function in human iPS cells in a manner similar to the transgene-based Zscan4 overexpression system used in mouse pluripotent stem cells. This example also demonstrates that synthetic mRNAs encoding human ZSCAN4 and Sendai virus vector expressing human ZSCAN4 can be used as therapeutic biologics for treating human pluripotent stem cells.

Materials and Methods

Cell Culture

Human foreskin fibroblast derived-induced pluripotent stem (hiPS) cells (System Biosciences, CA, USA) were cultured on mitotically-inactivated mouse embryonic fibroblasts (MEFs) and media supplemented with 20% knockout serum replacement and 10 ng/ml bFGF (Life Technologies, CA, USA) following manufacturer's instructions. The medium was changed every day and cells were passaged using accutase every 7 days.

Synthetic mRNA

For synthesis of modified mRNA, mRNA synthesis was performed as reported previously by Warren et al. (Warren et al., Cell Stem Cell, 2010 Nov. 5; 7(5):618-30). Using these protocol from Warren et al., mRNAs were synthesized by in vitro transcription of template DNAs encoding mouse Zscan4c, human ZSCAN4, or green fluorescent protein (GFP) with mixtures of modified dNTPs to increase RNA stability as well as translation efficiency in mammalian cells. The following modified dNTPs were used: 3'-0-Me-m7G (5')ppp(5')G ARCA cap analog, 5-methylcytidine triphosphate, and pseudouridine triphosphate Sendai Virus Vectors Sendai vectors that express either mouse Zscan4c (SeV18+mZscan4/ΔF) or human ZSCAN4 (SeV18+hZSCAN4/ΔF) were custom-made by MBL (Medical & Biological Laboratories Co, LTD). These vectors are referred to as "SeVmZscan4' or "SeVhZSCAN4", respectively, herein. As a control, the same Sendai vector was used, but the vector expressed a green fluorescent protein variant rather than Zscan4. These Sendai vectors lack the F protein, and thus, are not transmissible (Inoue et al., *J Virol.* 77: 23238-3246, 2003).

Sendai vectors that express either mouse Zscan4c fused to a Tamoxifen-controllable ERT2 domain (SeV18+mZERT2/ΔF), or human ZSCAN4 fused to Tamoxifen-controllable ERT2 domain (SeV18+hZERT2/ΔF) were custom-made by MBL (Medical & Biological Laboratories Co, LTD). These vectors are referred to as "SeVmZERT2' or "SeVhZERT2", respectively, herein. These Sendai vectors also lack the F protein, and thus, are not transmissible (Inoue et al., *J Virol.* 77: 23238-3246, 2003).

Additionally, temperature-sensitive Sendai vectors that express either mouse Zscan4 (SeV18+mZscan4/TS15ΔF) or human ZSCAN4 (SeV18+hZSCAN4/TS15ΔF) were custom-made by MBL (Medical & Biological Laboratories Co, LTD). These vectors are referred to as "SeVmZscan4-TS15" or "SeVhZSCAN4-TS15", respectively, herein. These Sendai vectors are functional at 35° C., and inactive at 37° C. (Ban et al., *Proc Natl Acad Sci USA.* 2011; 108(34):14234-14239). As a control, the same temperature-sensitive Sendai vector was used, but the vector expressed a green fluorescent protein variant rather than Zscan4. This vector is referred to as "SeVAG-TS15" herein. These Sendai vector also lacks the F protein, and thus, it is not transmissible (Inoue et al., *J Virol.* 77: 23238-3246, 2003).

Results

Figure 5:
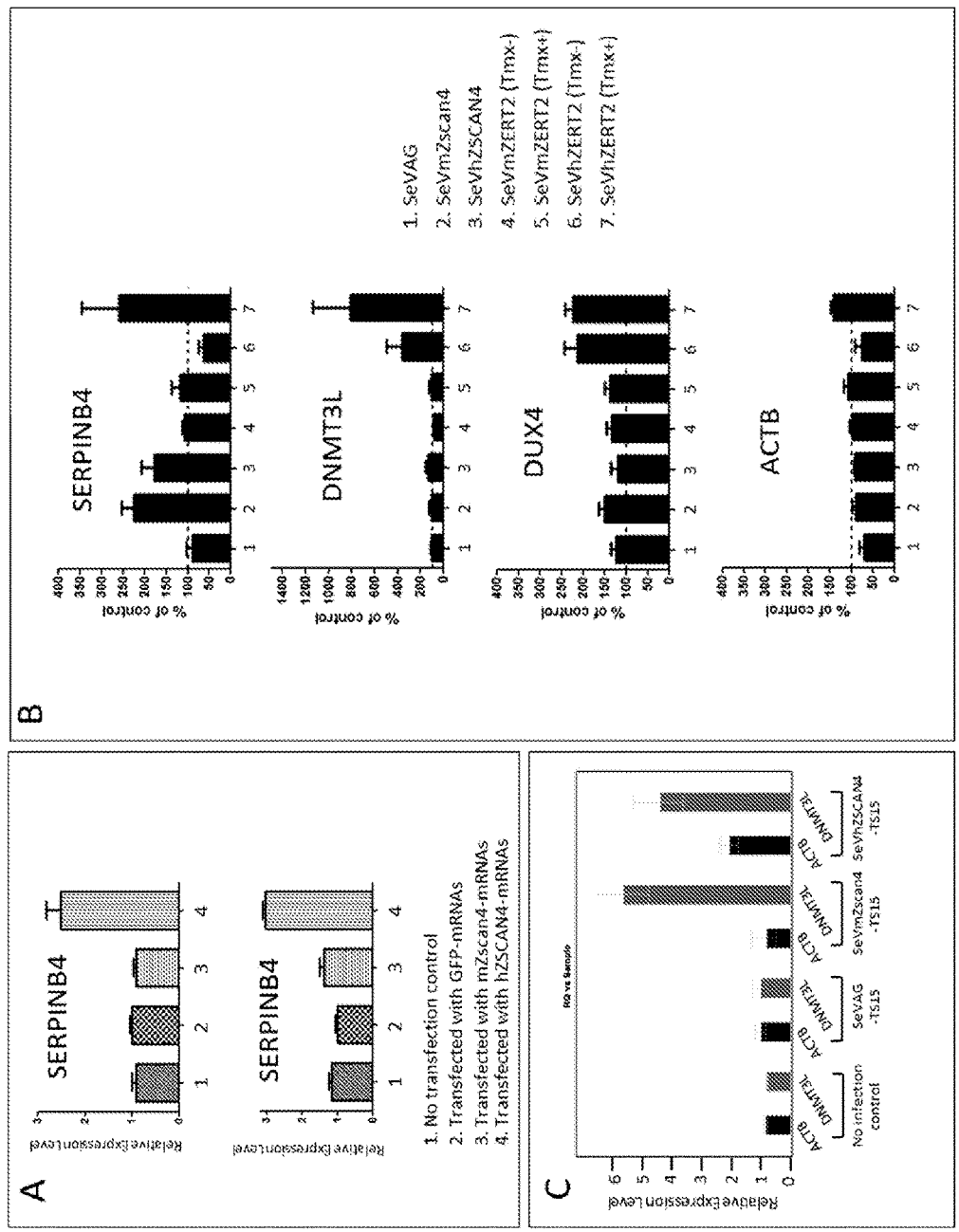
FIG. 5 depicts the effects of Zscan4 biologics on human iPS cells.

FIG. 5A shows that synthetic mRNAs encoding human ZSCAN4 can induce the expression of SERPINB4. FIG. 5B shows that SeVmZscan4, SeVhZSCAN4, SeVmZERT2 (Tmx+ condition), and SeVhZERT2 (Tmx+ condition) can induce the expression SERPINB4 and, to some extent, DNMT3L and DUX4. Similarly, temperature-sensitive Sendai vectors expressing either mouse Zscan4c or human ZSCAN4 can induce the expression of DNMT3L (FIG. 5C).

These results indicate that Zscan4 biologics, in the form of Sendai vectors expressing Zscan4 or synthetic Zscan4 mRNAs, can function in human pluripotent stem cells, e.g., human iPS cells, as Zscan4 induces markers (e.g., SERPINB4, DNMT3L, and DUX4) for the effects of Zscan4 on human iPS cells. These markers may also be useful for measuring the quality and effectiveness of Zscan4 biologics (Quality Control [QC]).

Example 4: Zscan4 Expression to Improve the Quality of Human Pluripotent Stem Cells This example describes the finding that Zscan4 biologics can improve the quality of human pluripotent stem cells, including but not limited to human embryonic stem (ES) cells and induced pluripotent stem (iPS) cells, by utilizing Zscan4 biologics (e.g., expression of Zscan4, either by a synthetic mRNA encoding Zscan4 or a Sendai virus vector expressing Zscan4) to correct one or more chromosome abnormalities and to correct one or more epigenetic errors. In particular, it is shown that a Zscan4 biologic can correct erroneous DNA methylation patterns in human iPS cells by transiently demethylating several DNA regions that are difficult to demethylate by other procedures. For example, there are regions in the genome where DNA methylation patterns are different between human iPS cells and human ES cells. It is thus important to correct such erroneous DNA methylation patterns in human iPS cells. It is believed that the ability of Zscan4 biologics to correct DNA methylation problems by merely exposing human iPS cells to a Zscan4 biologic may be a key technology for improving the safety of human iPS cells for therapeutic uses. The ability of Zscan4 biologics to correct DNA methylation problems in human iPS cells will also allow for the improvement of existing human iPS cells.

Example 5: Zscan4 Expression Extends the Lifespan of Human Dyskeratosis Congenita Fibroblast Cells and Extends Telomere Length in Human Dyskeratosis Congenita Fibroblast Cells This example describes the finding that expression of human ZSCAN4, either by a synthetic mRNA encoding ZSCAN4 or a Sendai virus vector expressing Zscan4, induces lifespan extension of human dyskeratosis congenita fibroblast cells, and also induces telomere length elongation in human dyskeratosis congenita fibroblast cells. This example also demonstrates that synthetic mRNAs encoding human ZSCAN4 and Sendai virus vector expressing human ZSCAN4 can be used as therapeutic biologics.

Materials and Methods

Cell Culture

Fibroblast cells isolated from a patient with dyskeratosis congenita (DKC: X-linked) were purchased from the Coriell Cell Repository (Catalog ID AG04646). According to the Coriell Catalog information, the cell donor, an 11 year old male Caucasian, is affected and presented with skin eruptions, anemia, nail dystrophy and esophageal abnormalities. Family history is negative. The biopsy was taken antemortem from uninvolved skin. The culture was initiated on Feb. 21, 1981 using explants of minced tissue. The cell morphology is fibroblast-like. The population doubling level (PDL) was 5.41 at freeze and the passage number was 5.

After receiving the DKC cells from the Coriell Cell Repository, the cells were cultured for a few more passages. The cells were cultured under condition recommended by the Coriell Cell Repository: Eagle's Minimum Essential Medium with Earle's salts and non-essential amino acids, supplemented with 15% fetal bovine serum (not inactivated).

Synthetic mRNA

For synthesis of modified mRNA, mRNA synthesis was performed as reported previously by Warren et al. (Warren et al., *Cell Stem Cell,* 2010 Nov. 5; 7(5):618-30). Using these protocol from Warren et al., mRNAs were synthesized by in vitro transcription of template DNAs encoding human ZSCAN4 or green fluorescent protein (GFP) with mixtures of modified dNTPs to increase RNA stability as well as translation efficiency in mammalian cells. The following modified dNTPs were used: 3'-0-Me-m7G(5')ppp(5')G ARCA cap analog, 5-methylcytidine triphosphate, and pseudouridine triphosphate.

Sendai Virus Vector

A Sendai vector that expresses human ZSCAN4 (SeV18+hZSCAN4/ΔF) was custom-made by MBL (Medical & Biological Laboratories Co, LTD). The vector is referred to as "SeVhZSCAN4" herein. This Sendai vector lacks the F protein, and thus, it is non-transmissible (Inoue et al., *J Virol.*

77:3238-3246, 2003). An MOI (multiplicity of infection) of 10 was used for the experiments.

Telomere Southern Blot Analysis

Telomere lengths of cells were measured by Southern blot analysis using the TeloTAGGG Telomere Length Assay kit (Roche Applied Sciences, Indiana, USA) according to the manufacturer's instruction.

Results

Synthetic mRNAs Encoding Human ZSCAN4 Extend the Lifespan of Human Dyskeratosis Congenita Fibroblast Cells DKC cells were plated in a 6 well dish at a concentration of $5 \times 10^4$ cells/well and then transfected with 1 µg of synthetic mRNAs using 5 µl of Lipofectamine (RNAiMAX: Life Technologies, California, USA). The medium was changed the next day. Every week cells were passaged at a ratio of 1:2 and transfected with synthetic mRNAs in the presence of 50 ng/ml B18R (Type I IFN inhibitor: eBiosciences, Inc., California, USA). Samples were prepared in triplicate. Cell number was counted using the Automated Cell Counter Moxi Z (ORFLO Technologies, Idaho, USA). Cell numbers were converted to PDL (population doubling level), starting at PDL=0 (normalized from passage 9, equivalent to approximately PDL=9 according to the information from the Coriell Cell Repository).

Figure 6:
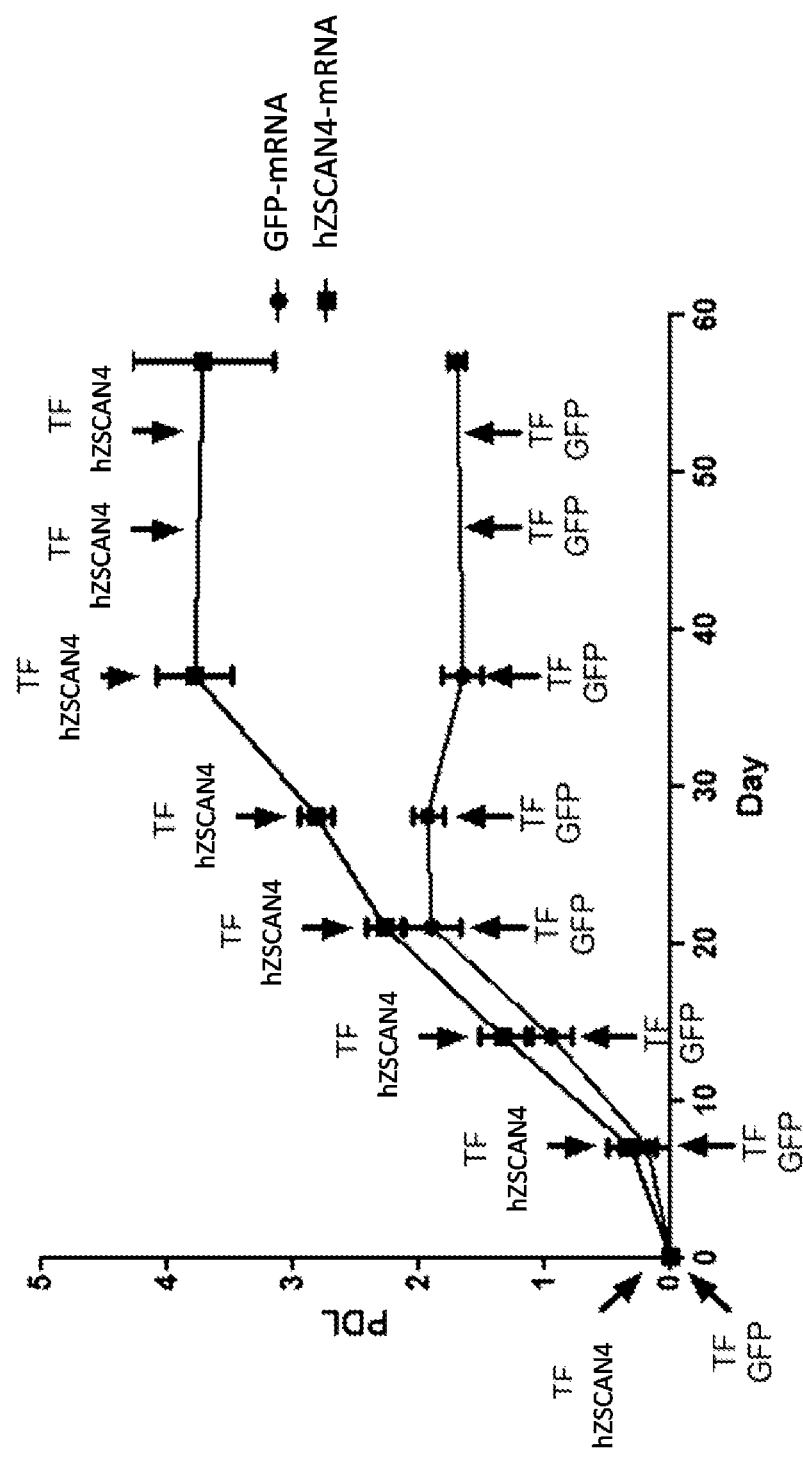
FIG. 6 depicts the results of a growth assay of human fibroblast cells from a DKC patient transfected with hZSCAN4 mRNAs or GFP mRNAs.

FIG. 6 shows the results of cell growth assays over 60 days. In control experiments, repeated transfections of GFP mRNAs do not change the growth patterns of DKC cells: after approximately 20 days in culture (approximately PDL=2), cells stop proliferating and undergo cellular senescence. By contrast, repeated transfections of human ZSCAN4 mRNAs extend the lifespan of the DKC cells and the cells continued to grow until ~40 days (~PDL=4). It is important to note that the hZSCAN4 treatment did not transform the cells into tumor-like cells with unlimited proliferation capacity. These results indicate that the hZSCAN4 treatment can extend the lifespan of cells from DKC patients without transforming the cells into tumors.

Sendai Virus Vectors Expressing Human ZSCAN4 Extend the Lifespan of Human Dyskeratosis Congenita Fibroblast Cells DKC cells were plated in a 6 well dish at a concentration of $5 \times 10^4$ cells/well, and 6 hours later the cells were contacted with SeVhZSCAN4 vector at an MOI of 10 for 24 hours. As a control, a second sample of DKC cells was cultured in the same manner, but without exposure to the SeVhZSCAN4 vector. Cells were passaged every one or two weeks. Cell number was counted by the Automated Cell Counter Moxi Z (ORFLO Technologies, Idaho, USA). Cell numbers were converted to PDL (population doubling level), starting at PDL=0 (normalized from passage 9, equivalent to approximately PDL=9 according to the information from the Coriell Cell Repository).

Figure 7:
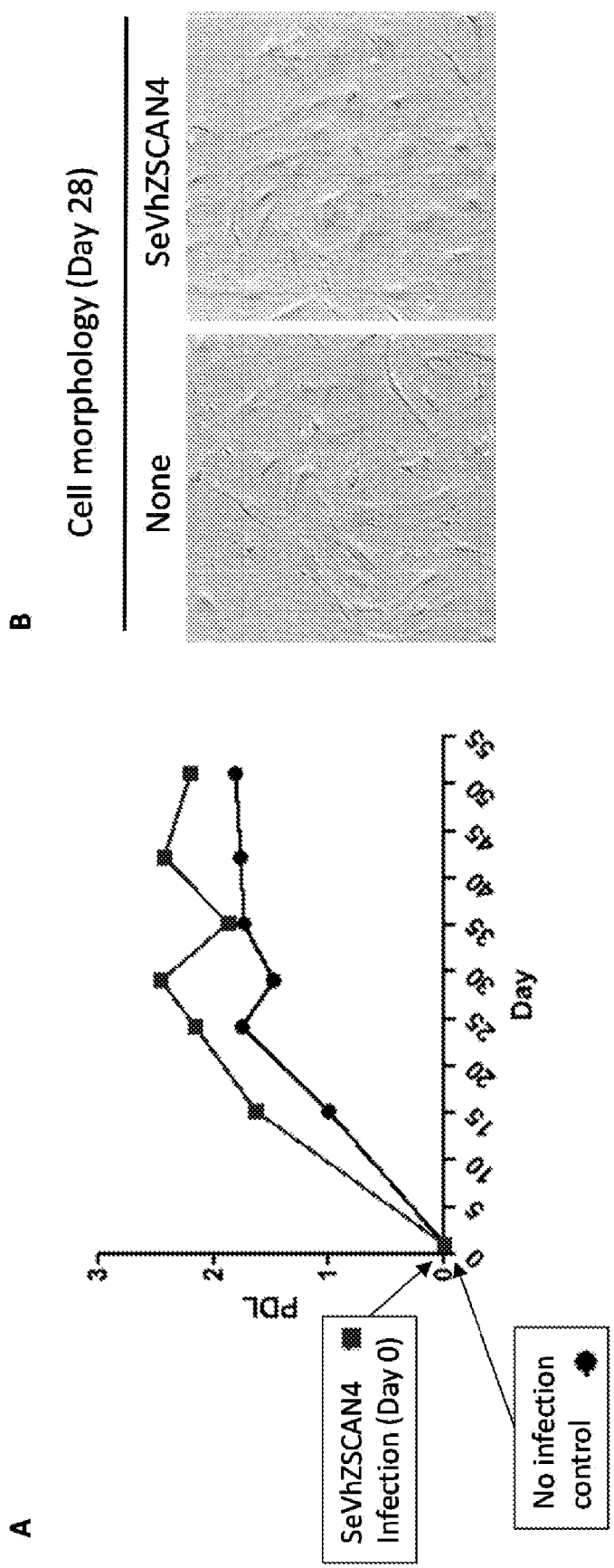
FIG. 7A depicts the results of a growth assay of human fibroblast cells from a DKC patient infected with SeVhZScan4.
FIG. 7B shows micrographs depicting the cell morphology of human fibroblast cells from a DKC patient infected with SeVhZScan4.

FIG. 7A shows the results of cell growth assays. In control experiments, DKC cells show a typical growth pattern: after approximately 25 days in culture (approximately PDL=2), cells stop proliferating and undergo cellular senescence. By contrast, DKC cells contacted with the SeVhZSCAN4 vector show an increase in cell lifespan. It is important to note that the SeVhZSCAN4-treatment does not change the cells into tumor-like cells with unlimited proliferation capacity.

FIG. 7B shows cell morphologies on day 28. SeVhZSCAN4-treated cells show a better morphology than the non-treated control cells.

These results indicate that the SeVhZSCAN4 treatment can extend the lifespan of cells from DKC patients without transforming the cells into tumors.

Figure 8:
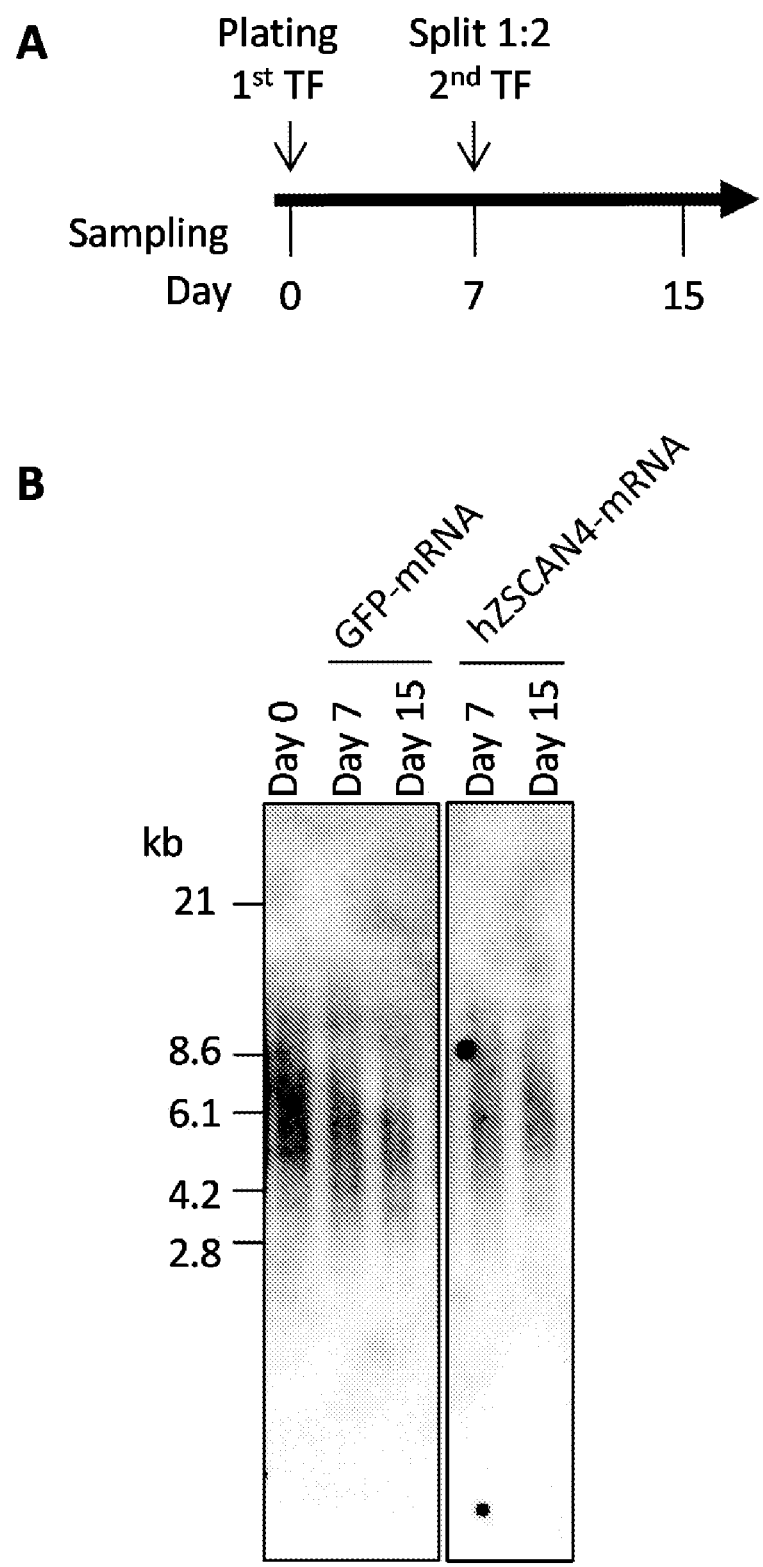
FIG. 8A depicts the experimental procedure.
FIG. 8B depicts the results of a telomere length assay of human fibroblast cells from a DKC patient transfected with hZSCAN4 mRNAs or GFP mRNAs.

Synthetic mRNAs Encoding Human ZSCAN4 Elongate Telomere Length in Human Dyskeratosis Congenita Fibroblast Cells FIG. 8A shows the procedure of the experiments. DKC cells were plated in 10 cm culture dishes at a concentration of $1 \times 10^5$ cells/10 cm culture dish. Cells in each 10-cm dish were then transfected with 5 µg of synthetic mRNAs using 25 µl of Lipofectamine (RNAiMAX: Life Technologies, California, USA). The medium was changed the next day. Cells from 1 dish were harvested on day 7 and genomic DNA was extracted. Cells from another dish were passaged at a 1:2 ratio and then transfected with 5 µg of synthetic mRNAs using 25 µl of Lipofectamine. Cells were harvested on day 15 and genomic DNA was extracted. The genomic DNA was then subjected to the telomere length assays.

FIG. 8B shows the results of telomere length assays. As previously reported (Wong J. M., Collins K. *Genes Dev.* (2006), 20(20), 2848-2858), telomere length of DKC fibroblast cells are shorter than that of normal cells and quickly become even shorter when the DKC cells are cultured. In control experiments, transfection with GFP-mRNAs did not change the telomere length shortening patterns of DKC cells. By contrast, transfection with human ZSCAN4-mRNAs elongated telomere length of the DKC cells and prevented telomere lengths from getting shorter. These results indicate that telomere length shortening of DKC cells, a primary cause of DKC disease phenotypes, can be rescued by treating cells with hZSCAN4-mRNAs.

Example 6: Zscan4 Expression Extends Lifespan of Human Werner Syndrome Cells

WS patients are characterized by the appearance of premature aging. Cells of WS patients in culture exhibit a higher rate of chromosomal breaks, translocations and deletions. Thus, WS patients are in need of a treatment that can enhance genome and/or chromosome stability.

This example demonstrates that synthetic mRNAs encoding Zscan4 can extend the lifespan of fibroblast cells isolated from a Werner syndrome (WS) patient. This example also demonstrates that synthetic mRNAs encoding human ZSCAN4 can be used as therapeutic biologics.

Materials and Methods

Cell Culture

Fibroblast cells isolated from a patient with Werner syndrome (WS) were purchased from the Coriell Cell Repository (Catalog ID AG03141). According to the Coriell Catalog information, "the donor was a 30 year old female Caucasian, and had features of premature aging, pigmented and atrophic skin, cataracts and hyperlipidemia type V. The biopsy was taken ante-mortem on Sep. 20, 1978. The culture was initiated using explants of minced skin tissue. The cell morphology is fibroblast-like. The karyotype is 46,XX with 80% of cells examined showing random chromosomal abnormalities. Homozygous for a C to T transition at nucleotide 2476 in the WRN gene (2476C>T), resulting in a stop codon at 748 {Gln748TER (Q748X)}. The cumulative population doubling level (PDL) was 17.97 at freeze and the passage number was 11." After receiving the WS cells from the Coriell Cell Repository, the cells were cultured for a few more passages. The cells were cultured in the condition recommended by the Coriell Cell Repository: Eagle's Minimum Essential Medium with Earle's salts Earle's salts: Dulbecco's modified MEM, supplemented with 15% fetal bovine serum (not inactivated).

Synthetic mRNA

For synthesis of modified mRNA, mRNA synthesis was performed as reported previously by Warren et al. (Warren et al., *Cell Stem Cell*, 2010 Nov. 5; 7(5):618-30). Using these protocol from Warren et al., mRNAs were synthesized by in vitro transcription of template DNAs encoding human ZSCAN4 or green fluorescent protein (GFP) with mixtures of modified dNTPs to increase RNA stability as well as translation efficiency in mammalian cells. The following modified dNTPs were used: 3'-0-Me-m7G(5')ppp(5')G ARCA cap analog, 5-methylcytidine triphosphate, and pseudouridine triphosphate.

Results

WS cells were plated in a 6 well dish at a concentration at $5 \times 10^4$ cells/well, and then transfected with 1 µg of synthetic mRNAs using 5 µl of Lipofectamine (RNAiMAX: Life Technologies, California, USA) at day 0. The medium was changed the next day. A second transfection with the same mRNAs was carried out on day 3. Dependent on the growth of the cells, the cells were passaged at a ratio of 1:2 every 1 or 2 weeks. Samples were prepared in triplicate. Cell numbers were converted to PDL, starting at a PDL of 0 (approximately equivalent to a cumulative PDL of 19, which is near cellular senescence according to the information from the Coriell Cell Repository).

Figure 9:
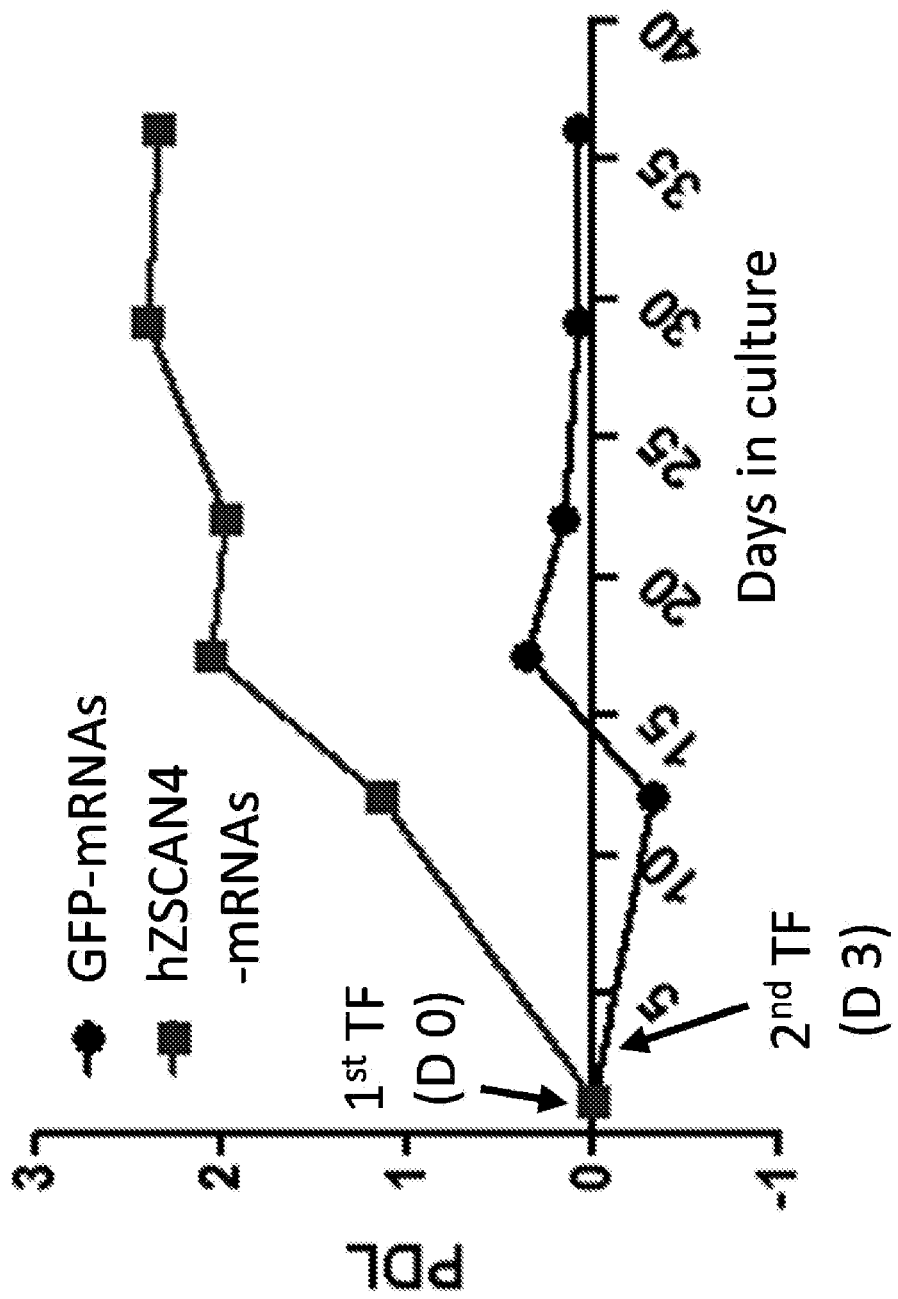
FIG. 9 depicts the results of a growth assay of fibroblast cells of a Werner syndrome (WS) patient transfected with hZSCAN4 mRNAs or GFP mRNAs.

FIG. 9 shows the results of cell growth assays. WS cells transfected with synthetic GFP mRNAs were used as a control. As shown in FIG. 9, WS cells transfected with synthetic GFP mRNAs underwent cellular senescence and stopped proliferating. By contrast, the transfection of WS cells with synthetic hZSCAN4 mRNAs provided WS cells with two more PDL, and thus extended the lifespan of the WS cells (FIG. 9). Importantly, the results demonstrate that synthetic hZSCAN4 mRNAs did not provide unlimited cell growth, as the cells stopped proliferating eventually. Similar to the results with synthetic hZSCAN4 mRNAs, lifespan extension of WS cells was also observed in cells contacted with SeVhZSCAN4 or SeVhZSCAN4-TS15 Sendai virus vectors that express human ZSCAN4. Without wishing to be bound by theory, it is believed that the use of ZSCAN4 as a therapeutic biologic does not appear to cause cell transformation and/or cancer in treated cells. These results indicate that hZSCAN4 treatment can extend the lifespan of cells in WS patients without transforming the cells into tumors.

Example 7: Zscan4 Expression to Treat Telomere Shortening in Patients

Figure 10:
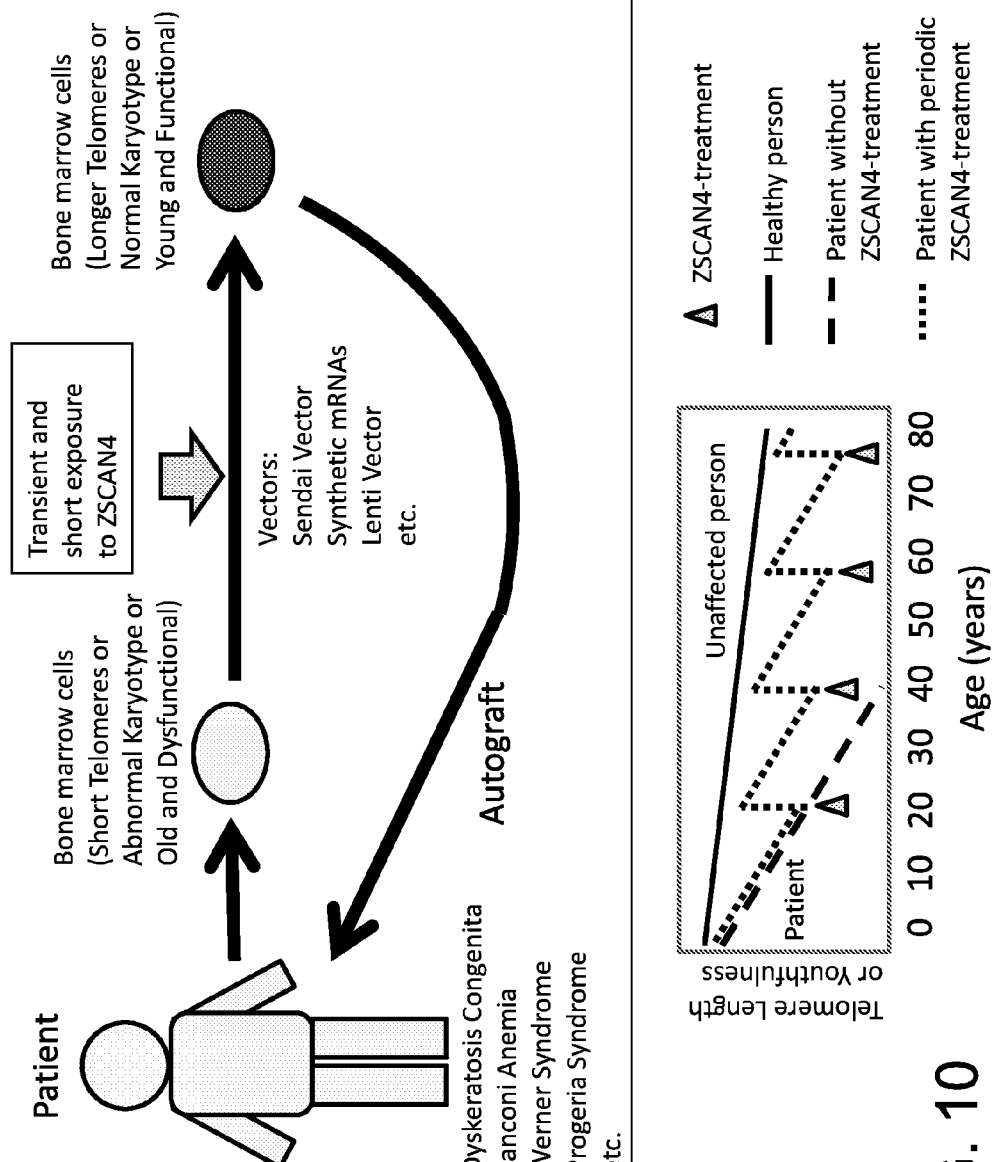
FIG. 10 depicts an exemplary treatment scheme using Zscan4.

FIG. 10 illustrates one mode of treatment using Zscan4. This procedure is very similar to the bone marrow transplantation procedures that have been done routinely in hospitals to treat patients with bone marrow failures and leukemia. Bone marrow, which includes hematopoietic stem cells and mesenchymal stem cells, will be aspirated from patients and then immediately exposed to Zscan4 (e.g., Sendai vector carrying human ZSCAN4). This exposure to Zscan4 will be transient and for a short time. Without wishing to be bound by theory, it is believed that the expression of Zscan4 will disappear when the bone marrow cells are administered back into the patient. Alternatively, temperature-sensitive Sendai vectors can be used, as the expression of Zscan4 can be turned off by switching the temperature. Alternatively, Sendai vectors carrying the fusion protein hZSCAN4-ERT2, which can be turned on by adding Tamoxifen and turned off by removing Tamoxifen, can be used. Alternatively, synthetic mRNAs such as hZS- CAN4-mRNAs can be used, as the production of ZSCAN4 protein is transient due to the limited half-life of synthetic mRNAs. The thusly Zscan4-rejuvenated bone marrow cells will then repopulate the patient's bone marrow and hematopoietic compartment. Based on the long term effects of this transient Zscan4 contact, and without wishing to be bound by theory, it is believed that this procedure is required only once or periodically after long intervals of time (e.g., many years). Without wishing to be bound by theory, it is believed that the Zscan4-rejuvenated bone marrow cells will out compete and thus replace sick bone marrow cells. Accordingly, it is believed that irradiation of bone marrow to eliminate sick bone marrow cells, which is performed during standard bone marrow transplantation, would not be necessary.

Example 8: Zscan4 Expression Extends Telomeres in Human Fibroblast Cells

This example describes the finding that Zscan4 overexpression induces telomere extension in human fibroblast cells.

Materials and Methods

Cell Culture

Primary adult human dermal fibroblasts (HDFa) isolated from adult skin (~30 year old) were purchased from Life Technologies (Cat. no. C-013-5C). Fibroblasts (GM01309) isolated from a Fanconi anemia, complementation group A (FANCA) patient were purchased from the Coriell Cell Repository. These cells were maintained under standard culture conditions: DMEM (Dulbecco's Modified Eagle Medium) supplemented with 10% Fetal Bovine Serum.

Telomere Quantification by qPCR

Telomere quantification by qPCR was conducted using procedures described previously (Cawthon, R. M. *Nucleic Acids Res.* 2002 May 15; 30(10):e47; and Callicott, R J et al. *Comparative Medicine*, 2006). Genomic DNA was extracted from $>5 \times 10^5$ fibroblast cells using the DNeasy blood and tissue kit (Qiagen). Quality of gDNA samples were assessed using Nanodrop. Genomic DNA samples with an A260/280 absorbance ratio greater than 1.8, and an A260/230 absorbance ratio of around 2 were used for qPCR to determine telomere length.

The primers used for telomere PCR were as follows:

```
                                           (SEQ ID NO: 41)
    tel1b: 5'-CGGTTT(GTTTGG)5GTT-3';
    and (SEQ ID NO: 42)
    tel2b: 5'-GGCTTG(CCTTAC)5CCT-3'
```

Each primer was used at a final concentration of 300 nM.

The primers used for single copy gene PCR were as follows:

```
                                           (SEQ ID NO: 43)
    36B4u: 5'-CAGCAAGTGGGAAGGTGTAATCC-3';
    and (SEQ ID NO: 44)
    36B4d: 5'-CCCATTCTATCATCAACGGGTACAA-3'
```

The 36B4u primer was used at a final concentration of 300 nM, and the 36B4d primer was used at a final concentration of 500 nM.

The final 20 µl qPCR reaction was place in one well of a 96-well plate and included 20 ng gDNA, primers, and 1×

Power SYBR green (Applied Biosystems). The telomere PCR thermal cycling program for the Tel1b/2b PCR was: 95° C. for 10 minutes, 40 cycles of 95° C. for 15 s, and 56° C. for 1 minute. The telomere PCR thermal cycling program for the 36B4 PCR was: 95° C. for 10 minutes, 40 cycles of 95° C. for 15 s, and 58° C. for 1 minute. The StepOne Plus qPCR machine (Applied Biosystems) was used to process the samples. Threshold level was set to obtain sample Ct values around 20-22. The delta delta Ct method was used to calculate the relative telomere/single copy gene ratio (relative T/S ratio) for assessment of telomere length in each sample.

Sendai Virus Vectors

Sendai vectors that express human ZSCAN4 (SeV18+ hZSCAN4/ΔF) were custom-made by MBL (Medical & Biological Laboratories Co, LTD). This Sendai vector lacks the F protein, and thus, it is non-transmissible (Inoue et al., *J Virol.* 77:3238-3246, 2003).

Results

Overexpression of Human ZSCAN4 Rapidly Increases Telomere Lengths in Normal Adult Human Fibroblast Cells Adult human dermal fibroblasts (HDFa) were cultured under standard culture conditions. On the day after passaging cells, one sample of cells was harvested for genomic DNA extraction (no treatment control). A second sample of cells was transduced with the SvhZSCAN4 Sendai viral vector.

Transduced cells were harvested 2 days (SeVhZSCAN4-treatment day 2) or 3 days (SeVhZSCAN4-treatment day 3) after transduction. Telomere length of harvested cells was then measured by qRT-PCR, and the relative telomere length (T/S ratio) to the control no treatment control cells was calculated.

Figure 11:
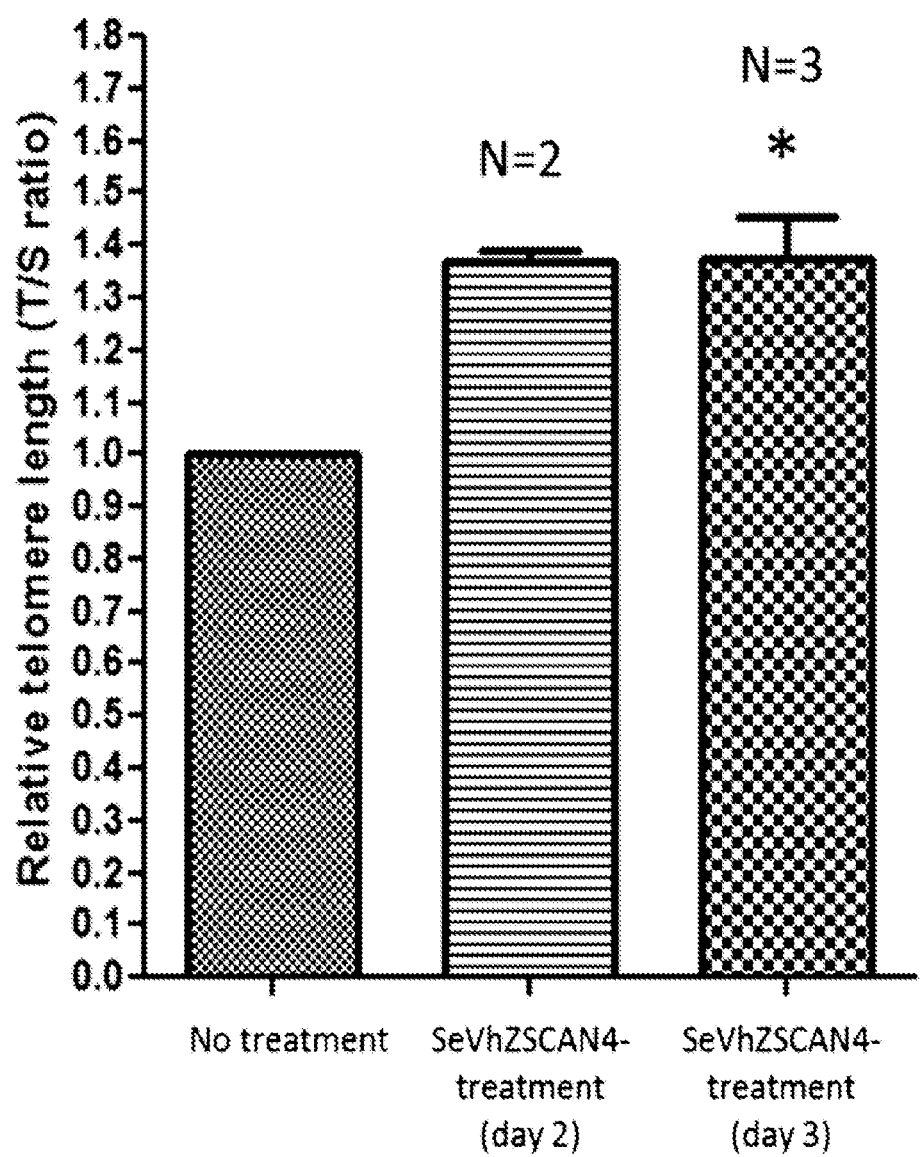
FIG. 11 depicts a bar graph showing that overexpression of human ZSCAN4 increases telomere length in normal adult human fibroblast cells. "N" indicates the number of replicates.

As shown in FIG. 11, the average length of telomeres increased after day 2 and after day 3. In particular, 2 days after transduction with ZSCAN4, the HDFa cells had a T/S ratio of about 1.4, while the control cells had a T/S ratio of 1.0 (FIG. 11). Similarly, 3 days after transduction with ZSCAN4, the HDFa cells had a T/S ratio of about 1.4 (FIG. 11). These results indicate that after two days of transduction with ZSCAN4, HDFa cells had about a 40% increase in relative telomere length, as compared to the control cells that were not transduced with ZSCAN4.

Overexpression of Human ZSCAN4 Rapidly Increases Telomere Lengths in Fibroblast Isolated from a Patient with Fanconi Anemia, Complementation Group A GM01309 fibroblasts isolated from a FANCA patient were cultured under standard culture conditions. On the day after passaging cells, one sample of cells was harvested for genomic DNA extraction (no treatment control). A second sample of cells was transduced with the SvhZSCAN4 Sendai viral vector.

Transduced cells were harvested 2 days (SeVhZSCAN4-treatment day 2) or 3 days (SeVhZSCAN4-treatment day 3) after transduction. Telomere length of harvested cells was then measured by qRT-PCR, and the relative telomere length (T/S ratio) to the control no treatment control cells was calculated.

Figure 12:
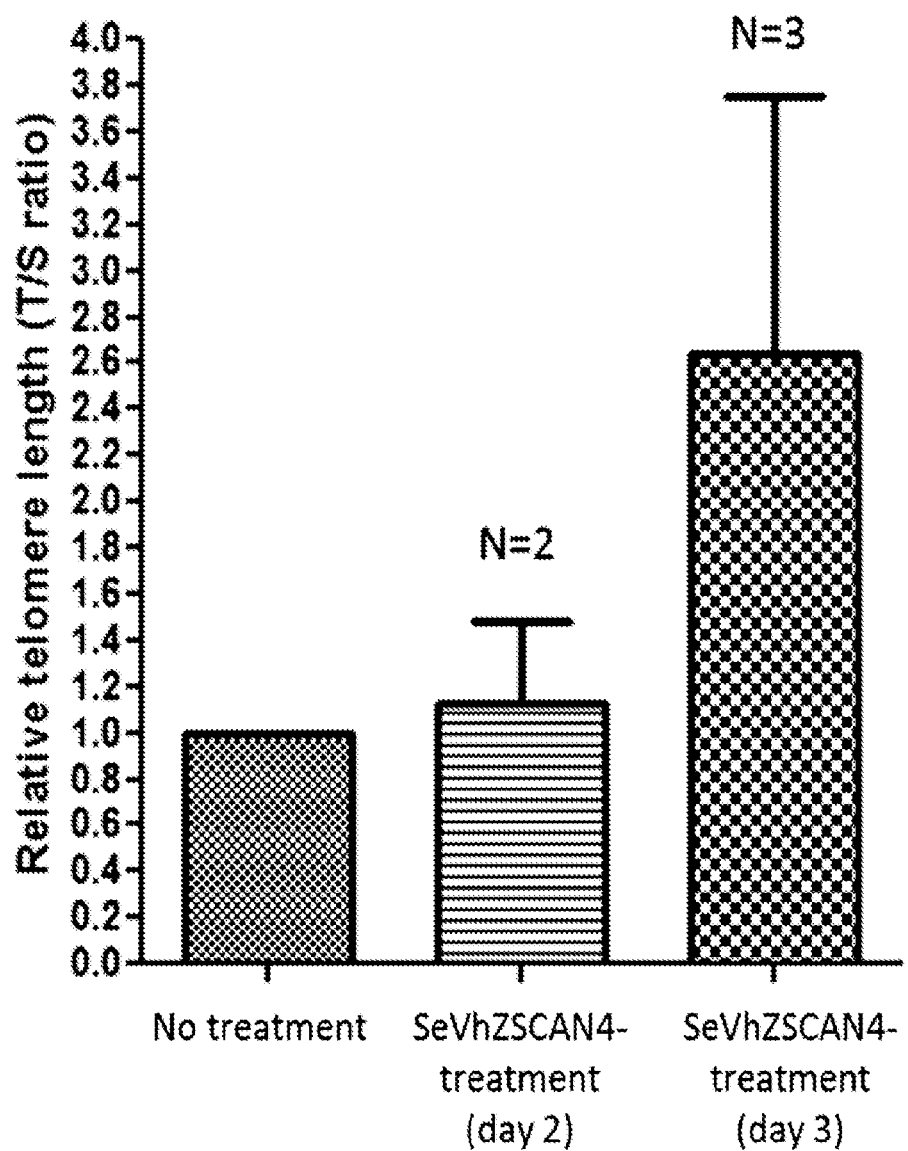
FIG. 12 depicts a bar graph showing that overexpression of human ZSCAN4 increases telomere length in human fibroblasts isolated from a patient with Fanconi anemia, complementation group A. "N" indicates the number of replicates.

As shown in FIG. 12, the average length of telomeres increased slightly after day 2 and dramatically after day 3. In particular, 2 days after transduction with ZSCAN4, the GM01309 cells had a T/S ratio of about 1.1, while the control cells had a T/S ratio of 1.0 (FIG. 12). This result indicates that after two days of transduction with ZSCAN4, GM01309 cells had about a 10% increase in relative telomere length, as compared to the control cells that were not transduced with ZSCAN4.

Three days after transduction with ZSCAN4, the GM01309 cells had a T/S ratio of about 2.6 (FIG. 12). This result indicates that after three days of transduction with ZSCAN4, GM01309 cells had about a 160% increase in relative telomere length, as compared to the control cells that were not transduced with ZSCAN4.

Example 9: Zscan4 Expression Extends Lifespan of Human Fibroblast Cells

This example describes the finding that synthetic mRNAs encoding human ZSCAN4 can extend the lifespan of dermal fibroblast cells isolated from a healthy adult. This example also demonstrates that synthetic mRNAs encoding human ZSCAN4 can be used as therapeutic biologics.

Materials and Methods

Cell Culture

Primary human dermal fibroblasts cells (HDFa) isolated from adult skin were purchased from Life Technologies. According to the manufacturer's information, the HDFa cells are capable of at least 12 population doublings (PDL). HDFa cells were cultured according to the manufacture's instruction. After receiving the HDFa cells, the cells were cultured for many passages such that the cells do not grow exponentially and are approaching cellular senescence.

Synthetic mRNA

For synthesis of modified mRNA, mRNA synthesis was performed as reported previously by Warren et al. (Warren et al., *Cell Stem Cell,* 2010 Nov. 5; 7(5):618-30). Using these protocol from Warren et al., mRNAs were synthesized by in vitro transcription of template DNAs encoding human ZSCAN4 or green fluorescent protein (GFP) with mixtures of modified dNTPs to increase RNA stability as well as translation efficiency in mammalian cells. The following modified dNTPs were used: 3'-0-Me-m7G(5')ppp(5')G ARCA cap analog, 5-methylcytidine triphosphate, and pseudouridine triphosphate.

Results

HDFa cells at a stage near cellular senescence were plated in a 6 well dish at a concentration of $1\times10^5$ cells/well, and then transfected with 1 μg of synthetic mRNAs using 5 μl of Lipofectamine (RNAiMAX: Life Technologies, California, USA) at day 0. The medium was changed the next day. A second transfection with the same mRNAs was carried out on day 3. Dependent on the growth of the cells, cells were passaged at a ratio of 1:2 every 1 or 2 weeks. Samples were prepared in triplicate. Cell numbers were converted to PDL, starting at a PDL of 0.

Figure 13:
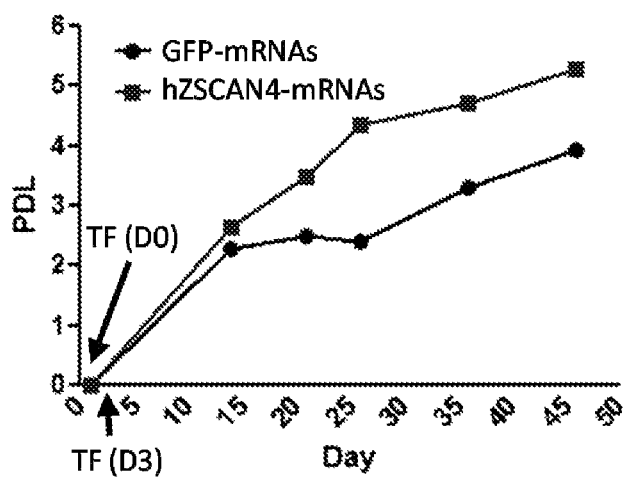
FIG. 13 depicts the results of growth assays of human adult dermal fibroblast (HDFa) cells transfected with hZSCAN4 mRNAs, mZscan4 mRNAs, or GFP mRNAs.
Figure 13:
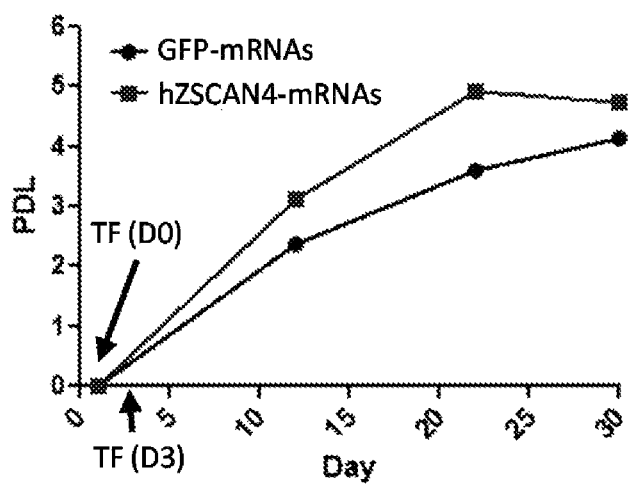
Figure 13:
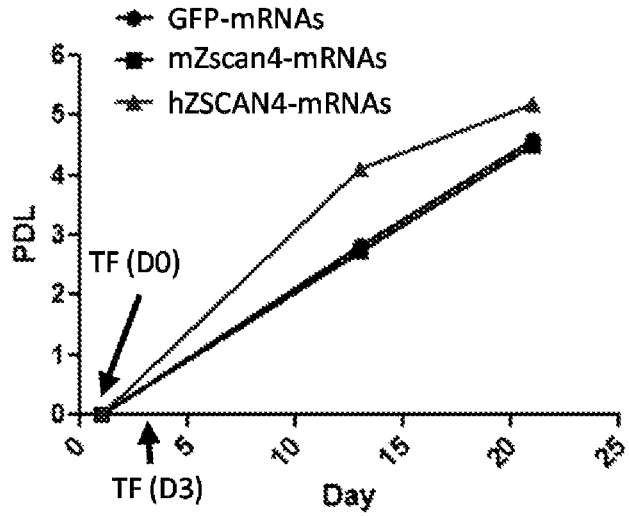

FIG. 13 shows the results of cell growth assays. HDFa cells transfected with synthetic GFP mRNAs were used as a control. After 2 weeks, HDFa cells transfected with synthetic GFP mRNAs underwent cellular senescence and proliferated slowly (FIG. 13). By contrast, HDFa cells transfected with synthetic hZSCAN4 mRNAs grew an additional 2 to 3 more PDLs, and thus, extended the lifespan of the HDFa cells near cellular senescence (FIGS. 13A and 13B). Synthetic mouse Zscan4 mRNAs did not appear to provide lifespan extension. This result indicates that human ZSCAN4 works better than mouse Zscan4c for extending the lifespan of HDFa cells (FIG. 13C). However, the synthetic hZSCAN4 mRNAs did not provide unlimited cell growth, as the cells slowed down or stopped proliferating eventually. Similar to the results with synthetic hZSCAN4 mRNAs, lifespan extension of HDFa cells was also observed in cells contacted with SeVhZSCAN4 or SeVhZSCAN4-TS15 Sendai virus vectors that express human ZSCAN4. Thus, the use of ZSCAN4 as a therapeutic biologic was not observed to cause cell transformation and/or cancer in treated cells. These results indicate that hZSCAN4 treatment can extend the lifespan of HDFa cells without transforming the cells into tumors.

Example 10: Telomere Length Elongation in Human Mesenchymal Stem (MS) Cells by Zscan4 Biologics This example describes the finding that a temperature-sensitive Sendai virus vector that expresses human ZSCAN4 can elongate telomere length in human mesenchymal stem (MS) cells. This example also demonstrates that Sendai virus vectors expressing human ZSCAN4 can be used as biologics to improve adult stem cells therapies including, without limitation, bone marrow transplants.

Materials and Methods

Cell Culture

Human adipose-derives mesenchymal stem cells (MSCs) were purchased from Life Technologies (CA, USA). According to the manufacturer's information, ADSCs have demonstrated very similar phenotypic and functional characteristics to bone marrow-derived mesenchymal stem cells. They can be expanded to 4-5 passages before they lose their ability to grow or differentiate into all potential phenotypes. The cells were cultured in the condition recommended by the manufacturer.

Sendai Virus Vectors

Temperature-sensitive Sendai vectors that express either mouse Zscan4 (SeV18+mZscan4/TS15ΔF) or human ZSCAN4 (SeV18+hZSCAN4/TS15ΔF) were custom-made by MBL (Medical & Biological Laboratories Co, LTD). These vectors are referred to as "SeVmZscan4-TS15" or "SeVhZSCAN4-TS15", respectively, herein. These Sendai vectors are functional at 35° C., and inactive at 37° C. (Ban et al., *Proc Natl Acad Sci USA.* 2011; 108(34):14234-14239). As a control, the same temperature-sensitive Sendai vector was used, but the vector expressed a green fluorescent protein variant rather than Zscan4. This vector is referred to as "SeVAG-TS15" herein. These Sendai vectors also lack the F protein, and thus, it is not transmissible (Inoue et al., *J Virol.* 77: 23238-3246, 2003).

Telomere Southern Blot Analysis

Telomere lengths of cells were measured by Southern blot analysis using the TeloTAGGG Telomere Length Assay kit (Roche Applied Sciences, Indiana, USA) according to the manufacturer's instruction.

Results

Human adipose-derives mesenchymal stem cells (MSCs) at passage 2 were plated in 10-cm dishes at a density of $1.5 \times 10^5$ cells, and contacted with temperature-sensitive Sendai vectors at an MOI of 10 (at day 0). Cells were incubated in media containing 10 μM $H_2O_2$ and kept at 35° C. for 3 days, followed by culturing at 37° C. Cells were passaged at a ratio of 1:2 on day 7. After another passaging on day 10, cells were contacted again with the temperature-sensitive Sendai vectors at an MOI of 10 and incubated 35° C. for 3 days, followed by culturing at 37° C. Subsequently, cells were passaged on day 14 (passage 3), day 20, day 27, day 42, and day 62 (passage 7). Cells were incubated in media containing 10 μM $H_2O_2$ so that telomere lengths get shorter faster than under typical cell culture conditions.

FIG. 14 shows the results of telomere length assays. Average telomere lengths (shown in the figure legend) were estimated based on Southern blot analysis according to manufacturer's protocol. As shown in FIG. 14, the human ZSCAN4 (SeVhZSCAN4-TS15) increased the telomere length of human MSCs, whereas mouse Zscan4 (SeVmZscan4-TS) did not appear to affect telomere length. These results indicate that telomere length shortening in human MSCs can be rescued by treating cells with human ZSCAN4 biologics. Without wishing to be bound by theory, it is believed that the effects of human ZSCAN4 described herein may be applied to other human tissue stem cells in culture. It is also believed that human ZSCAN4 biologics may also elongate telomere length (e.g., cell rejuvenation) in human tissue stem cells resident in human tissue (i.e., in vivo).

Example 11: Zscan4 Expression to Treat Patients with Defects in Resident Tissue Stem Cells There are many diseases that are caused by one or more deficiencies in resident tissue stem cells (i.e., tissue stem cells resident in the organ and/or tissue of the human body). For example, Duchenne muscular dystrophy is known to be associated with premature aging of muscle stem cells (satellite cells). Based on the results described herein that Zscan4 biologics (e.g., expression of Zscan4, either by a synthetic mRNA encoding Zscan4 or a Sendai virus vector expressing Zscan4) can rejuvenate tissue stem cells, it is believed that Zscan4 expression in resident tissue stem cells can correct disease-associated deficiencies in the cells. In the case of Duchene muscular dystrophy, it is thought that Zscan4 expression can be used to treat patients with Duchenne muscular dystrophy, by administering a Zscan4 biologic to muscle cells, particularly muscle stem cells, of a patient with Duchenne muscular dystrophy, to prevent the early deterioration of muscles cells.

Example 12: Zscan4 Expression to Treat Patients with Diabetes

It has been demonstrated that human ZSCAN4 is naturally, though rarely, expressed in some tissue stem cells in human pancreas. Based on the results described herein that Zscan4 biologics (e.g., expression of Zscan4, either by a synthetic mRNA encoding Zscan4 or a Sendai virus vector expressing Zscan4) can rejuvenate tissue stem cells and terminally differentiated cells, it is believed that ZSCAN4 expression can be used to treat patients with Diabetes, by administering a Zscan4 biologic to pancreatic cells, particularly resident pancreatic tissue stem cells, of a patient with Diabetes, to prevent pancreatic cells from further deterioration, and thereby facilitate the production of beta-cells.

Example 13: Zscan4 Expression to Treat Patients with Atopic Dermatitis and Other Skin Lesions Based on the results described herein that Zscan4 biologics (e.g., expression of Zscan4, either by a synthetic mRNA encoding Zscan4 or a Sendai virus vector expressing Zscan4) can rejuvenate tissue stem cells and terminally differentiated cells, it is believed that Zscan4 expression can be used to treat patients with atopic dermatitis or other skin lesions, by exposing a Zscan4 biologic (e.g., by topical administration) to the skin, particularly resident skin tissue stem cells, of a patient with atopic dermatitis or other skin lesions, to prevent the skin tissue stem cells and skin cells from further deterioration, and thereby facilitate the production of new skin tissue stem cells and skin cells.

Figure 15:
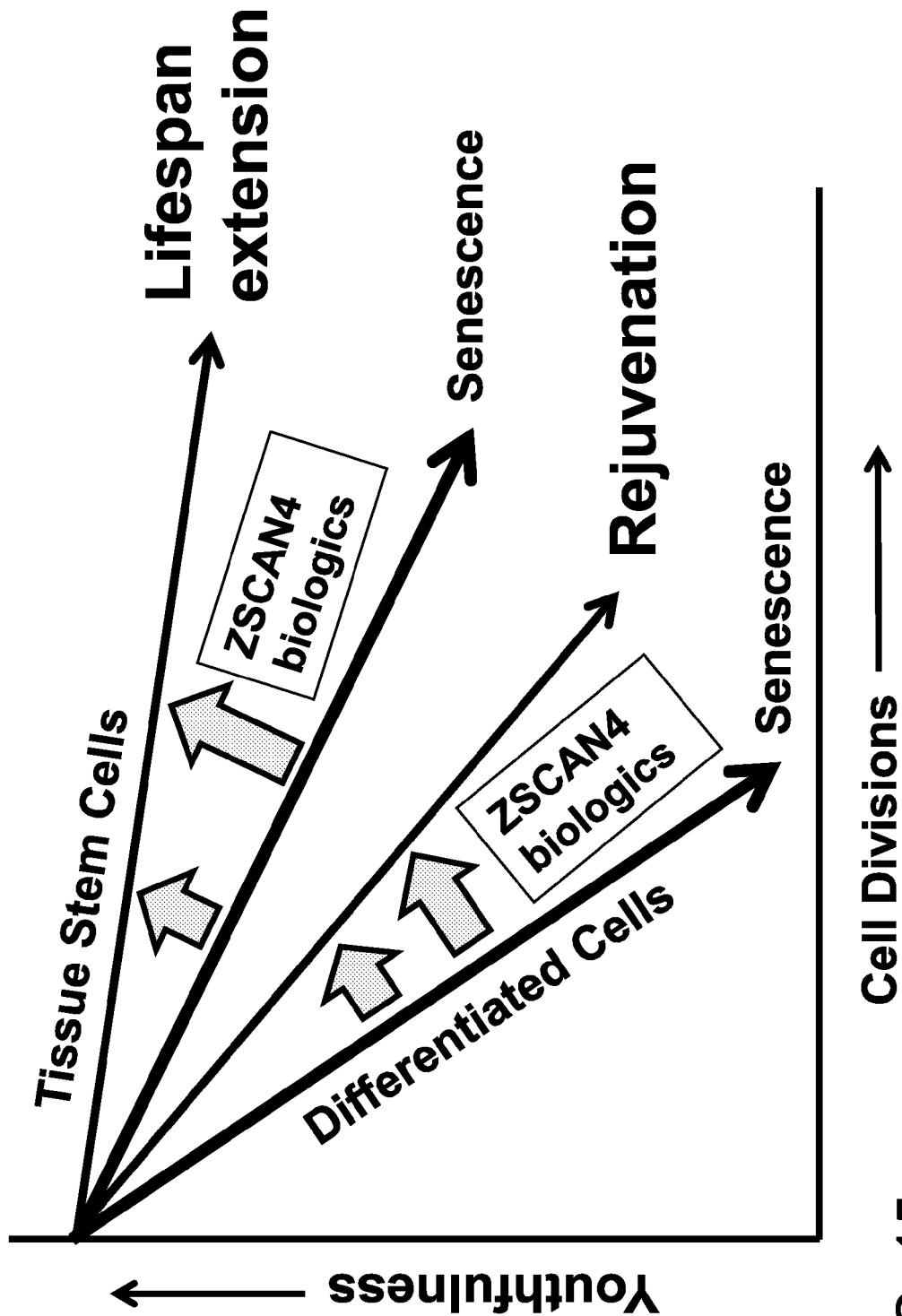
FIG. 15 depicts the effects of Zscan4 biologics on differentiated cells and tissue stem cells.

Example 14: Zscan4 Expression for Rejuvenating an Individual or for Slowing Down the Aging Process of an Individual by Rejuvenating Cells in the Body, Including Terminally Differentiated Cells, Progenitor Cells, or Resident Tissue Stem Cells It is thought that almost all the organs and tissues in the human body are maintained by resident tissue stem cells residing in the organs and tissues of the body. For example, the intestines are maintained by the continuous production of mature and differentiated cells from intestinal stem cells residing in the crypt of the intestine. Similarly, the skin is maintained by the continuous production of dermal epithelia from skin stem cells, whereas hairs are maintained by hair follicle stem cells. Compared to fully differentiated cells that age and deteriorate at a relatively fast pace, tissue stem cells tend to maintain their quality and youthfulness, e.g., by maintaining telomere length (FIG. 15). However, even tissue stem cells gradually lose their youthfulness (FIG. 15). Therefore, general aging and gradual loss of a youthful appearance and function can be considered to be the result of aging and deterioration of resident tissue stem cells.

Based on the results described herein that Zscan4 biologics (e.g., expression of Zscan4, either by a synthetic mRNA encoding Zscan4 or a Sendai virus vector expressing Zscan4) can rejuvenate embryonic stem (ES) cells and mesenchymal stem cells (MSCs), it is believed that Zscan4 expression in tissue stem cells residing in each organ and/or tissue of the human body can be rejuvenated and thus restore the organ and/or tissue to a normal (i.e., young) appearance and function. This is based on observations that human ZSCAN4 is naturally, though rarely, expressed in some tissue stem cells in the human pancreas. Furthermore, based on results described herein that Zscan4 biologics (e.g., expression of Zscan4, either by a synthetic mRNA encoding Zscan4 or a Sendai virus vector expressing Zscan4) can rejuvenate terminally differentiated cells, such as skin fibroblast cells, it is believed that Zscan4 expression in terminally differentiated cells and/or progenitor cells residing in each organ and/or tissue of the human body can be rejuvenated and thus restore the organ and/or tissue to a normal (i.e., young) appearance and function.

This example describes a procedure for expressing Zscan4 biologics (e.g., expression of Zscan4, either by a synthetic mRNA encoding Zscan4 or a Sendai virus vector expressing Zscan4) in tissue stem cells, terminally differentiated cells, and/or progenitor cells residing in organs and tissues of the human body to rejuvenated and thus restore the body a normal (i.e., young) appearance and function. In particular, a Zscan4 biologic as described herein is administered to a subject in need thereof by either directly injecting a Zscan4 biologic to each organ and tissue of the body or injecting a Zscan4 biologic to the circulating blood of the subject, thereby delivering the Zscan4 biologic to all the organs and tissues in the body. Alternatively, or additionally, the Zscan4 biologic may be injected into cerebrospinal fluids, thereby delivering the Zscan4 biologic to all nervous organs and tissues in the body. Alternatively, or additionally, the Zscan4 biologic may be injected into the lymphatic system, thereby delivering the Zscan4 biologic to all lymphatic organs and tissues in the body. Alternatively, or additionally, the Zscan4 biologic may be inhaled into the lung tissue, thereby delivering the Zscan4 biologic to the lung tissue, thereby delivering the Zscan4 biologic to the lung tissue. Alternatively, or additionally, the Zscan4 biologic may be ingested, thereby delivering the Zscan4 biologic to all the digestive organs and tissues, including the esophagus, stomach, and intestines of the body. Alternatively, or additionally, the Zscan4 biologic may be injected into portal veins, thereby delivering the Zscan4 biologic to the liver of the body. Alternatively, or additionally, the Zscan4 biologic may be topically applied to the skin or scalp, thereby delivering the Zscan4 biologic to the skin and skin appendages, such as hair follicles and sweat glands, of the body. These procedures will expose tissue stem cells, progenitor cells, and terminally differentiated cells in each organ and/or tissue of the subject to a Zscan4 biologic and thereby rejuvenate the tissue stem cells, progenitor cells, and/or terminally differentiated cells residing in the treated organ and/or tissue. It is believed that the overall effects of the rejuvenation of tissue stem cells, progenitor cells, and/or terminally differentiated cells in the treated subject are the rejuvenation of the subject and/or the slowing down of the aging process of the subject. It is also believed that rejuvenation of tissue stem cells, progenitor cells, and/or terminally differentiated cells in the treated subject will result in lifespan extension of the subject.

Example 15: Zscan4 Expression Corrects Trisomy 21 in Human Fibroblast Cells Isolated from a Down Syndrome Patient This example describes the finding that expression of human ZSCAN4, either by a synthetic mRNA encoding ZSCAN4 or a Sendai virus vector expressing ZSCAN4, can correct the trisomy 21 karyotype of fibroblast cells isolated from a Down syndrome patient. This example also demonstrates that synthetic mRNAs encoding human ZSCAN4 and Sendai virus vector expressing human ZSCAN4 can be used as therapeutic biologics.

Materials and Methods

Cell Culture

Fibroblast cells isolated from a patient with Down syndrome (DS, trisomy 21) were purchased from the Coriell Cell Repository (Catalog ID AG06872). According to the Coriell Catalog information, the donor was a 1 year old female Caucasian. The donor had typical features of Down syndrome (trisomy 21). The skin biopsy was taken postmortem on May 19, 1983. The culture was initiated using explants of minced skin tissue. The karyotype is 47,XX,+21. The cell morphology is fibroblast-like. The cumulative population doubling level (PDL) was 10.5 at freeze and the passage number was 5. After receiving the DS cells from the Coriell Cell Repository, the cells were cultured for a few more passages. The cells were cultured under the condition recommended by the Coriell Cell Repository: Eagle's Minimum Essential Medium with Earle's salts and non-essential amino acids, supplemented with 10% fetal bovine serum (not inactivated).

Synthetic mRNA

For synthesis of modified mRNA, mRNA synthesis was performed as reported previously by Warren et al. (Warren et al., *Cell Stem Cell*, 2010 Nov. 5; 7(5):618-30). Using these protocol from Warren et al., mRNAs were synthesized by in vitro transcription of template DNAs encoding human ZSCAN4 or green fluorescent protein (GFP) with mixtures of modified dNTPs to increase RNA stability as well as translation efficiency in mammalian cells. The following modified dNTPs were used: 3'-0-Me-m7G(5')ppp(5')G ARCA cap analog, 5-methylcytidine triphosphate, and pseudouridine triphosphate.

Sendai Virus Vectors

A Sendai vector that expresses human ZSCAN4 (SeV18+hZSCAN4/ΔF) was custom-made by MBL (Medical & Biological Laboratories Co, LTD). The vector is referred to as "SeVhZSCAN4" herein. This Sendai vector lacks the F protein, and thus, it is non-transmissible (Inoue et al., *J Virol.* 77:3238-3246, 2003). An MOI (multiplicity of infection) of 10 was used for the experiments.

Additionally, a temperature-sensitive Sendai vector that expresses human ZSCAN4 (SeV18+hZSCAN4/TS15ΔF) was custom-made by MBL (Medical & Biological Laboratories Co, LTD). This vector is referred to as "SeVhZS-CAN4-TS15" herein. This Sendai vector is functional at 35° C., and inactive at 37° C. (Ban et al., *Proc Natl Acad Sci USA*. 2011; 108(34):14234-14239). This Sendai vector also lacks the F protein, and thus, it is not transmissible (Inoue et al., *J Virol*. 77: 23238-3246, 2003). An MOI (multiplicity of infection) of 25 was used for this experiment.

Karyotype Analysis

In addition to regular karyotype analysis by G-banding, the copies of chromosome 21 present in each cultured cell was counted by fluorescence in situ hybridization (FISH) using a probe that specifically hybridizes to the centromeric region of chromosome 21 (CHR21-10-GR: Empire Genomics, New York, USA). In the interphase nucleus, the detection of 3 fluorescent dots indicates trisomy 21 (Down syndrome), whereas the detection of 2 fluorescent dots indicates normal copy number of chromosome 21 (normal).

Results

Synthetic mRNAs Encoding Human ZSCAN4 Correct Chromosome Abnormalities in Fibroblast Cells Isolated from a Down Syndrome Patient (Trisomy 21)

Down syndrome (DS) fibroblast cells at the passage 7 were plated in a 10 cm culture dish at a concentration of $5 \times 10^5$ cells/well and then transfected with 5 µg of synthetic mRNAs (hZSCAN4 or GFP) using 25 µl of Lipofectamine (RNAiMAX: Life Technologies, California, USA). In addition to cells transfected with GFP mRNAs, non-transfected cells were also used as a control. In one experiment (1× transfection), all the cells were passaged on day 5 and then karyotypes were analyzed on day 10 (passage 9). In another experiment (2× transfection), after passaging the cells on day 5, a second transfection with either GFP mRNAs or hZSCAN4 mRNAs was carried out, and then the karyotype was analyzed on day 10 (passage 9).

Figure 16:
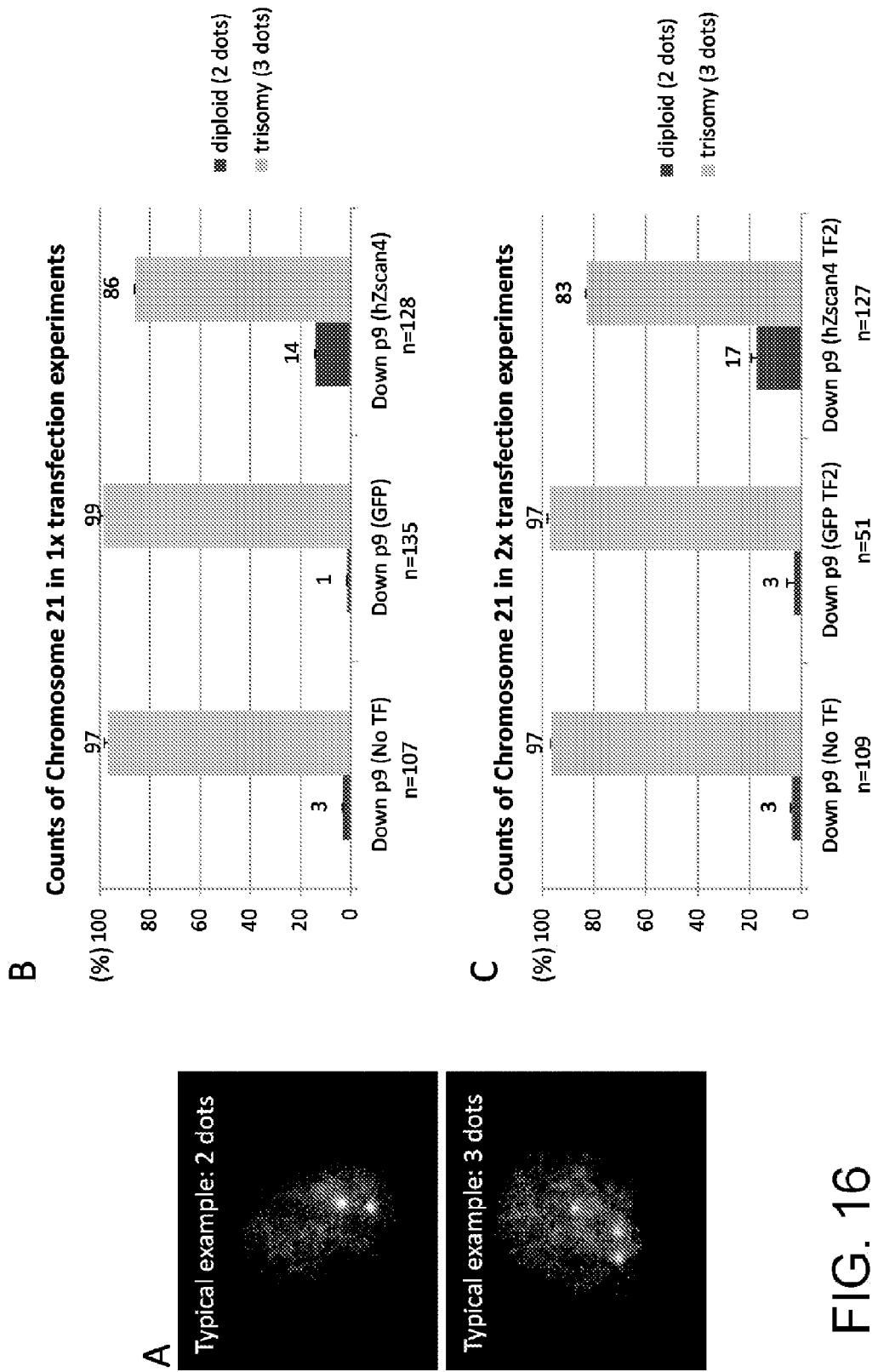
FIG. 16 depicts the ploidy number of chromosome 21 from fibroblast cells from a Down syndrome patient (DS cells) transfected with hZSCAN4 mRNAs.

FIG. 16A shows representative images of cell nuclei after carrying out FISH with chromosome 21 probes. Each dot indicates the number of chromosome 21 present in the nucleus. Two dots indicates a normal disomy of chromosome 21, whereas three dots indicates a trisomy of chromosome 21. FIG. 16B shows a summary of chromosome 21 counts in 1× transfection experiments: 10 days after transfecting human ZSCAN4 mRNAs, 14% of cells now have a normal number of Chromosome 21. FIG. 16C shows a summary of chromosome 21 counts in 2× transfection experiments: transfecting human ZSCAN4 mRNAs twice makes 17% of cells carry a normal number of chromosome 21. By contrast, both non-transfected cells and cells transfected with GFP mRNAs show only a small fraction (<3%) of cells with apparently normal chromosome 21. These are within the margin of error. These results indicate that the introduction of human ZSCAN4 mRNAs into cells can correct abnormalities in chromosome numbers.

Sendai Virus Vectors Expressing Human ZSCAN4 Correct Chromosome Abnormalities in Fibroblast Cells Isolated from a Down Syndrome Patient (Trisomy 21)

Figure 17:
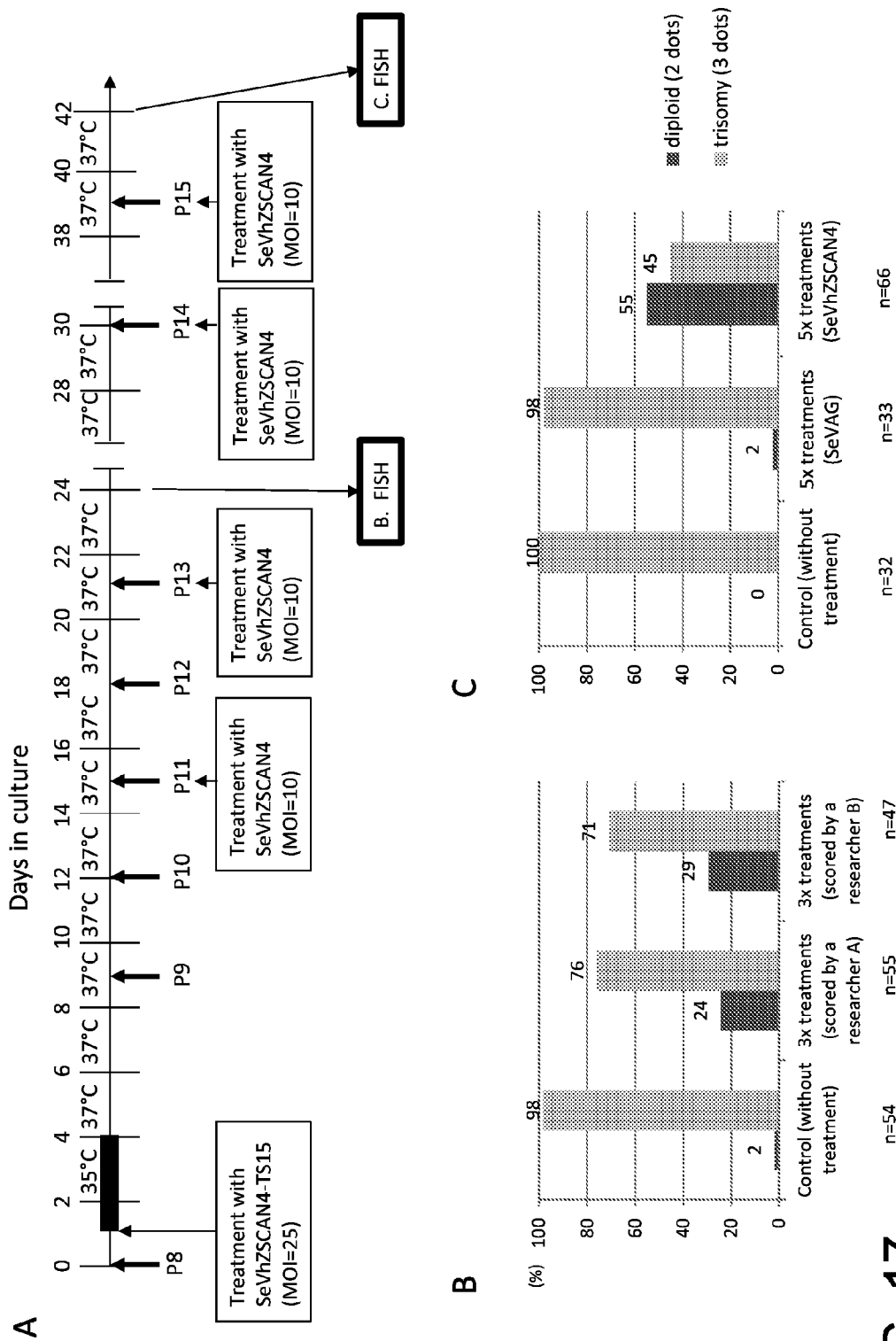
FIG. 17A depicts the experimental procedure.
FIG. 17B depicts the ploidy number of chromosome 21 from fibroblast cells from a Down Syndrome patient (DS cells) infected with SeVhZSCAN4-TS15 once, followed by infection with SeVhZSCAN4 twice.
FIG. 17C depicts the ploidy number of chromosome 21 from fibroblast cells from a Down Syndrome patient (DS cells) infected with SeVhZSCAN4-TS15 once, followed by infection with SeVhZSCAN4 four times.

FIG. 17A shows the experimental procedures. Down syndrome fibroblast (DS) cells were plated in a 6 well dish at a concentration of $5 \times 10^4$ cells/well at passage 8 (day 0). One day later, cells were treated with SeVhZSCAN4-TS15 at an MOI of 25 and kept at 35° C. for 3 days. Then, the dish was transferred to 37° C. and kept at 37° C. for the remainder of the experiment. The cells were passaged on day 9, day 12, and day 15. After passaging on day 15, cells were treated with SeVhZSCAN4 at an MO of 10. Subsequently, cells were passaged on day 18 and day 21. After passaging on day 21, cells were treated with SeVhZSCAN4 at an MOI of 10. Karyotype analysis was performed on day 24 by FISH (FIG. 17B). After passaging on day 30, cells were treated with SeVhZSCAN4 at an MOI of 10. After passaging on day 39, cells were treated with SeVhZSCAN4 at an MOI of 10. Karyotype analysis was performed on day 42 by FISH (FIG. 17C). Cells cultured in parallel without contacting the Sendai virus vector (no treatments) or cell cultured in parallel and contacted with the control Sendai vector expressing the GFP variant were used as controls. The FISH images were scored independently by two experienced researchers: 2 fluorescence dots (2× chromosome 21: Normal); 3 fluorescence dots (3× chromosome 21: trisomy 21, Down syndrome).

FIG. 17B shows a summary of chromosome 21 counts in the control cells and in cells treated once with SeVhZS-CAN4-TS15 and twice with SeVhZSCAN4 (3× treatments). The results demonstrated that treating Down syndrome fibroblast cells with the Sendai virus vector expressing human ZSCAN4 induces correction of trisomy 21 in nearly 30% of the cells.

FIG. 17C shows a summary of chromosome 21 counts in untreated control cells, in control cells treated with control Sendai vector, and in ells treated once with SeVhZSCAN4-TS15 and four-times with SeVhZSCAN4 (5× treatments). The results indicate that Down syndrome fibroblast cells treated repeatedly with the Sendai virus vector expressing human ZSCAN4 induces correction of trisomy 21 in nearly 55% of the cells.

These results indicate that the introduction of human ZSCAN4 into cells can correct abnormalities in chromosome numbers.

Example 16: Zscan4 Expression to Rejuvenate Oocytes and to Correct Chromosome Abnormalities in Oocytes and Preimplantation Embryos During maternal aging, the oocyte competence to be successfully fertilized dramatically declines and the risk of miscarriage and birth defects increases. Recent studies have revealed that maternal age-related miscarriage and birth defects are predominantly caused by chromosome segregation errors in oocytes. At this point, there has been no report that successfully reverse the ability of aged oocyte by preventing or correcting chromosome segregation errors.

In normal development of mouse preimplantation embryos, endogenous Zscan4 is expressed transiently and highly in 2-cell embryos (Falco et al., Dev Biol. 2007; 307: 539-50). We have also shown that the Zscan4 expression is critical for normal development (Falco et al., Dev Biol. 2007; 307: 539-50). Similarly, human ZSCAN4 is expressed transiently in human 6- to 8-cell stage embryos (Vassena et al., Development. 2011; 138: 3699-709). As the zygotic genome activation occurs in 2-cell stage in mouse and in 6- to 8-cell stage in human, it is considered that the expression of Zscan4 is required for human preimplantation embryo development.

This example describes the procedure that Zscan4 biologics can rejuvenate oocytes and correct chromosomal abnormalities in mouse preimplantation embryos. Based on the functional similarity between mouse Zscan4 and human ZSCAN4 genes shown in this patent application, and even superiority of the human ZSCAN4 gene, it is considered that the mouse embryo results can be directly applied to human embryos. These procedures can be implemented in the In Vitro Fertilization (IVF) clinic. These procedures can reduce the risk of Down syndrome and other karyotype problems for women of all ages, which can be especially beneficial for those older than 35 years old, according to the pregnancy risk guideline.

Materials and Methods

Oocyte Collection

Aged mice (i.e., mice over 45 weeks of age) and young mice (8 weeks of age) are purchased from the Jackson Laboratory. Oocytes at a germinal vesicle state (GV oocytes) are collected from the aged and young mice. Oocytes from the young mice are used as a control.

Synthetic mRNA

For synthesis of modified mRNA, mRNA synthesis is performed as reported previously by Warren et al. (Warren et al., *Cell Stem Cell*, 2010 Nov. 5; 7(5):618-30). Using the protocol from Warren et al., mRNAs are synthesized by in vitro transcription of template DNAs encoding mouse Zscan4c, human ZSCAN4, or green fluorescent protein (GFP) with mixtures of modified dNTPs to increase RNA stability as well as translation efficiency in mammalian cells. The following modified dNTPs were used: 3'-0-Me-m7G (5')ppp(5')G ARCA cap analog, 5-methylcytidine triphosphate, and pseudouridine triphosphate.

Sendai Virus Vectors

Sendai vectors that express either mouse Zscan4c (SeV18+mZscan4/ΔF) or human ZSCAN4 (SeV18+hZSCAN4/ΔF) are custom-made by MBL (Medical & Biological Laboratories Co, LTD). These vectors are referred to as "SeVmZscan4' or "SeVhZSCAN4'", respectively, herein. As a control, the same Sendai vector is used, but the vector expressed a green fluorescent protein variant rather than Zscan4. These Sendai vectors lack the F protein, and thus, are not transmissible (Inoue et al., *J Virol.* 77: 23238-3246, 2003).

Sendai vectors that express either mouse Zscan4c fused to a Tamoxifen-controllable ERT2 domain (SeV18+mZERT2/ΔF), or human ZSCAN4 fused to Tamoxifen-controllable ERT2 domain (SeV18+hZERT2/ΔF) are custom-made by MBL (Medical & Biological Laboratories Co, LTD). These vectors are referred to as "SeVmZERT2' or "SeVhZERT2'", respectively, herein. These Sendai vectors also lack the F protein, and thus, are not transmissible (Inoue et al., *J Virol.* 77: 23238-3246, 2003).

Additionally, temperature-sensitive Sendai vectors that express either mouse Zscan4 (SeV18+mZscan4/TS15ΔF) or human ZSCAN4 (SeV18+hZSCAN4/TS15ΔF) are custom-made by MBL (Medical & Biological Laboratories Co, LTD). These vectors are referred to as "SeVmZscan4-TS15" or "SeVhZSCAN4-TS15", respectively, herein. These Sendai vectors are functional at 35° C., and inactive at 37° C. (Ban et al., *Proc Natl Acad Sci USA.* 2011; 108(34):14234-14239). As a control, the same Sendai vector is used, but the vector expressed a green fluorescent protein variant rather than Zscan4. This vector is referred to as "SeVAG-TS15" herein. These Sendai vector also lacks the F protein, and thus, it is not transmissible (Inoue et al., *J Virol.* 77: 23238-3246, 2003).

Results

Oocytes at a germinal vesicle state (GV oocytes) are collected and subjected to in vitro maturation (IVM) for subsequent progression toward meiosis I and II. During IVM, oocytes are contacted with a Zscan4 biologic (e.g., either synthetic mRNAs encoding Zscan4 or Sendai virus vectors expressing Zscan4) and subsequently fertilized in vitro with sperm. Alternatively, fertilized oocytes/preimplantation embryos between the one-cell (zygote) stage and the blastocyst stage are contacted with a Zscan4 biologic (e.g., either synthetic mRNAs encoding Zscan4 or Sendai virus vectors expressing Zscan4). The methods of contact may include standard Lipofectamine transfection of synthetic mRNAs Zscan4 with, viral infection of Sendai virus vectors expressing Zscan4, and intracytoplasmic injection of a Zscan4 biologic by a micromanipulator.

The Zscan4-treated and fertilized oocytes are then cultured in KSOM culture medium for 96 hours at 37° C., 5% $CO_2$.

Without wishing to be bound by theory it is believed that Zscan4-treatment will result in oocytes from aged mice that are comparable to oocytes from young mice in terms of the number of zygotes that can successfully develop to the blastocyst stage. Resultant blastocysts are transferred to a recipient female mouse to check birth rate of healthy pups. It is believed that treatment with Zscan4 biologics improves the success rate of proper embryo development from aged oocytes by improving the karyotype and quality of embryos.

Figure 18:
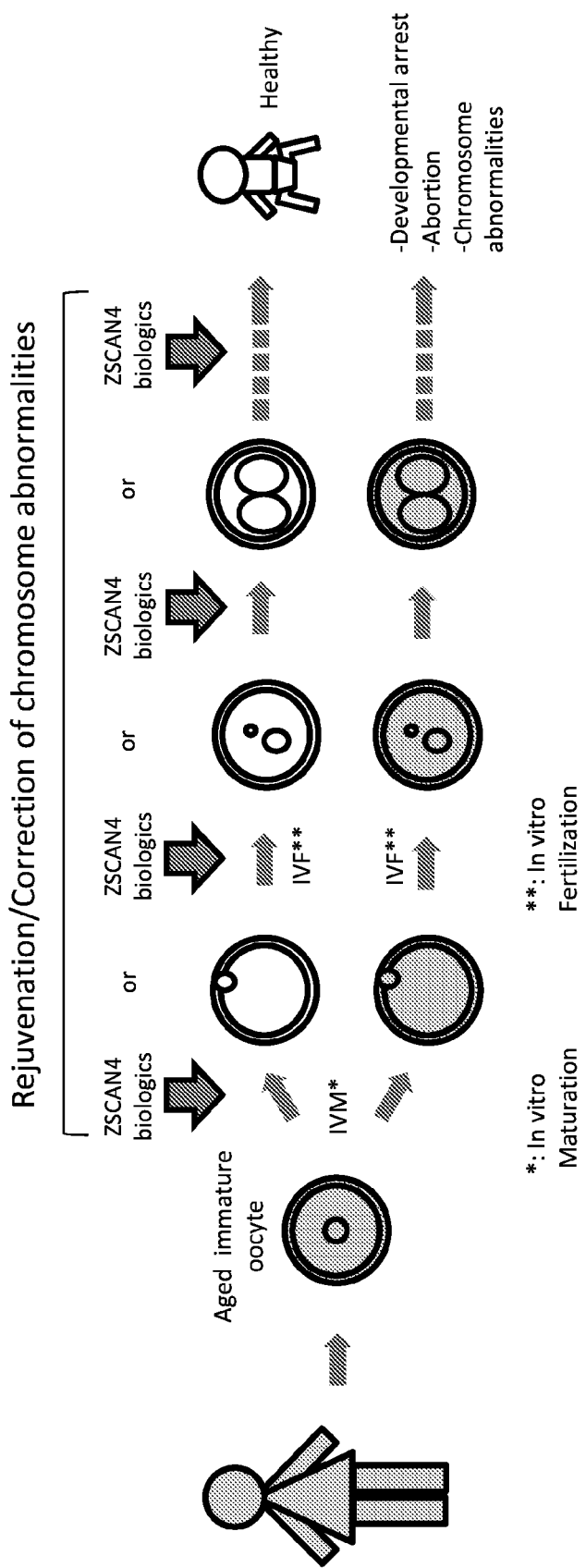
FIG. 18 depicts an exemplary treatment scheme for rejuvenating and/or correcting chromosome abnormalities in human oocytes, human fertilized oocytes, and human pre-implantation embryos using mouse Zscan4 or human ZSCAN4.

Without wishing to be bound by theory it is also believed that the above method can be applied to human oocytes and fertilized oocytes/preimplantation embryos to improve the success rate of proper embryo development from aged oocytes, and to improving the karyotype and quality of embryos (FIG. 18).

Example 17: Zscan4 Expression Represses Growth of Human Cancer Cells

This example describes the finding that a temperature-sensitive Sendai virus vector expressing either mouse Zscan4 or human ZSCAN4 can repress the proliferation of cancer cells. This example also demonstrates that Sendai virus vectors expressing Zscan4 can be used as therapeutic biologics.

Materials and Methods

Cell Culture

HCT116 human colorectal carcinoma cells were purchased from the American Type Culture Collection (ATCC). HCT116 cells are derived from colorectal carcinoma of human adult male. According to ATCC, "the stem line chromosome number is near diploid with the modal number at 45 (62%) and polyploids occurring at 6.8%. This line has a mutation in codon 13 of the ras proto-oncogene." HCT116 cells were cultured according to the ATCC's recommendation.

Sendai Virus Vectors

Temperature-sensitive Sendai vectors that express either mouse Zscan4 (SeV18+mZscan4/TS15ΔF) or human ZSCAN4 (SeV18+hZSCAN4/TS15ΔF) were custom-made by MBL (Medical & Biological Laboratories Co, LTD). These vectors are referred to as "SeVmZscan4-TS15" or "SeVhZSCAN4-TS15", respectively, herein. These Sendai vectors are functional at 35° C., and inactive at 37° C. (Ban et al., *Proc Natl Acad Sci USA.* 2011; 108(34):14234-14239). As a control, the same temperature-sensitive Sendai vector was used, but the vector expressed a green fluorescent protein variant rather than Zscan4. This vector is referred to as "SeVAG-TS15" herein. These Sendai vectors lack the F protein, and thus, it is not transmissible (Inoue et al., *J Virol.* 77: 23238-3246, 2003).

Results

HCT116 cell (passage 9) samples were cultured at a concentration of $8 \times 10^4$ cells/well. Cell samples were treated with one of the following Sendai vectors: SeVAG-TS15 (control), SeVmZscan4-TS15, or SeVhZSCAN4-TS15 at an MOI of 20 and incubated at 35° C. (day 0). Each of the three treatment samples was prepared in triplicate. On day 3, each treatment sample was passaged and treated with the same Sendai vector. Cell number was counted by the Automated Cell Counter Moxi Z (ORFLO Technologies, Idaho, USA). On day 7, each treatment sample was passaged and treated with the same Sendai vector. Cell number was counted (day 7). On day 10, each treatment sample was passaged and treated with the same Sendai vector. Cell numbers were counted (day 10). On day 14, each treatment sample was passaged and treated with the same Sendai vector. Cell numbers were counted (day 14). Cells were cultured at 35° C. throughout the experiments. Cell numbers were converted to PDL, starting at a PDL of 0 for day 0.

Figure 19:
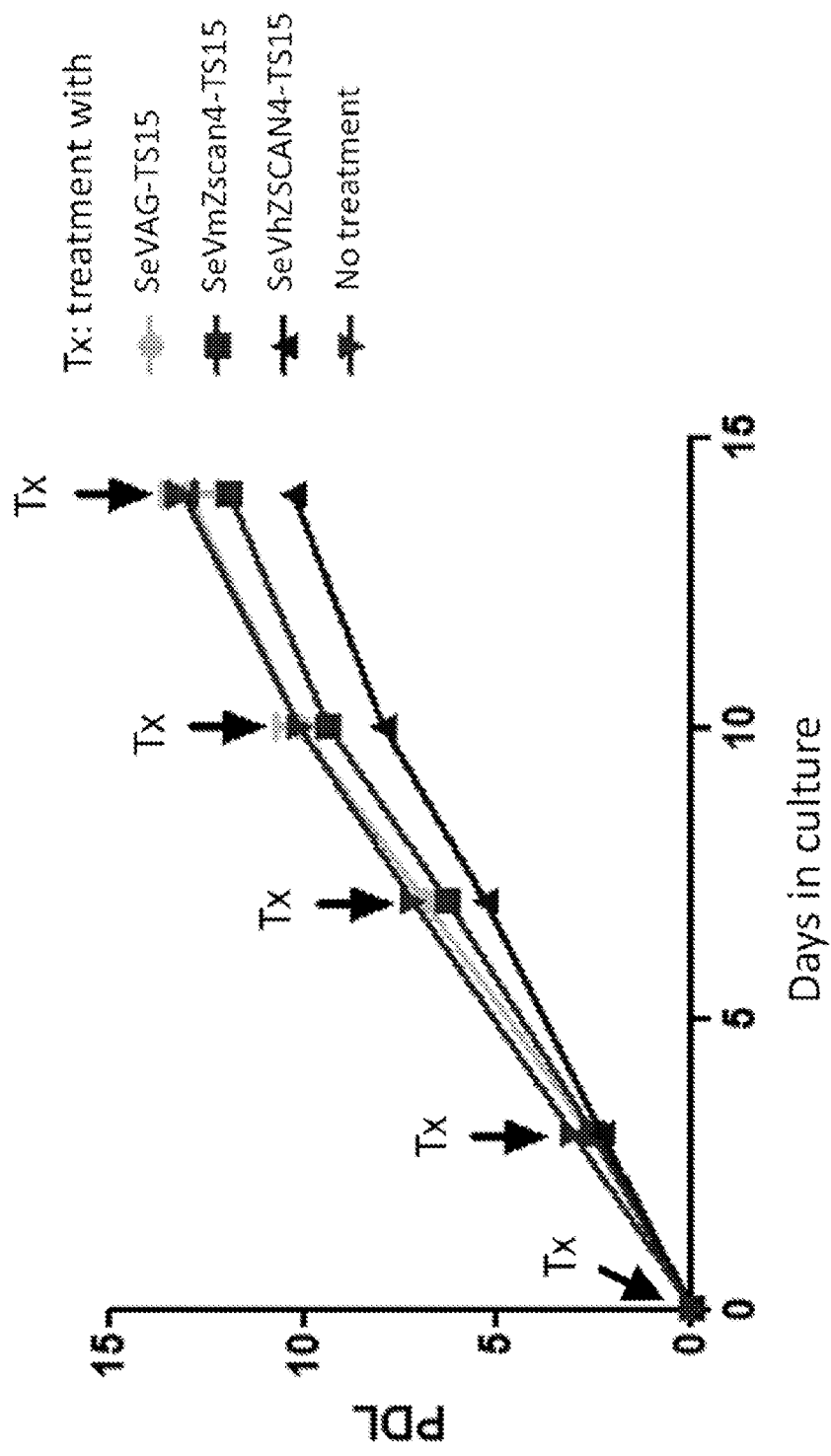
FIG. 19 depicts the repression of cell growth of HCT116 cancer cells infected with either SeVmZscan4-TS15 or SeVhZSCAN4-TS15.

FIG. 19 shows the growth curve of HTC116 cell samples. Compared to control groups (i.e., no treatment group and SeVAG-TS15-treated group), treatments with either SeVmZscan4-TS15 or SeVhZSCAN4-TS15 repressed the proliferation of HTC116 cells. As shown in FIG. 19, human ZSCAN4 was surprisingly better than mouse Zscan4 in repressing cancer cell growth. Thus, these results demonstrate that human ZSCAN4 produces surprisingly superior results over mouse Zscan4c. These results further indicate that the hZSCAN4 treatment can repress the growth of cancer cells. Without wishing to be bound by theory, it is believed that Zscan4-expressing agents may be used for cancer therapy.

Example 18: Zscan4 Expression for Increasing DNA Repair Capacity of Human Cells or Individuals This example describes the finding that Zscan4 biologics can increase the DNA repair capacity of human cells. It is known that genotoxic agents, such as mitomycin C or cisplatin, kills human cells in a dose-dependent manner. Cells exposed to a genotoxic agent and which are then treated with a Zscan4 biologic (e.g., expression of Zscan4, either by a synthetic mRNA encoding Zscan4 or a Sendai virus vector expressing Zscan4) become resistant to the genotoxic agent. It is found that resistance to genotoxic agents by the Zscan4 biologic is due to the heightened capacity of DNA repair induced by Zscan4 expression in the cells. Thus, Zscan4 biologics can be used to: (1) to improve the DNA repair capacity of patients with diseases associated with a DNA repair deficiency; (2) to protect specific tissues and/or organs, such as gonads, from being damaged by genotoxic agents, such as cancer therapeutics; and (3) to protect tissues, organs, and/or individuals from hazardous environments, such as the presence of toxic chemicals or nuclear fallouts.

Example 19: Repression of Zscan4 in Certain Cancer Stem Cells to Treat Cancer It is known that cancer tissues (e.g., tumors) contain cancer stem cells, which are not actively proliferating and are resistant to cancer chemotherapy (e.g., treatment with genotoxic agents such as cisplatin). It is believed that cancer stem cells can survive treatment with chemotherapy, and thus results in the recurrence of the cancer after the treatment. As the presence of Zscan4 can provide cells with resistance to genotoxic agents, it is believed that endogenous Zscan4 expression occurs in certain cancer stem cells, thus providing the cells with protection from the genotoxic agents. As such, it is believed that agents that reduce the expression of endogenous Zscan4, such as siRNAs or shRNAs specific for Zscan4, can be used to treat cancer stem cells in a patient with cancer to reduce or eliminate resistance to genotoxic agents in the cancer stem cells, and thus improve the patient's response to cancer therapy.

What is claimed:

1. A method of treating bone marrow failure associated with Fanconi anemia, dyskeratosis congenita or Hoyeraal-Hreidarsson syndrome, comprising:
   i. contacting one or more human bone marrow or blood cells with an isolated nucleic acid molecule encoding Zscan4 or a Zscan4 protein, and wherein the isolated nucleic acid molecule encoding the Zscan4 or the Zscan4 protein induces extension of telomeres in the one or more human bone marrow or blood cells; and
   ii. engrafting the contacted one or more human bone marrow or blood cells into the subject to treat the bone marrow failure associated with the Fanconi anemia, dyskeratosis congenita or Hoyeraal-Hreidarsson syndrome, wherein the bone marrow failure is caused by telomere shortening, and wherein the associated bone marrow failure is ameliorated.

2. The method of claim 1, wherein the one or more human bone marrow or blood cells are isolated from the subject suffering from the Fanconi anemia, dyskeratosis congenita or Hoyeraal-Hreidarsson syndrome.

3. The method of claim 1, wherein the one or more human bone marrow or blood cells are contacted with the isolated nucleic acid molecule encoding Zscan4.

4. The method of claim 3, wherein the isolated nucleic acid molecule is a synthetic mRNA.

5. The method of claim 3, wherein the isolated nucleic acid molecule is comprised in a vector.

6. The method of claim 5, wherein the vector is a Sendai virus vector.

7. The method of claim 3, wherein the Zscan4 is a Zscan4-ERT2 fusion protein or a Zscan4-ΔC protein.

8. The method of claim 3, wherein the Zscan4 is mouse Zscan4, human ZSCAN4, or a homolog thereof.

9. The method of claim 1, wherein the one or more human bone marrow or blood cells are contacted with the Zscan4 protein.

10. The method of claim 9, wherein the Zscan4 protein is fused to a cell-penetrating peptide.

11. The method of claim 9, wherein the Zscan4 protein is a mouse Zscan4 protein or a human ZSCAN4 protein.

12. The method of claim 1, wherein the blood cells are peripheral blood cells.

\* \* \* \* \*